United States Patent
Garcia et al.

(10) Patent No.: US 12,390,268 B2
(45) Date of Patent: Aug. 19, 2025

(54) SYSTEM AND METHOD FOR ESTIMATING TISSUE HEATING OF A TARGET ABLATION ZONE FOR ELECTRICAL-ENERGY BASED THERAPIES

(71) Applicant: Virginia Tech Intellectual Properties Inc., Blacksburg, VA (US)

(72) Inventors: Paulo A. Garcia, Somerville, MA (US); Christopher B. Arena, Blacksburg, VA (US); Michael B. Sano, Cary, NC (US); Rafael V. Davalos, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 247 days.

(21) Appl. No.: 17/591,992

(22) Filed: Feb. 3, 2022

(65) Prior Publication Data

US 2022/0151688 A1 May 19, 2022

Related U.S. Application Data

(60) Continuation of application No. 16/152,743, filed on Oct. 5, 2018, now Pat. No. 11,272,979, which is a (Continued)

(51) Int. Cl.
*A61B 18/14* (2006.01)
*A61B 34/10* (2016.01)
(Continued)

(52) U.S. Cl.
CPC .......... *A61B 18/1477* (2013.01); *A61B 34/10* (2016.02); *C12N 13/00* (2013.01);
(Continued)

(58) Field of Classification Search
CPC ........ A61B 18/1477; A61B 2018/0016; A61B 2018/00613; A61B 2018/00726;
(Continued)

(56) References Cited

U.S. PATENT DOCUMENTS

| 1,653,819 A | 12/1927 | Northcott |
| 3,730,238 A | 5/1973 | Butler |

(Continued)

FOREIGN PATENT DOCUMENTS

| AU | 2002315095 A1 | 12/2002 |
| AU | 2003227960 A1 | 12/2003 |

(Continued)

OTHER PUBLICATIONS

Beebe, S.J., et al., Nanosecond pulsed electric field (nsPEF) effects on cells and tissues: apoptosis induction and tumor growth inhibition. PPPS—2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

(Continued)

*Primary Examiner* — Michael F Peffley
(74) *Attorney, Agent, or Firm* — New River Valley IP Law, P.C.; Michele L. Mayberry; Ashley M. Gates

(57) ABSTRACT

Systems and methods are provided for modeling and for providing a graphical representation of tissue heating and electric field distributions for medical treatment devices that apply electrical treatment energy through one or a plurality of electrodes. In embodiments, methods comprise: providing one or more parameters of a treatment protocol for delivering one or more electrical pulses to tissue through a plurality of electrodes; modeling electric and heat distribution in the tissue based on the parameters; and displaying a (Continued)

graphical representation of the modeled electric and heat distribution. In another embodiment, a treatment planning module is adapted to generate an estimated target ablation zone based on a combination of one or more parameters for an irreversible electroporation protocol and one or more tissue-specific conductivity parameters.

19 Claims, 53 Drawing Sheets

Related U.S. Application Data continuation-in-part of application No. 14/808,679, filed on Jul. 24, 2015, now Pat. No. 11,655,466, and a continuation of application No. 14/558,631, filed on Dec. 2, 2014, now Pat. No. 10,117,707, which is a continuation-in-part of application No. 14/012,832, filed on Aug. 28, 2013, now Pat. No. 9,283,051, said application No. 14/808,679 is a continuation-in-part of application No. 13/332,133, filed on Dec. 20, 2011, now Pat. No. 10,448,989, and a division of application No. 12/906,923, filed on Oct. 18, 2010, now Pat. No. 9,198,733, which is a continuation-in-part of application No. 12/757,901, filed on Apr. 9, 2010, now Pat. No. 8,926,606, said application No. 13/332,133 is a continuation-in-part of application No. 12/757,901, filed on Apr. 9, 2010, now Pat. No. 8,926,606, said application No. 12/906,923 is a continuation-in-part of application No. 12/609,779, filed on Oct. 30, 2009, now Pat. No. 8,465,484, and a continuation-in-part of application No. 12/491,151, filed on Jun. 24, 2009, now Pat. No. 8,992,517, said application No. 14/012,832 is a continuation-in-part of application No. 12/491,151, filed on Jun. 24, 2009, now Pat. No. 8,992,517, which is a continuation-in-part of application No. 12/432,295, filed on Apr. 29, 2009, now Pat. No. 9,598,691.

(60) Provisional application No. 61/910,655, filed on Dec. 2, 2013, provisional application No. 61/694,144, filed on Aug. 28, 2012, provisional application No. 61/424,872, filed on Dec. 20, 2010, provisional application No. 61/285,618, filed on Dec. 11, 2009, provisional application No. 61/252,445, filed on Oct. 16, 2009, provisional application No. 61/171,564, filed on Apr. 22, 2009, provisional application No. 61/167,997, filed on Apr. 9, 2009, provisional application No. 61/075,216, filed on Jun. 24, 2008, provisional application No. 61/125,840, filed on Apr. 29, 2008.

(51) Int. Cl.
  *C12N 13/00* (2006.01)
  *A61B 18/00* (2006.01)
  *A61B 34/00* (2016.01)
  *A61B 90/00* (2016.01)

(52) U.S. Cl.
  CPC ............... *A61B 2018/0016* (2013.01); *A61B 2018/00613* (2013.01); *A61B 2018/00779* (2013.01); *A61B 2018/00875* (2013.01); *A61B 2018/00886* (2013.01); *A61B 2018/00892* (2013.01); *A61B 2018/1425* (2013.01); *A61B 2034/104* (2016.02); *A61B 34/25* (2016.02); *A61B 2034/256* (2016.02); *A61B 90/37* (2016.02)

(58) Field of Classification Search
  CPC ........... A61B 2018/00761; A61B 2018/00779; A61B 2018/00791; A61B 2018/00827; A61B 2018/00875; A61B 2018/00886; A61B 2018/00892; A61B 2018/1425; A61B 2018/143; A61B 2034/104; A61B 2034/256; A61B 2090/374; A61B 2090/3762; A61B 2090/378; A61B 34/10; A61B 34/25; A61B 90/37; C12N 13/00
  See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |

(56) References Cited

U.S. PATENT DOCUMENTS

| | | |
|---|---|---|
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Vu Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak, III |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton et al. |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |

(56) References Cited

U.S. PATENT DOCUMENTS

| | | | |
|---|---|---|---|
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,478,793 B1 * | 11/2002 | Cosman ............... A61B 34/20 606/49 |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |

(56) References Cited

U.S. PATENT DOCUMENTS

| | | |
|---|---|---|
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 * | 2/2010 | Long .................. A61B 1/06 600/103 |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| 7,871,406 B2 * | 1/2011 | Nields .................. A61B 6/4464 606/34 |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 * | 11/2011 | Davalos .............. A61B 18/1233 606/32 |
| 8,055,323 B2 * | 11/2011 | Sawyer .................. A61N 5/1049 600/407 |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,403,925 B2 | 3/2013 | Miller et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,670,816 B2 * | 3/2014 | Green .................. A61B 17/221 600/424 |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 * | 12/2015 | Neal, II .................. A61B 18/12 |
| 9,283,051 B2 | 3/2016 | Garcia et al. |
| 9,414,881 B2 | 8/2016 | Callas et al. |
| 9,598,691 B2 | 3/2017 | Davalos |
| 9,700,368 B2 | 7/2017 | Callas et al. |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 11,254,926 B2 | 2/2022 | Garcia et al. |
| 11,272,979 B2 | 3/2022 | Garcia et al. |
| 11,311,329 B2 | 4/2022 | Davalos et al. |
| 11,382,681 B2 | 7/2022 | Arena et al. |
| 11,406,820 B2 | 8/2022 | Sano et al. |
| 11,453,873 B2 | 9/2022 | Davalos et al. |
| 11,607,271 B2 | 3/2023 | Garcia et al. |
| 11,607,537 B2 | 3/2023 | Latouche et al. |
| 11,638,603 B2 | 5/2023 | Sano et al. |
| 11,655,466 B2 | 5/2023 | Neal et al. |
| 11,737,810 B2 | 8/2023 | Davalos et al. |
| 11,890,046 B2 | 2/2024 | Neal et al. |
| 11,903,690 B2 | 2/2024 | Davalos et al. |
| 11,925,405 B2 | 3/2024 | Davalos et al. |
| 11,950,835 B2 | 4/2024 | O'Brien et al. |
| 11,952,568 B2 | 4/2024 | Neal, II et al. |
| 11,974,800 B2 | 5/2024 | Sano et al. |
| 12,059,197 B2 | 8/2024 | Davalos et al. |
| 12,173,280 B2 | 12/2024 | Neal, II et al. |
| 12,214,189 B2 | 2/2025 | Lorenzo et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077627 A1 | 6/2002 | Johnson et al. |
| 2002/0077676 A1 | 6/2002 | Schroeppel et al. |
| 2002/0082543 A1 | 6/2002 | Park et al. |

(56) References Cited

U.S. PATENT DOCUMENTS

| | | |
|---|---|---|
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0112141 A1 | 5/2005 | Terman |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016125 A1 | 1/2007 | Wong et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129720 A1 | 6/2007 | Demarais et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |

(56) References Cited

U.S. PATENT DOCUMENTS

| | | |
|---|---|---|
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0009102 A1 | 1/2008 | Yang et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0071264 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1* | 8/2009 | Esser ............... A61N 1/327 606/41 |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1* | 9/2010 | Pearson ............. A61B 18/1206 703/2 |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1* | 5/2011 | Neal, II ............. A61B 18/12 607/2 |
| 2011/0112531 A1 | 5/2011 | Landis et al. |
| 2011/0118727 A1 | 5/2011 | Fish et al. |
| 2011/0118732 A1* | 5/2011 | Rubinsky ........... A61B 18/14 606/41 |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley, I |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071870 A1 | 3/2012 | Salahieh et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0139734 A1 | 6/2012 | Olde et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |

(56) References Cited

U.S. PATENT DOCUMENTS

| | | |
|---|---|---|
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0023871 A1 | 1/2013 | Collins |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Li et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0276748 A1 | 9/2014 | Ku et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0086713 A1 | 3/2017 | Pushpala et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0319851 A1 | 11/2017 | Athos et al. |
| 2017/0348525 A1 | 12/2017 | Sano et al. |
| 2017/0360326 A1 | 12/2017 | Davalos |
| 2018/0028260 A1 | 2/2018 | Onik et al. |
| 2018/0036529 A1 | 2/2018 | Jaroszeski et al. |
| 2018/0071014 A1 | 3/2018 | Neal et al. |
| 2018/0125565 A1 | 5/2018 | Sano et al. |
| 2018/0132922 A1 | 5/2018 | Neal, II |
| 2018/0161086 A1 | 6/2018 | Davalos et al. |
| 2018/0177543 A1 | 6/2018 | You et al. |
| 2018/0198218 A1 | 7/2018 | Regan et al. |
| 2019/0023804 A1 | 1/2019 | Onik et al. |
| 2019/0029749 A1 | 1/2019 | Garcia et al. |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |
| 2021/0022795 A1 | 1/2021 | Davalos et al. |
| 2021/0023362 A1 | 1/2021 | Lorenzo et al. |
| 2021/0052882 A1 | 2/2021 | Wasson et al. |
| 2021/0113265 A1 | 4/2021 | D'Agostino et al. |
| 2021/0137410 A1 | 5/2021 | O'Brien et al. |
| 2021/0186600 A1 | 6/2021 | Davalos et al. |
| 2021/0361341 A1 | 11/2021 | Neal et al. |
| 2021/0393312 A1 | 12/2021 | Davalos et al. |
| 2022/0151688 A1 | 5/2022 | Garcia et al. |
| 2022/0161027 A1 | 5/2022 | Aycock et al. |
| 2022/0290183 A1 | 9/2022 | Davalos et al. |
| 2022/0362549 A1 | 11/2022 | Sano et al. |
| 2023/0157759 A1 | 5/2023 | Garcia et al. |
| 2023/0212551 A1 | 7/2023 | Neal, II et al. |
| 2023/0248414 A1 | 8/2023 | Sano et al. |
| 2023/0355293 A1 | 11/2023 | Davalos et al. |
| 2023/0355968 A1 | 11/2023 | Davalos et al. |
| 2024/0008911 A1 | 1/2024 | Davalos et al. |
| 2024/0074804 A1 | 3/2024 | Neal et al. |
| 2024/0173063 A1 | 5/2024 | Neal, II et al. |
| 2024/0268878 A1 | 8/2024 | Davalos et al. |
| 2024/0277245 A1 | 8/2024 | Davalos et al. |
| 2024/0299076 A1 | 9/2024 | O'Brien et al. |
| 2025/0000569 A1 | 1/2025 | Davalos et al. |
| 2025/0120762 A1 | 4/2025 | Neal, II et al. |
| 2025/0152230 A1 | 5/2025 | Davalos et al. |
| 2025/0177741 A1 | 6/2025 | Lorenzo et al. |
| 2025/0205481 A1 | 6/2025 | Davalos et al. |

FOREIGN PATENT DOCUMENTS

| | | |
|---|---|---|
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |

(56) References Cited

FOREIGN PATENT DOCUMENTS

| | | |
|---|---|---|
| DE | 4000893 A1 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |
| WO | 2024081749 A2 | 4/2024 |

OTHER PUBLICATIONS

Beebe, S.J., et al.,, "Nanosecond, high-intensity pulsed electric fields induce apoptosis in human cells", FASEB J, 17(9): p. 1493-5 (2003).

Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.

Belehradek, J., et al., "Electropermeabilization of Cells in Tissues Assessed by the Qualitative and Quantitative Electroloading of Bleomycin", Biochimica Et Biophysica Acta—Biomembranes, 1190(1): p. 155-163 (1994).

Ben-David, E. et al., "Irreversible Electroporation: Treatment Effect Is Susceptible to Local Environment and Tissue Properties," Radiology, vol. 269, No. 3, 2013, 738-747.

Ben-David, E.,et al., "Characterization of Irreversible Electroporation Ablation in In Vivo Procine Liver" Am. J. Roentgenol. 198(1), W62-W68 (2012).

Benz, R., et al. "Reversible electrical breakdown of lipid bilayer membranes: a charge-pulse relaxation study". J Membr Biol, 48(2): p. 181-204 (1979).

(56) References Cited

OTHER PUBLICATIONS

Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.

Bhonsle, S., M. F. Lorenzo, A. Safaai Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.

Blad, et al., Impedance Spectra of Tumour Tissue in Comparison with Normal Tissue; a Possible Clinical Application for Electrical Impedance Tomography, Physiol. Meas. 17 (1996) A105-A115.

Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.

Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.

Bondarenko, A. and G. Ragoisha, Eis spectrum analyser (the program is available online at http://www.abc.chemistry.bsu.by/vi/analyser/.

Boone, K., Barber, D. & Brown, B. Review—Imaging with electricity: report of the European Concerted Action on Impedance Tomography. J. Med. Eng. Technol. 21, 201-232 (1997).

Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.

Bower et al., "Irreversible electroporation of the pancreas: definitive local therapy without systemic effects." Journal of surgical oncology, 2011. 104(1): p. 22-28.

BPH Management Strategies: Improving Patient Satisfaction, Urology Times, May 2001, vol. 29, Supplement 1.

Brown, et al., Blood Flow Imaging Using Electrical Impedance Tomography, Clin. Phys. Physiol. Meas., 1992, vol. 13, Suppl. A, 175-179.

Brown, S.G., Phototherapy of tumors. World J. Surgery, 1983. 7: p. 700-9.

Bulvik, B. E. et al. "Irreversible Electroporation versus Radiofrequency Ablation: A Comparison of Local and Systemic Effects in a Small Animal Model," Radiology, vol. 280, No. 2, 2016, 413-424.

Cannon et al., "Safety and early efficacy of irreversible electroporation for hepatic tumors in proximity to vital structures." Journal of Surgical Oncology, 6 pages (2012).

Carpenter A.E. et al., "CellProfiler: image analysis software for identifying and quantifying cell phenotypes." Genome Biol. 2006; 7(10): R100. Published online Oct. 31, 2006, 11 pages.

Castellvi, Q., B. Mercadal, and A. Ivorra, "Assessment of electroporation by electrical impedance methods," in Handbook of electroporation. Springer-Verlag, 2016, pp. 671-690.

Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Chang, D.C., "Cell Poration and Cell-Fusion Using an Oscillating Electric-Field". Biophysical Journal, 56(4): p. 641-652 (1989).

Charpentier, K.P., et al., "Irreversible electroporation of the pancreas in swine: a pilot study." HPB: the official journal of the International Hepato Pancreato Biliary Association, 2010. 12(5): p. 348-351.

Chen et al., "Classification of cell types using a microfluidic device for mechanical and electrical measurement on single cells." Lab on a Chip, vol. 11, pp. 3174-3181 (2011).

Chen, M.T., et al., "Two-dimensional nanosecond electric field mapping based on cell electropermeabilization", PMC Biophys, 2(1):9 (2009).

Clark et al., "The electrical properties of resting and secreting pancreas." The Journal of Physiology, vol. 189, pp. 247-260 (1967).

Coates, C.W.,et al., "The Electrical Discharge of the Electric Eel, Electrophorous Electricus," Zoologica, 1937, 22(1), pp. 1-32.

Cook, et al., ACT3: A High-Speed, High-Precision Electrical Impedance Tomograph, IEEE Transactions on Biomedical Engineering, vol. 41, No. 8, Aug. 1994.

Corovic et al., "Analytical and numerical quantification and comparison of the local electric field in the tissue for different electrode configurations," Biomed Eng Online, 6, 14 pages, 2007.

Cowley, Good News for Boomers, Newsweek, Dec. 30, 1996/Jan. 6, 1997.

Cox, et al., Surgical Treatment of Atrial Fibrillation: A Review, Europace (2004) 5, S20-S-29.

Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.

Crowley, Electrical Breakdown of Biomolecular Lipid Membranes as an Electromechanical Instability, Biophysical Journal, vol. 13, pp. 711-724, 1973.

Dahl et al., "Nuclear shape, mechanics, and mechanotransduction." Circulation Research vol. 102, pp. 1307-1318 (2008).

Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).

Daud, A.I., et al., "Phase I Trial of Interleukin-12 Plasmid Electroporation in Patients With Metastatic Melanoma," Journal of Clinical Oncology, 26, 5896-5903, Dec. 20, 2008.

Davalos et al., "Electrical impedance tomography for imaging tissue electroporation," IEEE Transactions on Biomedical Engineering, 51, pp. 761-767, 2004.

Davalos et al., "Theoretical analysis of the thermal effects during in vivo tissue electroporation." Bioelectrochemistry, vol. 61(1-2): pp. 99-107, 2003.

Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.

Davalos, et al., Tissue Ablation with Irreversible Electroporation, Annals of Biomedical Engineering, vol. 33, No. 2, p. 223-231, Feb. 2005.

Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).

Davalos, Real-Time Imaging for Molecular Medicine through Electrical Impedance Tomography of Electroporation, Dissertation for Ph.D. in Engineering—Mechanical Engineering, Graduate Division of University of California, Berkeley, 2002.

De Senneville, B. D. et al., "MR thermometry for monitoring tumor ablation," European radiology, vol. 17, No. 9, pp. 2401-2410, 2007.

De Vuyst, E., et al., "In situ bipolar Electroporation for localized cell loading with reporter dyes and investigating gap functional coupling", Biophysical Journal, 94(2): p. 469-479 (2008).

Dean, Nonviral Gene Transfer to Skeletal, Smooth, and Cardiac Muscle in Living Animals, Am J. Physiol Cell Physiol 289: 233-245, 2005.

Demirbas, M. F., "Thermal Energy Storage and Phase Change Materials: An Overview" Energy Sources Part B 1(1), 85-95 (2006).

(Neal, Robert E. et al.) Co-pending U.S. Appl. No. 16/404,392, filed May 6, 2019, and published as U.S. Publication No. 2019/0256839 on Aug. 22, 2019, Specification, Claims, Figures.

(Neal, Robert E. et al.) Co-pending U.S. Appl. No. 16/865,772, filed May 4, 2020, Specification, Claims, Figures.

(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.

(Neal, Robert E. et al.) Co-Pending U.S. Appl. No. 14/940,863, filed Nov. 13, 2015 and Published as US 2016/0066977 on Mar. 10, 2016, Specification, Claims, Figures.

(56) References Cited

OTHER PUBLICATIONS (Neal, Robert et al.) Co-pending U.S. Appl. No. 16/280,511, filed Feb. 20, 2019, and published as U.S. Publication No. 2019/0175248 on Jun. 13, 2019, Specification, Claims, Figures.
(Neal, Robert et al.) Co-pending U.S. Appl. No. 17/338,960, filed Jun. 4, 2021, Specification, Claims, Figures.
(Neal, Robert et al.) Co-Pending Application No. EP 10824248.8, filed May 9, 2012, Amended Claims (3 pages), Specification and Figures (See PCT/US10/53077).
(O'Brien, Timothy J. et al.) Co-Pending U.S. Appl. No. 16/915,760, filed Jun. 29, 2020, Specification, Claims, Figures.
(O'Brien, Timothy J. et al.) Co-Pending U.S. Appl. No. 17/152,379, filed Jan. 19, 2021, Specification, Claims, Figures.
(Pearson, Robert M. et al.) Co-pending Application No. PCT/US2010/029243, filed Mar. 30, 2010, published as WO 2010/117806 on Oct. 14, 2010, Specification, Claims, Figures.
(Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al) Co-Pending Application No. PCT/US2015/030429, Filed May 12, 2015, Published on Nov. 19, 2015 as WO 2015/175570, Specification, Claims, Figures.
(Sano, Michael B. et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-pending U.S. Appl. No. 15/843,888, filed Dec. 15, 2017, and published as U.S. Publication No. 2018/0125565 on May 10, 2018, Specification, Claims, Figures.
(Sano, Michael B. et al.) Co-pending U.S. Appl. No. 16/443,351, filed Jun. 17, 2019 (published as 20190328445 on Oct. 31, 2019), Specification, Claims, Figures.
(Sano, Michael B. et al.) Co-pending U.S. Appl. No. 16/520,901, filed Jul. 24, 2019, and published as U.S. Publication No. 2019/0351224 on Nov. 21, 2019, Specification, Claims, Figures.
(Sano, Michael B. et al.) Co-Pending U.S. Appl. No. 16/747,219, filed Jan. 20, 2020, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-Pending Application No. JP 2019-133057 filed Jul. 18, 2019, 155 pgs, Specification, Claims, Figures (See PCT/US15/30429 for English Version of documents as filed).
(Sano, Michael et al.) Co-Pending Application No. PCT/US11/62067, filed Nov. 23, 2011, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Alinezhadbalalami, N. et al., "Generation of Tumor-activated T cells Using Electroporation", Bioelectrochemistry 142 (2021) 107886, Jul. 13, 2021, 11 pages.
Al-Sakere et al., "Tumor ablation with irreversible electroporation," PLoS ONE, 2, e1135, 2007, 8 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)—Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Pakhomova, O. N., Gregory, B., Semenov I., and Pakhomov, A. G., BBA—Biomembr., 2014, 1838, 2547-2554.
Paszek et al., "Tensional homeostasis and the malignant phenotype." Cancer Cell, vol. 8, pp. 241-254 (2005).
Pavselj, N. et al. The course of tissue permeabilization studied on a mathematical model of a subcutaneous tumor in small animals. IEEE Trans Biomed Eng 52, 1373-1381 (2005).
Pavselj, N., et al., "A numerical model of skin electroporation as a method to enhance gene transfection in skin. 11th Mediterranean

(56) References Cited

OTHER PUBLICATIONS

Conference on Medical and Biological Engineering and Computing", vols. 1 and 2, 16(1-2): p. 597-601 (2007).
PCT Application No. PCT/2011/062067, International Preliminary Report on Patentability dated May 28, 2013.
PCT Application No. PCT/2011/066239, International Preliminary Report on Patentability dated Jun. 25, 2013.
PCT Application No. PCT/US09/62806, International Search Report (Jan. 19, 2010), Written Opinion (Jan. 19, 2010), and International Preliminary Report on Patentability (Jan. 4, 2010), 15 pgs.
PCT Application No. PCT/US10/53077, International Search Report (Aug. 2, 2011), Written Opinion (Aug. 2, 2011), and International Preliminary Report on Patentability (Apr. 17, 2012).
PCT Application No. PCT/US15/30429, International Search Report and Written Opinion dated Oct. 16, 2015, 19 pages.
PCT Application No. PCT/US15/30429, International Report on Patentability dated Nov. 15, 2016.
PCT Application No. PCT/US15/65792, International Search Report (Feb. 9, 2016), Written Opinion (Feb. 9, 2016), and International Preliminary Report on Patentability (Jun. 20, 2017), 15 pages.
PCT Application No. PCT/US19/51731, International Preliminary Report on Patentability dated Mar. 23, 2021, 13 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
PCT Application No. PCT/US2004/043477, International Search Report (Aug. 26, 2005), Written Opinion (Aug. 26, 2005), and International Preliminary Report on Patentability (Jun. 26, 2006).
PCT Application No. PCT/US2009/042100, International Search Report (Jul. 9, 2009), Written Opinion (Jul. 9, 2009), and International Preliminary Report on Patentability (Nov. 2, 2010).
PCT Application No. PCT/US2010/029243, International Search Report, 4 pgs, (Jul. 30, 2010), Written Opinion, 7 pgs, (Jul. 30, 2010), and International Preliminary Report on Patentability, 8 pgs, (Oct. 4, 2011).
PCT Application No. PCT/US2010/030629, International Search Report (Jul. 15, 2010), Written Opinion (Jul. 15, 2010), and International Preliminary Report on Patentability (Oct. 11, 2011).
PCT Application No. PCT/US2011/062067, International Search Report and Written Opinion dated Jul. 25, 2012.
PCT Application No. PCT/US2011/066239, International Search Report (Aug. 22, 2012), and Written Opinion (Aug. 22, 2012).
Pending Application No. PCT/US21/51551, International Search Report and Written Opinion dated Dec. 29, 2021, 14 pages.
Pending U.S. Appl. No. 14/686,380, Advisory Action dated Oct. 20, 2021, 3 pages.
Pending U.S. Appl. No. 14/686,380, Appeal Brief filed Nov. 5, 2021, 21 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiner's Answer to Appeal Brief, dated Feb. 18, 2022, 16 pages.
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Oct. 6, 2020 Final Office Action with RCE, dated Jan. 6, 2020, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement Jul. 19, 2017, 7 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 14/808,679, 3rd Renewed Petition, Dec. 9, 2019 and Petition Decision Dec. 18. 2019, 11 pages.
Pending U.S. Appl. No. 14/808,679, Appeal Brief, filed Jun. 3, 2021, 25 pages.
Pending U.S. Appl. No. 14/808,679, Examiner's Answer to Appeal Brief, dated Sep. 15, 2021, 6 pages.
Pending U.S. Appl. No. 14/808,679, Final Office Action dated Dec. 28, 2020, 11 pages.
Pending U.S. Appl. No. 14/808,679, Final Office Action dated Jan. 11, 2019, 12 pages.
Pending U.S. Appl. No. 14/808,679, Interview Summary, Apr. 26, 2019, 3 pages.
Pending U.S. Appl. No. 14/808,679, Non-Final Office Action dated Jun. 12, 2020, 10 pages.
Pending U.S. Appl. No. 14/808,679, Non-Final Office Action dated Sep. 10, 2018, 12 pages.
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).

(56) References Cited

OTHER PUBLICATIONS

Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster RS, "High-intensity focused ultrasound in the treatment of prostatic disease", European Urology, 1993, vol. 23 Suppl 1, pp. 29-33.
Foster, R.S., et al., Production of Prostatic Lesions in Canines Using Transrectally Administered High-Intensity Focused Ultrasound. Eur. Urol., 1993; 23: 330-336.
Fox, et al., Sampling Conductivity Images via MCMC, Mathematics Department, Auckland University, New Zealand, May 1997.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Garcia et al., "Irreversible electroporation (IRE) to treat brain cancer." ASME Summer Bioengineering Conference, Marco Island, FL, Jun. 25-29, 2008, 2 pages.
Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.
Garcia P.A., et al., "Pilot study of irreversible electroporation for intracranial surgery", Conf Proc IEEE Eng Med Biol Soc, 2009:6513-6516, 2009.
Garcia, et al., "A Parametric Study Delineating Irreversible Electroporation from Thermal Damage Based on a Minimally Invasive Intracranial Procedure," Biomed Eng Online, vol. 10:34, 22 pages, 2011.
Garcia, P. A., et al., "Towards a predictive model of electroporation-based therapies using pre-pulse electrical measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Garcia, P. et al. Intracranial nonthermal irreversible electroporation: in vivo analysis. J Membr Biol 236, 127-136 (2010).
Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.
Garcia-Sánchez, T., A. Azan, I. Leray, J. Rosell-Ferrer, R. Bragos, and L. M. Mir, "Interpulse multifrequency electrical impedance measurements during electroporation of adherent differentiated myotubes," Bioelectrochemistry, vol. 105, pp. 123-135, 2015.
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.

Gehl, et al., In Vivo Electroporation of Skeletal Muscle: Threshold, Efficacy and Relation to Electric Field Distribution, Biochimica et Biophysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., The Use of Magnetic Resonance Imaging Data and the Inclusion of Anisotropic Regions in Electrical Impedance Tomography, Biomed. Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.
Griffiths, et al., A Dual-Frequency Electrical Impedance Tomography System, Phys. Med. Biol., 1989, vol. 34, No. 10, pp. 1465-1476.
Griffiths, The Importance of Phase Measurement in Electrical Impedance Tomography, Phys. Med. Biol., 1987, vol. 32, No. 11, pp. 1435-1444.
Griffiths, Tissue Spectroscopy with Electrical Impedance Tomography: Computer Simulations, IEEE Transactions on Biomedical Engineering, vol. 42, No. 9, Sep. 1995.
Gumerov, et al., The Dipole Approximation Method and Its Coupling with the Regular Boundary Element Method for Efficient Electrical Impedance Tomography, Boundary Element Technology XIII, 1999.
Hapala, Breaking the Barrier: Methods for Reversible Permeabilization of Cellular Membranes, Critical Reviews in Biotechnology, 17(2): 105-122, 1997.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maček Lebar and Miklavčič, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.

(56) References Cited

OTHER PUBLICATIONS

Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.

Marszalek et al., "Schwan equation and transmembrane potential induced by alternating electric field." Biophysical Journal, vol. 58, pp. 1053-1058 (1990).

Martin, n.R.C.G., et al., "Irreversible electroporation therapy in the management of locally advanced pancreatic adenocarcinoma." Journal of the American College of Surgeons, 2012. 215(3): p. 361-369.

Martinsen, O. G. and Grimnes, S., Bioimpedance and bioelectricity basics. Academic press, 2011.

Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.

Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.

Miklavčič, et al., The Importance of Electric Field Distribution for Effective in Vivo Electroporation of Tissues, Biophysical Journal, vol. 74, May 1998, pp. 2152-2158.

Miller, L., et al., Cancer cells ablation with irreversible electroporation, Technology in Cancer Research and Treatment 4 (2005) 699-706.

Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.

Min, M., U. Pliquett, T. Nacke, A. Barthel, P. Annus, and R. Land, "Broadband excitation for short-time impedance spectroscopy," Physiological measurement, vol. 29, No. 6, p. S185, 2008.

Mir et al., "Mechanisms of Electrochemotherapy" Advanced Drug Delivery Reviews 35:107-118 (1999).

Mir, et al., Effective Treatment of Cutaneous and Subcutaneous Malignant Tumours by Electrochemotherapy, British Journal of Cancer, vol. 77, No. 12, pp. 2336-2342, 1998.

Mir, et al., Electrochemotherapy Potentiation of Antitumour Effect of Bleomycin by Local Electric Pulses, European Journal of Cancer, vol. 27, No. 1, pp. 68-72, 1991.

Mir, et al., Electrochemotherapy, a Novel Antitumor Treatment: First Clinical Trial, C.R. Acad. Sci. Paris, Ser. III, vol. 313, pp. 613-618, 1991.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, L.M., et al., Electric Pulse-Mediated Gene Delivery to Various Animal Tissues, in Advances in Genetics, Academic Press, 2005, p. 83-114.

Mir, Therapeutic Perspectives of In Vivo Cell Electropermeabilization, Bioelectrochemistry, vol. 53, pp. 1-10, 2000.

Mulhall et al., "Cancer, pre-cancer and normal oral cells distinguished by dielectrophoresis." Analytical and Bioanalytical Chemistry, vol. 401, pp. 2455-2463 (2011).

Narayan, et al., Establishment and Characterization of a Human Primary Prostatic Adenocarcinoma Cell Line (ND-1), The Journal of Urology, vol. 148, 1600-1604, Nov. 1992.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Naslund, Michael J., Transurethral Needle Ablation of the Prostate, Urology, vol. 50, No. 2, Aug. 1997.

Neal II et al., "A Case Report on the Successful Treatment of a Large Soft-Tissue Sarcoma with Irreversible Electroporation," Journal of Clinical Oncology, 29, pp. 1-6, 2011.

Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.

Neal II, R. E. et al. In Vitro and Numerical Support for Combinatorial Irreversible Electroporation and Electrochemotherapy Glioma Treatment. Annals of Biomedical Engineering, Oct. 29, 2013, 13 pages.

Neal II, R. E., et al., "Successful Treatment of a Large Soft Tissue Sarcoma with Irreversible Electroporation", Journal of Clinical Oncology, 29:13, e372-e377 (2011).

Neal II, R.E., et al., "Treatment of breast cancer through the application of irreversible electroporation using a novel minimally invasive single needle electrode." Breast Cancer Research and Treatment, 2010. 123(1): p. 295-301.

Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.

Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.

Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).

Neumann, et al., Gene Transfer into Mouse Lyoma Cells by Electroporation in High Electric Fields, J. Embo., vol. 1, No. 7, pp. 841-845, 1982.

Neumann, et al., Permeability Changes Induced by Electric Impulses in Vesicular Membranes, J. Membrane Biol., vol. 10, pp. 279-290, 1972.

Nikolova, B., et al., "Treatment of Melanoma by Electroporation of Bacillus Calmette-Guerin". Biotechnology & Biotechnological Equipment, 25(3): p. 2522-2524 (2011).

Nuccitelli, R., et al., "A new pulsed electric field therapy for melanoma disrupts the tumor's blood supply and causes complete remission without recurrence", Int J Cancer, 125(2): p. 438-45 (2009).

O'Brien et al., "Investigation of the Alamar Blue (resazurin) fluorescent dye for the assessment of mammalian cell cytotoxicity." European Journal of Biochemistry, vol. 267, pp. 5421-5426 (2000).

O'Brien, T. J. et al., "Effects of internal electrode cooling on irreversible electroporation using a perfused organ model," Int. J. Hyperth., vol. 35, No. 1, pp. 44-55, 2018.

Okino, et al., Effects of High-Voltage Electrical Impulse and an Anticancer Drug on In Vivo Growing Tumors, Japanese Journal of Cancer Research, vol. 78, pp. 1319-1321, 1987.

Onik, et al., Sonographic Monitoring of Hepatic Cryosurgery in an Experimental Animal Model, AJR American J. of Roentgenology, vol. 144, pp. 1043-1047, May 1985.

Onik, et al., Ultrasonic Characteristics of Frozen Liver, Cryobiology, vol. 21, pp. 321-328, 1984.

Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.

Onik, G., P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Apply. Neurophysiol., 1976. 39: p. 69-76.

Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

(56) References Cited

OTHER PUBLICATIONS (Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.
(Arena, Christopher B. et al.) Co-pending U.S. Appl. No. 16/372,520, filed Apr. 2, 2019, which published as 20190223938 on Jul. 25, 2019, Specification, Claims, Figures.
(Arena, Christopher B. et al.) Co-Pending Application No. PCT/US11/66239, filed Dec. 20, 2011, Specification, Claims, Figures.
(Arena, Christopher B. et al.) Co-Pending U.S. Appl. No. 13/332,133, filed Dec. 20, 2011 and published as U.S. Publication No. 2012/0109122 on May 3, 2012, Specification, Claims, Figures.
(Aycock, Kenneth N. et al.) Co-pending U.S. Appl. No. 17/535,742, filed Nov. 26, 2021, Specification, Claims, and Figures.
(Davalos, Rafael et al.) Co-Pending Application No. PCT/US21/51551, filed Sep. 22, 2021, Specification, Claims, Figures.
(Davalos, Rafael et al.) Co-pending U.S. Appl. No. 10/571,162, filed Oct. 18, 2006 (published as 2007/0043345 on Feb. 22, 2007), Specification, Figures, Claims.
(Davalos, Rafael et al.) Co-Pending U.S. Appl. No. 12/757,901, filed Apr. 9, 2010, Specification, Claims, Figures.
(Davalos, Rafael et al.) Co-Pending Application No. PCT/US04/43477, filed Dec. 21, 2004, Specification, Claims, Figures.
(Davalos, Rafael V. et al.) Co-Pending Application No. PCT/US10/53077, filed Oct. 18, 2010, Specification, Claims, Figures.
(Davalos, Rafael V. et al.) Co-Pending U.S. Appl. No. 12/491,151, filed Jun. 24, 2009, and published as U.S. Publication No. 2010/0030211 on Feb. 4, 2010, Specification, Claims, Figures.
(Davalos, Rafael V. et al.) Co-Pending U.S. Appl. No. 12/609,779, filed Oct. 30, 2009, and published as U.S. Publication No. 2010/0331758 on Dec. 30, 2010, Specification, Claims, Figures.
(Davalos, Rafael V. et al.) Co-Pending U.S. Appl. No. 13/919,640, filed Jun. 17, 2013, and published as U.S. Publication No. 2013/0281968 on Oct. 24, 2013, Specification, Claims, Figures.
(Davalos, Rafael V. et al.) Co-Pending U.S. Appl. No. 14/686,380, filed Apr. 14, 2015 and Published as US 2015/0289923 on Oct. 15, 2015, Specification, Claims, Figures.
(Davalos, Rafael V. et al.) Co-Pending U.S. Appl. No. 15/424,335, filed Feb. 3, 2017, and published as U.S. Publication No. 2017/0189579 on Jul. 6, 2017, Specification, Claims, Figures.
(Davalos, Rafael V. et al.) Co-Pending U.S. Appl. No. 15/536,333, filed Jun. 15, 2017, and published as U.S. Publication No. 2017/0360326 on Dec. 21, 2017, Specification, Claims, Figures.
(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.
(Davalos, Rafael V. et al.) Co-pending U.S. Appl. No. 16/177,745, filed Nov. 1, 2018, and published as U.S. Publication No. 2019/0069945 on Mar. 7, 2019, Specification, Claims, Figures.
(Davalos, Rafael V. et al.) Co-pending U.S. Appl. No. 16/232,962, filed Dec. 26, 2018, and published as U.S. Publication No. 2019/0133671 on May 9, 2019, Specification, Claims, Figures.
(Davalos, Rafael V. et al.) Co-pending U.S. Appl. No. 16/275,429, filed Feb. 14, 2019, which published as 2019/0175260 on Jun. 13, 2019, Specification, Claims, Figures.
(Davalos, Rafael V. et al.) Co-pending U.S. Appl. No. 16/352,759, filed Mar. 13, 2019, Specification, Claims, Figures.
(Davalos, Rafael V. et al.) Co-pending U.S. Appl. No. 16/535,451, filed Aug. 8, 2019, and Published as U.S. Publication No. 2019/0376055 on Dec. 12, 2019, Specification, Claims, Figures.
(Davalos, Rafael V. et al.) Co-pending U.S. Appl. No. 16/865,031, filed May 1, 2020, Specification, Claims, Figures.
(Davalos, Rafael V. et al.) Co-pending U.S. Appl. No. 17/069,359, filed Oct. 13, 2020, Specification, Claims, Drawings.
(Davalos, Rafael V. et al.) Co-pending U.S. Appl. No. 17/172,731, filed Feb. 10, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-pending Application No. 19861489.3 filed Apr. 16, 2021, Specification, figures (See PCT/US19/51731), and claims (3 pages).
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending Application No. PCT/US09/62806, filed Oct. 30, 2009, Specification, Claims, Figures.
(Davalos, Rafael V. et al.) Co-Pending Application No. PCT/US10/30629, filed Apr. 9, 2010, Specification, Claims, Figures.
(Davalos, Rafael V. et al.) Co-pending application No. PCT/US19/51731 filed Sep. 18, 2019, Specification, Claims, Figures.
(Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.
(Davalos, Rafael V. et al.) Co-Pending U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending U.S. Appl. No. 12/432,295, filed Apr. 29, 2009, and published as U.S. Publication No. 2009/0269317-A1 on Oct. 29, 2009, Specification, Figures, Claims.
(Davalos, Rafael V.) Co-pending U.S. Appl. No. 15/423,986, filed Feb. 3, 2017, and published as U.S. Publication No. 2017/0209620 on Jul. 27, 2017, Specification, Claims, Figures.
(Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Davalos, Rafael V.) Co-Pending Application No. PCT/US09/42100, filed Apr. 29, 2009, Specification, Claims, Figures.
(Garcia, Paulo A. et al.) Co-Pending U.S. Appl. No. 14/012,832, filed Aug. 28, 2013, and published as U.S. Publication No. 2013/0345697 on Dec. 26, 2013, Specification, Claims, Figures.
(Garcia, Paulo A. et al.) Co-Pending U.S. Appl. No. 14/558,631, filed Dec. 2, 2014, and published as U.S. Publication No. 2015/0088120 on Mar. 26, 2015, Specification, Claims, Figures.
(Garcia, Paulo A. et al.) Co-Pending U.S. Appl. No. 15/011,752, filed Feb. 1, 2016, and published as U.S. Publication No. 2016/0143698 on May 26, 2016, Specification, Claims, Figures.
(Garcia, Paulo A. et al.) Co-Pending U.S. Appl. No. 16/655,845, filed Oct. 17, 2019, Specification, Claims, Figures.
(Garcia, Paulo A. et al.) Co-pending U.S. Appl. No. 16/152,743, filed Oct. 5, 2018, Specification, Claims, Figures.
(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Lorenzo, Melvin F. et al.) Co-pending U.S. Appl. No. 16/938,778, filed Jul. 24, 2020, Specification, Claims, Figures.
(Mahajan, Roop L. et al.) Co-Pending U.S. Appl. No. 13/958,152, filed Aug. 2, 2013, Specification, Claims, Figures.
(Neal, Robert E. et al.) Co-Pending U.S. Appl. No. 12/906,923, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-pending U.S. Appl. No. 16/375,878, filed Apr. 5, 2019, which published on Aug. 1, 2019 as US 2019-0233809 A1, Specification, Claims, Figures.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, Communication Pursuant to Article 94(3) EPC, dated May 3, 2021, 4 pages.

(56) References Cited

OTHER PUBLICATIONS

Pending Application No. EP 15793361.5, European Search Report dated Dec. 4, 2017, 9 pages.
Pending Application No. EP 15793361.5, Response to May 3, 2021 Communication Pursuant to Article 94(3) EPC, dated Nov. 12, 2021, 12 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2016-567747, Decision to Grant with English Version of allowed claims, 9 pages.
Pending Application No. JP 2019-133057, amended claims (English language version) filed Aug. 14, 2019, 5 pages.
Pending Application No. JP 2019-133057, Office Action dated Sep. 1, 2021, 3 pages (and English translation, 4 pages).
Pending Application No. JP 2019-133057, Office Action dated Sep. 14, 2020, 5 pages (and English translation, 6 pages).
Pending Application No. JP 2019-133057, Request for Amendment and Appeal filed Dec. 23, 2021 (8 pages) with English Translation of the Amended Claims (2 pages).
Pending Application No. JP 2019-133057, Response to Sep. 14, 2020 Office Action filed Mar. 18, 2021 (6 pages) with English Version of claims and response (5 pages).
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid eukaemia Cells, Apoptosis, vol. 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," AUTOMATIKA 52(2011) 1, 12-19.
Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.
Rols, M.P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. Vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Salford, L.G., et al., "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the EEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Helczynska et al., "Hypoxia promotes a dedifferentiated phenotype in ductal breast carcinoma in situ." Cancer Research, vol. 63, pp. 1441-1444 (2003).
Heller, et al., Clinical Applications of Electrochemotherapy, Advanced Drug Delivery Reviews, vol. 35, pp. 119-129, 1999.

(56) References Cited

OTHER PUBLICATIONS

Hjouj, M., et al., "Electroporation-Induced BBB Disruption and Tissue Damage Depicted by MRI", Neuro-Oncology 13: Issue suppl 3, abstract ET-32 (2011).
Hjouj, M., et al., "MRI Study on Reversible and Irreversible Electroporation Induced Blood Brain Barrier Disruption", PLOS ONE, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, page iii114.
Ho, et al., Electroporation of Cell Membranes: A Review, Critical Reviews in Biotechnology, 16(4): 349-362, 1996.
Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.
Hu, Q., et al., "Simulations of transient membrane behavior in cells subjected to a high-intensity ultrashort electric pulse", Physical Review E, 71(3) (2005).
Huang, et al., Micro-Electroporation: Improving the Efficiency and Understanding of Electrical Permeabilization of Cells, Biomedical Microdevices, vol. 2, pp. 145-150, 1999.
Hughes, et al., An Analysis of Studies Comparing Electrical Impedance Tomography with X-Ray Videofluoroscopy in the Assessment of Swallowing, Physiol. Meas. 15, 1994, pp. A199-A209.
Ibey et al., "Selective cytotoxicity of intense nanosecond-duration electric pulses in mammalian cells." Biochimica Et Biophysica Acta—General Subjects, vol. 1800, pp. 1210-1219 (2010).
Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.
Ivanuša, et al., MRI Macromolecular Contrast Agents as Indicators of Changed Tumor Blood Flow, Radiol. Oncol. 2001; 35(2): 139-47.
Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra et al., "In vivo electrical conductivity measurements during and after tumor electroporation: conductivity changes reflect the treatment outcome." Physics in Medicine and Biology, vol. 54, pp. 5949-5963 (2009).
Ivorra, "Bioimpedance monitoring for physicians: an overview." Biomedical Applications Group, 35 pages (2002).
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
Jarm et al., "Antivascular effects of electrochemotherapy: implications in treatment of bleeding metastases." Expert Rev Anticancer Ther. vol. 10, pp. 729-746 (2010).
Jaroszeski, et al., In Vivo Gene Delivery by Electroporation, Advanced Drug Delivery Review, vol. 35, pp. 131-137, 1999.
Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).
Jordan, D.W., et al., "Effect of pulsed, high-power radiofrequency radiation on electroporation of mammalian cells". IEEE Transactions on Plasma Science, 32(4): p. 1573-1578 (2004).

Jossinet et al., Electrical Impedance Endo-Tomography: Imaging Tissue From Inside, IEEE Transactions on Medical Imaging, vol. 21, No. 6, Jun. 2002, pp. 560-565.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita and Tsong, "Formation and resealing of pores of controlled sizes in human erythrocyte membrane." Nature, vol. 268 (1977) pp. 438-441.
Kinosita and Tsong, "Voltage-induced pore formation and hemolysis of human erythrocytes." Biochimica et Biophysica Acta (BBA)—Biomembranes, 471 (1977) pp. 227-242.
Kinosita et al., "Electroporation of cell membrane visualized under a pulsed-laser fluorescence microscope." Biophysical Journal, vol. 53, pp. 1015-1019 (1988).
Kinosita, et al., Hemolysis of Human Erythrocytes by a Transient Electric Field, Proc. Natl. Acad. Sci. USA, vol. 74, No. 5, pp. 1923-1927, 1977.
Kirson et al., "Alternating electric fields arrest cell proliferation in animal tumor models and human brain tumors." Proceedings of the National Academy of Sciences vol. 104, pp. 10152-10157 (2007).
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed to electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses. Part II. Reduced electrolytic contamination", Bioelectrochemistry, 54(1): p. 91-5 (2001).
Kotnik, T., et al., "Role of pulse shape in cell membrane electropermeabilization", Biochimica Et Biophysica Acta—Biomembranes, 1614(2): p. 193-200 (2003).
Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Laufer et al., "Electrical impedance characterization of normal and cancerous human hepatic tissue." Physiological Measurement, vol. 31, pp. 995-1009 (2010).
Lebar et al., "Inter-pulse interval between rectangular voltage pulses affects electroporation threshold of artificial lipid bilayers." IEEE Transactions on NanoBioscience, vol. 1 (2002) pp. 116-120.
Lee, E. W. et al. Advanced Hepatic Ablation Technique for Creating Complete Cell Death : Irreversible Electroporation. Radiology 255, 426-433, doi:10.1148/radiol.10090337 (2010).
Lee, E.W., et al., "Imaging guided percutaneous irreversible electroporation: ultrasound and immunohistological correlation", Technol Cancer Res Treat 6: 287-294 (2007).
Lee, R. C., D. J. Canaday, and S. M. Hammer. Transient and stable ionic permeabilization of isolated skeletal muscle cells after electrical shock. J. Burn Care Rehabil. 14:528- 540, 1993.

(56) References Cited

OTHER PUBLICATIONS

Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses". Ieee Transactions on Biomedical Engineering, 58(8) (2011).
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Pending U.S. Appl. No. 14/808,679, Panel Decision from Pre-Appeal Brief Review, dated Apr. 26, 2021, 2 pages.
Pending U.S. Appl. No. 14/808,679, Petition Decision, dated Oct. 1, 2019, 5 pages.
Pending U.S. Appl. No. 14/808,679, Petition Decision, dated Oct. 23, 2019, 6 pages.
Pending U.S. Appl. No. 14/808,679, Petition Decision, Dec. 3, 2019, 5 pages.
Pending U.S. Appl. No. 14/808,679, Petition for Priority and Supplemental Response, filed May 8, 2019, 25 pages.
Pending U.S. Appl. No. 14/808,679, Petition Supplement, Sep. 25, 2019, 10 pages.
Pending U.S. Appl. No. 14/808,679, Petition, May 8, 2019, 2 pages.
Pending U.S. Appl. No. 14/808,679, Pre-Appeal Brief Reasons for Request for Review, dated Mar. 29, 2021, 5 pages.
Pending U.S. Appl. No. 14/808,679, Preliminary Amendment Jul. 24, 2015, 6 pages.
Pending U.S. Appl. No. 14/808,679, Preliminary Amendment, filed Jul. 27, 2015, 9 pages.
Pending U.S. Appl. No. 14/808,679, RCE filed Apr. 11, 2019, 8 pages.
Pending U.S. Appl. No. 14/808,679, Renewed Petition, filed Oct. 9, 2019, 1 pages.
Pending U.S. Appl. No. 14/808,679, Reply Brief, dated Nov. 15, 2021, 5 pages.
Pending U.S. Appl. No. 14/808,679, Response to Mar. 19, 2018 Restriction Requirement dated May 21, 2018, 2 pages.
Pending U.S. Appl. No. 14/808,679, Response to Non-Final Office Action dated Jun. 12, 2020, filed Sep. 14, 2020, 9 pages.
Pending U.S. Appl. No. 14/808,679, Response to Sep. 10, 2018 Non-Final Office Action dated Dec. 10, 2018, 9 pages.
Pending U.S. Appl. No. 14/808,679, Restriction Requirement dated Mar. 19, 2018, 7 pages.
Pending U.S. Appl. No. 14/808,679, Second Renewed Petition, filed Oct. 31, 2019, 3 pages.
Pending U.S. Appl. No. 14/808,679, Supplemental Response, May 8, 2019, 16 pages.
Pending U.S. Appl. No. 16/152,743 Preliminary Amendment filed Oct. 5, 2018, 7 pages.
Pending U.S. Appl. No. 16/152,743, Final Office Action dated Jul. 15, 2021, 8 pages.
Pending U.S. Appl. No. 16/152,743, Non-Final Office Action dated Sep. 25, 2020, 10 pages.
Pending U.S. Appl. No. 16/152,743, Notice of Allowance, dated Oct. 27, 2021, 8 pages.
Pending U.S. Appl. No. 16/152,743, Petition for Delayed Claim for Priority dated Dec. 28, 2020, 2 pages.
Pending U.S. Appl. No. 16/152,743, Response to Jul. 15, 2021 Final Office Action, filed Oct. 13, 2021, 6 pages.
Pending U.S. Appl. No. 16/152,743, Response to Notice to File Corrected Application Papers, filed Jan. 7, 2022, 8 pages.
Pending U.S. Appl. No. 16/152,743, Response to Sep. 25, 2020 Non-Final Office Action dated Dec. 28, 2020, 9 pages.
Pending U.S. Appl. No. 16/152,743, Second Preliminary Amendment filed May 2, 2019, 6 pages.
Pending U.S. Appl. No. 16/210,771, Applicant-Initiated Interview Summary dated Aug. 13, 2021, 4 bages.
Pending U.S. Appl. No. 16/210,771, Final Office Action dated May 14, 2021, 13 pages.
Pending U.S. Appl. No. 16/210,771, Non-Final Office Action dated Oct. 7, 2021, 10 pages.
Pending U.S. Appl. No. 16/210,771, Non-Final Office Action dated Sep. 3, 2020, 9 pages.
Pending U.S. Appl. No. 16/210,771, Preliminary Amendment filed Dec. 5, 2018, 8 pages.
Pending U.S. Appl. No. 16/210,771, Response to May 14, 2021 Final Office Action, filed Aug. 16, 2021, 6 pages.
Pending U.S. Appl. No. 16/210,771, Response to Oct. 7, 2021 Non-Final Office Action, dated Jan. 7, 2022, 7 pages.
Pending U.S. Appl. No. 16/210,771, Response to Restriction Requirement, filed Jul. 8, 2020, 7 pages.
Pending U.S. Appl. No. 16/210,771, Response to Sep. 3, 2020 Non-Final Office Action filed Jan. 4, 2021, 11 pages.
Pending U.S. Appl. No. 16/210,771, Restriction Requirement, dated Jun. 9, 2020, 7 pages.
Pending U.S. Appl. No. 16/210,771, Rule 1.132 Declaration dated Jan. 7, 2022, 3 pages.
Pending U.S. Appl. No. 16/210,771, Second Preliminary Amendment filed Oct. 14, 2019, 7 pages.
Pending U.S. Appl. No. 16/352,759, Corrected Notice of Allowability and Examiner's Amendment, dated Feb. 22, 2022, 6 pages.
Pending U.S. Appl. No. 16/352,759, Non-Final Office Action dated Jun. 30, 2021, 7 pages.
Pending U.S. Appl. No. 16/352,759, Notice of Allowance dated Nov. 10, 2021, 7 pages.
Pending U.S. Appl. No. 16/352,759, Response to Non-Final Office Action dated Sep. 27, 2021, 6 pages.
Pending U.S. Appl. No. 16/372,520 Preliminary Amendment filed Apr. 9, 2019, 7 pages.
Pending U.S. Appl. No. 16/375,878, Non-Final Office Action dated Jun. 24, 2021, 8 pages.
Pending U.S. Appl. No. 16/375,878, Preliminary Amendment, filed Apr. 9, 2019, 9 pages.
Pending U.S. Appl. No. 16/375,878, Response to Jun. 24, 2021 Non-Final Office Action, dated Dec. 22, 2021, 8 pages.
Pending U.S. Appl. No. 16/375,878, Second Preliminary Amendment, filed Feb. 5, 2020, 3 pages.
Pending U.S. Appl. No. 16/443,351, Preliminary amendment filed Feb. 3, 2020.
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Shao, Qi et al. Engineering T cell response to cancer antigens by choice of focal therapeutic conditions, International Journal of Hyperthermia, 2019, DOI: 10.1080/02656736.2018.1539253.
Sharma, A. , et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al., Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).

(56) References Cited

OTHER PUBLICATIONS

Talele, S. and P. Gaynor, "Non-linear time domain model of electropermeabilization: Effect of extracellular conductivity and applied electric field parameters", Journal of Electrostatics, 66(5-6): p. 328-334 (2008).

Talele, S. and P. Gaynor, "Non-linear time domain model of electropermeabilization: Response of a single cell to an arbitrary applied electric field", Journal of Electrostatics, 65(12): p. 775-784 (2007).

Talele, S., et al., "Modelling single cell electroporation with bipolar pulse parameters and dynamic pore radii". Journal of Electrostatics, 68(3): p. 261-274 (2010).

Teissie, J. and T.Y. Tsong, "Electric-Field Induced Transient Pores in Phospholipid-Bilayer Vesicles". Biochemistry, 20(6): p. 1548-1554 (1981).

Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.

Thompson, et al., To determine whether the temperature of 2% lignocaine gel affects the initial discomfort which may be associated with its instillation into the male urethra, BJU International (1999), 84, 1035-1037.

Thomson et al., "Investigation of the safety of irreversible electroporation in humans," J Vasc Interv Radiol, 22, pp. 611-621, 2011.

Tibbitt et al., "Hydrogels as Extracellular Matrix Mimics for 3D Cell Culture", Jul. 2009, Biotechnol Bioeng, 103(4),655-663.

TUNA—Suggested Local Anesthesia Guidelines, no date available.

U.S. Appl. No. 12/491,151 (U.S. Pat. No. 8,992,517), file history through Feb. 2015, 113 pages.

U.S. Appl. No. 12/609,779 (U.S. Pat. No. 8,465,484), file history through May 2013, 100 pages.

U.S. Appl. No. 12/757,901 (U.S. Pat. No. 8,926,606), file history through Jan. 2015, 165 pages.

U.S. Appl. No. 12/906,923 (U.S. Pat. No. 9,198,733), file history through Nov. 2015, 55 pages.

U.S. Appl. No. 13/332,133 (U.S. Pat. No. 10,448,989), file history through Sep. 2019, 226 pages.

U.S. Appl. No. 13/550,307 (U.S. Pat. No. 10,702,326), file history through May 2020, 224 pages.

U.S. Appl. No. 13/919,640 (U.S. Pat. No. 8,814,860), file history through Jul. 2014, 41 pages.

U.S. Appl. No. 13/958,152, file history through Dec. 2019, 391 pages.

U.S. Appl. No. 13/989,175 (U.S. Pat. No. 9,867,652), file history through Dec. 2017, 200 pages.

U.S. Appl. No. 14/012,832 (U.S. Pat. No. 9,283,051), file history through Nov. 2015, 17 pages.

U.S. Appl. No. 14/017,210 (U.S. Pat. No. 10,245,098), file history through Jan. 2019, 294 pages.

U.S. Appl. No. 14/558,631 (U.S. Pat. No. 10,117,707), file history through Jul. 2018, 58 pages.

U.S. Appl. No. 14/627,046 (U.S. Pat. No. 10,245,105), file history through Feb. 2019, 77 pages.

U.S. Appl. No. 14/940,863 (U.S. Pat. No. 10,238,447), file history through Oct. 2019, 23 pages.

U.S. Appl. No. 15/011,752 (U.S. Pat. No. 10,470,822), file history through Jul. 2019, 54 pages.

U.S. Appl. No. 15/186,653 (U.S. Pat. No. 10,292,755), file history through Mar. 2019, 21 pages.

U.S. Appl. No. 15/310,114 (U.S. Pat. No. 10,471,254), file history through Aug. 2019, 44 pages.

U.S. Appl. No. 15/423,986 (U.S. Pat. No. 10,286,108), file history through Jan. 2019, 124 pages.

U.S. Appl. No. 15/424,335 (U.S. Pat. No. 10,272,178), file history through Feb. 2019, 67 pages.

U.S. Appl. No. 15/536,333 (U.S. Pat. No. 10,694,972), file history through Apr. 2020, 78 pages.

U.S. Appl. No. 15/843,888 (U.S. Pat. No. 10,537,379), file history through Sep. 2019, 33 pages.

U.S. Appl. No. 15/881,414 (U.S. Pat. No. 10,154,874), file history through Nov. 2018, 43 pages.

U.S. Appl. No. 16/177,745 (U.S. Pat. No. 10,828,085), file history through Jun. 2020, 57 pages.

U.S. Appl. No. 16/232,962 (U.S. Pat. No. 10,828,086), file history through Jun. 2020, 44 pages.

U.S. Appl. No. 16/275,429 (U.S. Pat. No. 10,959,772), file history through Feb. 2021, 18 pages.

U.S. Appl. No. 16/280,511, file history through Aug. 2021, 31 pages.

U.S. Appl. No. 16/404,392 (U.S. Pat. No. 11,254,926), file history through Jan. 2022, 153 pages.

Van Den Bos, W. et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.

Verbridge et al., "Oxygen-Controlled Three-Dimensional Cultures to Analyze Tumor Angiogenesis." Tissue Engineering, Part A vol. 16, pp. 2133-2141 (2010).

Vernier, P.T., et al., "Nanoelectropulse-driven membrane perturbation and small molecule permeabilization", Bmc Cell Biology, 7 (2006).

Vidamed, Inc., Transurethral Needle Ablation (TUNA): Highlights from Worldwide Clinical Studies, Vidamed's Office TUNA System, 2001.

Voyer, D., A. Silve, L. M. Mir, R. Scorretti, and C. Poignard, "Dynamical modeling of tissue electroporation," Bioelectrochemistry, vol. 119, pp. 98-110, 2018.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.

Weaver et al., "A brief overview of electroporation pulse strength-duration space: A region where additional intracellular effects are expected." Bioelectrochemistry vol. 87, pp. 236-243 (2012).

Weaver, Electroporation: A General Phenomenon for Manipulating Cells and Tissues, Journal of Cellular Biochemistry, 51: 426-435, 1993.

Weaver, et al., Theory of Electroporation: A Review, Bioelectrochemistry and Bioenergetics, vol. 41, pp. 136-160, 1996.

Weaver, J. C., Electroporation of biological membranes from multicellular to nano scales, IEEE Trns. Dielectr. Electr. Insul. 10, 754-768 (2003).

Weaver, J.C., "Electroporation of cells and tissues", IEEE Transactions on Plasma Science, 28(1): p. 24-33 (2000).

Weisstein: Cassini Ovals. From MathWorld—A. Wolfram Web Resource; Apr. 30, 2010; http://mathworld.wolfram.com/ (updated May 18, 2011).

Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.

Yang et al., "Dielectric properties of human leukocyte subpopulations determined by electrorotation as a cell separation criterion." Biophysical Journal, vol. 76, pp. 3307-3314 (1999).

Yao et al., "Study of transmembrane potentials of inner and outer membranes induced by pulsed-electric-field model and simulation." IEEE Trans Plasma Sci, 2007. 35(5): p. 1541-1549.

Zhang, Y., et al., MR imaging to assess immediate response to irreversible electroporation for targeted ablation of liver tissues: preclinical feasibility studies in a rodent model. Radiology, 2010. 256(2): p. 424-32.

Zhao, J. et al. "Irreversible electroporation reverses resistance to immune checkpoint blockade in pancreatic cancer", Nature Communications (2019) 10:899, 14 pages.

Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.

Zimmermann, et al., Dielectric Breakdown of Cell Membranes, Biophysical Journal, vol. 14, No. 11, pp. 881-899, 1974.

(56) References Cited

OTHER PUBLICATIONS

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp 894-899.
Pending U.S. Appl. No. 16/520,901, Non-Final Office Action, dated Oct. 13, 2021, 9 pages.
Pending U.S. Appl. No. 16/520,901, Preliminary Amendment filed Aug. 14, 2019.
Pending U.S. Appl. No. 16/520,901, Response to Oct. 13, 2021 Non-Final Office Action, dated Mar. 8, 2022, 11 pages.
Pending U.S. Appl. No. 16/520,901, Second Preliminary Amendment filed Feb. 4, 2020.
Pending U.S. Appl. No. 16/535,451 Final Office Action, dated Feb. 4, 2022, 7 pages.
Pending U.S. Appl. No. 16/535,451 Non-Final Office Action, dated Jun. 24, 2021, 12 pages.
Pending U.S. Appl. No. 16/535,451 Preliminary Amendment filed Aug. 8, 2019, 3 pages.
Pending U.S. Appl. No. 16/535,451 Response to Jun. 24, 2021 Non-Final Office Action, dated Oct. 26, 2021, 10 pages.
Pending U.S. Appl. No. 16/535,451 Second Preliminary Amendment filed Oct. 9, 2019, 15 pages.
Pending U.S. Appl. No. 16/535,451 Third Preliminary Amendment filed Nov. 5, 2019, 4 pages.
Pending U.S. Appl. No. 16/655,845, Non-Final Office Action, dated Mar. 1, 2022, 8 pages.
Pending U.S. Appl. No. 16/655,845, Preliminary Amendment filed Oct. 16, 2020, 6 pages.
Pending U.S. Appl. No. 16/655,845, Response to Oct. 21, 2021 Restriction Requirement, dated Dec. 21, 2021, 7 pages.
Pending U.S. Appl. No. 16/655,845, Restriction Requirement, dated Oct. 21, 2021, 6 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/865,031, Preliminary Amendment filed May 1, 2020, 7 pages.
Pending U.S. Appl. No. 16/865,031, Second Preliminary Amendment, filed Sep. 17, 2021, 10 pages.
Pending U.S. Appl. No. 16/865,772, Preliminary Amendment filed May 4, 2020, 6 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 16/915,760, Preliminary Amendment filed Jul. 6, 2020, 5 pages.
Pending U.S. Appl. No. 17/069,359, Preliminary Amendment, filed Sep. 17, 2021, 6 pages.
Pending U.S. Appl. No. 17/172,731, Preliminary Amendment, filed Sep. 17, 2021, 7 pages.
Pending U.S. Appl. No. 17/277,662 Preliminary Amendment filed Mar. 18, 2021, 8 pages.
Pending U.S. Appl. No. 17/338,960, Response to Notice to File Missing Parts and Amendment, filed Aug. 16, 2021, 7 pages.
Pending Application No. 19861489.3 Response to Communication pursuant to Rules 161(2) and 162 EPC, filed Nov. 16, 2021, 7 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, Certificate of Grant dated Feb. 10, 2022, 1 page.
Pending Application No. AU 2015259303, First Examination Report dated Oct. 26, 2020, 6 pages.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
Pending Application No. CN 201580025135.6, Response to First Office Action, Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. CN 202011281572.3, Amendment filed Sep. 8, 2021 (16 pages) with English Version of the Amended Claims (7 pages).
Pending Application No. EP 09739678.2 Extended European Search Report dated May 11, 2012, 7 pages.
Pending Application No. EP 09739678.2, Communication pursuant to Rule 94.3, Apr. 16, 2014, 3 pages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (Jan. 20, 2014), 6 pages.
Pending Application No. EP 10824248.8, Invitation Pursuant to rule 62a(1) EPC (Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (Sep. 25, 2013), Response filed Nov. 18, 2013.
Pending Application No. 19861489.3 Response to May 16, 2022 Extended European Search Report, dated Dec. 13, 2022, 136 pages.
Pending Application No. EP 15793361.5, Communication dated Feb. 8, 2024, 4 pages.
Pending Application No. EP 15793361.5, Communication Pursuant to Article 94(3) EPC, dated Apr. 4, 2023, 4 pages.
Pending Application No. EP 15793361.5, Response to Apr. 4, 2023 Communication Pursuant to Article 94(3) EPC, dated Oct. 16, 2023, 13 pages.
Pending Application No. PCT/US23/15118, International Search Report and Written Opinion dated Jul. 31, 2023, 18 pages.
Pending Application No. PCT/US23/15118, Invitation to Pay Additional Fees dated May 17, 2023, 3 pages.
Pending Application No. PCT/US23/76626, International Search Report and Written Opinion, dated Apr. 17, 2024, 12 pages.
Pending Application No. PCT/US23/76626, Invitation to Pay Additional Fees dated Feb. 21, 2024, 2 pages.
Polajžer, T. et al., "Cancellation effect is present in high-frequency reversible and irreversible electroporation," Bioelectrochemistry, vol. 132, 2020, 11 pages.
Reilly, J. P. et al., "Sensory Effects of Transient Electrical Stimulation—Evaluation with a Neuroelectric Model," IEEE Trans. Biomed. Eng., vol. BME-32, No. 12, 1001-1011, 1985, 11 pages.
Reti, I. M. and Davydow, D. S., "Electroconvulsive Therapy and Antibiotics: A Case Report", J. ECT, vol. 23, No. 4, Dec. 2007, pp. 289-290.

(56) References Cited

OTHER PUBLICATIONS

Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Rubinsky, L. et al., "Electrolytic Effects During Tissue Ablation by Electroporation," Technol. Cancer Res. Treat., vol. 15, No. 5, NP95-103, 2016, 9 pages.
Sano, M. B. et al., "Burst and continuous high frequency irreversible electroporation protocols evaluated in a 3D tumor model," Phys. Med. Biol., vol. 63, No. 13, 2018, 17 pages.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
U.S. Appl. No. 14/686,380, file history through Dec. 2023, 265 pages.
U.S. Appl. No. 14/808,679 (U.S. Pat. No. 11,655,466), file history through Aug. 2022, 253 pages.
U.S. Appl. No. 16/152,743 (U.S. Pat. No. 11,272,979), file history through Jan. 2022, 89 pages.
U.S. Appl. No. 16/210,771 (U.S. Pat. No. 11,607,537), file history through Dec. 2022, 139 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/443,351 (U.S. Pat. No. 11,638,603), file history through Mar. 2023, 114 pages.
U.S. Appl. No. 16/520,901 (U.S. Pat. No. 11,406,820), file history through May 2022, 39 pages.
U.S. Appl. No. 16/535,451 (U.S. Pat. No. 11,453,873), file history through Aug. 2022, 85 pages.
U.S. Appl. No. 16/655,845 (U.S. Pat. No. 11,607,271), file history through Jan. 2023, 68 pages.
U.S. Appl. No. 16/865,772, file history through Aug. 2023, 110 pages.
U.S. Appl. No. 17/069,359 (U.S. Pat. No. 11,737,810), file history through Apr. 2023, 27 pages.
Valdez, C. M. et al., "The interphase interval within a bipolar nanosecond electric pulse modulates bipolar cancellation," Bioelectromagnetics, vol. 39, No. 6, 441-450, 2018, 28 pages.
Verma, A. et al., "Primer on Pulsed Electrical Field Ablation: Understanding the Benefits and Limitations," Circ. Arrhythmia Electrophysiol., No. September, pp. 1-16, 2021, 16 pages.
Vižintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Pending U.S. Appl. No. 16/747,219, Response to Nov. 10, 2022 Final Office Action, dated Feb. 10, 2023, 6 pages.
Pending U.S. Appl. No. 16/865,031, Final Office Action dated May 24, 2023, 18 pages.
Pending U.S. Appl. No. 16/865,031, Non-Final Office Action dated Nov. 28, 2022, 16 pages.
Pending U.S. Appl. No. 16/865,031, Notice of Allowance dated Oct. 4, 2023, 10 pages.
Pending U.S. Appl. No. 16/865,031, Response to May 24, 2023 Final Office Action, dated Jul. 25, 2023, 8 pages.
Pending U.S. Appl. No. 16/865,031, Response to Nov. 28, 2022 Non-Final Office Action, dated Feb. 27, 2023, 10 pages.
Pending U.S. Appl. No. 16/915,760, Applicant-Initiated Interview Summary dated Aug. 8, 2023, 2 pages.
Pending U.S. Appl. No. 16/915,760, Final Office Action dated Aug. 10, 2023, 9 pages.
Pending U.S. Appl. No. 16/915,760, Final Office Action dated Jun. 2, 2023, 8 pages.
Pending U.S. Appl. No. 16/915,760, Non-Final Office Action dated Jan. 19, 2023, 8 pages.
Pending U.S. Appl. No. 16/915,760, Notice of Allowance dated Nov. 29, 2023, 7 pages.
Pending U.S. Appl. No. 16/915,760, Response to Aug. 10, 2023 Final Office Action, dated Nov. 10, 2023, 6 pages.
Pending U.S. Appl. No. 16/915,760, Response to Jan. 19, 2023 Non-Final Office Action, dated Apr. 19, 2023, 8 pages.
Pending U.S. Appl. No. 16/915,760, Response to Sep. 20, 2022 Restriction Requirement, filed Nov. 21, 2022, 2 pages.
Pending U.S. Appl. No. 16/915,760, Restriction Requirement dated Sep. 20, 2022, 6 pages.
Pending U.S. Appl. No. 16/938,778, Non-Final Office Action dated Jan. 2, 2024, 12 pages.
Pending U.S. Appl. No. 16/938,778, Response to Jan. 2, 2024 Non-Final Office Action, dated Apr. 2, 2024, 13 pages.
Pending U.S. Appl. No. 16/938,778, Response to Oct. 24, 2023 Restriction Requirement, dated Dec. 13, 2023, 3 pages.
Pending U.S. Appl. No. 16/938,778, Restriction Requirement dated Oct. 24, 2023, 6 pages.
Pending U.S. Appl. No. 17/000,049, Final Office Action dated Mar. 29, 2024, 15 pages.
Pending U.S. Appl. No. 17/000,049, Non-Final Office Action dated Dec. 11, 2023, 13 pages.
Pending U.S. Appl. No. 17/000,049, Response to Dec. 11, 2023 Non-Final Office Action, dated Mar. 11, 2024, 9 pages.
Pending U.S. Appl. No. 17/000,049, Response to Jul. 31, 2023 Restriction Requirement dated Nov. 9, 2023, 8 pages.
Pending U.S. Appl. No. 17/000,049, Restriction Requirement dated Jul. 31, 2023, 6 pages.
Pending U.S. Appl. No. 17/152,379, Non-Final Office Action dated Apr. 23, 2024, 14 pages.
Pending U.S. Appl. No. 17/172,731, Final Office Action dated Apr. 10, 2024, 5 pages.
Pending U.S. Appl. No. 17/172,731, Final Office Action dated Jul. 12, 2023, 11 pages.
Pending U.S. Appl. No. 17/172,731, Non-Final Office Action dated Feb. 15, 2023, 7 pages.
Pending U.S. Appl. No. 17/172,731, Non-Final Office Action dated Oct. 31, 2023, 13 pages.
Pending U.S. Appl. No. 17/172,731, Preliminary Amendment, filed Jun. 27, 2022, 9 pages.
Pending U.S. Appl. No. 17/172,731, Response to Feb. 15, 2023 Non-Final Office Action, dated May 15, 2023, 8 pages.
Pending U.S. Appl. No. 17/172,731, Response to Jul. 12, 2023 Final Office Action, dated Oct. 12, 2023, 10 pages.
Pending U.S. Appl. No. 17/172,731, Response to Oct. 31, 2023 Non-Final Office Action, dated Jan. 31, 2024, 7 pages.
Pending U.S. Appl. No. 17/277,662 Non-Final Office Action dated May 5, 2023, 9 pages.
Pending U.S. Appl. No. 17/277,662 Notice of Allowance dated Oct. 2, 2023, 7 pages.
Pending U.S. Appl. No. 17/277,662 Response to May 5, 2023 Non-Final Office Action, dated Aug. 7, 2023, 8 pages.
Pending U.S. Appl. No. 17/338,960, Ex Parte Quayle Action dated May 24, 2023, 6 pages.
Pending U.S. Appl. No. 17/338,960, Response to May 24, 2023 Ex Parte Quayle Action, dated Aug. 8, 2023, 6 pages.
Pending U.S. Appl. No. 18/027,824, Preliminary Amendment dated Mar. 22, 2023, 8 pages.
Pending U.S. Appl. No. 18/100,835, Preliminary Amendment filed Jan. 26, 2023, 8 pages.
Pending U.S. Appl. No. 18/100,835, Second Preliminary Amendment filed Feb. 6, 2023, 6 pages.
Pending U.S. Appl. No. 18/120,158, Preliminary Amendment dated Mar. 13, 2023, 195 pages.
Pending U.S. Appl. No. 18/123,719, Preliminary Amendment dated Jun. 6, 2023, 6 pages.

(56) References Cited

OTHER PUBLICATIONS

Pending U.S. Appl. No. 18/130,330, Preliminary Amendment dated Jun. 20, 2023, 8 pages.
Pending U.S. Appl. No. 18/130,330, Second Preliminary Amendment dated Feb. 26, 2024, 3 pages.
Pending U.S. Appl. No. 18/348,605, Preliminary Amendment dated Oct. 31, 2023, 7 pages.
Pending U.S. Appl. No. 18/402,231, Preliminary Amendment dated Mar. 5, 2024, 5 pages.
Pending U.S. Appl. No. 18/404,473, Preliminary Amendment dated May 13, 2024, 6 pages.
Pending U.S. Appl. No. 18/502,967, Preliminary Amendment filed Nov. 6, 2023, 6 pages.
Pending Application No. 19861489.3 Extended European Search Report dated May 16, 2022 (8 pages).
(Davalos, Rafael et al.) Co-Pending Application No. PCT/US23/15118, filed Mar. 13, 2023, Specification, Claims, Figures.
(Davalos, Rafael et al.) Co-Pending Application No. PCT/US23/76626, filed Oct. 11, 2023, Specification, Claims, Figures.
(Davalos, Rafael V. et al.) Co-Pending U.S. Appl. No. 18/027,824, filed Mar. 22, 2023, Specification, Claims, and Figures.
(Davalos, Rafael V. et al.) Co-Pending U.S. Appl. No. 18/130,330, filed Apr. 3, 2023, Specification, Claims, Figures.
(Davalos, Rafael V. et al.) Co-pending U.S. Appl. No. 18/348,605, filed Jul. 7, 2023, Specification, Claims, Drawings.
(Davalos, Rafael V. et al.) Co-pending U.S. Appl. No. 18/402,231, filed Jan. 2, 2024, Specification, Claims, Figures.
(Davalos, Rafael V. et al.) Co-pending U.S. Appl. No. 18/404,473, filed Jan. 4, 2024, Specification, Claims, Figures.
(Garcia, Paulo A. et al.) Co-Pending U.S. Appl. No. 18/100,835, filed Jan. 24, 2023, Specification, Claims, Figures.
(Neal, Robert E. et al.) Co-pending U.S. Appl. No. 18/120,158, filed Mar. 10, 2023, Specification, Claims, Figures.
(Neal, Robert E. et al.) Co-pending U.S. Appl. No. 18/502,967, filed Nov. 6, 2023, Specification, Claims, Figures.
(Neal, Robert et al.) Co-pending U.S. Appl. No. 18/528,051, filed Dec. 4, 2023, Specification, Claims, Figures.
(O'Brien, Timothy J. et al.) Co-Pending U.S. Appl. No. 18/608,958, filed Mar. 19, 2024, Specification, Claims, Figures.
(Sano, Michael B. et al.) Co-pending U.S. Appl. No. 17/862,486, filed Jul. 12, 2022, Specification, Claims, Figures.
(Sano, Michael B. et al.) Co-pending U.S. Appl. No. 18/123,719, filed Mar. 20, 2023, Specification, Claims, Figures.
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Buist et al., "Efficacy of multi-electrode linear irreversible electroporation," Europace, vol. 23, No. 3, pp. 464-468, 2021, 5 pages.
Butikofer, R. et al., "Electrocutaneous Nerve Stimulation—I: Model and Experiment," IEEE Trans. Biomed. Eng., vol. BME-25, No. 6, 526-531, 1978, 6 pages.
Butikofer, R. et al., "Electrocutaneous Nerve Stimulation—II: Stimulus Waveform Selection," IEEE Trans. Biomed. Eng., vol. BME-26, No. 2, 69-75, 1979, abstract only, 2 pages.
Cosman, E. R. et al., "Electric and Thermal Field Effects in Tissue Around Radiofrequency Electrodes," Pain Med., vol. 6, No. 6, 405-424, 2005, 20 pages.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Korohoda, W. et al. "Reversible and Irreversible Electroporation of Cell Suspensions Flowing Through a Localized DC Electric Field", Cellular & Molecular Biology Letters, vol. 18 (2013), pp. 102-119 (published Dec. 27, 2012).

Lv, Y. et al. "The Englargement of Ablation Area by Electrolytic Irreversible Electroporation (E-IRE) Using Pulsed Field with Bias DC Field", Annals of Biomedical Engineering, vol. 50, No. 12, Dec. 2022, 10 pages.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
Mercadal, B. et al., "Avoiding nerve stimulation in irreversible electroporation: A numerical modeling study," Phys. Med. Biol., vol. 62, No. 20, 8060-8079, 2017, 28 pages.
Mercadal, Borja et al. "Dynamics of Cell Death After Conventional IRE and H-FIRE Treatments", Annals of Biomedical Engineering, vol. 48, No. 5, 2020, p. 1451-1462.
Miklavčič, D et al., "The effect of high frequency electric pulses on muscle contractions and antitumor efficiency in vivo for a potential use in clinical electrochemotherapy," Bioelectrochemistry, vol. 65, 121-128, 2004, 8 pages.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.
Patent No. JP 7051188, Notice of Reasons for Revocation dated Jan. 30, 2023 (3 pages) with English translation (5 pages).
Patent No. JP 7051188, Opposition dated Jul. 4, 2022 (16 pages) with English translation (13 pages).
Patent No. JP 7051188, Response to Jan. 30, 2023 Notice of Reasons for Revocation, dated Apr. 27, 2023 (9 pages) with English translation (10 pages).
Patent No. JP 7051188, Response to Opposition dated Aug. 22, 2023 (21 pages) with English translation (25 pages).
Pending U.S. Appl. No. 16/375,878, Applicant-Initiated Interview Summary dated Aug. 23, 2022, 7 pages.
Pending U.S. Appl. No. 16/375,878, Final Office Action dated Apr. 15, 2022, 8 pages.
Pending U.S. Appl. No. 16/375,878, Final Office Action dated Aug. 18, 2023, 11 pages.
Pending U.S. Appl. No. 16/375,878, Non-Final Office Action dated Jan. 23, 2023, 8 pages.
Pending U.S. Appl. No. 16/375,878, Notice of Allowance dated Nov. 15, 2023, 6 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Aug. 18, 2023 Final Office Action, dated Oct. 18, 2023, 9 pages.
Pending U.S. Appl. No. 16/375,878, Response to Jan. 23, 2023 Non-Final Office Action, dated Apr. 24, 2023, 10 pages.
Pending U.S. Appl. No. 16/747,219, Applicant-Initiated Interview Summary dated Aug. 3, 2022, 4 pages.
Pending U.S. Appl. No. 16/747,219, Final Office Action dated Nov. 10, 2022, 12 pages.
Pending U.S. Appl. No. 16/747,219, Non-Final Office Action dated Mar. 31, 2022, 12 pages.
Pending U.S. Appl. No. 16/747,219, Non-Final Office Action dated May 25, 2023, 13 pages.
Pending U.S. Appl. No. 16/747,219, Notice of Allowance dated Dec. 26, 2023, 12 pages.
Pending U.S. Appl. No. 16/747,219, Response to Mar. 31, 2022 Non-Final Office Action, dated Aug. 1, 2022, 8 pages.
Pending U.S. Appl. No. 16/747,219, Response to May 25, 2023 Non-Final Office Action, dated Aug. 25, 2023, 9 pages.
(Davalos, Rafael et al.) Co-Pending U.S. Appl. No. 18/846,198, filed Sep. 11, 2024, Specification, Claims, Figures.
(Davalos, Rafael V. et al.) Co-pending U.S. Appl. No. 18/767,746, filed Jul. 9, 2024, Specification, Claims, Figures.
Pending U.S. Appl. No. 17/000,049, Examiner Interview Summary dated Jul. 8, 2024, 7 pages.

(56) References Cited

OTHER PUBLICATIONS

Pending U.S. Appl. No. 17/152,379, Response to Apr. 23, 2024 Non-Final Office Action, filed Aug. 23, 2024, 7 pages.
Pending U.S. Appl. No. 18/100,835, Response to Jun. 28, 2024 Restriction Requirement, dated Aug. 28, 2024, 5 pages.
Pending U.s. Appl. No. 18/120,158, Response to Jun. 20, 2024 Non-Final Office Action, dated Sep. 20, 2024, 8 pages.
Pending U.S. Appl. No. 18/348,605, Non-Final Office Action dated Sep. 5, 2024, 10 pages.
Pending U.S. Appl. No. 18/502,967, Response to Jun. 18, 2024 Non-Final Office Action dated Sep. 18, 2024, 12 pages.
Pending U.S. Appl. No. 18/846,198, Preliminary Amendment dated Sep. 11, 2024, 8 pages.
Pending Application No. EP 15793361.5, Brief Communication from the EPO, dated Aug. 19, 2024, 1 page.
Pending Application No. EP 15793361.5, EPO Result of Consultation, Aug. 12, 2024, 3 pages.
Pending Application No. EP 15793361.5, Response to Feb. 8, 2024 Communication, Filed Aug. 2, 2024, 40 pages.
Pending Application No. EP 15793361.5, Supplemental Response to Feb. 8, 2024 Communication, Filed Aug. 16, 2024, 9 pages.
(Davalos, Rafael V. et al.) Co-pending U.S. Appl. No. 19/026,703, filed Jan. 17, 2025, Specification, Claims, Drawings.
(Lorenzo, Melvin F. et al.) Co-pending U.S. Appl. No. 19/044,045, filed Feb. 3, 2025, Specification, Claims, Figures.
(Neal, Robert E. et al.) Co-pending U.S. Appl. No. 18/930,252, filed Oct. 29, 2024, Specification, Claims, Figures.
(Neal, Robert E. et al.) Co-pending U.S. Appl. No. 19/019,625, filed Jan. 14, 2025, Specification, Claims, Figures.
Co-pending U.S. Appl. No. 17/535,742, Non-final Office Action dated Dec. 13, 2024, 12 pages.
Pending U.S. Appl. No. 16/938,778, Interview Summary dated Jun. 21, 2024, 1 page.
Pending U.S. Appl. No. 16/938,778, Notice of Allowance dated Jun. 21, 2024, 10 pages.
Pending U.S. Appl. No. 17/152,379, Final Office Action dated Dec. 11, 2024, 8 pages.
Pending U.S. Appl. No. 17/172,731, Notice of Allowance dated Jun. 27, 2024, 7 pages.
Pending U.S. Appl. No. 17/172,731, Response to Apr. 10, 2024 Final Office Action, dated Jun. 10, 2024, 6 pages.
Pending U.S. Appl. No. 18/100,835, Non-Final Office Action dated Oct. 23, 2024, 10 pages.
Pending U.S. Appl. No. 18/100,835, Response to Oct. 23, 2024 Non-Final Office Action, dated Jan. 23, 2025, 8 pages.
Pending U.S. Appl. No. 18/100,835, Restriction Requirement dated Jun. 28, 2024, 6 pages.
Pending U.S. Appl. No. 18/120,158, Non-Final Office Action dated Jun. 20, 2024, 13 pages.
Pending U.S. Appl. No. 18/120,158, Notice of Allowance dated Oct. 2, 2024, 5 pages.
Pending U.S. Appl. No. 18/348,605, Final Office Action dated Feb. 5, 2025, 9 pages.
Pending U.S. Appl. No. 18/348,605, Response to Sep. 5, 2024 Non-Final Office Action, dated Dec. 5, 2024, 7 pages.
Pending U.S. Appl. No. 18/402,231, Non-Final Office Action dated Dec. 13, 2024, 8 pages.
Pending U.S. Appl. No. 18/502,967, Non-Final Office Action dated Jun. 18, 2024, 25 pages.
Pending U.S. Appl. No. 18/502,967, Notice of Allowance dated Dec. 2, 2024, 9 pages.
Pending U.S. Appl. No. 18/767,746, Preliminary amendment dated Oct. 4, 2024, 5 pages.
(Davalos, Rafael et al.) Co-Pending U.S. Appl. No. 19/120,676, filed Apr. 11, 2025, Specification, Claims, Figures.
Pending U.S. Appl. No. 17/535,742, Final Office Action dated Apr. 29, 2025, 11 pages.
Pending U.S. Appl. No. 17/535,742, Response to Dec. 13, 2024 Non-final Office Action, dated Apr. 14, 2025, 9 pages.
Pending U.S. Appl. No. 18/100,835, Non-Final Office Action dated Jun. 23, 2025, 12 pages.
Pending U.S. Appl. No. 18/100,835, Response to Mar. 6, 2025 Final Office Action, dated Jun. 6, 2025, 12 pages.
Pending U.S. Appl. No. 18/348,605, Examiner Interview Summary dated Jun. 6, 2025, 3 pages.
Pending U.S. Appl. No. 18/402,231, Notice of Allowance dated Apr. 10, 2025, 7 pages.
Pending U.S. Appl. No. 18/930,252, Preliminary Amendment dated Apr. 25, 2025, 118 pages.
Pending U.S. Appl. No. 19/019,625, Preliminary Amendment dated Apr. 4, 2025, 194 pages.
Pending U.S. Appl. No. 19/120,676, Preliminary Amendment dated Apr. 11, 2025, 8 pages.

* cited by examiner

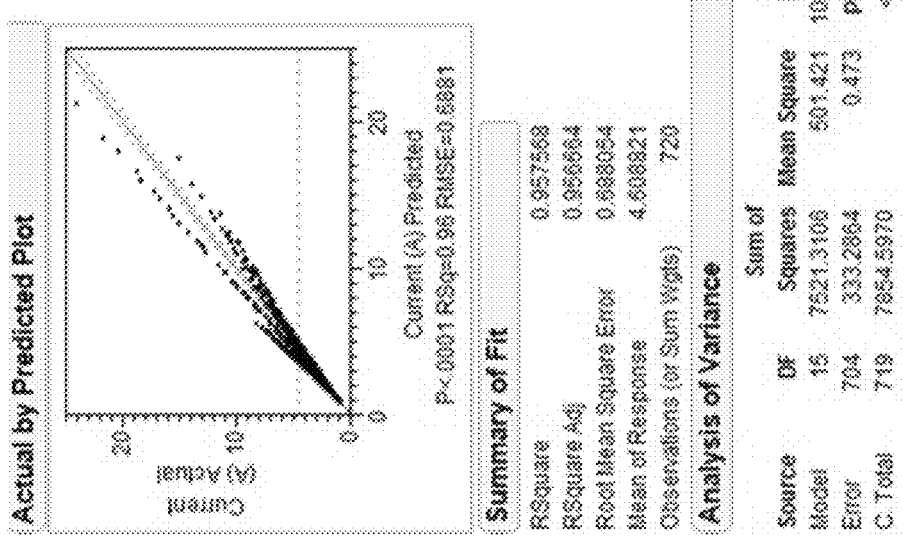
FIG. 8C
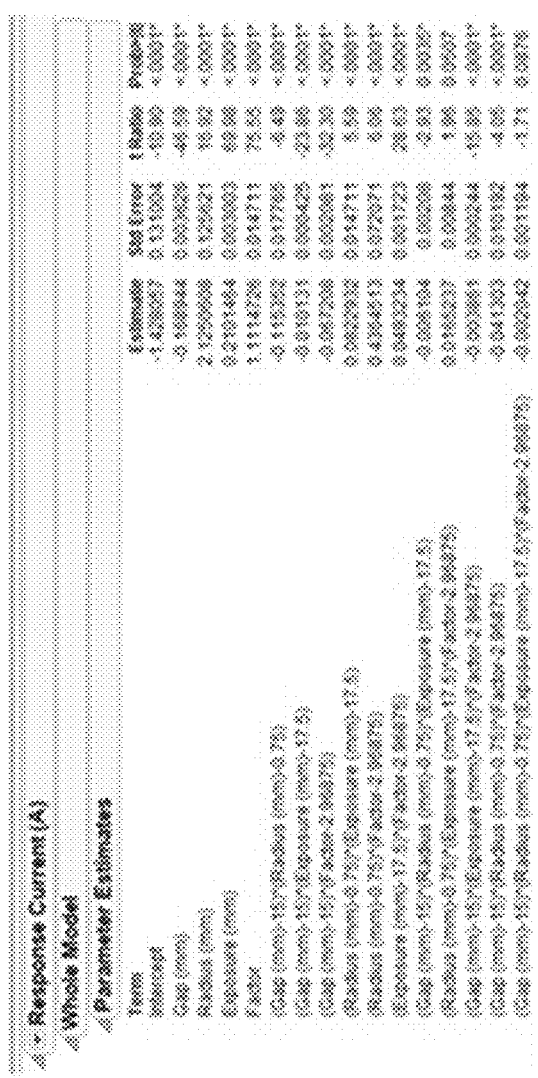
FIG. 8A
FIG. 8B

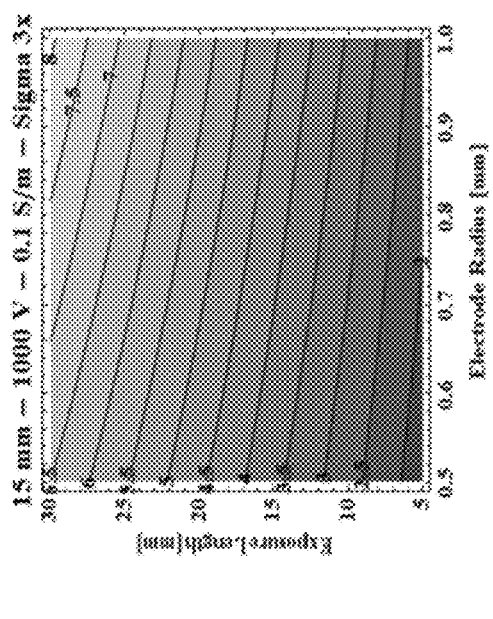
FIG. 9A
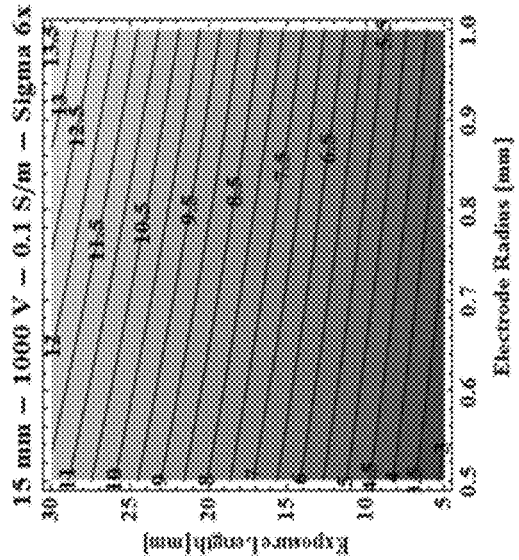
FIG. 9D
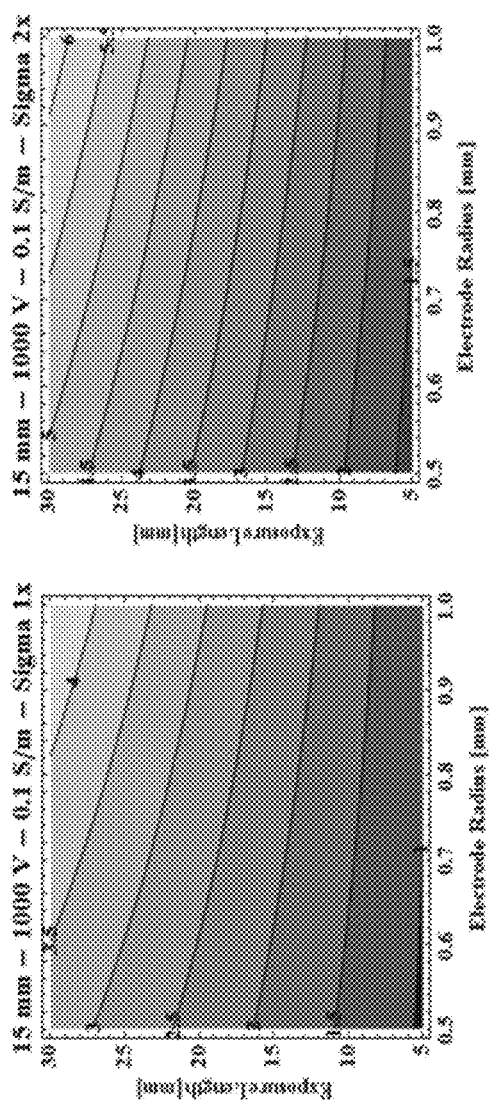
FIG. 9B
FIG. 9C
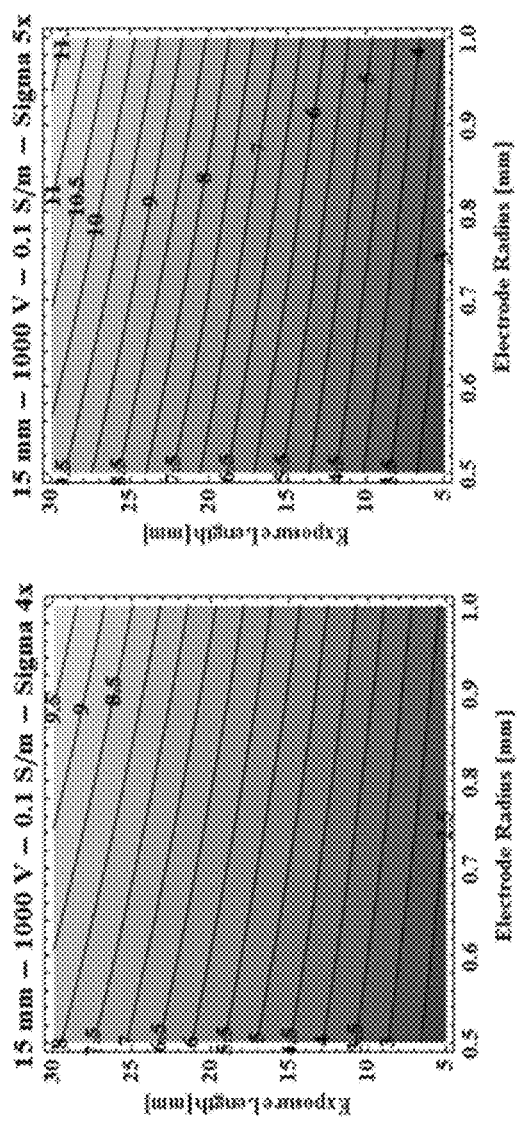
FIG. 9E
FIG. 9F

Potato Experiment # 1:

| Timing | Voltage (V) | Current (A) Onset | Current (A) End | Static Conductivity Onset σ (S/m) | Static Conductivity End σ (S/m) | Dynamic Conductivity Onset σ (S/m) | Dynamic Conductivity End σ (S/m) | Static Conductivity Onset σ_sample/σ_ref | Static Conductivity End σ_sample/σ_ref | Dynamic Conductivity Onset σ_sample/σ_ref | Dynamic Conductivity End σ_sample/σ_ref |
|---|---|---|---|---|---|---|---|---|---|---|---|
| Pre-IRE | 24 | - | 0.018 | - | 0.021 | - | 0.020 | - | 1.0 | - | 1.0 |
| Pre-IRE | 48 | - | 0.036 | - | 0.021 | - | 0.020 | - | 1.0 | - | 1.0 |
| Pre-IRE | 72 | - | 0.061 | - | 0.023 | - | 0.023 | - | 1.1 | - | 1.2 |
| Pre-IRE | 96 | 0.108 | 0.126 | 0.031 | 0.036 | 0.034 | 0.041 | 1.5 | 1.7 | 1.7 | 2.1 |
| Pre-IRE | 123 | 0.165 | 0.232 | 0.037 | 0.052 | 0.043 | 0.063 | 1.8 | 2.5 | 2.1 | 3.2 |
| IRE | 984 | 15.4 (1") | 19.2 (90") | 0.430 | 0.536 | 0.589 | 0.727 | 20.9 | 26.0 | 29.5 | 36.9 |
| Post-IRE | 24 | 0.384 | 0.348 | 0.440 | 0.399 | 0.602 | 0.545 | 21.3 | 19.3 | 30.2 | 27.3 |
| Post-IRE | 48 | 0.78 | 0.72 | 0.447 | 0.412 | 0.612 | 0.564 | 21.7 | 20.0 | 30.6 | 28.2 |
| Post-IRE | 72 | 1.2 | 1.14 | 0.458 | 0.435 | 0.628 | 0.596 | 22.2 | 21.1 | 31.4 | 29.8 |
| Post-IRE | 96 | 1.54 | 1.48 | 0.441 | 0.424 | 0.604 | 0.580 | 21.4 | 20.6 | 30.2 | 29.0 |
| Post-IRE | 120 | 1.92 | 1.86 | 0.440 | 0.426 | 0.602 | 0.583 | 21.3 | 20.7 | 30.2 | 29.2 |

FIG. 10A

Potato Experiment # 2

| Timing | Voltage (V) | Current (A) Onset | Current (A) End | Static Conductivity Onset σ (S/m) | Static Conductivity End σ (S/m) | Dynamic Conductivity Onset σ (S/m) | Dynamic Conductivity End σ (S/m) | Static Onset $\sigma_{end}/\sigma_{max}$ | Static End $\sigma_{end}/\sigma_{max}$ | Dynamic Onset $\sigma_{end}/\sigma_{max}$ | Dynamic End $\sigma_{end}/\sigma_{max}$ |
|---|---|---|---|---|---|---|---|---|---|---|---|
| Pre-IRE | 21 | - | 0.018 | - | 0.024 | - | 0.023 | - | 1.0 | - | 1.0 |
| Pre-IRE | 48 | - | 0.036 | - | 0.021 | - | 0.020 | - | 0.9 | - | 0.8 |
| Pre-IRE | 72 | 0.071 | 0.079 | 0.027 | 0.030 | 0.026 | 0.029 | 1.2 | 1.3 | 1.2 | 1.4 |
| Pre-IRE | 96 | 0.134 | 0.17 | 0.038 | 0.049 | 0.043 | 0.058 | 1.6 | 2.1 | 1.9 | 2.5 |
| Pre-IRE | 120 | 0.24 | 0.336 | 0.055 | 0.077 | 0.066 | 0.097 | 2.3 | 3.3 | 2.9 | 4.2 |
| IRE | 996 | 14.6 (1*) | 19 (90*) | 0.403 | 0.524 | 0.550 | 0.719 | 17.1 | 22.3 | 24.1 | 31.5 |
| Post-IRE | 24 | 0.4 | 0.36 | 0.458 | 0.412 | 0.627 | 0.563 | 19.4 | 17.5 | 27.4 | 24.7 |
| Post-IRE | 48 | 0.79 | 0.74 | 0.452 | 0.424 | 0.619 | 0.579 | 19.2 | 18.0 | 27.1 | 25.4 |
| Post-IRE | 72 | 1.15 | 1.11 | 0.439 | 0.424 | 0.600 | 0.579 | 18.6 | 18.0 | 26.3 | 25.4 |
| Post-IRE | 96 | 1.6 | 1.52 | 0.458 | 0.435 | 0.627 | 0.595 | 19.4 | 18.5 | 27.4 | 26.0 |
| Post-IRE | 123 | 1.96 | 1.92 | 0.438 | 0.429 | 0.599 | 0.586 | 18.6 | 18.2 | 26.2 | 25.7 |

FIG. 10B

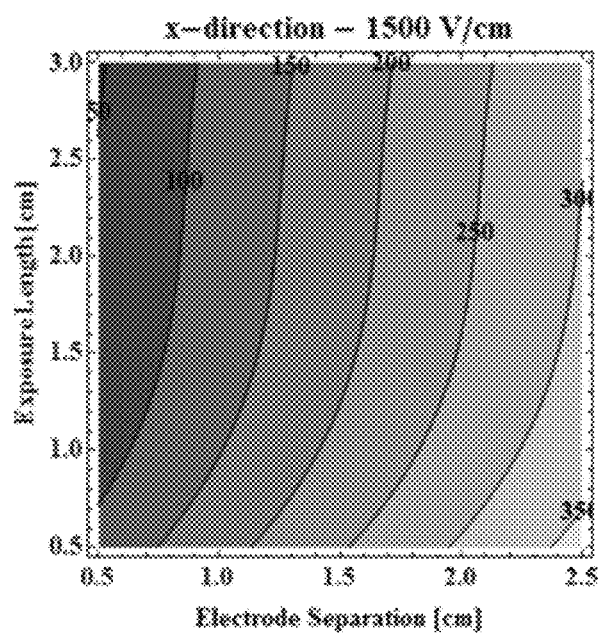
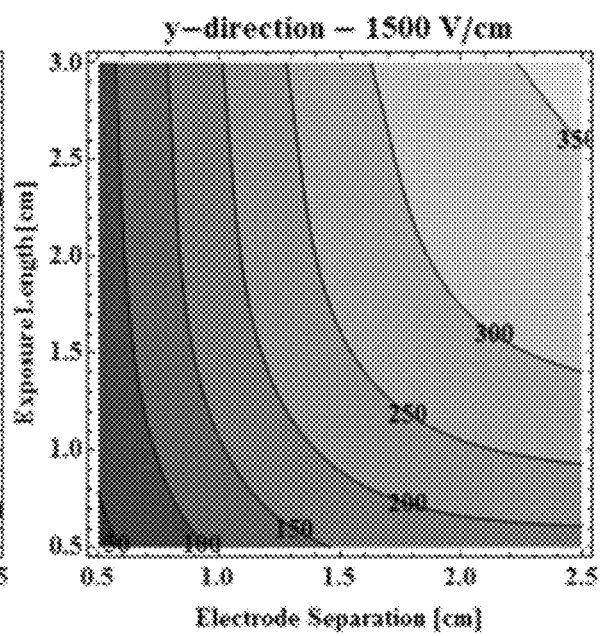
FIG. 12A  FIG. 12B
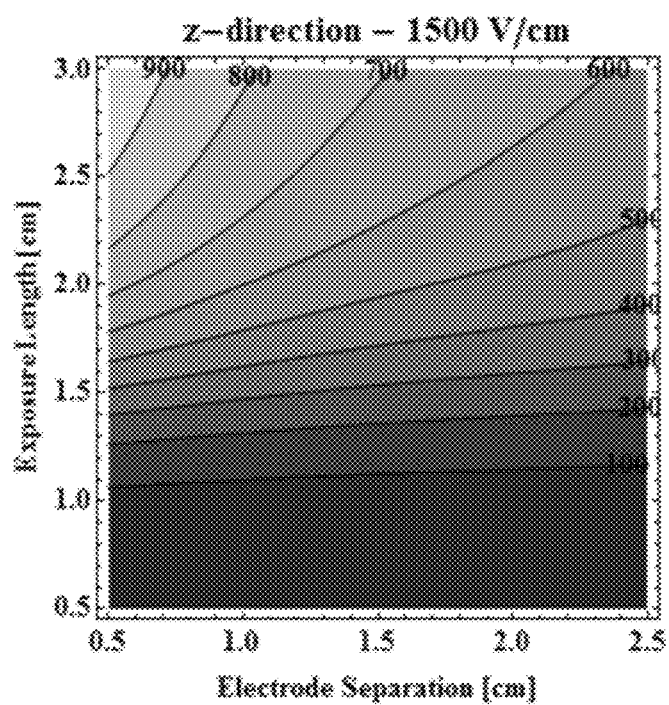
FIG. 12C

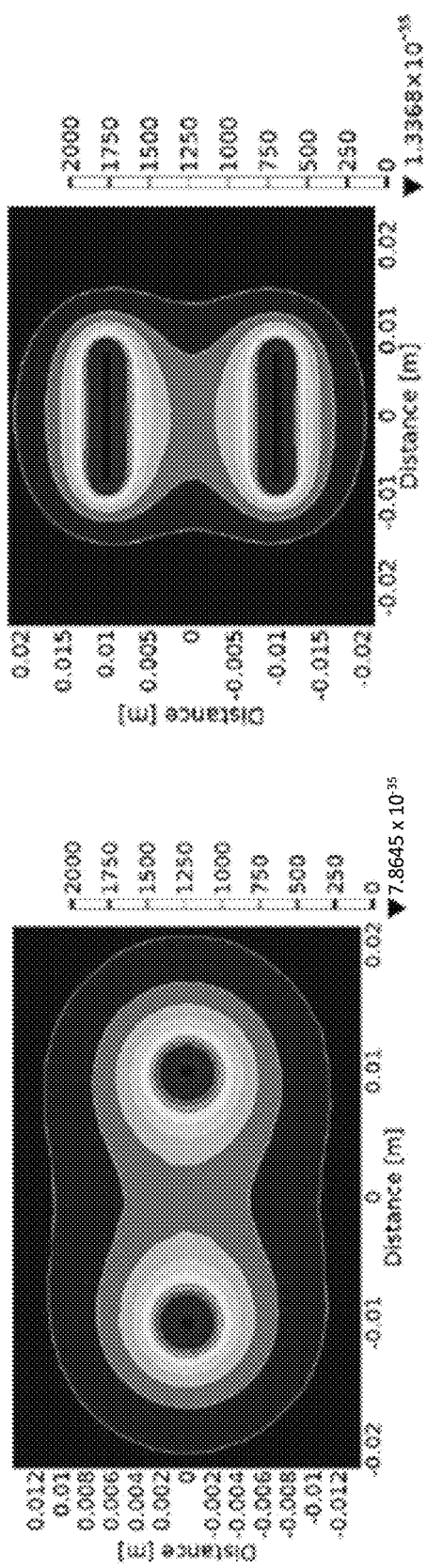
FIG. 20B
FIG. 20A
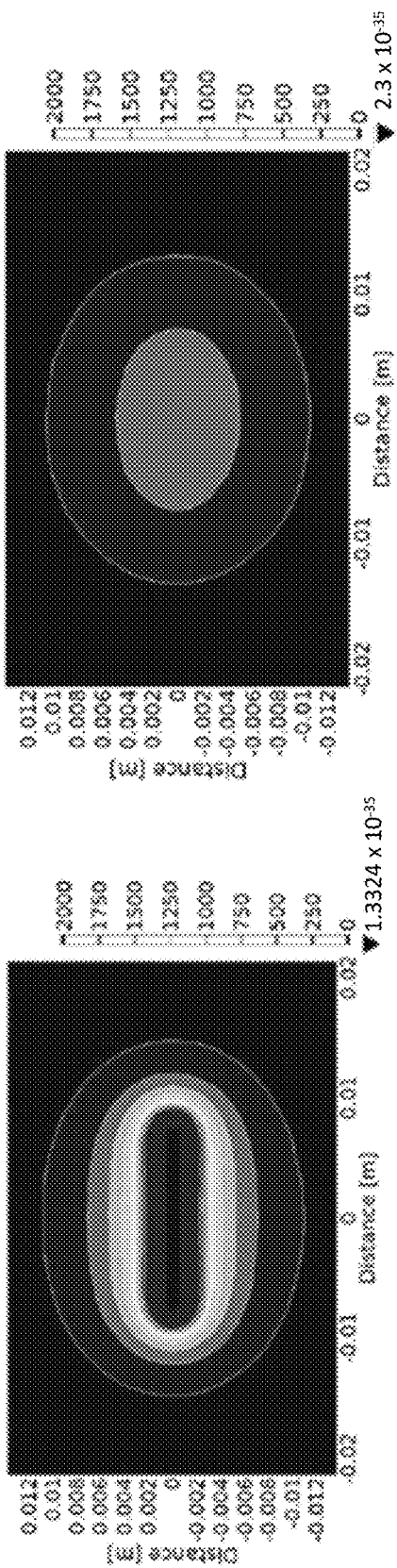
FIG. 20D
FIG. 20C

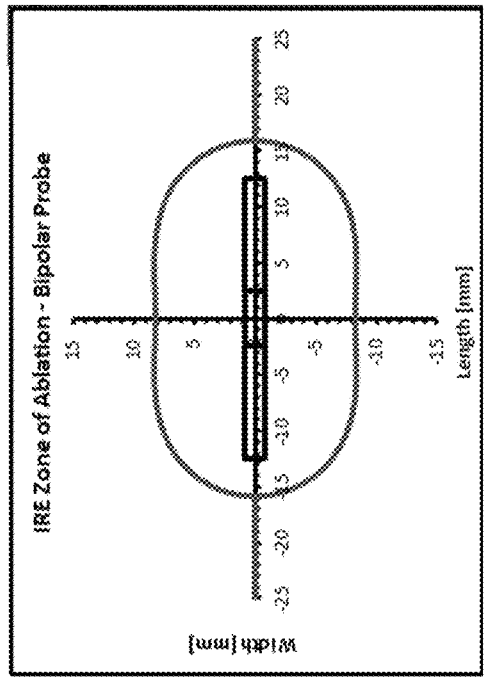
FIG. 36A
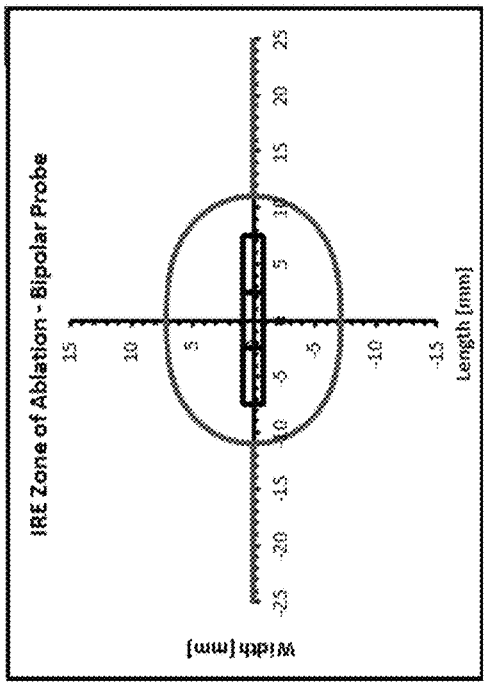
FIG. 36C
FIG. 36B
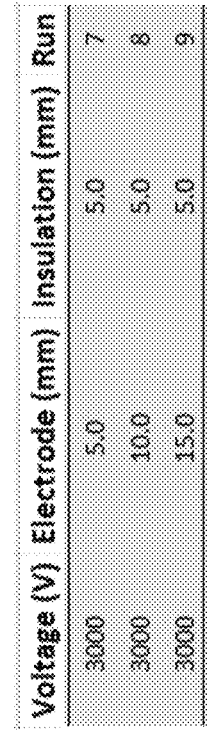
FIG. 36D
FIG. 36E
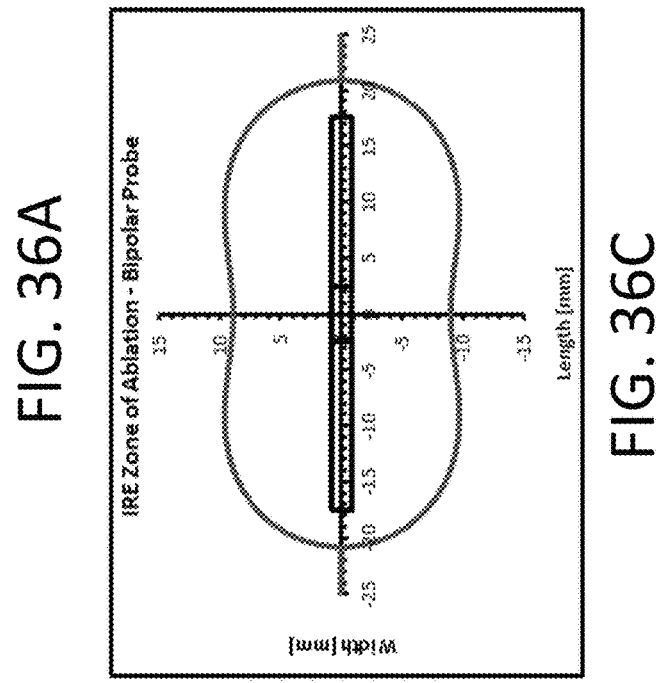

FIGS. 43A-D

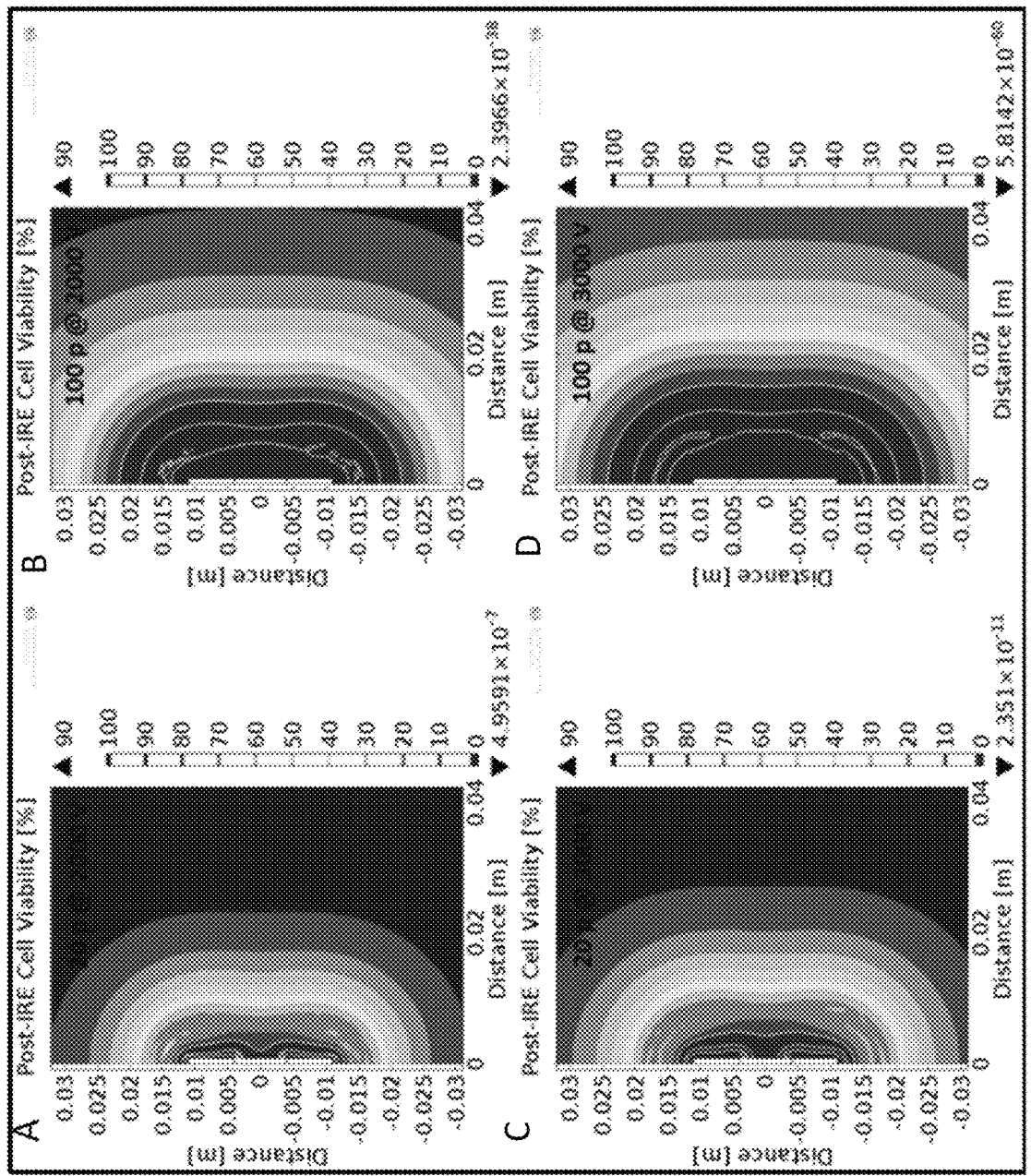
FIGS. 46A-D

Parametric study on bipolar electrode configuration as a function of electrode length, separation distance, and diameter in the resulting IRE area and volume.

| Number | Electrode Length (mm) | Insulation Length (mm) | Diameter (mm) | IRE Area (cm²) | IRE Volume (cm³) |
|---|---|---|---|---|---|
| 1 | 5.00 | 4.00 | 1.27 | 0.943 | 1.590 |
| 2 | 5.00 | 4.00 | 1.65 | 1.025 | 1.880 |
| 3 | 5.00 | 4.00 | 2.11 | 1.120 | 2.241 |
| 4 | 5.00 | 8.00 | 1.27 | 1.100 | 1.844 |
| 5 | 5.00 | 8.00 | 1.65 | 1.199 | 2.204 |
| 6 | 5.00 | 8.00 | 2.11 | 1.309 | 2.645 |
| 7 | 5.00 | 12.00 | 1.27 | 1.116 | 1.792 |
| 8 | 5.00 | 12.00 | 1.65 | 1.253 | 2.208 |
| 9 | 5.00 | 12.00 | 2.11 | 1.395 | 2.721 |
| 10 | 5.00 | 16.00 | 1.27 | 1.042 | 1.689 |
| 11 | 5.00 | 16.00 | 1.65 | 1.160 | 2.058 |
| 12 | 5.00 | 16.00 | 2.11 | 1.283 | 2.493 |
| 13 | 7.50 | 4.00 | 1.27 | 1.274 | 2.346 |
| 14 | 7.50 | 4.00 | 1.65 | 1.371 | 2.738 |
| 15 | 7.50 | 4.00 | 2.11 | 1.483 | 3.215 |
| 16 | 7.50 | 8.00 | 1.27 | 1.440 | 2.620 |
| 17 | 7.50 | 8.00 | 1.65 | 1.548 | 3.066 |
| 18 | 7.50 | 8.00 | 2.11 | 1.680 | 3.652 |
| 19 | 7.50 | 12.00 | 1.27 | 1.478 | 2.575 |
| 20 | 7.50 | 12.00 | 1.65 | 1.622 | 3.097 |
| 21 | 7.50 | 12.00 | 2.11 | 1.777 | 3.732 |
| 22 | 7.50 | 16.00 | 1.27 | 1.379 | 2.423 |
| 23 | 7.50 | 16.00 | 1.65 | 1.511 | 2.886 |
| 24 | 7.50 | 16.00 | 2.11 | 1.660 | 3.462 |
| 25 | 10.00 | 4.00 | 1.27 | 1.596 | 3.087 |
| 26 | 10.00 | 4.00 | 1.65 | 1.718 | 3.628 |
| 27 | 10.00 | 4.00 | 2.11 | 1.850 | 4.253 |
| 28 | 10.00 | 8.00 | 1.27 | 1.764 | 3.368 |
| 29 | 10.00 | 8.00 | 1.65 | 1.901 | 3.973 |
| 30 | 10.00 | 8.00 | 2.11 | 2.037 | 4.640 |

FIG. 48A

| | | | | | |
|---|---|---|---|---|---|
| 31 | 10.00 | 12.00 | 1.27 | 1.809 | 3.319 |
| 32 | 10.00 | 12.00 | 1.65 | 1.972 | 3.974 |
| 33 | 10.00 | 12.00 | 2.11 | 2.139 | 4.733 |
| 34 | 10.00 | 16.00 | 1.27 | 1.694 | 3.123 |
| 35 | 10.00 | 16.00 | 1.65 | 1.848 | 3.708 |
| 36 | 10.00 | 16.00 | 2.11 | 2.015 | 4.386 |
| 37 | 12.50 | 4.00 | 1.27 | 1.922 | 3.868 |
| 38 | 12.50 | 4.00 | 1.65 | 2.049 | 4.475 |
| 39 | 12.50 | 4.00 | 2.11 | 2.199 | 5.228 |
| 40 | 12.50 | 8.00 | 1.27 | 2.087 | 4.130 |
| 41 | 12.50 | 8.00 | 1.65 | 2.234 | 4.824 |
| 42 | 12.50 | 8.00 | 2.11 | 2.383 | 5.611 |
| 43 | 12.50 | 12.00 | 1.27 | 2.132 | 4.059 |
| 44 | 12.50 | 12.00 | 1.65 | 2.303 | 4.793 |
| 45 | 12.50 | 12.00 | 2.11 | 2.484 | 5.680 |
| 46 | 12.50 | 16.00 | 1.27 | 1.998 | 3.796 |
| 47 | 12.50 | 16.00 | 1.65 | 2.169 | 4.474 |
| 48 | 12.50 | 16.00 | 2.11 | 2.354 | 5.297 |
| 49 | 15.00 | 4.00 | 1.27 | 2.242 | 4.626 |
| 50 | 15.00 | 4.00 | 1.65 | 2.382 | 5.324 |
| 51 | 15.00 | 4.00 | 2.11 | 2.537 | 6.164 |
| 52 | 15.00 | 8.00 | 1.27 | 2.399 | 4.855 |
| 53 | 15.00 | 8.00 | 1.65 | 2.569 | 5.693 |
| 54 | 15.00 | 8.00 | 2.11 | 2.720 | 6.533 |
| 55 | 15.00 | 12.00 | 1.27 | 2.444 | 4.767 |
| 56 | 15.00 | 12.00 | 1.65 | 2.642 | 5.661 |
| 57 | 15.00 | 12.00 | 2.11 | 2.816 | 6.580 |
| 58 | 15.00 | 16.00 | 1.27 | 2.317 | 4.528 |
| 59 | 15.00 | 16.00 | 1.65 | 2.499 | 5.288 |
| 60 | 15.00 | 16.00 | 2.11 | 2.705 | 6.232 |

FIG. 48B

Parametric study on bipolar electrode configuration as a function of applied voltage and pulse number in the resulting IRE area and volume.

| Run | Voltage (V) | Pulse Number | IRE Area (cm²) | IRE Volume (cm³) | IRE Area > 670.1 V/cm (cm²) | IRE Volume > 670.1 V/cm (cm³) |
|---|---|---|---|---|---|---|
| 1 | 2000 | 0 | 0.00000 | 0.00000 | 0.96961 | 1.57498 |
| 2 | 2000 | 20 | 0.21547 | 0.35000 | 0.96961 | 1.57498 |
| 3 | 2000 | 40 | 0.43094 | 0.69999 | 0.96961 | 1.57498 |
| 4 | 2000 | 60 | 0.64641 | 1.04999 | 0.96961 | 1.57498 |
| 5 | 2000 | 80 | 0.86188 | 1.39998 | 0.96961 | 1.57498 |
| 6 | 2000 | 100 | 1.07734 | 1.74998 | 0.96961 | 1.57498 |
| 7 | 2250 | 0 | 0.00000 | 0.00000 | 1.12614 | 2.07358 |
| 8 | 2250 | 20 | 0.25025 | 0.46080 | 1.12614 | 2.07358 |
| 9 | 2250 | 40 | 0.50051 | 0.92159 | 1.12614 | 2.07358 |
| 10 | 2250 | 60 | 0.75076 | 1.38239 | 1.12614 | 2.07358 |
| 11 | 2250 | 80 | 1.00101 | 1.84318 | 1.12614 | 2.07358 |
| 12 | 2250 | 100 | 1.25127 | 2.30398 | 1.12614 | 2.07358 |
| 13 | 2500 | 0 | 0.00000 | 0.00000 | 1.23823 | 2.32864 |
| 14 | 2500 | 20 | 0.27516 | 0.51748 | 1.23823 | 2.32864 |
| 15 | 2500 | 40 | 0.55032 | 1.03495 | 1.23823 | 2.32864 |
| 16 | 2500 | 60 | 0.82549 | 1.55243 | 1.23823 | 2.32864 |
| 17 | 2500 | 80 | 1.10065 | 2.06990 | 1.23823 | 2.32864 |
| 18 | 2500 | 100 | 1.37581 | 2.58738 | 1.23823 | 2.32864 |
| 19 | 2750 | 0 | 0.00000 | 0.00000 | 1.34103 | 2.67481 |
| 20 | 2750 | 20 | 0.29801 | 0.59440 | 1.34103 | 2.67481 |
| 21 | 2750 | 40 | 0.59601 | 1.18880 | 1.34103 | 2.67481 |
| 22 | 2750 | 60 | 0.89402 | 1.78321 | 1.34103 | 2.67481 |
| 23 | 2750 | 80 | 1.19203 | 2.37761 | 1.34103 | 2.67481 |
| 24 | 2750 | 100 | 1.49003 | 2.97201 | 1.34103 | 2.67481 |
| 25 | 3000 | 0 | 0.00000 | 0.00000 | 1.49312 | 3.17126 |
| 26 | 3000 | 20 | 0.33180 | 0.70472 | 1.49312 | 3.17126 |
| 27 | 3000 | 40 | 0.66361 | 1.40945 | 1.49312 | 3.17126 |
| 28 | 3000 | 60 | 0.99541 | 2.11417 | 1.49312 | 3.17126 |
| 29 | 3000 | 80 | 1.32722 | 2.81890 | 1.49312 | 3.17126 |
| 30 | 3000 | 100 | 1.65902 | 3.52362 | 1.49312 | 3.17126 |

FIG. 49

Parametric study on bipolar electrode configuration as a function of pulse number in the resulting IRE area and volume with an applied voltage of 3000 V.

| Run | Voltage (V) | Pulse Number | IRE Area (cm²) | IRE Volume (cm³) | IRE Area > 670.1 V/cm (cm²) | IRE Volume > 670.1 V/cm (cm³) |
|---|---|---|---|---|---|---|
| 1 | 3000 | 0 | 0.00000 | 0.00000 | 1.49312 | 3.17126 |
| 2 | 3000 | 20 | 0.33180 | 0.70472 | 1.49312 | 3.17126 |
| 3 | 3000 | 40 | 0.66361 | 1.40945 | 1.49312 | 3.17126 |
| 4 | 3000 | 60 | 0.99541 | 2.11417 | 1.49312 | 3.17126 |
| 5 | 3000 | 80 | 1.32722 | 2.81890 | 1.49312 | 3.17126 |
| 6 | 3000 | 100 | 1.65902 | 3.52362 | 1.49312 | 3.17126 |
| 7 | 3000 | 120 | 1.99083 | 4.22835 | 1.49312 | 3.17126 |
| 8 | 3000 | 140 | 2.32263 | 4.93307 | 1.49312 | 3.17126 |
| 9 | 3000 | 160 | 2.65444 | 5.63780 | 1.49312 | 3.17126 |
| 10 | 3000 | 180 | 2.98624 | 6.34252 | 1.49312 | 3.17126 |
| 11 | 3000 | 200 | 3.31804 | 7.04724 | 1.49312 | 3.17126 |
| 12 | 3000 | 220 | 3.64985 | 7.75197 | 1.49312 | 3.17126 |
| 13 | 3000 | 240 | 3.98165 | 8.45669 | 1.49312 | 3.17126 |
| 14 | 3000 | 260 | 4.31346 | 9.16142 | 1.49312 | 3.17126 |
| 15 | 3000 | 280 | 4.64526 | 9.86614 | 1.49312 | 3.17126 |
| 16 | 3000 | 300 | 4.97707 | 10.57087 | 1.49312 | 3.17126 |
| 17 | 3000 | 320 | 5.30887 | 11.27559 | 1.49312 | 3.17126 |
| 18 | 3000 | 340 | 5.64068 | 11.98032 | 1.49312 | 3.17126 |
| 19 | 3000 | 360 | 5.97248 | 12.68504 | 1.49312 | 3.17126 |

FIG. 50

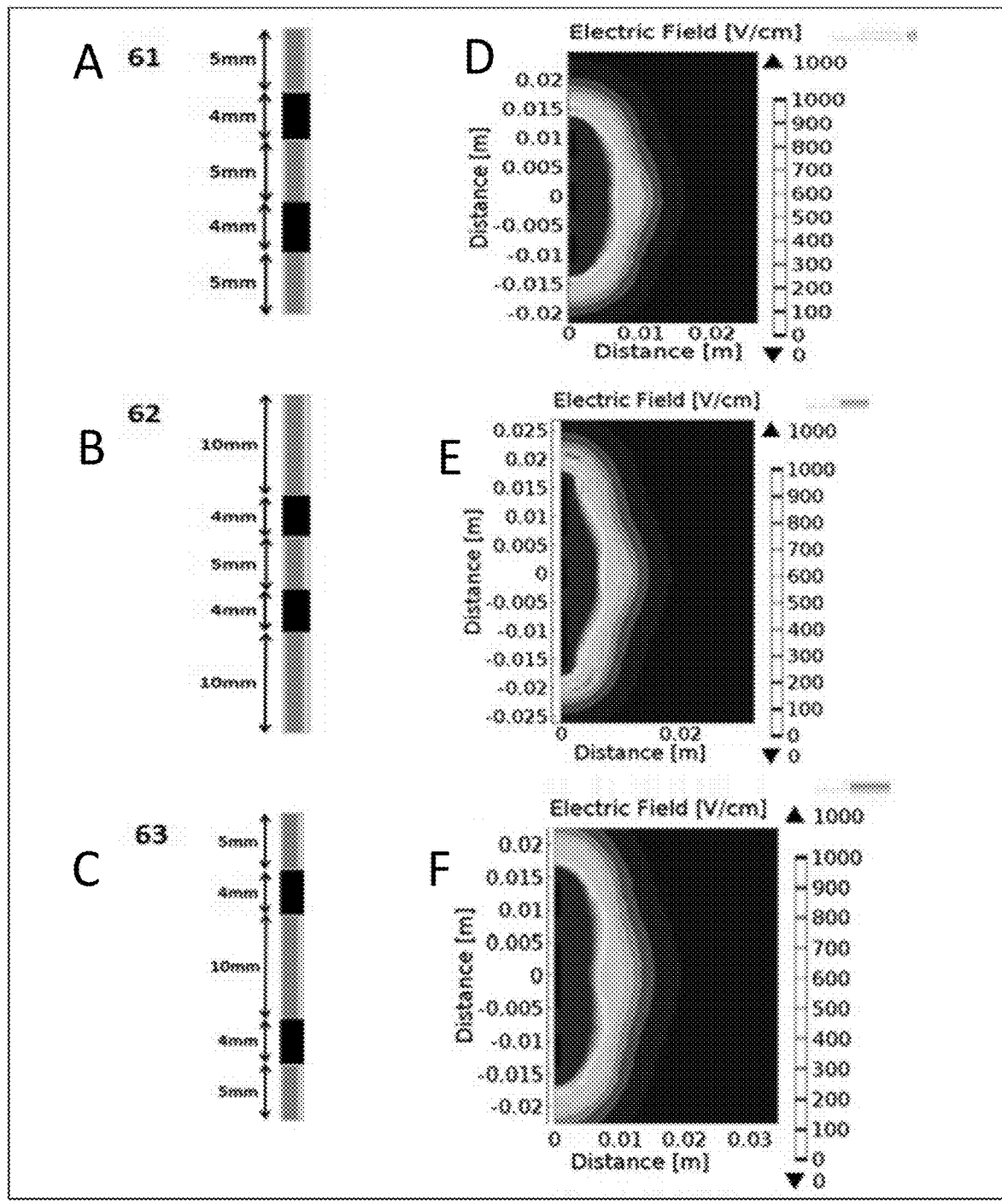
FIG. 51A-F

SYSTEM AND METHOD FOR ESTIMATING TISSUE HEATING OF A TARGET ABLATION ZONE FOR ELECTRICAL-ENERGY BASED THERAPIES

CROSS-REFERENCE TO RELATED APPLICATIONS

The present application is a Continuation of U.S. patent application Ser. No. 16/152,743 filed Oct. 5, 2018, which published as U.S. Patent Application Publication No. 2019/0029749 on Jan. 31, 2019 and which issued as U.S. Pat. No. 11,272,979 on Mar. 15, 2022, which application is a Continuation of U.S. patent application Ser. No. 14/558,631 filed Dec. 2, 2014, which published as U.S. Patent Application Publication No. 2015/0088120 on Mar. 26, 2015, and which issued as U.S. Pat. No. 10,117,707 on Nov. 6, 2018. The '631 application is a Continuation-in-Part (CIP) of U.S. patent application Ser. No. 14/012,832, filed on Aug. 28, 2013, which published as U.S. Patent Application Publication No. 2013/0345697 on Dec. 26, 2013 and issued as U.S. Pat. No. 9,283,051 on Mar. 15, 2016. The '832 application relies on and claims the benefit of the filing date of U.S. Provisional Application No. 61/694,144, filed on Aug. 28, 2012. The '832 application is also a CIP of U.S. application Ser. No. 12/491,151, filed on Jun. 24, 2009, which '151 application published as U.S. Patent Application Publication No. 2010/0030211 on Feb. 4, 2010 and issued as U.S. Pat. No. 8,992,517 on Mar. 31, 2015. The '151 application relies on and claims the benefit of the filing dates of U.S. Provisional Patent Application Nos. 61/171,564, filed on Apr. 22, 2009, 61/167,997, filed on Apr. 9, 2009, and 61/075,216, filed on Jun. 24, 2008. The '151 application is also a CIP of U.S. patent application Ser. No. 12/432,295, filed on Apr. 29, 2009, which '295 application published as U.S. Patent Application Publication No. 2009/0269317 and issued as U.S. Pat. No. 9,598,691 on Mar. 21, 2017. The '295 application relies on and claims the benefit of the filing date of U.S. Provisional Patent Application No. 61/125,840, filed on Apr. 29, 2008. The '631 application also relies on and claims priority to and the benefit of the filing date of U.S. Provisional Application No. 61/910,655, filed Dec. 2, 2013. The Ser. No. 16/152,743 application is also a CIP Application of U.S. patent application Ser. No. 14/808,679 filed Jul. 24, 2015, which published as U.S. Patent Application Publication No. 2015/0327944 on Nov. 19, 2015 and which issued as U.S. Pat. No. 11,655,466 on May 23, 2023. The '679 application is a Divisional application of U.S. patent application Ser. No. 12/906,923 filed Oct. 18, 2010, which published as U.S. Patent Application Publication No. 2011/0106221 on May 5, 2011 and issued as U.S. Pat. No. 9,198,733 on Dec. 1, 2015. The '923 application claims priority to and the benefit of the filing date of U.S. Provisional Application No. 61/252,445 filed Oct. 16, 2009. The '923 application is a CIP of the '151 application. The '923 application is also a CIP of U.S. patent application Ser. No. 12/609,779 filed Oct. 30, 2009, which published as U.S. Patent Application Publication No. 2010/0331758 on Dec. 30, 2010 and issued as U.S. Pat. No. 8,465,484 on Jun. 18, 2013. The '923 application is also a CIP of U.S. patent application Ser. No. 12/757,901 filed Apr. 9, 2010, which published as U.S. Patent Application Publication No. 2010/0261994 on Oct. 14, 2010 and issued as U.S. Pat. No. 8,926,606 on Jan. 6, 2015. The '901 application claims priority to and the benefit of the filing date of U.S. Provisional Application Nos. 61/285,618 filed Dec. 11, 2009 and 61/167,997 filed Apr. 9, 2009. The '679 application is a CIP of U.S. patent application Ser. No. 13/332,133 filed Dec. 20, 2011, which published as U.S. Patent Application Publication No. 2012/0109122 on May 3, 2012 and issued as U.S. Pat. No. 10,448,989 on Oct. 22, 2019. The '133 application is a CIP of the '901 application. The '133 application claims priority to and the benefit of the filing date of U.S. Provisional application No. 61/424,872 filed Dec. 20, 2010. The disclosures of these patent applications are hereby incorporated by reference herein in their entireties.

FIELD OF THE INVENTION

The present invention is related to medical therapies involving the administering of electrical treatment energy. More particularly, embodiments of the present invention provide systems and methods for modeling and providing a graphical representation of tissue heating and electric field for a medical treatment device that applies electrical treatment energy through a plurality of electrodes defining a target treatment area. Embodiments of the present invention also provide systems and methods providing a graphical representation of a target ablation zone based on one or more electrical conductivity parameters that are specific for the tissue to be treated.

DESCRIPTION OF RELATED ART

Electroporation-based therapies (EBTs) are clinical procedures that utilize pulsed electric fields to induce nanoscale defects in cell membranes. Typically, pulses are applied through minimally invasive needle electrodes inserted directly into the target tissue, and the pulse parameters are tuned to create either reversible or irreversible defects. Reversible electroporation facilitates the transport of molecules into cells without directly compromising cell viability. This has shown great promise for treating cancer when used in combination with chemotherapeutic agents or plasmid DNA (M. Marty et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006; A. I. Daud et al., "Phase I Trial of Interleukin-12 Plasmid Electroporation in Patients With Metastatic Melanoma," Journal of Clinical Oncology, 26, 5896-5903, Dec. 20 2008). Alternatively, irreversible electroporation (IRE) has been recognized as a non-thermal tissue ablation modality that produces a tissue lesion, which is visible in real-time on multiple imaging platforms (R. V. Davalos, L. M. Mir, and B. Rubinsky, "Tissue ablation with irreversible electroporation," Ann Biomed Eng, 33, 223-31, February 2005; R. V. Davalos, D. M. Otten, L. M. Mir, and B. Rubinsky, "Electrical impedance tomography for imaging tissue electroporation," IEEE Transactions on Biomedical Engineering, 51, 761-767, 2004; L. Appelbaum, E. Ben-David, J. Sosna, Y. Nissenbaum, and S. N. Goldberg, "US Findings after Irreversible Electroporation Ablation: Radiologic-Pathologic Correlation," Radiology, 262, 117-125, Jan. 1, 2012). Because the mechanism of cell death does not rely on thermal processes, IRE spares major nerve and blood vessel architecture and is not subject to local heat sink effects when using a specific protocol that does not exceed the thermal damage threshold. (B. Al-Sakere, F. Andre, C. Bernat, E. Connault, P. Opolon, R. V. Davalos, B. Rubinsky, and L. M. Mir, "Tumor ablation with irreversible electroporation," PLoS ONE, 2, e1135, 2007). These unique benefits have translated to the successful treatment of several surgically "inoperable" tumors (K. R. Thomson et al., "Investigation of the safety of irreversible electroporation in humans," J Vasc Intery Radiol, 22, 611-21, May 2011; R. E. Neal II et al., "A Case Report on the Successful Treatment of a Large Soft-Tissue Sarcoma with Irreversible Electroporation," Journal of Clinical Oncology, 29, 1-6, 2011; P. A. Garcia et al., "Non-thermal irreversible electroporation (N-TIRE) and adjuvant fractionated radiotherapeutic multimodal therapy for intracranial malignant glioma in a canine patient," Technol Cancer Res Treat, 10, 73-83, 2011).

In EBTs, the electric field distribution is the primary factor for dictating defect formation and the resulting volume of treated tissue (J. F. Edd and R. V. Davalos, "Mathematical modeling of irreversible electroporation for treatment planning," Technology in Cancer Research and Treatment, 6, 275-286, 2007 ("Edd and Davalos, 2007"); D. Miklavcic, D. Semrov, H. Mekid, and L. M. Mir, "A validated model of in vivo electric field distribution in tissues for electrochemotherapy and for DNA electrotransfer for gene therapy," Biochimica et Biophysica Acta, 1523, 73-83, 2000). The electric field is influenced by both the geometry and positioning of the electrodes as well as the dielectric tissue properties. Because the pulse duration is typically much longer than the pulse rise/fall time, static solutions of the Laplace's equation incorporating only electric conductivity are sufficient for predicting the electric field distribution. In tissues with uniform conductivity, solutions can be obtained analytically for various needle electrode configurations if the exposure length is much larger than the separation distance (S. Corovic, M. Pavlin, and D. Miklavcic, "Analytical and numerical quantification and comparison of the local electric field in the tissue for different electrode configurations," Biomed Eng Online, 6, 2007; R. Neal II et al., "Experimental Characterization and Numerical Modeling of Tissue Electrical Conductivity during Pulsed Electric Fields for Irreversible Electroporation Treatment Planning," Biomedical Engineering, IEEE Transactions on, PP, 1-1, 2012 ("Neal et al., 2012")). This is not often the case in clinical applications where aberrant masses with a diameter on the order of 1 cm are treated with an electrode exposure length of similar dimensions. Additionally, altered membrane permeability due to electroporation influences the tissue conductivity in a non-linear manner. Therefore numerical techniques may be used to account for any electrode configuration and incorporate a tissue-specific function relating the electrical conductivity to the electric field distribution (i.e. extent of electroporation).

Conventional devices for delivering therapeutic energy such as electrical pulses to tissue include a handle and one or more electrodes coupled to the handle. Each electrode is connected to an electrical power source. The power source allows the electrodes to deliver the therapeutic energy to a targeted tissue, thereby causing ablation of the tissue.

Once a target treatment area is located within a patient, the electrodes of the device are placed in such a way as to create a treatment zone that surrounds the treatment target area. In some cases, each electrode is placed by hand into a patient to create a treatment zone that surrounds a lesion. The medical professional who is placing the electrodes typically watches an imaging monitor while placing the electrodes to approximate the most efficient and accurate placement.

However, if the electrodes are placed by hand in this fashion, it is very difficult to predict whether the locations selected will ablate the entire treatment target area because the treatment region defined by the electrodes vary greatly depending on such parameters as the electric field density, the voltage level of the pulses being applied, size of the electrode and the type of tissue being treated. Further, it is often difficult or sometimes not possible to place the electrodes in the correct location of the tissue to be ablated because the placement involves human error and avoidance of obstructions such as nerves, blood vessels and the like.

Conventionally, to assist the medical professional in visualizing a treatment region defined by the electrodes, an estimated treatment region is generated using a numerical model analysis such as complex finite element analysis. One problem with such a method is that even a modest two dimensional treatment region may take at least 30 minutes to several hours to complete even in a relatively fast personal computer. This means that it would be virtually impossible to try to obtain on a real time basis different treatment regions based on different electrode positions.

In IRE treatments, the electric field distribution is the primary factor for dictating defect formation and the resulting volume of treated tissue (See J. F. Edd and R. V. Davalos, "Mathematical modeling of irreversible electroporation for treatment planning," Technol Cancer Res Treat, vol. 6, pp. 275-286, 2007; D. Sel, et al., "Sequential finite element model of tissue electropermeabilization," IEEE Trans Biomed Eng, vol. 52, pp. 816-27, May 2005). The electric field is influenced by both the geometry and positioning of the electrodes as well as the dielectric tissue properties. The application of an electric field across any conductive media will result in some degree of resistive losses in which energy is dissipated as heat. Though cell death in IRE is attributed to non-thermal mechanisms, it is possible to inadvertently elevate tissue temperatures above thermal damage thresholds if parameters are not chosen carefully. Since a major advantage of IRE is the ablation of tissue without deleterious thermal effects and the therapy is often applied in regions which cannot clinically sustain thermal injury, it is important to identify safe operating parameters. Transient heating of tissue in proximity to the electrode can result in the denaturing of the extracellular matrix, scar formation, or damage to local blood vessels and nerves. To avoid these effects, it is important to understand the extent and geometry of tissue heating.

Therefore, it would be desirable to provide an improved system and method to predict a treatment region that avoids electrical and thermal overexposure and damage in order to determine safe and effective pulse protocols for administering electrical energy based therapies, such IRE.

SUMMARY OF THE INVENTION

In one embodiment, the invention provides a system for treating a tissue, which system applies electrical treatment energy through one or more electrodes, such as a plurality of electrodes, defining a target treatment area of the tissue. The system comprises a memory, a display device, a processor coupled to the memory and the display device, and a treatment planning module stored in the memory and executable by the processor. In one embodiment, the treatment planning module is adapted to generate an estimated heat distribution and/or electrical field distribution in the display device based on one or more parameters for an electrical energy based protocol, such as an irreversible electroporation (IRE) protocol. In another embodiment, the treatment planning module is adapted to generate an estimated target ablation zone based on a combination of one or more parameters for an electrical energy based protocol, such as an IRE-based protocol, and one or more tissue-specific conductivity parameters.

In another embodiment, the invention provides a method of treating a tissue with a medical treatment device that applies electrical treatment energy through a one or more or a plurality of electrodes defining a target treatment area of the tissue and comprises a display device. The method may be executed partially or completely using the system of the invention. In a specific embodiment, one or more steps are executed through the treatment planning module.

In embodiments, the treatment planning module can be used to determine a temperature distribution to determine tissue heating at or around a target ablation zone prior to or during treatment. The treatment planning module can be used to graphically display contour lines which represent a specific temperature of tissue heating. In one embodiment, the treatment planning module estimates the temperature rise within tissue due to Joule heating effects, and plots a contour line according to a temperature specified by a user. Further, the treatment planning module may further plot a contour line representing an electric field intensity such that temperature and electric field intensity can be correlated. The treatment planning module may plot the temperature distribution and electric field distribution for a bipolar and single needle electrodes. This capability may allow a user (e.g. treating physician) to determine heating to surrounding tissues during treatment planning and adjust parameters to prevent thermal damage to critical surrounding structures such as nerves and blood vessels. In one embodiment, the contour lines are Cassini oval approximations performed according to the equations and procedure in Example 7.

In embodiments, the treatment planning module can be used to provide the electric field distributions using different configurations of bipolar probes and include the dynamic change in electrical conductivity from the non-electroporated baseline tissue electrical conductivity. The treatment planning module may plot contour lines representing electric field distributions based on a specific combination of electrode length, separation distance, and applied voltage. The treatment planning module may incorporate the dynamic change in electrical conductivity from the baseline during treatment to account for treatment-related changes in conductivity for particular tissues such as liver, kidney, brain, etc. This capability may allow the treating physician to determine electric field distributions and zones of ablation based on the capacity for a specific target tissue to change in conductivity during treatment. In one embodiment, the contour lines are Cassini oval approximations performed according to the equations and procedure in Example 7.

In embodiments, the treatment planning module can be based on a parametric study of the dynamic conductivity curve so that variables related to the dynamic conductivity could be used to fit tissue specific behavior. In embodiments, the treatment planning module may provide input for one or more electrical conductivity parameters such as the baseline (e.g., non-electroporated) conductivity, change in conductivity, the transition zone (how rapidly the conductivity increases), the electric field at which the change in conductivity occurs, and the electric field at which irreversible electroporation occurs. These parameters may be experimentally derived for different tissues and stored in a database. This capability may allow the treating physician to account for different conductivity parameters as they apply to different target tissues when designing a treatment protocol. Thus, when considering a specific tissue, the treating physician may optimize the calculation of an ablation zone for that tissue by inputting one or more of the tissue-specific conductivity parameters for the tissue of interest.

BRIEF DESCRIPTION OF THE DRAWINGS

The accompanying drawings illustrate certain aspects of embodiments of the present invention, and should not be used to limit or define the invention. Together with the written description the drawings serve to explain certain principles of the invention.

FIGS. 8A and 8B are tables showing Whole Model Parameter Estimates and Effect Tests, respectively.

FIG. 8C is a graph showing a plot of Actual Current vs. Predicted Current.

FIGS. 9A-9F are graphs showing the representative (15 mm gap) correlation between current vs. exposure length and electrode radius for maximum electrical conductivities (1×-6×, respectively).

FIG. 10A is a table showing experimental validation of the code for determining the tissue/potato dynamic from in vitro measurements, referred to as potato experiment #1.

FIG. 10B is a table showing experimental validation of the code for determining the tissue/potato dynamic from in vitro measurements, referred to as potato experiment #2.

FIGS. 12A-12C are graphs showing representative contour plots of the electric field strength at 1.0 cm from the origin using an edge-to-edge voltage-to-distance ratio of 1500 V/cm assuming z=1, wherein FIG. 12A is a plot of the x-direction, FIG. 12B is a plot of the y-direction, and FIG. 12C is a plot of the z-direction.

FIGS. 20A-D are representations of the Electric Field [V/cm] Distributions from the 3D Non-Electroporated (Baseline) Models of FIG. 19, wherein FIG. 20A represents the x-y plane mid-electrode length, FIG. 20B represents the x-z plane mid-electrode diameter, FIG. 20C represents the y-z plane mid-electrode diameter, and FIG. 20D represents the y-z plane between electrodes.

FIGS. 22A-22D are representations of the Electric Field [V/cm] Distributions from the 3D Electroporated Models with 1.5-cm Electrodes at a Separation of 2.0 cm and 3000 V (cross-sections) assuming $\sigma_{max}/\sigma_0=3.6$, wherein FIG. 22A represents the x-y plane mid-electrode length, FIG. 22B represents the x-z plane mid-electrode diameter, FIG. 22C represents the y-z plane mid-electrode diameter, and FIG. 22D represents the y-z plane between electrodes.

FIGS. 36A-36C show a representation of a visualization tool providing the 650 V/cm electric field distributions using different configurations of bipolar probes and includes dynamic change (3.6×) in electrical conductivity from the non-electroporated baseline for runs 7, 8, and 9 of the visualization.

FIG. 36D is a table showing parameters of runs 7, 8, and 9 including electrode length, separation distance (insulation), and applied voltage.

FIG. 36E is a table showing lesion dimensions for runs 7, 8, and 9. The results show that as the length of the bipolar electrode increases the size of the zone of ablation increases.

FIG. 37 shows the conductivity changes from 0.1 to 0.35 at an electric field centered at 500 V/cm.

FIGS. 46A-D are representative contour plots showing post-IRE cell viability, wherein A) corresponds to 20 pulses at 2000 volts, B) corresponds to 20 pulses at 3000 volts, C) corresponds to 100 pulses at 2000 volts, and D) corresponds to 100 pulses at 3000 volts.

FIGS. 48A and 48B are a table showing the results of a parametric study on bipolar electrode configuration as a function of electrode length, separation distance, and diameter in the resulting IRE area and volume.

FIG. 49 is a table showing the results of a parametric study on bipolar electrode configuration as a function of applied voltage and pulse number in the resulting IRE area and volume with 7 mm long electrodes separated by an 8 mm insulation shaft.

FIG. 50 is a table showing the results of a parametric study on bipolar electrode configuration as a function of pulse number in the resulting IRE area and volume with an applied voltage of 3000 V with 7 mm long electrodes separated by an 8 mm insulation shaft.

FIGS. 51A-C are schematics of representative electrode geometries.

FIGS. 51D-F are representative contour plots showing the resulting electric field distribution corresponding to the electrode geometries of FIGS. 51A-C.

DETAILED DESCRIPTION OF VARIOUS EMBODIMENTS OF THE INVENTION

Reference will now be made in detail to various exemplary embodiments of the invention. Embodiments described in the description and shown in the figures are illustrative only and are not intended to limit the scope of the invention. Changes may be made in the specific embodiments described in this specification and accompanying drawings that a person of ordinary skill in the art will recognize are within the scope and spirit of the invention.

Throughout the present teachings, any and all of the features and/or components disclosed or suggested herein, explicitly or implicitly, may be practiced and/or implemented in any combination, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Embodiments of the invention include a method for visualization of heat and electric field distribution within a target treatment area, the method comprising: selecting as inputs an applied voltage, electrode spacing, and treatment duration corresponding to a desired treatment protocol for a target treatment area; using the inputs in a Cassini approximation of data, wherein the data comprises measured voltage, electrode spacing, and time of actual treatment protocols, and determining an expected temperature distribution and expected electric field distribution of the target treatment area; and displaying a graphical representation of a selected temperature and a selected electric field of the expected temperature and electric field distributions. Such methods can further comprise as inputs one or more of a baseline conductivity for the target treatment area, a change in conductivity for the target treatment area, or a conductivity for a specific tissue type.

Such methods can include a method of treatment planning for medical therapies involving administering electrical treatment energy, the method comprising: providing one or more parameters of a treatment protocol for delivering one or more electrical pulses to tissue through one or more a plurality of electrodes; modeling heat distribution in the tissue based on the parameters; and displaying a graphical representation of the modeled heat distribution.

Figure 1:
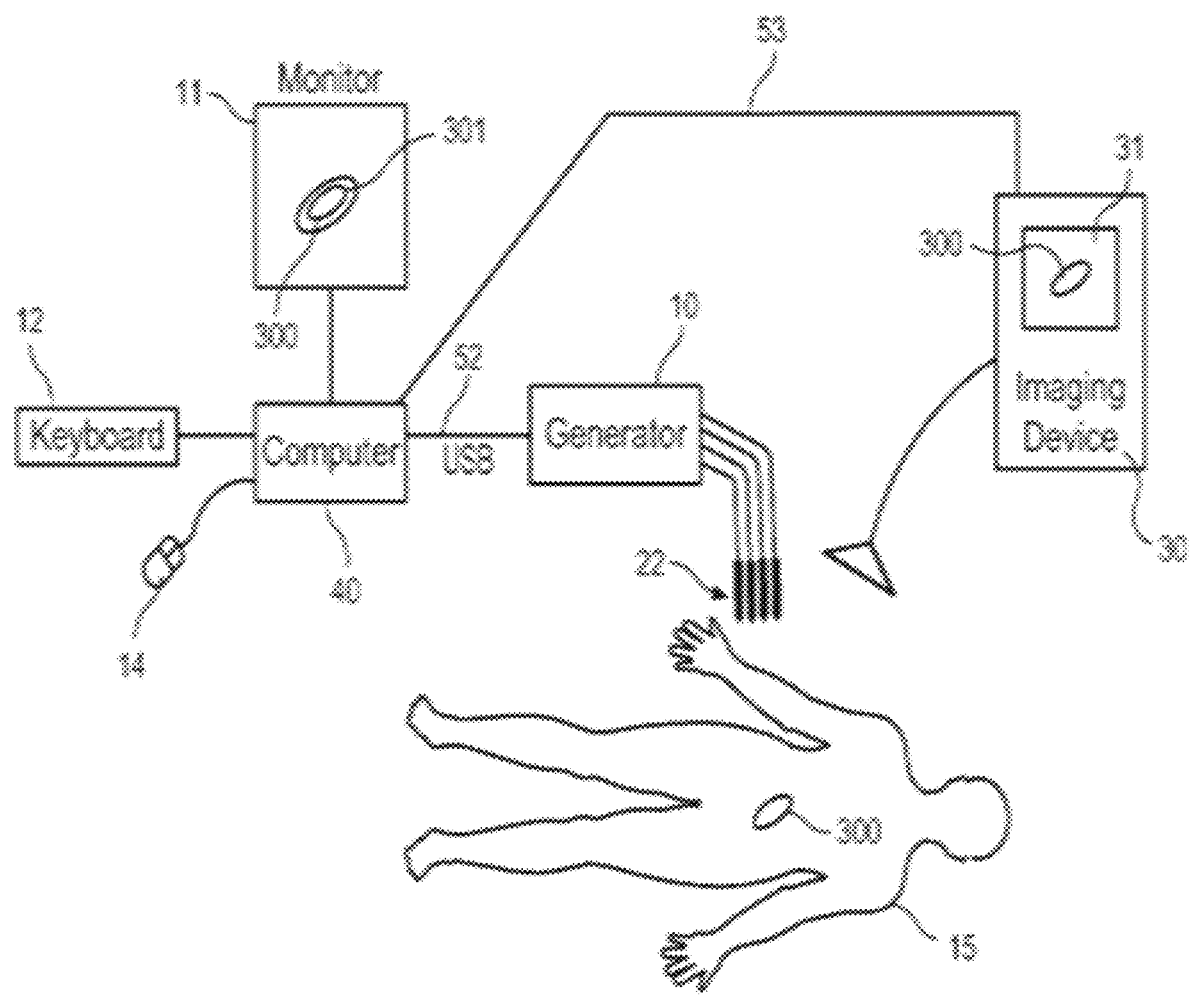
FIG. 1 is a schematic diagram of a representative system of the invention.
Figure 2:
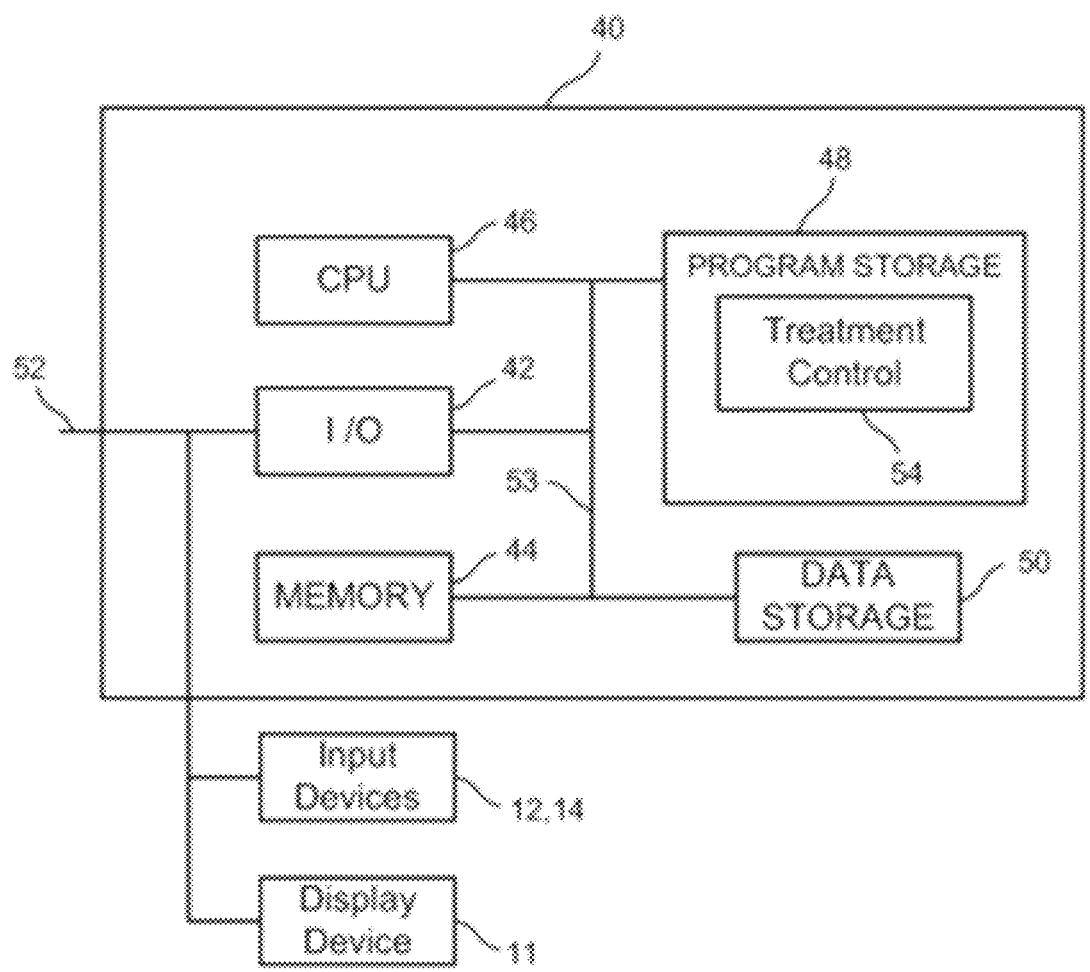
FIG. 2 is a schematic diagram of a representative treatment control computer of the invention.

One embodiment of the present invention is illustrated in FIGS. 1 and 2. Representative components that can be used with the present invention can include one or more of those that are illustrated in FIG. 1. For example, in embodiments, one or more probes 22 can be used to deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

For example, a treatment protocol according to the invention could include a one or more or a plurality of electrodes. According to the desired treatment pattern, the plurality of electrodes can be disposed in various positions relative to one another. In a particular example, a plurality of electrodes can be disposed in a relatively circular pattern with a single electrode disposed in the interior of the circle, such as at approximately the center. Any configuration of electrodes is possible and the arrangement need not be circular but any shape periphery can be used depending on the area to be treated, including any regular or irregular polygon shape, including convex or concave polygon shapes. The single centrally located electrode can be a ground electrode while the other electrodes in the plurality can be energized. Any number of electrodes can be in the plurality such as from about 1 to 20. Indeed, even 3 electrodes can form a plurality of electrodes where one ground electrode is disposed between two electrodes capable of being energized, or 4 electrodes can be disposed in a manner to provide two electrode pairs (each pair comprising one ground and one electrode capable of being energized). During treatment, methods of treating can involve energizing the electrodes in any sequence, such as energizing one or more electrode simultaneously, and/or energizing one or more electrode in a particular sequence, such as sequentially, in an alternating pattern, in a skipping pattern, and/or energizing multiple electrodes but less than all electrodes simultaneously, for example.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein in its entirety. The pulse generator 10 is connected to a treatment control computer 40 having input devices such as keyboard 12 and a pointing device 14, and an output device such as a display device 11 for viewing an image of a target treatment area such as a lesion 300 surrounded by a safety margin 301. The therapeutic energy delivery device 22 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment planning module 54) which assists a user to plan for, execute, and review the results of a medical treatment procedure, as will be discussed in more detail below. For example, the treatment planning module 54 assists a user to plan for a medical treatment procedure by enabling a user to more accurately position each of the probes 22 of the therapeutic energy delivery device 20 in relation to the lesion 300 in a way that will generate the most effective treatment zone. The treatment planning module 54 can display the anticipated treatment zone based on the position of the probes and the treatment parameters. The treatment planning module 54 may also display a zone of temperature heating according to cutoff values inputted by the treating physician and correlate this with a value for the electric field distribution. The treatment planning module may also allow the treating physician to display the anticipated treatment zone, or target ablation zone, according to one or more tissue-specific conductivity parameters inputted by the treating physician. The conductivity parameters may include the baseline conductivity of the tissue to be treated, the ratio of the baseline conductivity to the maximum conductivity of the tissue that is reached during treatment, the rate at which the conductivity increases from the baseline to the maximum conductivity, and/or the electric field at which the conductivity changes during treatment.

The treatment planning module 54 can display the progress of the treatment in real time and can display the results of the treatment procedure after it is completed. This information can be displayed in a manner such that it can be used for example by a treating physician to determine whether the treatment was successful and/or whether it is necessary or desirable to re-treat the patient.

For purposes of this application, the terms "code", "software", "program", "application", "software code", "computer readable code", "software module", "module" and "software program" are used interchangeably to mean software instructions that are executable by a processor. The "user" can be a physician or other medical professional. The treatment planning module 54 executed by a processor outputs various data including text and graphical data to the monitor 11 associated with the generator 10.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment planning module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. In a preferred embodiment, the communication link 52 is a USB link. In one embodiment, the imaging device 30 is a stand-alone device which is not connected to the computer 40. In the embodiment as shown in FIG. 1, the computer 40 is connected to the imaging device 30 through a communications link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid (not shown) of the display device (monitor) 11 of the computer running the treatment planning module 54. This embodiment would provide an accurate representation of the lesion image on the grid, and may eliminate the step of manually inputting the dimensions of the lesion in order to create the lesion image on the grid. This embodiment would also be useful to provide an accurate representation of the lesion image if the lesion has an irregular shape.

It should be noted that the software can be used independently of the pulse generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment. Additionally, the software can be used for hypothetical illustration of zones of ablation, temperature thresholds or cutoffs, and electrical field thresholds or cutoffs for training purposes to the user on therapies that deliver electrical energy. For example, the data can be evaluated by a human to determine or estimate favorable treatment protocols for a particular patient rather than programmed into a device for implementing the particular protocol.

Figure 3:
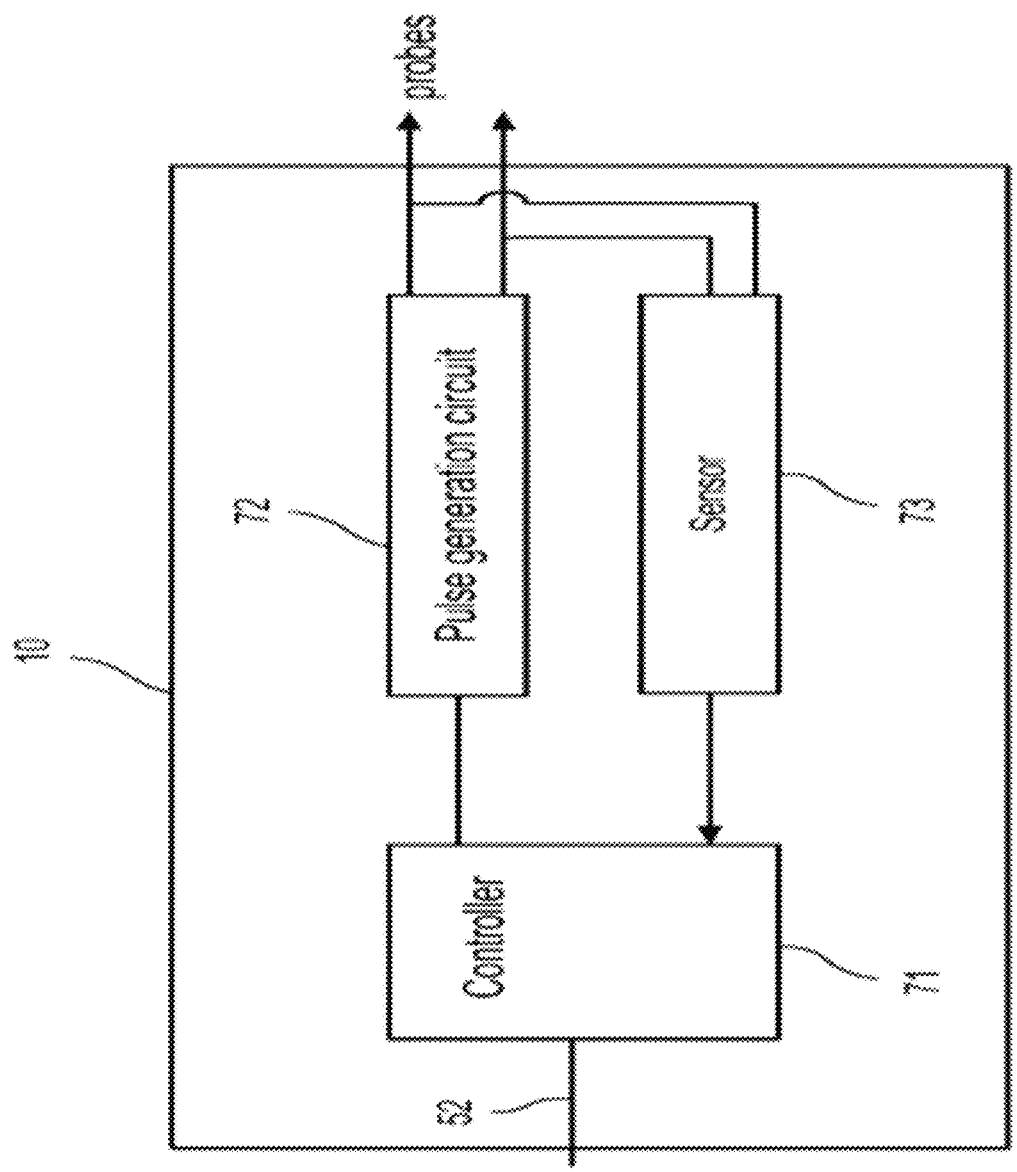
FIG. 3 is schematic diagram illustrating details of the generator shown in the system of FIG. 1, including elements for detecting an over-current condition.

FIG. 3 illustrates one embodiment of a circuitry to detect an abnormality in the applied pulses such as a high current, low current, high voltage or low voltage condition. This circuitry is located within the generator 10 (see FIG. 1). A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes are shown. However, the generator 10 can accommodate any number of probes/electrodes (e.g., from 1-10, such as 6 probes) and energizing multiple electrodes simultaneously for customizing the shape of the ablation zone. In the embodiment shown, the pulses are applied one pair of electrodes at a time, and then switched to another pair. The pulse generation circuit 72 includes a switch, preferably an electronic switch, that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes. The treatment planning module 54 can further include a feature that tracks the treatment progress and provides the user with an option to automatically retreat for low or missing pulses, or over-current pulses (see discussion below). Also, if the generator stops prematurely for any reason, the treatment planning module 54 can restart at the same point where it terminated, and administer the missing treatment pulses as part of the same treatment. In other embodiments, the treatment planning module 54 is able to detect certain errors during treatment, which include, but are not limited to, "charge failure", "hardware failure", "high current failure", and "low current failure".

General treatment protocols for the destruction (ablation) of undesirable tissue through electroporation are known. They involve the insertion (bringing) electroporation electrodes to the vicinity of the undesirable tissue and in good electrical contact with the tissue and the application of electrical pulses that cause irreversible electroporation of the cells throughout the entire area of the undesirable tissue. The cells whose membrane was irreversible permeabilized may be removed or left in situ (not removed) and as such may be gradually removed by the body's immune system. Cell death is produced by inducing the electrical parameters of irreversible electroporation in the undesirable area.

Electroporation protocols involve the generation of electrical fields in tissue and are affected by the Joule heating of the electrical pulses. When designing tissue electroporation protocols it is important to determine the appropriate electrical parameters that will maximize tissue permeabilization without inducing deleterious thermal effects. It has been shown that substantial volumes of tissue can be electroporated with reversible electroporation without inducing damaging thermal effects to cells and has quantified these volumes (Davalos, R. V., B. Rubinsky, and L. M. Mir, Theoretical analysis of the thermal effects during in vivo tissue electroporation. Bioelectrochemistry, 2003. Vol. 61(1-2): p. 99-107).

The electrical pulses used to induce irreversible electroporation in tissue are typically larger in magnitude and duration from the electrical pulses required for reversible electroporation. Further, the duration and strength of the pulses for irreversible electroporation are different from other methodologies using electrical pulses such as for intracellular electro-manipulation or thermal ablation. The methods are very different even when the intracellular (nano-seconds) electro-manipulation is used to cause cell death, e.g. ablate the tissue of a tumor or when the thermal effects produce damage to cells causing cell death.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see published U.S. application 2002/0010491 published Jan. 24, 2002.

The pulse is typically administered at voltage of about 100 V/cm to 7,000 V/cm or 200 V/cm to 2000 V/cm or 300V/cm to 1000 V/cm about 600 V/cm for irreversible electroporation. This is substantially lower than that used for intracellular electro-manipulation which is about 10,000 V/cm, see U.S. application 2002/0010491 published Jan. 24, 2002.

The voltage expressed above is the voltage gradient (voltage per centimeter). The electrodes may be different shapes and sizes and be positioned at different distances from each other. The shape may be circular, oval, square, rectangular or irregular etc. The distance of one electrode to another may be 0.5 to 10 cm, 1 to 5 cm, or 2-3 cm. The electrode may have a surface area of 0.1-5 sq. cm or 1-2 sq. cm.

The size, shape and distances of the electrodes can vary and such can change the voltage and pulse duration used. Those skilled in the art will adjust the parameters in accordance with this disclosure to obtain the desired degree of electroporation and avoid thermal damage to surrounding cells.

Additional features of protocols for electroporation therapy are provided in U.S. Patent Application Publication No. US 2007/0043345 A1, the disclosure of which is hereby incorporated by reference in its entirety.

In one aspect, the systems and methods may have the capability for estimating a volume of tissue that will be heated at or above a cutoff value and a volume of tissue that will receive an electric field at or above a cutoff value for the above medical treatment device. The cut-off values may be user-specified values determined by a treating physician or technician. The systems and methods are provided so that the treating physician may recognize treatments that produce overheating in the vicinity of the electrodes of the treatment device. This additional capability of the treatment device may be based on the Joule heating equations of Example 8. The values may be plotted as contour lines which may be displayed with a graphical representation of the estimated treatment volume above. In one embodiment, the contour lines are Cassini oval approximations performed according to the equations and procedure in Example 7.

In another aspect, the systems and methods may have the additional capability for providing the electric field distributions using different configurations of bipolar probes and include the dynamic change in electrical conductivity from the baseline non-electroporated tissue. The systems and methods may allow a user to incorporate tissue-specific values for the dynamic change in conductivity in estimating a treatment volume. This additional capability is further described in Example 9. In one embodiment, the contour lines are Cassini oval approximations performed according to the equations and procedure in Example 7.

In another aspect, the systems and methods may have the additional capability for inputting or adjusting one or more variables related to the dynamic conductivity so that tissue-specific behavior can be accounted for when estimating a treatment volume. In embodiments, the treatment planning module may provide input for parameters such as the baseline conductivity, change in conductivity, the transition zone (how rapidly the conductivity increases), the electric field at which the change in conductivity occurs, and the electric field at which irreversible electroporation occurs. These parameters may allow the treating physician to fine-tune the ablation zone based on the conductivity characteristics of the target tissue. The present inventors have recognized that the conductivity characteristics of the tissue, such as baseline and maximum conductivities, should be determined before the therapy in order to determine safe and effective pulse protocols. This additional capability is further described in Example 10.

The numerical models and algorithms of the invention, as provided in the Examples, such as Cassini Oval equations of Example 7 and the Joule Heating Model equations of Example 8, can be implemented in a system for estimating a 3-dimensional treatment volume for a medical treatment device that applies treatment energy through one or more or a plurality of electrodes defining a treatment area. In one embodiment, the numerical models and algorithms are implemented in an appropriate computer readable code as part of the treatment planning module 54 of the system of the invention. Computing languages available to the skilled artisan for programming the treatment planning module 54 include general purpose computing languages such as the C and related languages, and statistical programming languages such as the "S" family of languages, including R and S-Plus. The computer readable code may be stored in a memory 44 of the system of the invention. A processor 46 is coupled to the memory 44 and a display device 11 and the treatment planning module 54 stored in the memory 44 is executable by the processor 46. Treatment planning module 54, through the implemented numerical models, is adapted to generate a graphical display of an estimated temperature or electric field or target ablation zone in the display device 11.

In one embodiment, the invention provides for a system for estimating and graphically displaying a thermal and/or electric field value for a medical treatment device that applies treatment energy through one or more or a plurality of electrodes 22 defining a treatment area, the system comprising a memory 44, a display device 11, a processor 46 coupled to the memory 44 and the display device 11, and a treatment planning module 54 stored in the memory 44 and executable by the processor 46, the treatment planning module 54 adapted to generate one or more isocontours representing a value of a temperature and/or electric field for display in the display device 11 based on modeling of the temperature distributions or electrical field distributions according to one or more parameters defining an electrical energy based protocol (e.g., irreversible electroporation). The results of modeling the temperature distributions and electrical field distributions may be stored in a database or calculated in real-time. The treatment planning module may generate the isocontours based on the modeling results.

In another embodiment, the invention provides for a system for estimating a target ablation zone for a medical treatment device that applies treatment energy through one or more or a plurality of electrodes 22 defining a treatment area, the system comprising a memory 44, a display device 11, a processor 46 coupled to the memory 44 and the display device 11, and a treatment planning module 54 stored in the memory 44 and executable by the processor 46, the treatment planning module 54 adapted to generate a target ablation zone in the display device 11 based on a combination of one or more parameters for a treatment protocol for irreversible electroporation and one or more tissue-specific conductivity parameters.

The foregoing description provides additional instructions and algorithms for a computer programmer to implement in computer readable code a treatment planning module 54 that may be executable through a processor 46 to generate an estimated temperature or electrical field for display in the display device 11 based on modeling of a tissue according to one or more parameters for electroporation, such as IRE. The computer readable code may also estimate a temperature value and an electric field value according to equations described in Example 8 and graphically display these value as contour lines in the display device. In one embodiment, the contour lines are Cassini oval approximations performed according to the equations and procedure in Example 7. The computer readable code may also provide for input on one or more conductivity parameters for estimating the target ablation zone as described in Examples 9 and 10.

Figure 4:
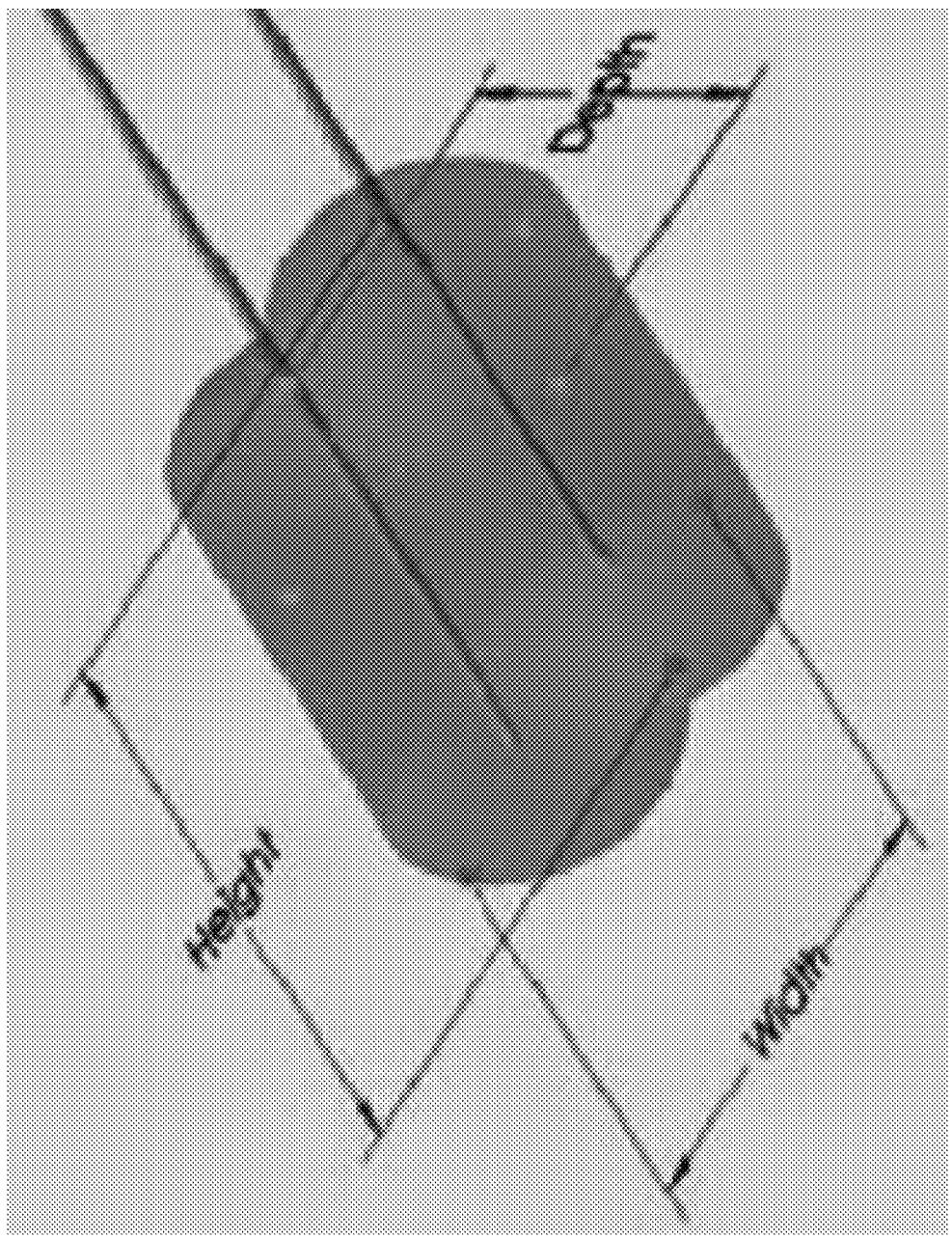
FIG. 4 is a schematic diagram showing IRE zones of ablation nomenclature (see E. Ben-David, et al., "Characterization of Irreversible Electroporation Ablation in In Vivo Porcine Liver," Am J Roentgenol, vol. 198, pp. W62-W68, January 2012).
Figures 16A, 16B:
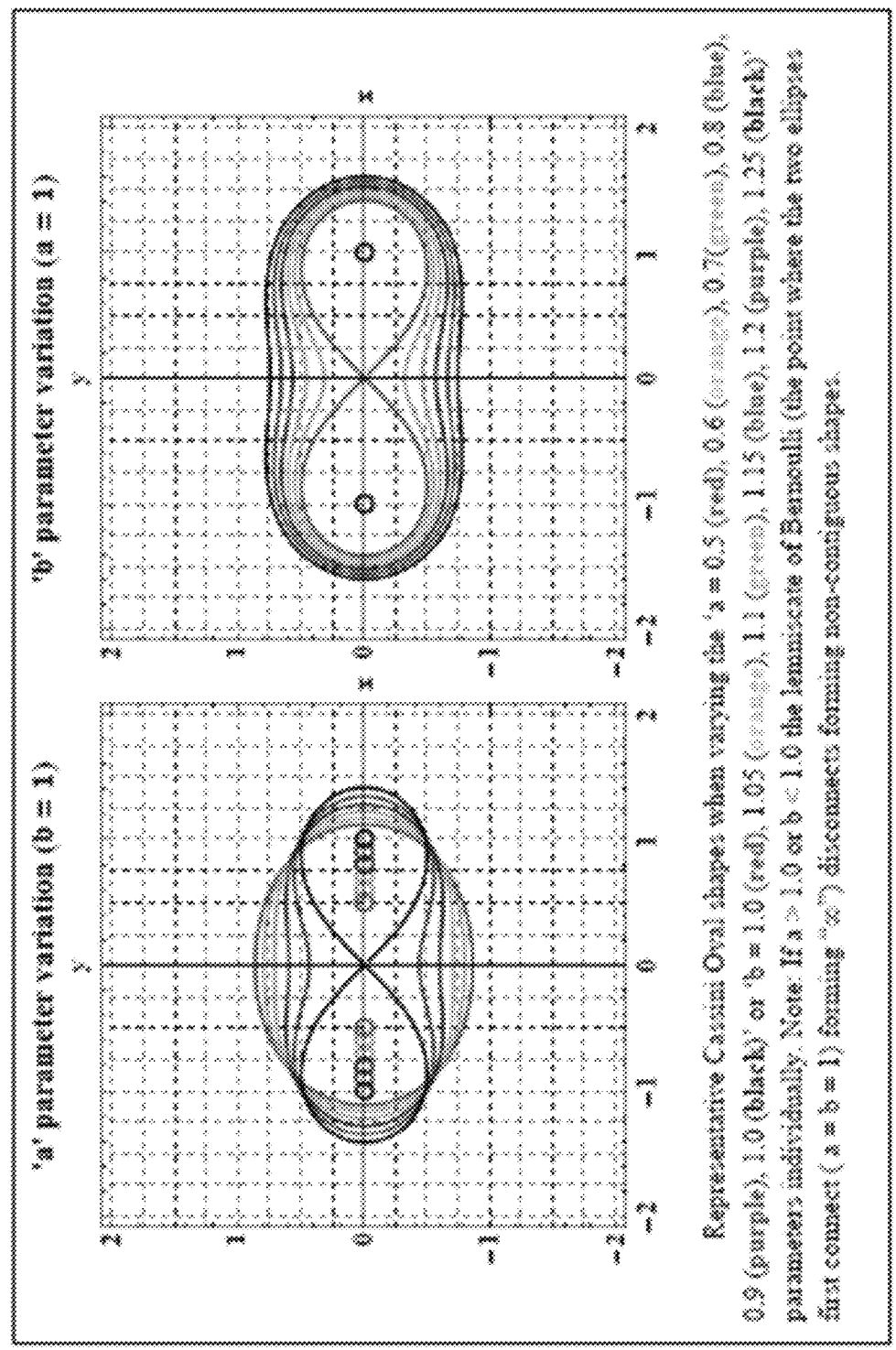
FIGS. 16A and 16B are representative Cassini Oval shapes when varying the 'a=0.5 (red), 0.6 (orange), 0.7 (green), 0.8 (blue), 0.9 (purple), 1.0 (black)' or 'b=1.0 (red), 1.05 (orange), 1.1 (green), 1.15 (blue), 1.2 (purple), 1.25 (black)' parameters individually. Note: If a>1.0 or b<1.0 the lemniscate of Bernoulli (the point where the two ellipses first connect (a=b=1) forming "∞") disconnects forming non-contiguous shapes.

FIG. 4 is a schematic diagram showing a three-dimensional zone of ablation occurring during irreversible electroporation. The width and depth of this zone of ablation may be modeled two-dimensionally using the Cassini oval equation. Further, the mathematical fit of the zone of ablation has similar shape characteristics as the actual and simulated electric field and temperature values. For example, a typical single bi-polar probe will be configured to have a first and second electrode spaced apart from each other at the distal end of the single probe. Since the lesion formed by this bi-polar arrangement closely resembles the 8-like shape of the electric field, the method of the invention can be used to accurately predict the electric field and temperature contours. FIGS. 16A and 16B show variations of 'a' and 'b' parameters that will closely resemble the 8-like shape of the electric field according to the Cassini Equation.

The method of the invention fits data extracted from numerical simulations to both the 'a' and 'b' parameters from the Cassini Equation, providing the flexibility to match potentially any shape of electric field created by the specific pulse parameters employed. Also, as illustrated in FIGS. 16A and 16B since the 'a' or 'b' parameters are not related to the separation distance or geometry of the electrodes, the electric field and temperature contours of the bi-polar probe can be captured according to the techniques described above.

Additionally, by adding the cumulative effects of electrode pairs, the electric field and thermal contours of alternative multi-electrode arrangements of three or more probes can be determined. For example, a four single probe electrode box can be captured by calculating treatment regions based on each combination of electrode pairs for the fit according to the techniques described above. Thus, for example, if the four probe electrode box is configured for treatment using pulses that cycle through probe combinations 1-2, 3-4, 1-3, 2-4, 2-3 and 1-4 the approximation tool can find electric field and temperature contours for each probe combination, then superimpose the results to display the cumulative effect of that particular pulse protocol in the treatment region.

In one embodiment, the treatment planning module 54 provides for a method for modeling and graphical display of tissue heating according to a set of parameters defining a treatment protocol. In a specific embodiment, the set of parameters correspond to a treatment protocol for inducing irreversible electroporation in a tissue.

The treatment planning module 54 may provide one or more parameters of a treatment protocol for delivering one or more electrical pulses to a tissue through one or more or a plurality of electrodes.

The treatment planning module 54 may model a heat distribution in a tissue surrounding the one or more or the plurality of electrodes based on the one or more parameters.

The treatment planning module 54 may provide a graphical representation of the heat distribution based on the modeled heat distribution.

The treatment planning module 54 may allow a user to optionally modify one or more of the parameters of the treatment protocol through input devices 12, 14 based on the graphical representation of the heat distribution.

The treatment planning module 54 may be in operable connection with a controller 71 capable of delivering one or more electrical pulses to the tissue based on the one or more parameters stored in the treatment planning module 54.

The treatment planning module 54 may model the heat distribution in the tissue based on the Joule heating in the tissue.

The treatment planning module 54 may calculate the heat distribution as:

$$\rho C_p \frac{\partial T}{\partial t} = \nabla \cdot (k \nabla T) + Q_{jh} \left[ \frac{W}{m^3} \right]$$

where $\rho$ is the density, $C_p$ is the heat capacity, k is the thermal conductivity, and $Q_{jh}$ are the resistive losses $$Q_{jh} = J \cdot E \left[ \frac{W}{m^3} \right]$$

where J is the induced current density $$J = \sigma E \left[ \frac{A}{m^2} \right]$$

and $\sigma$ is the tissue conductivity and E is the electric field $$E = -\nabla \phi \left[ \frac{V}{m} \right]$$

The treatment planning module may further calculate the resistive losses as $jh.Qrh=((jh.Jix+jh.Jex)*duty\_cycly*jh.Ex+(jh.Jiy+$
$jh.Jey)*duty\_cycle*jh.Ey+(jh.Jiz+jh.Jez)$
$*duty\_cycle*jh.Ez)*(t<=90)+0*(t>90)$ according to the Joule Heating Model described in Example 8.

The treatment planning module 54 may allow a user to specify a heat distribution value (i.e. temperature) and may provide a graphical representation of the temperature as an isocontour line.

The treatment planning module 54 may model an electric field distribution in a tissue surrounding the one or more or a plurality of electrodes based on the one or more parameters of the treatment protocol.

The treatment planning module 54 may provide a graphical representation of the electric field distribution based on the modeled electrical field distribution.

The treatment planning module may calculate the electric field distribution as:

$$\nabla^2 \phi = 0$$

where $\phi$ is the electric potential, this equation is solved with boundary conditions:

$\vec{n} \cdot \vec{J} = 0$ at the boundaries
$\phi = V_{in}$ at the boundary of the first electrode
$\phi = 0$ at the boundary of the second electrode wherein $\vec{n}$ is the normal vector to the surface, $\vec{J}$ is the electrical current and $V_{in}$ is the electrical potential applied.

The treatment planning module 54 may allow a user to specify a value for an electrical field distribution and provide a graphical representation of the electrical field distribution value as an isocontour line.

The treatment planning module 54 may display isocontour lines representing the heat and electrical field distributions by calculating a Cassini oval according to Example 7. The Cassini oval may be calculated by first modeling the temperature and electrical field distributions, storing the values in a database, and then calculating the specific Cassini oval based on parameters chosen by the user.

The treatment planning module 54 may allow a user to specify the one or more parameters of a treatment protocol including voltage, gap between electrodes, duration, pulse width, and electric field intensity.

Alternatively, or in addition, the treatment planning module 54 may allow a user to input one or more of the tissue-specific conductivity parameters described herein and model the electric field distribution and tissue heating. The treatment planning module 54 may then provide graphical representations of one or more values of the electrical field intensity and tissue temperature.

The treatment planning module 54 may provide a graphical representation of an electrical field distribution and a heat distribution through a variety of modes of operation. First, the treatment planning module 54 may model the electrical field distribution and heat distribution for each set of parameters that are entered through input devices 12, 14. Thus, every time the treating physician altered one or more parameters of the treatment protocol, the treatment planning module 54 software would model the electrical field and heat distributions according to those parameters and then graphically display them on the display device 11. In a second approach, the software would first run the modeling of the heat and electrical field distributions for a wide range of parameter combinations and store the resulting distributions in the database stored in memory 44. In this approach, when the treating physician enters a particular combination of parameters, the treatment planning module 54 retrieves the heat distribution and electrical field distribution from values stored in the database. These values are then used as a basis for Cassini oval calculations to determine specific contours for the particular combination of parameters. The Cassini oval calculations are performed according to the equations and procedure described in Example 7. The Cassini ovals are then graphically displayed on the display device 11 in real time. In embodiments, specific contours are provided according to values for temperature or electrical field intensity set by the user.

The treatment planning module 54 may model the heat and electric field distributions according to mathematical formulas. In a specific embodiment, the treatment planning module 54 may model the heat distribution and the electrical field distribution according to the formulas in Example 8.

In another embodiment, the invention provides a system for treating a tissue, which system applies electrical treatment energy through one or more or a plurality of electrodes defining a target treatment area of the tissue. The system comprises a computer 40 comprising: a memory 44, a display device 11, a processor 46 coupled to the memory 44 and the display device 11; and a treatment planning module 54 stored in the memory 44 and executable by the processor 46. In this embodiment, the treatment planning module 54 is adapted to: provide one or more parameters of a treatment protocol for delivering one or more electrical pulses to a tissue through one or more or a plurality of electrodes; model a heat distribution in a tissue surrounding the at least electrode based on the one or more parameters; provide a graphical representation of the heat distribution on the display device 11 based on the modeled heat distribution. The system further comprises input devices 12, 14 in operable connection with computer 40, which input devices are capable of modifying the one or more parameters of the treatment protocol in the treatment planning module 54. The system further comprises a generator 10 in operable connection with the computer through a controller 71, which controller 71 is capable of instructing the generator 10 to deliver the one or more electrical pulses to the target tissue through the one or more or the plurality of electrodes 22 based on the one or more parameters of the treatment protocol stored in the treatment planning module 54. The system may further comprise one or more databases stored in the memory 44 for storing the modeled heat distributions or modeled electric field distributions for a plurality of sets of parameters for a treatment protocol.

In another embodiment, the treatment planning module 54, in addition to providing one or more parameters of a treatment protocol for delivering one or more electrical pulses to a tissue through one or more or a plurality of electrodes, may also provide one or more conductivity parameters specific for the tissue to be treated.

The treatment planning module 54 may estimate the target ablation zone based on the one or more parameters of the treatment protocol and the one or more electrical flow characteristics. The treatment planning module may also display a graphical representation of the estimation in the display device 11.

The treatment planning module 54 may optionally allow for modification of one or more of the parameters of the treatment protocol through input devices 12, 14 based on the graphical representation of the target ablation zone.

Additionally, the treatment planning module 54 may be in operable communication with a controller 77 and provide one or more parameters to the controller for delivering one or more electrical pulses to the tissue.

The treatment planning module 54 may provide one or more parameters of a treatment protocol comprise voltage, gap between electrodes, duration, pulse width, and electric field intensity.

Additionally, the one or more conductivity parameters provided by the treatment planning module 54 may comprise the baseline conductivity of the tissue to be treated, the ratio of the baseline conductivity to the maximum conductivity of the tissue that is reached during treatment, the rate at which the conductivity increases from the baseline to the maximum conductivity, or the electric field at which the conductivity changes during treatment.

Additionally, one or more conductivity parameters for a plurality of tissues may be provided in a database stored in memory 44.

In another embodiment, the invention provides a system for treating a tissue, which system applies electrical treatment energy through one or more or a plurality of electrodes 22 defining a target treatment area of the tissue. The system may comprise a computer 40 comprising a memory 44, a display device 11, a processor 46 coupled to memory 44 and the display device 11, and a treatment planning module 54 stored in the memory 44 and executable by the processor 46. The treatment planning module 54 may be adapted to provide one or more parameters of a treatment protocol for delivering one or more electrical pulses to a tissue through one or more or a plurality of electrodes, provide one or more conductivity parameters specific for the tissue to be treated, estimate the target ablation zone and display a graphical representation of the estimation in the display device based on the one or more parameters of the treatment protocol and the one or more conductivity parameters. The system may further comprise input devices 12, 14 in operable connection with the computer 40, which input devices 12, 14 are capable of allowing a user to modify the one or more parameters of the treatment protocol in the treatment planning module 54. The system may further comprise a generator 10 in operable connection with the computer 40 through a controller 71, which controller 71 is capable of instructing the generator 10 to deliver the one or more electrical pulses to a tissue through the one or more or the plurality of electrodes 22 based on the one or more parameters of the treatment protocol stored in the treatment planning module 54. Additionally, the system may comprise a database of conductivity parameters for a plurality of tissues stored in the memory 44.

The systems of the invention may be further configured to include software for displaying a Graphical User Interface in the display device with various screens for input and display of information, including those for inputting various parameters or display of graphical representations of zones of temperature, electrical field, and ablation. Additionally, the Graphical User Interface (GUI) may allow a user to input one or more values related to an irreversible electroporation protocol and tissue-specific conductivity measurements through the use of text fields, check boxes, pull-downs, sliders, command buttons, tabs, and the like.

In one embodiment, the invention provides a method of treating a tissue with a medical treatment device that applies electrical treatment energy through one or more or a plurality of electrodes defining a target treatment area of the tissue and that comprises a display device. The method may comprise providing one or more parameters of a treatment protocol for delivering one or more electrical pulses to a tissue through one or more or a plurality of electrodes, modeling a heat distribution in a tissue surrounding the at least electrode based on the one or more parameters, displaying a graphical representation of the heat distribution based on the modeled heat distribution in the display device, modifying one or more of the parameters of the treatment protocol based on the graphical representation of the heat distribution, and implanting one or a plurality of electrodes in the tissue and delivering one or more electrical pulses to the tissue through the electrodes based on the one or more modified parameters.

In an exemplary implementation of the method, a treating physician identifies a target treatment area in a tissue of a patient. For example, the target treatment area may be a tumor that is unresectable by conventional surgical methods. The treating physician then uses input devices 12, 14 such as a keyboard or mouse to interact with the treatment planning module 54 to select and input one or more parameters for designing an irreversible electroporation treatment protocol for ablating the tumor. The treating physician then selects a temperature value to graphically display a temperature contour profile in the target treatment area on the display device 11. For example, the treating physician may select a value of 50° C. The treating physician then may correlate this temperature contour with imaging from the treatment area, by overlaying the temperature contour with the imaging on the display device 11. By visualizing the temperature contour relative to the imaging, the treating physician then may identify structures surrounding the treatment area such as nerves and blood vessels that may be subject to thermal damage. The treating physician then may modify the irreversible electroporation parameters so that the temperature contour no longer indicates that critical structures may be subject to overheating. Irreversible electroporation parameters that may be modified include the voltage, distance between electrodes, electrode diameter, period of treatment, pulse width, number of pulses, and electric field. Similarly, the treatment planning module 54 may allow the treating physician to visualize a temperature contour relative to an electric field contour. Through one or more iterations of adjustment of the irreversible electroporation parameters and visualization of the temperature contour and electric field contour on the display device, the treating physician may ultimately select a final set of irreversible electroporation parameters to be used for treatment. The treating physician may then implant a pair of electrodes at the target treatment area in the tissue and deliver a plurality of electrical pulses to the treatment area based on the final set of irreversible electroporation parameters.

Thus, one embodiment of the method may comprise one or more of: 1. identifying a target treatment area in a tissue of a patient; 2. selecting and inputting one or more parameters for designing an irreversible electroporation treatment protocol for the target treatment area; 3. selecting a temperature value to graphically display a temperature contour in a simulation of the target treatment area; 4. correlating the temperature contour with imaging from the treatment area; 5. Identifying structures within or surrounding the target treatment area such as nerves and blood vessels that may be subject to thermal damage based on the temperature contour; 6. modifying the irreversible electroporation parameters through one or more iterations so that the temperature contour no longer indicates that critical structures may be subject to overheating; 7. selecting a final set of irreversible electroporation parameters to be used for treatment; and 8. implanting a pair of electrodes at the target treatment area in the tissue and delivering a plurality of electrical pulses to the treatment area based on the final set of irreversible electroporation parameters.

The target treatment area may be imaged through a variety of imaging modalities including Computed Tomography (CT), Magnetic Resonance Imaging (MRI), Ultrasound, Positron Emission Tomography (PET), and the like. The imaging devices may be operably connected with the display device 11 so that results of the imaging may overlap or otherwise be available for comparison with the graphical display of the temperature and electric field contours.

In another embodiment, the invention provides a method of treating a tissue with a medical treatment device that applies electrical treatment energy through one or more or a plurality of electrodes defining a target treatment area of the tissue, which medical treatment device comprises a display device. The method may comprise providing one or more parameters of a treatment protocol for delivering one or more electrical pulses to a tissue through one or a plurality of electrodes, and one or more conductivity parameters specific for the tissue to be treated, estimating the target ablation zone and displaying a graphical representation of the estimation in the display device based on the one or more parameters of the treatment protocol and the one or more conductivity parameters, modifying one or more of the parameters of the treatment protocol based on the graphical representation of the target ablation zone, and implanting one or a plurality of electrodes in the tissue and delivering one or more electrical pulses to the tissue through the electrodes based on the one or more modified parameters. In the context of this specification, when referring to implanting an electrode, one or more of the electrode(s) can alternatively or in addition be placed near, or contact, or otherwise be operably disposed in a manner to administer electrical energy to the tissue.

In an exemplary implementation of the method, a treating physician identifies a target treatment area in a tissue of a patient. For example, the target treatment area may be a tumor that is unresectable by conventional surgical methods. The treating physician then uses input devices 12, 14 such as a keyboard or mouse to interact with the treatment planning module 54 to select and input one or more parameters for designing an irreversible electroporation treatment protocol for ablating the tumor. The treatment planning module 54 then graphically displays an ablation zone on the display device 11 based on the one or more parameters of the irreversible electroporation treatment protocol. The treating physician then selects one or more conductivity parameters based on the type of tissue to be treated. The one or more conductivity parameters may be tissue-specific values based on experimental data that is stored in a database in memory 44 or may be obtained by the physician and entered into the treatment planning module 54 using the keyboard or other input, such as a hands-free input. In embodiments, tissue-specific conductivity values may be provided for heart, kidney, liver, lung, spleen, pancreas, brain, prostrate, breast, small intestine, large intestine, and stomach.

The one or more conductivity parameters may include the baseline conductivity, change in conductivity, the transition zone (how rapidly the conductivity increases), the electric field at which the change in conductivity occurs, and the electric field at which irreversible electroporation occurs. After selecting the one or more conductivity parameters, the treatment planning module 54 may display a modified ablation zone on the display device 11 based on the tissue-specific conductivity characteristics inputted by the physician. The treating physician then may alter the one or more parameters of the irreversible electroporation protocol to modify the target ablation zone on the display device 11 to fit a desired area of treatment. The treating physician may then strategically place (e.g., implant) a pair of electrodes at the target treatment area in the tissue and deliver a plurality of electrical pulses to the treatment area based on the final set of irreversible electroporation parameters.

Thus, one embodiment of the method may comprise one or more of: 1. identifying a target treatment area in a tissue of a patient; 2. selecting and inputting one or more parameters for designing an irreversible electroporation treatment protocol for the target treatment area; 3. displaying a graphical representation of a target ablation zone on a display device; 4. selecting and inputting one or more conductivity characteristics based on the specific tissue to be treated; 5. displaying a modified graphical representation of the target ablation zone based on the tissue-specific conductivity characteristics; 6. modifying the one or more parameters of the irreversible electroporation protocol to fit a desired area of treatment; and 7. disposing/implanting a pair of electrodes at the target treatment area in the tissue and delivering a plurality of electrical pulses to the treatment area based on the modified IRE parameters.

As will be apparent to a skilled artisan, the systems and methods described above may be compatible with a variety of bi-polar and mono-polar probe combinations and configurations. Additionally, the calculations may be extended to not only display an electric field and temperature but also using that information to calculate an electrical damage and thermal damage component which take into account the time of exposure to the electric field and temperatures and can be tissue-specific such as for liver, kidney, etc. The systems and methods may be capable of displaying information such as "electric damage" or "thermal damage" once the electric field and temperature contours are determined, based on predetermined values for electric damage and thermal damage in the given tissue type. "Electric damage" and "thermal damage" regions can be visualized in place of or in combination with electric field and temperature as isocontour lines, shaded or highlighted areas, or other forms of graphical representation. In addition, the inclusion of tissue-specific in-vivo derived data including blood flow, metabolic heat generation, and one or more conductivity parameters such as tissue conductivity and ratios of changing conductivity can be included to reflect dynamic changes within a specific tissue type.

Additional details of the algorithms and numerical models disclosed herein will be provided in the following Examples, which are intended to further illustrate rather than limit the invention.

In Example 1, the present inventors provide a numerical model that uses an asymmetrical Gompertz function to describe the response of porcine renal tissue to electroporation pulses. However, other functions could be used to represent the electrical response of tissue under exposure to pulsed electric fields such as a sigmoid function, ramp, and/or interpolation table. This model can be used to determine baseline conductivity of tissue based on any combination of electrode exposure length, separation distance, and non-electroporating electric pulses. In addition, the model can be scaled to the baseline conductivity and used to determine the maximum electric conductivity after the electroporation-based treatment. By determining the ratio of conductivities pre- and post-treatment, it is possible to predict the shape of the electric field distribution and thus the treatment volume based on electrical measurements. An advantage of this numerical model is that it is easy to implement in computer software code in the system of the invention and no additional electronics or numerical simulations are needed to determine the electric conductivities.

The system and method of the invention can also be adapted for other electrode geometries (sharp electrodes, bipolar probes), electrode diameter, and other tissues/tumors once their response to different electric fields has been fully characterized.

The present inventors provide further details of this numerical modeling as well as experiments that confirm this numerical modeling in Example 2. In developing this work, the present inventors were motivated to develop an IRE treatment planning method and system that accounts for real-time voltage/current measurements. As a result of this work, the system and method of the invention requires no electronics or electrodes in addition to the NANOKNIFE® System, a commercial embodiment of a system for electroporation-based therapies. The work shown in Example 2 is based on parametric study using blunt tip electrodes, but can be customized to any other geometry (sharp, plate, bipolar). The numerical modeling in Example 2 provides the ability to determine a baseline tissue conductivity based on a low voltage pre-IRE pulse (non-electroporating ~50 V/cm), as well as the maximum tissue conductivity based on high voltage IRE pulses (during electroporation) and low voltage post-IRE pulse (non-electroporating ~50 V/cm). Two numerical models were developed that examined 720 or 1440 parameter combinations. Results on IRE lesion were based on in vitro measurements. A major finding of the modeling in Example 2 is that the electric field distribution depends on conductivity ratio pre- and post-IRE. Experimental and clinical IRE studies may be used to determine this ratio. As a result, one can determine e-field thresholds for tissue and tumor based on measurements. The 3-D model of Example 2 captures depth, width, and height e-field distributions.

In Example 3, as a further extension of the inventors work, the inventors show prediction of IRE treatment volume based on 1000 V/cm, 750 v/cm, and 500 V/cm IRE thresholds as well as other factors as a representative case of the numerical modeling of the invention.

In Example 4, the inventors describe features of the Specific Conductivity and procedures for implementing it in the invention.

In Example 5, the inventors describe in vivo experiments as a reduction to practice of the invention.

In Example 6, the inventors describe how to use the ratio of maximum conductivity to baseline conductivity in modifying the electric field distribution and thus the Cassini oval equation.

In Example 7, the inventors describe the Cassini oval equation and its implementation in the invention.

In Example 8, the inventors describe mapping of electric field and thermal contours using a simplified data cross-referencing approach.

In Example 9, the inventors describe visualization of electric field distributions using different configurations of bipolar probes.

In Example 10, the inventors describe a method for determining the IRE threshold for different tissues according to one or more conductivity parameters.

In Example 11, the inventors describe correlating experimental and numerical IRE lesions using the bipolar probe.

EXAMPLES

Example 1

Materials And Methods

The tissue was modeled as a 10-cm diameter spherical domain using a finite element package (Comsol 4.2a, Stockholm, Sweden). Electrodes were modeled as two 1.0-mm diameter blunt tip needles with exposure lengths (Y) and edge-to-edge separation distances (X) given in Table 1. The electrode domains were subtracted from the tissue domain, effectively modeling the electrodes as boundary conditions.

TABLE 1

Electrode configuration and relevant electroporation-based treatment values used in study.

| | PARAMETER VALUES | MEAN |
|---|---|---|
| W [V/cm] | 500, 1000, 1500, 2000, 2500, 3000 | 1750 |
| X [cm] | 0.5, 1.0, 1.5, 2.0, 2.5 | 1.5 |
| Y [cm] | 0.5, 1.0, 1.5, 2.0, 2.5, 3.0 | 1.75 |
| Z [cm] | 1.0, 1.25, 1.5, 2.0, 3.0, 4.0, 5.0, 6.0 | 2.96875 |

The electric field distribution associated with the applied pulse is given by solving the Laplace equation:

$$\nabla \cdot (\sigma(|E|)\nabla\varphi) = 0 \quad (1)$$

where $\sigma$ is the electrical conductivity of the tissue, E is the electric field in V/cm, and $\varphi$ is the electrical potential (Edd and Davalos, 2007). Boundaries along the tissue in contact with the energized electrode were defined as $\varphi = V_o$, and boundaries at the interface of the other electrode were set to ground. The applied voltages were manipulated to ensure that the voltage-to-distance ratios (IN) corresponded to those in Table 1. The remaining boundaries were treated as electrically insulating, $\partial\varphi/\partial n = 0$.

Figure 5:
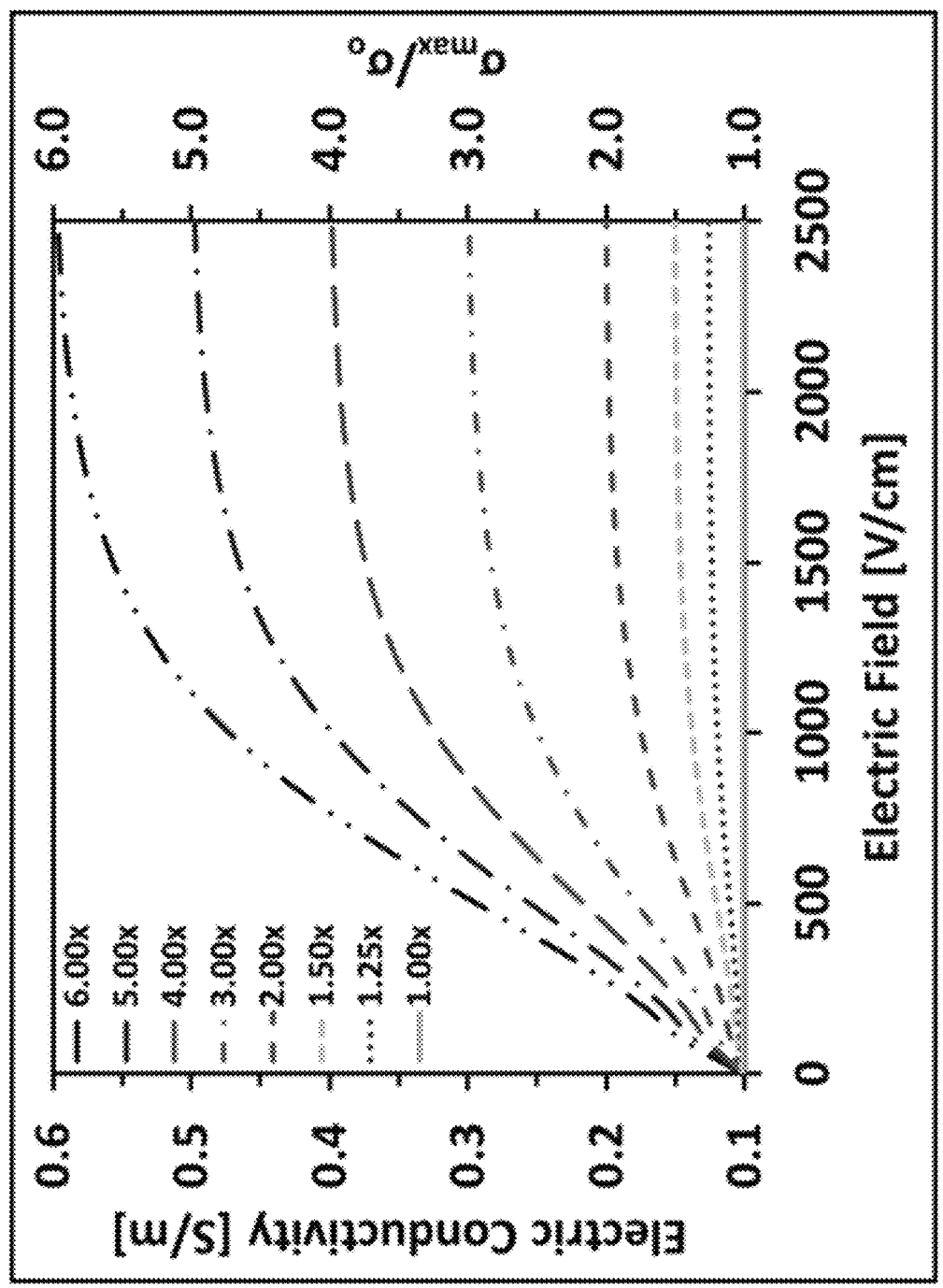
FIG. 5 is a graph of the asymmetrical Gompertz function showing tissue electric conductivity as a function of electric field.

The analyzed domain extends far enough from the area of interest (i.e. the area near the electrodes) that the electrically insulating boundaries at the edges of the domain do not significantly influence the results in the treatment zone. The physics-controlled finer mesh with ~100,000 elements was used. The numerical models have been adapted to account for a dynamic tissue conductivity that occurs as a result of electroporation, which is described by an asymmetrical Gompertz curve for renal porcine tissue (Neal et al., 2012):

$$\sigma(|E|) = \sigma_0 + (\sigma_{max} - \sigma_0)\exp[-A \cdot \exp[-B \cdot E]] \quad (2)$$

where $\sigma_o$ is the non-electroporated tissue conductivity and $\sigma_{max}$ is the maximum conductivity for thoroughly permeabilized cells, A and B are coefficients for the displacement and growth rate of the curve, respectively. Here, it is assumed that $\sigma_o = 0.1$ S/m but this value can be scaled by a factor to match any other non-electroporated tissue conductivity or material as determined by a pre-treatment pulse. In this work the effect of the ratio of maximum conductivity to baseline conductivity in the resulting electric current was examined using the 50-μs pulse parameters (A=3.05271; B=0.00233) reported by Neal et al. (Neal et. al., 2012). The asymmetrical Gompertz function showing the tissue electric conductivity as a function of electric field is, for example, shown in FIG. 5.

The current density was integrated over the surface of the ground electrode to determine the total current delivered. A regression analysis on the resulting current was performed to determine the effect of the parameters investigated and their interactions using the NonlinearModelFit function in Wolfram Mathematica 8.0. Current data from the numerical simulations were fit to a mathematical expression that accounted for all possible interactions between the parameters:

$$I = \text{factor} \cdot [aW + bX + cY + dZ + e(W-\overline{W})(X-\overline{X}) + f(W-\overline{W})(Y-\overline{Y}) + g(W-\overline{W})(Z-\overline{Z}) + h(X-\overline{X})(Y-\overline{Y}) + i(X-\overline{X})(Z-\overline{Z}) + j(Y-\overline{Y})(Z-\overline{Z}) + k(W-\overline{W})(X-\overline{X})(Y-\overline{Y}) + l(X-\overline{X})(Y-\overline{Y})(Z-\overline{Z}) + m(W-\overline{W})(Y-\overline{Y})(Z-\overline{Z}) + n(W-\overline{W})(X-\overline{X})(Z-\overline{Z}) + o(W-\overline{W})(X-\overline{X})(Y-\overline{Y})(Z-\overline{Z}) + p]$$ (3)

where I is the current in amps, W is the voltage-to-distance ratio [V/cm], X is the edge-to-edge distance [cm], Y is the exposure length [cm], and Z is the unitless ratio $\sigma_{max}/\sigma_o$. The $\overline{W}$, $\overline{X}$, $\overline{Y}$, and $\overline{Z}$ are means for each of their corresponding parameters (Table 1) and the coefficients (a, b, c, . . . , n, o, p) were determined from the regression analysis (Table 2).

Results.

A method to determine electric conductivity change following treatment based on current measurements and electrode configuration is provided. The best-fit statistical (numerical) model between the W, X, Y, and Z parameters resulted in Eqn. 3 with the coefficients in Table 2 ($R^2$=0.999646). Every coefficient and their interactions had statistical significant effects on the resulting current (P<0.0001*). With this equation one can predict the current for any combination of the W, Y, X, Z parameters studied within their ranges (500 V/cm≤W≤3000 V/cm, 0.5 cm≤X≤2.5 cm, 0.5 cm≤Y≤3.0 cm, and 1.0≤Z≤6.0). Additionally, by using the linear results (Z=1), the baseline tissue conductivity can be extrapolated for any blunt-tip electrode configuration by delivering and measuring the current of a non-electroporating pre-treatment pulse. The techniques described in this specification could also be used to determine the conductivity of other materials, such as non-biological materials, or phantoms.

TABLE 2

Coefficients (P < 0.0001*) from the Least Square analysis using the NonlinearModelFit function in Mathematica.

| | ESTIMATE |
|---|---|
| a → | 0.00820 |
| b → | 7.18533 |
| c → | 5.80997 |
| d → | 3.73939 |
| e → | 0.00459 |
| f → | 0.00390 |
| g → | 0.00271 |
| h → | 3.05537 |
| i → | 2.18763 |
| j → | 1.73269 |
| k → | 0.00201 |
| l → | 0.92272 |
| m → | 0.00129 |
| n → | 0.00152 |
| o → | 0.00067 |
| p → | −33.92640 |

Figure 6:
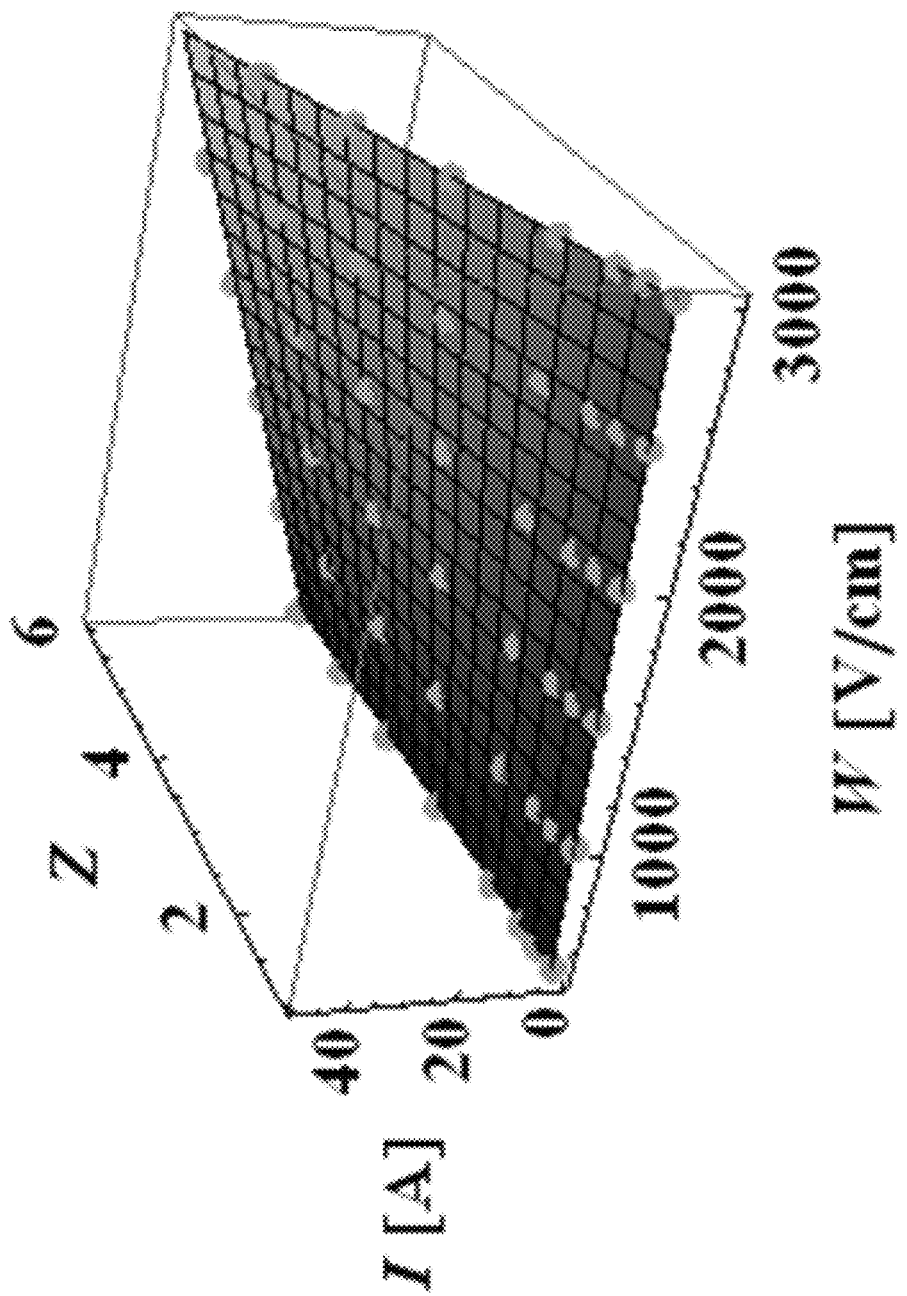
FIG. 6 is a graph showing a representative 3D plot of current [A] as a function of Z ($\sigma_{max}/\sigma_o$) and voltage-to-distance ratio (W) for a separation distance of 1.5 cm and an electrode exposure length of 2.0 cm as used by Ben-David et al.

FIG. 6 shows a representative case in which the effect of the W and Z are studied for electroporation-based therapies with 2.0 cm electrodes separated by 1.5 cm. The 3D plot corroborates the quality of the model which shows every data point from the numerical simulation (green spheres) being intersected by the best-fit statistical (numerical) model. This 3D plot also shows that when Z is kept constant, the current increases linearly with the voltage-to-distance ratio (W). Similarly, the current increases linearly with Z when the voltage-to-distance ratio is constant. However, for all the other scenarios there is a non-linear response in the current that becomes more drastic with simultaneous increases in W and Z.

Figure 7B:
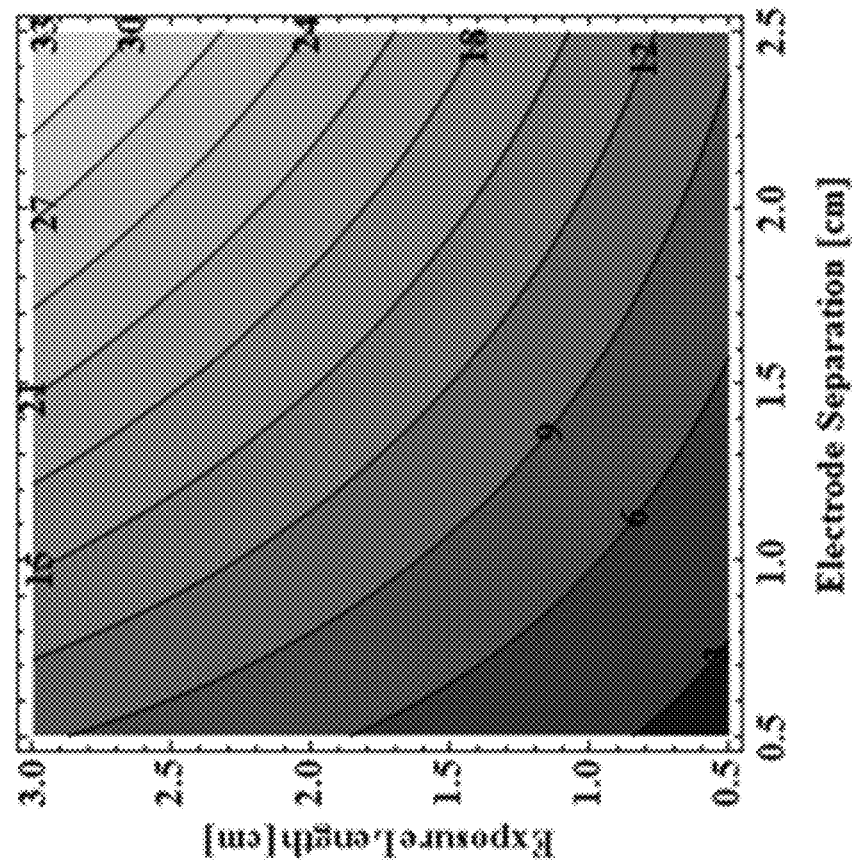
FIGS. 7A and 7B are graphs showing representative contour plots of current [A] as a function of electrode exposure and separation distance using 1500 V/cm for Z=1 (FIG. 7A) and Z=4 (FIG. 7B).
Figure 7A:
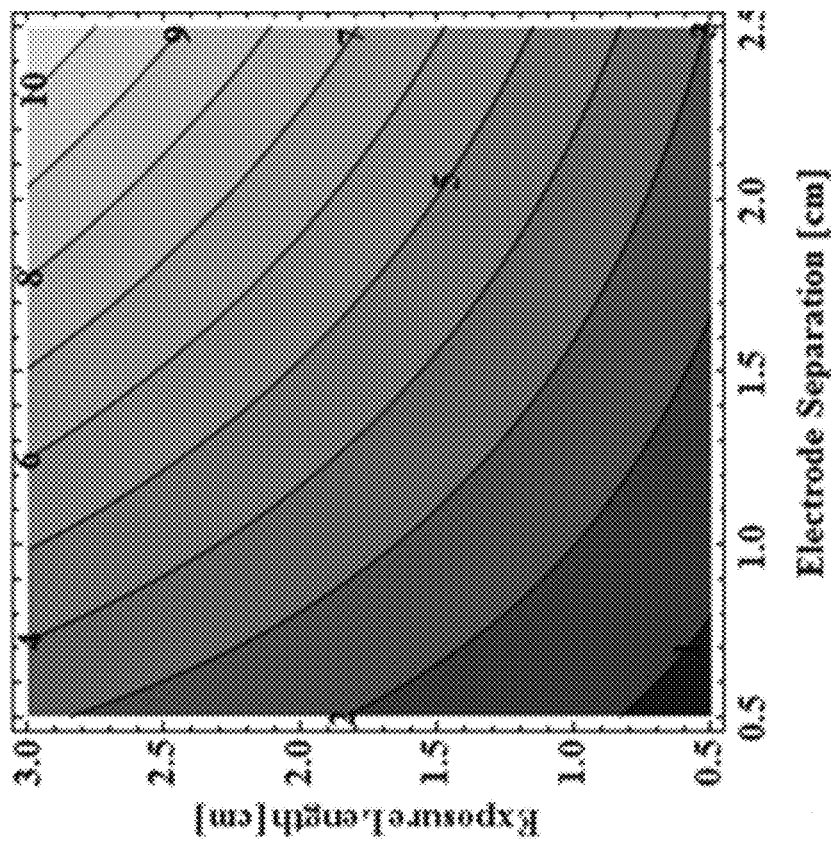

In order to fully understand the predictive capability of the statistical (numerical) model, two cases in which the current is presented as a function of the exposure length and electrode separation are provided. FIG. 7A shows the linear case (Z=1) in which the current can be scaled to predict any other combination of pulse parameters as long as the pulses do not achieve electroporation. For example, one can deliver a non-electroporation pulse (~50 V/cm) and measure current. The current can then be scaled to match one of the W values investigated in this study. By using Eqn. 3 and solving for the factor, the baseline electric conductivity of the tissue can be determined and used for treatment planning. FIG. 7B is the case in which the maximum electric conductivity was 0.4 S/m (Z=4) after electroporation. The trends are similar to the ones described in FIG. 5 in that if exposure length is constant, the current increases linearly with increasing electrode separation and vice versa. However, even though the conductivity within the treated region increases by a factor of 4, the current increases non-linearly only by a factor of 3. This can be seen by comparing the contours in FIG. 7A with those in FIG. 7B which consistently show that the curves are increased by a factor of 3.

Example 2. Determining the Relationship Between Blunt Tip Electrode Configuration and Resulting Current after IRE Treatment Model Assumptions:
Gompertz Conductivity: Pulse duration=50 μs, Ex-vivo kidney tissue
Baseline Conductivity: σ=0.1 S/m
Spherical Domain: diameter=10 cm
Applied Voltage: Voltage=1000 V
Parametric Study:
Total Combinations: 720 models
Maximum Conductivity: 1.0×, 1.25×, 1.5×, 2×, 3×, 4×, 5×, 6× the baseline
Edge-to-edge Distance: 5, 10, 15, 20, 25 mm
Electrode Exposure: 5, 10, 15, 20, 25, 30 mm
Electrode Radius: 0.5, 0.75, 1.0 mm
The output of statistical analysis software (JMP 9.0) used to fit model and determine the coefficients for all parameter combinations is shown in the tables of FIGS. 8A and 8B and the plot of FIG. 8C.

Parameters of Best Fit for Dynamic Conductivity Changes Between 1×-6× the Baseline Conductivity ($R^2$=0.96):
  a=−1.428057; (*Intercept Estimate*)
  b=−0.168944; (*Gap Estimate*)
  c=2.1250608; (*Radius Estimate*)
  d=0.2101464; (*Exposure Estimate*)
  e=1.1114726; (*Factor Estimate*)
  f=−0.115352; (*Gap–Radius Estimate*)
  g=−0.010131; (*Gap–Exposure Estimate*)
  h=−0.067208; (*Gap–Factor*)
  i=0.0822932; (*Radius–Exposure Estimate*)
  j=0.4364513; (*Radius–Factor Estimate*)
  k=0.0493234; (*Exposure–Factor Estimate*)
  l=−0.006104; (*Gap–Radius–Exposure Estimate*)
  m=0.0165237; (*Radius–Exposure–Factor Estimate*)*)
  n=−0.003861; (*Gap–Exposure–Factor Estimate*)
  o=−0.041303; (*Gap–Radius–Factor Estimate*)
  p=−0.002042; (*Gap–Radius–Exposure–Factor Estimate*)

Analytical Function for Dynamic Conductivity Changes Between 1×-6× the Baseline Conductivity ($R^2$=0.96):

5 mm<gap=x<25 mm, 0.5 mm<radius=y<1.0 mm,
5 mm<exposure=z<30 mm, 1<factor=w<6

Default conductivity of 0.1 S/m and 1000 V which can be scaled for dynamic conductivities. The function is a linear combination of all iterations examined in the parametric study:

$$\text{Current}(w,x,y,z)=a+bx+cy+dz+ew+f(x+bb)(y+cc)+g(x+bb)(z+dd)+h(x+bb)(w+e)+i(y+cc)(z+dd)+j(y+cc)(w+ee)+k(z+dd)(w+ee)+l(x+bb)(y+cc)+m(y+cc)(z+dd)(w+ee)+n(x+bb)(z+dd)(w+ee)+o(x+bb)(y+cc)(w+ee)+p(x+bb)(y+cc)(z+dd)(w+ee)$$

FIGS. 9A-9F show the representative (15 mm gap) correlation between current vs. exposure length and electrode radius for maximum conductivities (1×-6×, respectively).

FIGS. 10A and 10B are tables showing experimental validation of the code for determining the tissue/potato dynamic conductivity from in vitro measurements.

Determining the Relationship Between Blunt Tip Electrode Configuration and e-Field Distribution after IRE Treatment Model Assumptions:
Gompertz Conductivity: Pulse duration=50-µs, Ex-vivo kidney tissue
Baseline Conductivity: σ=0.1 S/m
Spherical Domain: diameter=10 cm
Electrode Radius: r=0.5 mm
Parametric Study:
Total Combinations: 1440 models
Maximum Conductivity: 1.0×, 1.25×, 1.5×, 2×, 3×, 4×, 5×, 6× the baseline
Edge-to-edge Distance: 5, 10, 15, 20, 25 mm
Electrode Exposure: 5, 10, 15, 20, 25, 30 mm
Voltage-to-distance Ratio: 500, 1000, 1500, 2000, 2500, 3000 V/cm Example 3

Comparison of analytical solutions with statistical (numerical) model to calculate current and explanation of procedure that results in 3D IRE volume.

Figure 11A:
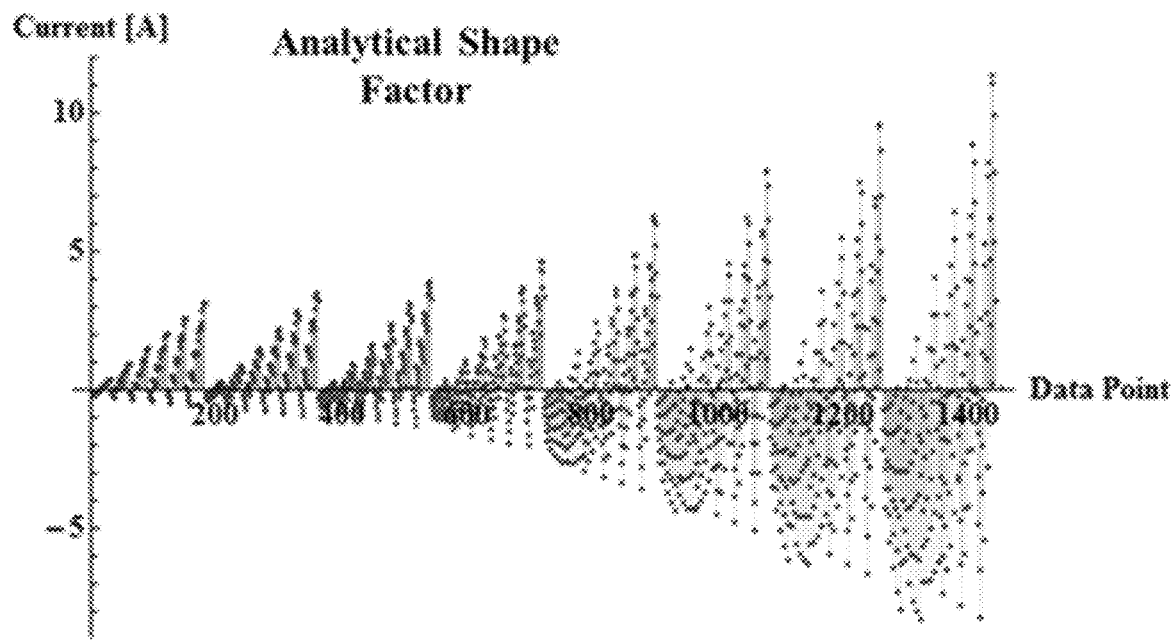
FIGS. 11A and 11B are graphs plotting residual current versus data point for analytical shape factor (FIG. 11A) and statistical (numerical) non-linear conductivity (FIG. 11B).
Figure 11B:
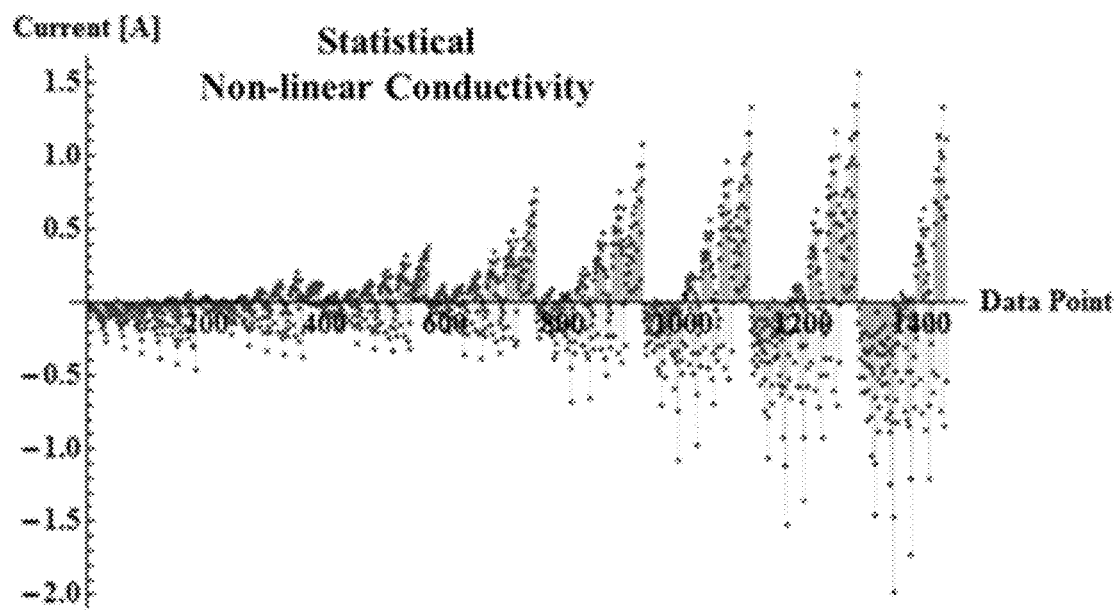

The process of backing-out the electrical conductivity using the analytical solutions and the one proposed in the "Towards a Predictive Model of Electroporation-Based Therapies using Pre-Pulse Electrical Measurements" abstract presented in the IEEE Engineering in Medicine and Biology Conference in Aug. 28, 2012 in San Diego, California were compared. A method to determine the predictive power of the equations to calculate current is analyzing the residuals of the 1440 combinations of parameters examined. In the context of this specification, a residual is the difference between the predicted current and the actual current. As can be seen in FIGS. 11A and 11B with increasing non-linear change in conductivity due to electroporation and increasing applied electric field there is an increase in the residual for both cases. The main message though is that using the shape factor (analytical) method the maximum residual is 11.3502 A and with the statistical (numerical) model the maximum is 1.55583 A. This analysis suggests that the shape factor method may be inadequate to predict the non-linear changes in current that occur during electroporation and for reliable predictions the statistical (numerical) method may be better.

In terms of the prediction of the volume treated a representative method is to map out the electric field 5 cm in the directions along the (x,0,0), (0,y,0), and (0,0,z) axes from the origin. In addition, the electric field can be extracted along a line that starts at the origin and ends at 3 cm along each of the axes. These plots contain the information for determining the distances at which a particular IRE threshold occurs. In embodiments, 1440 different parameter combinations were simulated that resulted in data sets of 28,692 (x-direction), 20,538 (y-direction), 27,306 (z-direction), and 25,116 (xyz-direction) for homogeneous conductivity. Even though these simulations only include dynamic conductivity changes due to electroporation, it is believed that an identical analysis for simulations that also include the changes in conductivity due to temperature could also be performed. In this manner, it would be possible to determine irreversible electroporation thresholds as a function of temperature and electroporation. Manipulating these large data sets is challenging but it provides all the necessary information to study the effect of electrode separation, electrode length, dynamic conductivity factor, and voltage-to-distance ratio for any position along the described paths. In order to be able to manipulate the data and extract the distance for different IRE thresholds, the function NonlinearModelFit (Mathematica) was used in order to come up with analytical expressions that would closely match the electric field. A different function was used for each of the directions studied in the positive directions along the Cartesian coordinate system. The Micheilis Menten function was used along the x-direction ($R^2$=0.978978), the analytical solution to the Laplace equation along the y-direction ($R^2$=0.993262), and the Logistic equation in the z-direction ($R^2$=0.983204). Each of those functions was scaled by a 3rd order polynomial function that enabled the fit to incorporate the electrode separation and electrode exposure as well. Even though the described functions were used to fit the data from the numerical data, there might be other functions that are also appropriate and this will be explored further in order to use the most reliable fit. In FIGS. 12A-12C provided are representative contour plots of the electric field strength at 1.0 cm from the origin using an edge-to-edge voltage-to-distance ratio of 1500 V/cm assuming a z=1 which is the case for non-electroporated electrical conductivity. It is important to note that in this case the y and z data are starting from (0, 0, 0) and the x-data starts outside the external electrode-tissue boundary. One representative case is presented, but any of the 1440 parameters combinations that were disclosed in the conference proceeding could be plotted as well.

The following functions describe the electric field [V/cm] distributions along the x-axis ($E_x$), y-axis ($E_y$), and z-axis ($E_z$) as a function of voltage-to-distance (W), edge-to-edge separation between the electrodes (X), exposure length (Y), maximum conductivity to baseline conductivity (Z), and distance in the x-direction (xx), y-direction (yy), and z-direction (zz).

Micheilis Menten Equation (Electric Field in the x-Direction)

$$E_x(W,X,Y,Z,xx)=W*(a*\text{Exp}[-b \cdot xx]+c)*(dX^3+eX^2+fX+gY^3+hY^2+iY+j)+k$$

The coefficients for the NonlinearModelFit are given below:

a=−0.447392, b=8.98279, c=−0.0156167, d=−0.0654974, e=0.468234, f=−6.17716, g=0.326307, h=−2.33953, I=5.90586, j=−4.83018, k−9.44083

Laplace Equation (Electric Field in the y-Direction)

$$E_y(W, X, Y, Z, yy) = a + (X^3 + X^2 + bX + cY^3 + dY^2 + eY + f) *$$
$$\left(h + \frac{(gWXZ)}{2} * \left(\frac{1}{\text{Log}\left[\frac{X+0.1}{0.05}\right]}\right) * \text{Abs}\left[\frac{1}{i \cdot yy - \frac{X}{2} - 0.05} - \frac{1}{i \cdot yy + \frac{X}{2} + 0.05}\right]\right)$$

The coefficients for the NonlinearModelFit are given below:
a=−56.6597, b=−42.9322, c=6.66389, d=−50.8391, e=141.263, f=138.934, g=0.00417123, h=0.184109

Logistic Equation (Electric Field in the z-Direction)

$$E_z(W, X, Y, Z, zz) =$$
$$a + \frac{bWZ}{1 + c \cdot \text{Exp}\left[d \cdot \left(\frac{2zz}{y} - e\right)\right]} \cdot (fX^3 + gX^2 + hX + i) \cdot (jY^3 + kY^2 + lY + m)$$

The coefficients for the NonlinearModelFit are given below:
a=49.0995, b=−0.00309563, c=1.39341, d=4.02546, e=1.24714, f=0.276404, g=−1.84076, h=4.93473, I=−9.13219, j=0.699588, k=−5.0242, l=12.8624, m=19.9113.

In order to visualize the predicted IRE shape the equation of an ellipsoid was used and the semi-axes were forced to intersect with the locations at which the IRE threshold wants to be examined. Therefore, the provided functions can be adjusted in real-time to display the IRE volume for any electric field threshold. This is important since different tissues have different IRE thresholds that depend on the temperature, dielectric properties of the tissue, the electrode configuration, and the pulse parameters used. Once again, even though the equation for an ellipsoid is used to represent the IRE volume, other functions may be evaluated that may also be appropriate to replicate the morphology of the zones of ablation being achieved experimentally such as the Cassini curve. A 1500 V/cm was used as the voltage-to-distance ratio, electrode exposure 2 cm, and electrode separation 1.5 cm to generate 3 different IRE zones using 1000 V/cm, 750 V/cm, and 500 V/cm as the IRE thresholds with z=1.

Figure 13A:
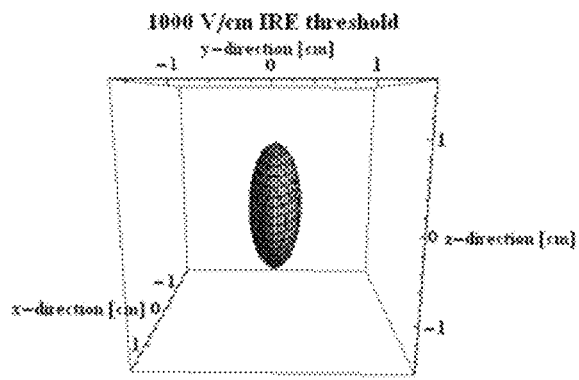
FIGS. 13A-13C are 3D plots representing zones of ablation for a 1500 V/cm ratio, electrode exposure of 2 cm, and electrode separation of 1.5 cm, at respectively a 1000 V/cm IRE threshold (FIG. 13A), 750 V/cm IRE threshold (FIG. 13B), and 500 V/cm IRE threshold (FIG. 13C) using the equation for an ellipsoid.
Figure 13B:
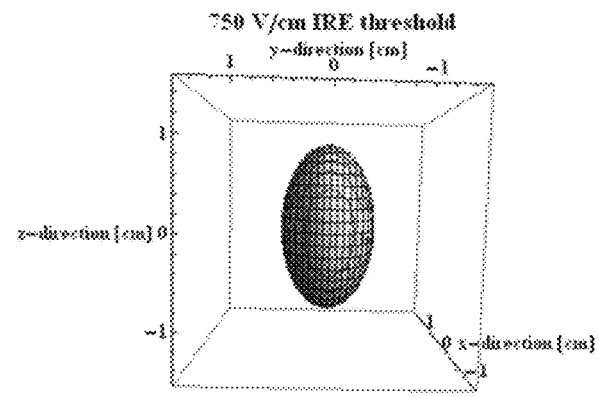
Figure 13C:
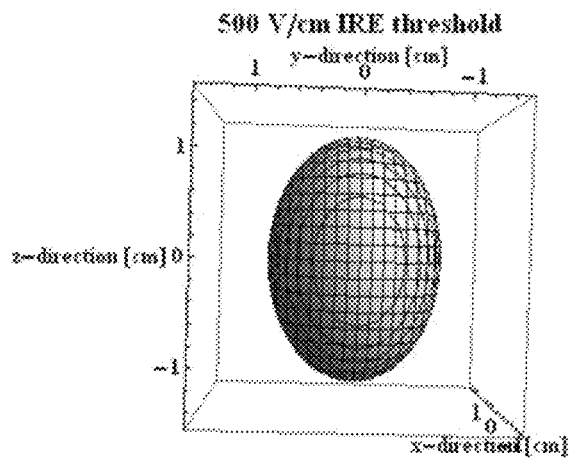

From the 3D plots representing the zones of ablation shown in FIGS. 13A-13C it can be seen that if the IRE threshold is reduced from 1000 V/cm to either 750 V/cm or 500 V/cm, the volume becomes larger. This is representative of how different tissues may have different thresholds and this code may provide the ability to simulate the fields in a broad/generic manner that can then be applied to any tissue. Incorporating the xyz-data that was extracted from the parametric study will help modify the "roundness" of the current depictions of the zone of IRE ablation in order to more realistically replicate the experimental results. However, to the best of the inventors' knowledge there is no such adaptable code currently available to provide a 3D IRE volume as a function of measured current, electrode length, electrode exposure, applied voltage-to-distance ratio, and customizable electric field threshold so it is believed that this will greatly help the medical community in planning and verifying the clinical treatments of patients being treated with the IRE technology.

Example 4

Specific Conductivity

Specific conductivity can be important in embodiments for treatment planning of irreversible electroporation (IRE). For many applications, especially when treating tumors in the brain, the volume (area) of IRE should be predicted to maximize the ablation of the tumorous tissue while minimizing the damage to surrounding healthy tissue. The specific electrical conductivity of tissue during an irreversible electroporation (IRE) procedure allows the physicians to: determine the current threshold; minimize the electric current dose; decrease the Joule heating; and reduce damage to surrounding healthy tissue. To measure the specific conductivity of tissue prior to an IRE procedure the physician typically performs one or more of the following: establishes the electrode geometry (shape factor); determines the physical dimensions of the tissue; applies a small excitation AC voltage signal (1 to 10 mV); measures the AC current response; calculates the specific conductivity ($\sigma$) using results from the prior steps. This procedure tends to not generate tissue damage (low amplitude AC signals) and will supply the physician (software) with the required information to optimize IRE treatment planning, especially in sensitive organs like the brain which is susceptible to high electrical currents and temperatures. Thus, the IRE procedure is well monitored and can also serve as a feedback system in between series of pulses and even after the treatment to evaluate the area of ablation.

Special Cases for electrode geometry
Nomenclature (units in brackets):
$V_e$=voltage on the hot electrode (the highest voltage), [V]
G=electroporation voltage gradient (required for electroporation), [V/m]
$R_1$=radius of electrode with highest voltage (inner radius), [m]
$R_2$=radius at which the outer electrodes are arranged (outer radius), [m]
i=total current, [A]
L=length of cylindrical electrode, [m]
A=area of plate electrode, [m$^2$]
$\sigma$=electrical conductivity of tissue, [S/m]
$\rho$=density
c=heat capacity Case 1

Electrical conduction between a two-cylinder (needle) arrangement of length L in an infinite medium (tissue). It is important to note that this formulation is most accurate when L≫$R_1$, $R_2$ and L≫w. The electrical conductivity can be calculated from, $$\sigma = \frac{i \cdot S}{V_e}$$

where the shape factor (S) corresponding to the electrode dimensions and configuration is given by, $$\frac{2 \cdot \pi \cdot L}{\cosh^{-1}\left(\frac{4 \cdot w^2 - (2 \cdot R_1)^2 - (2 \cdot R_2)^2}{8 \cdot R_1 \cdot R_2}\right)}$$

Case 2

Cylindrical arrangement in which the central electrode is a cylinder (needle) with radius $R_1$ and the outer electrodes are arranged in a cylindrical shell with a shell radius of $R_2$ (not the radius of the electrodes). The voltage on the central electrode is $V_e$. The voltage distribution in the tissue may be determined as a function of radius, r:

$$V = V_e \frac{\ln\frac{r}{R_2}}{\ln\frac{R_1}{R_2}}$$

The required voltage on the central electrode to achieve IRE:

$$V_e = GR_2 \ln\frac{R_2}{R_1}$$

The required current on the central electrode:

$$i = \frac{2\pi L \sigma V_e}{\ln\frac{R_2}{R_1}}$$

The specific conductivity ($\sigma$) of the tissue can be calculated since the voltage signal ($V_e$) and the current responses (i) are known.

Explanation of electrical concepts.

By using the bipolar electrode described previously in US Patent Application Publication No. 2010/0030211 A1, one can apply a small excitation AC voltage signal (for example from about 1 to 10 mV), $$V(t) = V_0 \sin(\omega t)$$

where V(t) is the potential at time t, $V_0$ is the amplitude of the excitation signal and $\omega$ is the frequency in radians/s. The reason for using a small excitation signal is to get a response that is pseudo-linear since in this manner the value for the impedance can be determined indicating the ability of a system (tissue) to resist the flow of electrical current. The measured AC current (response) that is generated by the excitation signal is described by $$I(t) = I_0 \sin(\omega t + \theta)$$

where I(t) is the response signal, Io is the amplitude of the response ($I_0 \neq V_0$) and $\theta$ is the phase shift of the signal. The impedance (Z) of the system (tissue) is described by, $$Z = (V(t))/(I(t)) = (V_0 \sin(\omega t))/(I_0 \sin(\omega t + \theta)) = Z_0(\sin(\omega t))/(\sin(\omega t + \theta))$$

It is important to note that the measurement of the response is at the same excitation frequency as the AC voltage signal to prevent interfering signals that could compromise the results. The magnitude of the impedance $|Z_0|$ is the electrical resistance of the tissue. The electrical resistivity ($\Omega m$) can be determined from the resistance and the physical dimensions of the tissue in addition to the electrode geometry (shape factor). The reciprocal of the electrical resistivity is the electrical conductivity (S/m). Therefore, after deriving the electrical resistivity from the methods described above, the conductivity may be determined.

As described in U.S. Patent Application No. 61/694,144 the analytical solution (Table 4) assumes that the length of the electrodes is much larger than the electrode radius or separation distance between the electrodes. Additionally, the analytical solution is not capable of capturing the non-linear electrical response of the tissue during electroporation procedures. The proposed statistical algorithm (Table 3) is preferably used in order to capture the response in treatments that are being conducted clinically and show how the analytical overestimates the baseline and maximum current that uses the experimental data.

TABLE 3

Determination of conductivity using the statistical model and in vivo data from pre-pulse and IRE pulses in canine kidney tissue using identical electrode configuration that the experimental one described below.

|  | Current [A] | Voltage [V] | Volt-2-Dist [V/cm] | Conductivity [S/m] | Z = $\sigma_{max}/\sigma_{min}$ |
|---|---|---|---|---|---|
| Pre-Pulse | 0.258 | 48 | 53 | 0.365 | — |
| IRE-Pulse | 20.6 | 1758 | 1953 | 1.037 | 2.841 |
| IRE-Pulse | 23.7 | 1758 | 1953 | 1.212 | 3.320 |
| IRE-Pulse | 23.6 | 1758 | 1953 | 1.207 | 3.305 |
| Avg. IRE | 22.6 | 1758 | 1953 | 1.150 | 3.150 |
| IRE-Pulse | 10.4 | 1259 | 1399 | 0.727 | 1.990 |
| IRE-Pulse | 11.1 | 1257 | 1397 | 0.789 | 2.162 |
| IRE-Pulse | 11 | 1257 | 1397 | 0.781 | 2.138 |
| Avg. IRE | 10.8 | 1257 | 1397 | 0.763 | 2.090 |
| Pre-Pulse | 0.343 | 73.3 | 52 | 0.341 | — |
| IRE-Pulse | 23.6 | 2262 | 1616 | 1.007 | 2.952 |
| IRE-Pulse | 24.3 | 2262 | 1616 | 1.041 | 3.051 |
| IRE-Pulse | 25.4 | 2262 | 1616 | 1.094 | 3.207 |
| Avg. IRE | 24.5 | 2262 | 1616 | 1.050 | 3.080 |

TABLE 4

Determination of conductivity using the analytical model and in vivo data from pre-pulse and IRE pulses in canine kidney tissue using identical electrode configuration than the experimental one described below. Assumption: Length >> radius, Length >> width, 2 cylindrical electrodes in an infinite medium.

|  | Current [A] | Voltage [V] | Volt-2-Dist [V/cm] | Shape Factor [m] | Conductivity [S/m] |
|---|---|---|---|---|---|
| Pre-Pulse | 0.258 | 48 | 53 | 0.01050 | 0.512 |
| IRE-Pulse | 20.6 | 1758 | 1953 | 0.01050 | 1.116 |
| IRE-Pulse | 23.7 | 1758 | 1953 | 0.01050 | 1.284 |
| IRE-Pulse | 23.6 | 1758 | 1953 | 0.01050 | 1.279 |
| Avg. IRE | 22.6 | 1758 | 1953 | 0.01050 | 1.225 |
| IRE-Pulse | 10.4 | 1259 | 1399 | 0.01050 | 0.787 |
| IRE-Pulse | 11.1 | 1257 | 1397 | 0.01050 | 0.841 |
| IRE-Pulse | 11 | 1257 | 1397 | 0.01050 | 0.834 |
| Avg. IRE | 10.8 | 1257 | 1397 | 0.01050 | 0.819 |
| Pre-Pulse | 0.343 | 73.3 | 52 | 0.00924 | 0.506 |
| IRE-Pulse | 23.6 | 2262 | 1616 | 0.00924 | 1.129 |
| IRE-Pulse | 24.3 | 2262 | 1616 | 0.00924 | 1.163 |
| IRE-Pulse | 25.4 | 2262 | 1616 | 0.00924 | 1.215 |
| Avg. IRE | 24.5 | 2262 | 1616 | 0.00924 | 1.172 |

Example 5

In Vivo Experiments

1) Animals.

IRE ablations were performed in canine kidneys in a procedure approved by the local animal ethics committee. Male canines weighing approximately 30 kg were premedicated with acetylpromazine (0.1 mg/kg), atropine (0.05 mg/kg), and morphine (0.2 mg/kg) prior to general anesthesia induced with propofol (6 mg/kg, then 0.5 mg/kg/min) and maintained with inhaled isofluorane (1-2%). Anesthetic depth was monitored by bispectral index monitoring (Covidien, Dublin, Ireland) of EEG brain activity. After ensuring adequate anesthesia, a midline incision was made and mesenchymal tissue was maneuvered to access the kidney. Pancuronium was delivered intravenously to mitigate electrically mediated muscle contraction, with an initial dose of 0.2 mg/kg, and adjusted if contractions increased.

2) Experimental Procedure.

Figure 14A:
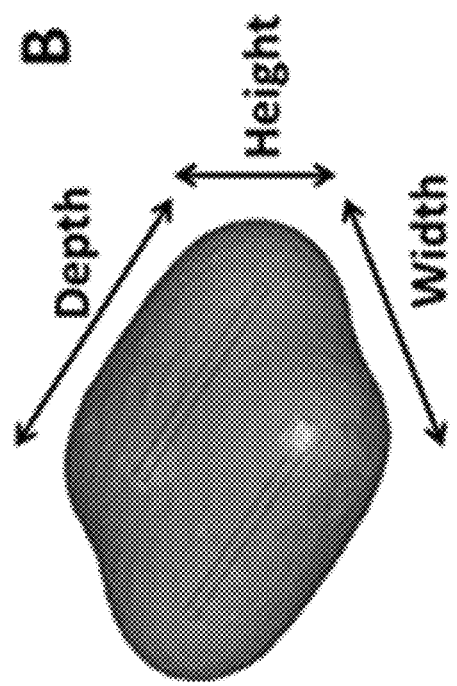
FIG. 14A is a schematic diagram showing an experimental setup of an embodiment of the invention.
Figure 14B:
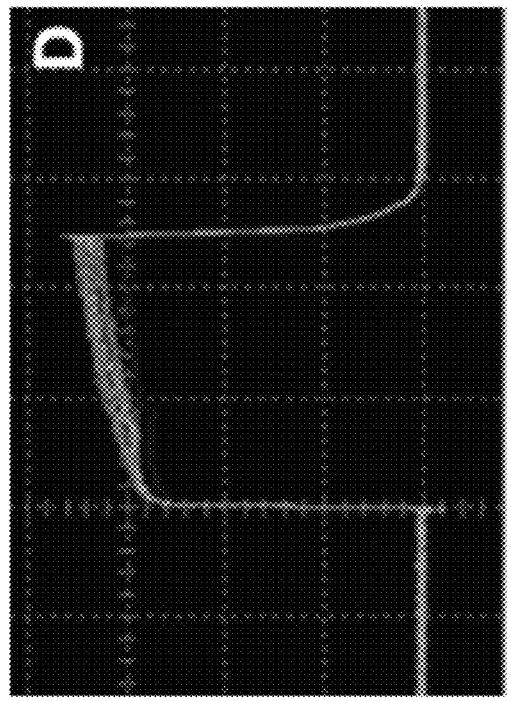
FIG. 14B is a schematic diagram showing dimension labeling conventions.
Figure 14C:
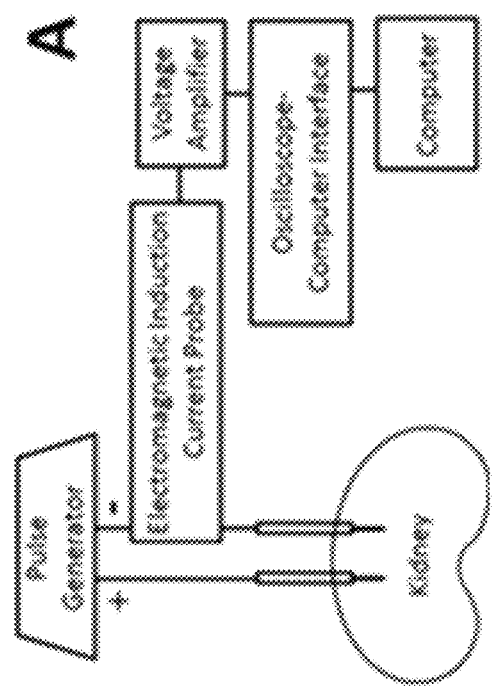
FIG. 14C is a waveform showing 50 V pre-pulse electrical current at 1 cm separation, grid=0.25 A, where the lack of rise in intrapulse conductivity suggests no significant membrane electroporation during pre-pulse delivery.
Figure 14D:
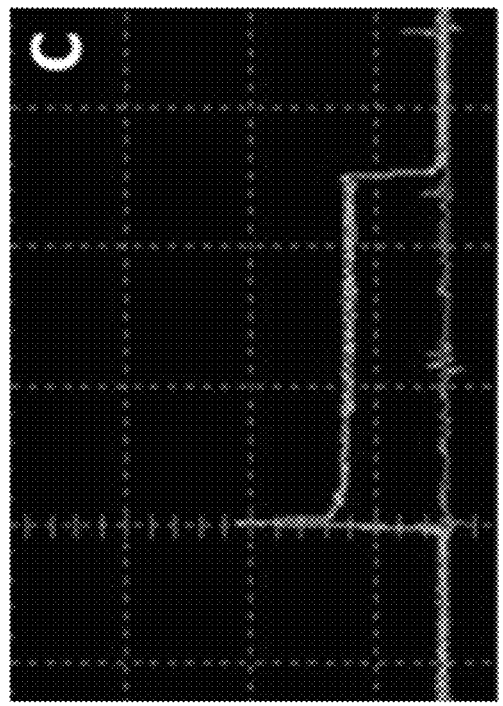
FIG. 14D is a waveform showing electrical current for pulses 40-50 of 1750 V at 1 cm separation, grid=5 A, where progressive intrapulse current rise suggests continued conductivity increase and electroporation.

Two modified 18 gauge needle electrodes (1.0 mm diameter and 1.0 cm in exposure) were inserted as pairs into the superior, middle, or inferior lobe of the kidney, with lobes being randomly selected. A BTX ECM830 pulse generator (Harvard Apparatus, Cambridge, Mass.) was used to deliver an initial 100 μs pre-pulse of 50 V/cm voltage-to-distance ratio (center-to-center) between the electrodes to get an initial current able to be used to determine baseline conductivity. Electrical current was measured with a Tektronix TCP305 electromagnetic induction current probe connected to a TCPA300 amplifier (both Tektronix, Beaverton, OR). A Protek DSO-2090 USB computer-interface oscilloscope provided current measurements on a laptop using the included DSO-2090 software (both GS Instruments, Incheon, Korea). A schematic of the experimental setup can be found in FIG. 14A. Following the pre-pulse, a series of 100 pulses, each 100 μs long, at a rate of 1 pulse per second was delivered, reversing polarity after 50 pulses. A five second pause was encountered after pulses 10 and 50 to save data. A schematic diagram showing dimension labeling conventions is shown in FIG. 14B. Representative current waveforms from a pre-pulse and experimental pulse can be found in FIGS. 14C and 14D, respectively. Electrode exposure lengths were set to 1 cm for all trials. The separation distance between electrodes and applied voltage may be found in Table 5. After completing pulse delivery, the electrodes were removed. Two additional ablations were performed in the remaining lobes before repeating the procedure on the contralateral kidney, resulting in a total of three ablations per kidney and six per canine.

TABLE 5

KIDNEY EXPERIMENT PROTOCOLS IN CANINE SUBJECTS

| Setup | Separation, cm | Voltage, V | Voltage-Distance Ratio, V/cm | n |
|---|---|---|---|---|
| 1 | 1 | 1250 | 1250 | 4 |
| 2 | 1 | 1750 | 1750 | 4 |
| 3 | 1.5 | 2250 | 1500 | 6 |

3) Kidney Segmentation and 3D Reconstruction.

Numerical models provide an advantageous platform for predicting electroporation treatment effects by simulating electric field, electrical conductivity, and temperature distributions. By understanding the electric field distribution, one can apply an effective lethal electric field threshold for IRE, EIRE, to predict ablation lesion dimensions under varying pulse protocols (electrode arrangements and applied voltages). However, in order to do so, these models should first be calibrated with experimental data. Here, the numerical simulation algorithm developed from porcine kidneys was expanded that accounts for conductivity changes using an asymmetrical sigmoid function (R. E. Neal, 2nd, et al., "Experimental characterization and numerical modeling of tissue electrical conductivity during pulsed electric fields for irreversible electroporation treatment planning," IEEE Trans Biomed Eng., vol. 59, pp. 1076-85. Epub 2012 Jan. 6, 2012 ("R. E. Neal, $2^{nd}$, et al., 2012")). The model is calibrated to the experimental lesions to determine an effective electric field threshold under the three experimental setups used. In addition, static and linear conductivity functions are also correlated to the lesion dimensions. The three functions are used to evaluate which numerical technique will result in better accuracy in matching lesion shapes and resulting current from actual IRE ablations in mammalian tissue, particularly for kidney.

The imaging-based computational model domains were constructed from a magnetic resonance imaging (MRI) scan of a kidney from a canine subject of similar size to those in the study. The scans were scaled by 1.21 times in all directions to better match the experimental kidney dimensions while maintaining the anatomical characteristics. Mimics 14.1 image analysis software (Materialise, Leuven, BG) was used to segment the kidney geometry from the surrounding tissues. The kidney was traced in each of the two-dimensional (2D) MRI axial slices, which were then integrated into a three-dimensional (3D) solid representation of the kidney volume which was refined and exported to 3-matic version 6.1 (Materialise, Leuven, BG) to generate a volumetric mesh compatible with Comsol Multiphysics finite element modeling software (Comsol Multiphysics, v.4.2a, Stockholm, Sweden).

Electrodes were simulated as paired cylinders, each 1 cm long and 1 mm in diameter, and separated by 1 or 1.5 cm to represent the two experimental conditions. The pairs were inserted into the 3D kidney mesh in two configurations, representing both experimental approaches that used either the superior/inferior (vertical) or middle (horizontal) lobe of the kidney, both with tips 1.5 cm deep. The finite element model simulated the electric field distribution in the kidney, which was used to determine cell death EIRE by correlating the electric field values with the average in vivo lesion height and width dimensions.

4) Electric Field Distribution and Lethal EIRE Determination.

The electric field distribution is determined according to $$-\nabla \cdot (\sigma(|E|)\nabla \phi) = 0 \qquad (1)$$

where σ is the electrical conductivity of the tissue, E is the electric field in V/cm, and φ is the electrical potential. Tissue-electrode boundaries for the cathode and anode were defined as $\phi = V_o$ and ground, respectively. The remaining boundaries were treated as electrically insulating, $d\phi/dn=0$, since the kidneys were isolated from the surrounding mesenchymal tissue during the experimental procedures. The current density was integrated over a mid-plane parallel to both electrodes to determine simulated electric current.

The model was solved for the vertical and horizontal electrode configurations, each considering three electrical conductivity tissue responses. These responses included a homogeneous static conductivity ($\sigma_0$) as well as two that accounted for electroporation based conductivity changes in tissue that result from cell membrane permeabilization. The dynamic models are based on a relationship between a minimum baseline and a maximum conductivity. The static conductivity model was used to determine the baseline conductivity, $\sigma_0$, by matching simulated electrical current with the pre-pulse experimental data, where the field strength should be below that able to permeabilize any cells in the tissue. The maximum conductivity, $\sigma_{max}$, occurs when the number of cells electroporated in the tissue has saturated, and the cellular membranes no longer restrict the extent of interstitial electrolyte mobility. The statistical model discussed in (P. A. Garcia, et al., "Towards a predictive model of electroporation-based therapies using pre-pulse electrical measurements," Conf Proc IEEE Eng Med Biol Soc, vol. 2012, pp. 2575-8, 2012 ("P. A. Garcia, et al., 2012")) was used to predict $\sigma_{max}$ from previously characterized tissue response to pre-pulse $\sigma_0$ and electrical data.

The $\sigma_0$ and $\sigma_{max}$ values provide the required parameters to define the electric field-dependent conductivity, $\sigma(|E|)$, of renal tissue in vivo. One model assumed a linear relationship that grew between the minimum and maximum conductivities over a range from 200 to 2000 V/cm, $\sigma_L(|E|)$, and the second used an asymmetrical sigmoid Gompertz curve, $\sigma_S(|E|)$, derived from the work described in (R. E. Neal, 2nd, et al., 2012) using the equation:

$$\sigma_s(|E|) = \sigma_0 + (\sigma_{max} - \sigma_0) \cdot \exp[-A \cdot \exp(-B \cdot E)] \tag{2}$$

where A and B are unitless coefficients that vary with pulse length, t(s). This function was fit using curve parameters for a 100 µs long pulse, where A=3.053 and B=0.00233 (R. E. Neal, $2^{nd}$, et al., 2012)

The electric field distribution along a width and height projection based at the midpoint length of the electrodes was used to determine the electric field magnitude that matched experimental lesion dimensions. This was performed for all three conductivity scenarios in all three experimental protocol setups in order to determine which model best matched the IRE ablations, providing the optimum conductivity modeling technique for mammalian tissue.

5) Results: In Vivo Experiments.
Electrical Currents.

All animals survived the procedures without adverse event until euthanasia. Electrical pre-pulse currents were 0.258±0.036 A (mean±SD) for the 1 cm electrode separation trials and 0.343±0.050 A for the 1.5 cm separation trials. Electrical currents from the trials for pulses 1-10, 40-50, and 90-100 are reported in Table 6. Although currents are typically reported to increase with consecutive pulses, there is no statistically significant correlation between pulse number and measured current. Therefore, all numerical calibrations to match electrical current and determine $\sigma_{max}$ used the average current from all captured pulses for each experimental setup.

TABLE 6

EXPERIMENTAL ELECTRIC CURRENTS
TO CALIBRATE NUMERICAL MODELS

| Setup | Separation, cm | Average Delivered Voltage, V | Pulse Number | Average Electric Current, A* |
|---|---|---|---|---|
| Pre 1 | 1 | 48 | 1750 | 0.258 (0.036) |
| Pre 2 | 1.5 | 73 | 1250 | 0.343 (0.050) |
| 1 | 1 | 1258 | 1-10 | 10.4 (1.7) |
|  |  |  | 40-50 | 11.1 (1.1) |
|  |  |  | 90-100 | 11.0 (1.7) |
| 2 | 2 | 1758 | 1-10 | 20.6 (3.2) |
|  |  |  | 40-50 | 23.7 (5.1) |
|  |  |  | 90-100 | 23.6 (3.8) |
| 3 | 1.5 | 2262 | 1-10 | 23.6 (1.47) |
|  |  |  | 40-50 | 24.3 (3.25) |
|  |  |  | 90-100 | 25.4 (3.27) |

*Currents given as "average (standard deviation)"

6) Determination of Dynamic Conductivity Function.

Pre-pulse electrical current was used to calculate the baseline conductivity, $\sigma_0$, used in the static numerical simulation. In addition, the baseline and maximum, $\sigma_{max}$, electrical conductivities required for generating the asymmetrical sigmoid and linear dynamic conductivity functions were calculated according to the procedure outlined in (P. A. Garcia, et al., 2012) and are provided in Table 7. The ratio between these conductivities was calculated and demonstrates an increase in conductivity between 2.09 and 3.15 times, consistent with values determined in the literature for other organs (N. Payselj, et al., "The course of tissue permeabilization studied on a mathematical model of a subcutaneous tumor in small animals," IEEE Trans Biomed Eng, vol. 52, pp. 1373-81, August 2005).

TABLE 7

BASELINE AND MAXIMUM ELECTRIC CONDUCTIVITIES

| Setup | Gap, cm | V/d Ratio, V/cm | $\sigma_0$ | $\sigma_{max}$ | $\sigma_{max}/\sigma_0$ |
|---|---|---|---|---|---|
| 1 | 1 | 1250 | 0.365 | 0.763 | 2.09 |
| 2 | 1 | 1750 | 0.365 | 1.150 | 3.15 |
| 3 | 1.5 | 1500 | 0.341 | 1.050 | 3.08 |

Example 6

How to Use the Ratio of Maximum Conductivity to Baseline Conductivity in Modifying the Electric Field Distribution and Thus the Cassini Oval Equation.

Irreversible electroporation (IRE) is a promising new method for the focal ablation of undesirable tissue and tumors. The minimally invasive procedure involves placing electrodes into the region of interest and delivering a series of low energy electric pulses to induce irrecoverable structural changes in cell membranes, thus achieving tissue death. To achieve IRE, the electric field in the region of interest needs to be above a critical threshold, which is dependent on a variety of conditions such as the physical properties of the tissue, electrode geometry and pulse parameters. Additionally, the electric conductivity of the tissue changes as a result of the pulses, redistributing the electric field and thus the treatment area. The effect of a dynamic conductivity around the electrodes where the highest electric fields are generated was investigated in order to better predict the IRE treatment for clinical use.

The electric field distribution associated with the electric pulse is given by solving the governing Laplace equation, $\nabla \cdot (\sigma \nabla \varphi) = 0$, where $\sigma$ is the tissue electrical conductivity (baseline 0.2 S/m) and $\varphi$ the electrical potential (3000 V). The dynamic changes in electrical conductivity due to electroporation were modeled with the flc2hs Heaviside function within the finite element modeling software used in the study (Comsol Multiphysics 3.5a, Stockholm, Sweden). The dynamic conductivity factor ranged between 2.0-7.0 times the baseline value in the regions exceeding 3000 V/cm. The total electrical current, volumes, and lesion shapes from the IRE treatment were evaluated.

Figures 15A, 15B:
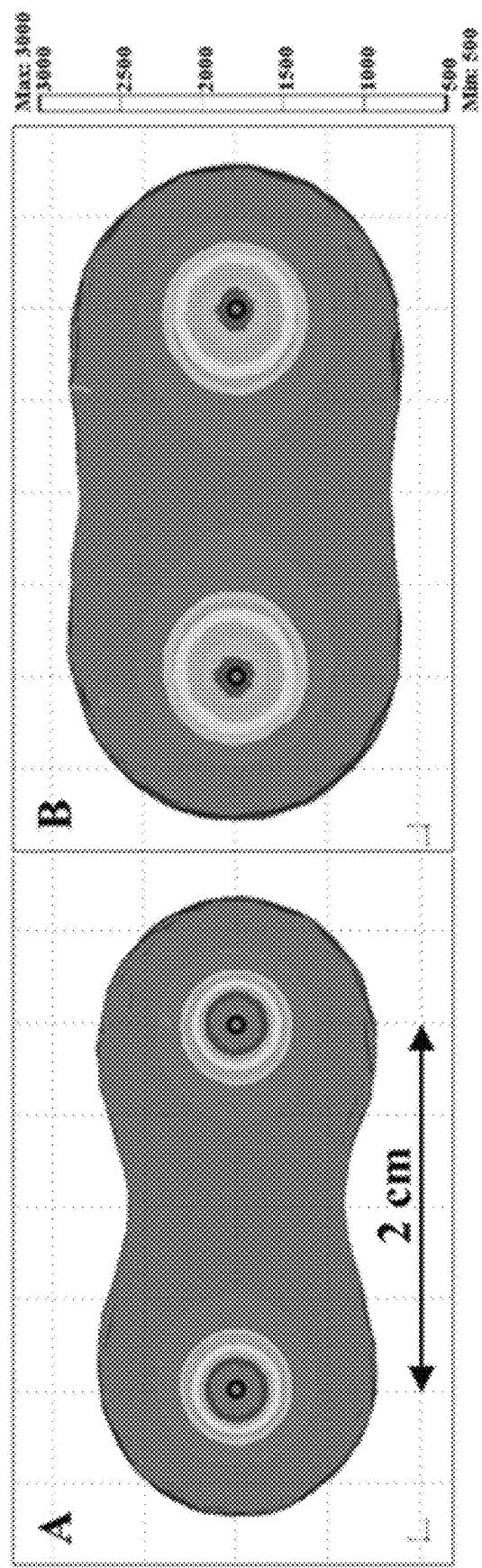
FIGS. 15A and 15B are electric field [V/cm] isocontours for non-electroporated tissue (FIG. 15A) and electroporated tissue (FIG. 15B) maps assuming a maximum conductivity to baseline conductivity ratio of 7.0×.

FIGS. 15A and 15B display the electric field distributions for the non-electroporated (baseline conductivity) and electroporated (maximum/baseline conductivity) maps, respectively. The electric field from using the baseline conductivity resulted in a "peanut" shape distribution (FIG. 15A). By incorporating the conductivity ratio between $\sigma_{max}/\sigma_0$, there is a redistribution of the electric field and thus the volumes, currents and lesion shapes are modified as well. The electric field distribution for a 7.0× factor (FIG. 15B), shows a more gradual dissipation of the electric field and a rounder predicted IRE lesion.

A method to predict IRE lesions and incorporate the dynamic changes in conductivity due to electroporation around the electrodes is presented in this example. This procedure provides additional tools to better approximate the electric field distributions in tissue and thus help to generate more reliable IRE treatment planning for clinical use using Finite Element Analysis (FEA) models.

Specifically in order to adapt the Cassini Oval to match experimental lesions or electric field distributions the following procedure should be used:

In IRE treatments, the electric field distribution is the primary factor for dictating defect formation and the resulting volume of treated tissue (J. F. Edd and R. V. Davalos, "Mathematical modeling of irreversible electroporation for treatment planning," Technol Cancer Res Treat, vol. 6, pp. 275-286, 2007; D. Sel, et al., "Sequential finite element model of tissue electropermeabilization," IEEE Trans Biomed Eng, vol. 52, pp. 816-27, May 2005; S. Mahnic-Kalamiza, et al., "Educational application for visualization and analysis of electric field strength in multiple electrode electroporation," BMC Med Educ, vol. 12, p. 102, 2012 ("S. Mahnic-Kalamiza, et al., 2012")). The electric field is influenced by both the geometry and positioning of the electrodes as well as the dielectric tissue properties. Additionally, altered membrane permeability due to electroporation influences the tissue conductivity in a non-linear manner. Therefore numerical techniques are preferably used to account for different electrode configurations and incorporate tissue-specific functions relating the electrical conductivity to the electric field distribution (i.e. extent of electroporation). The inventors are currently using imaging-based computational models for IRE treatment planning that use the physical properties of the tissue and patient-specific 3D anatomical reconstructions to generate electric field distributions (P. A. Garcia, et al., "Non-thermal irreversible electroporation (N-TIRE) and adjuvant fractionated radiotherapeutic multimodal therapy for intracranial malignant glioma in a canine patient," Technol Cancer Res Treat, vol. 10, pp. 73-83, 2011 ("P. A. Garcia, et al, 2011")).

Oftentimes in clinical practice, there is need to rapidly visualize the estimated zone of ablation without relying on complex and time consuming numerical simulations. As an alternative, analytical solutions are powerful techniques that provide valuable insight and offer the ability to rapidly visualize electric field distributions (S. Mahnic-Kalamiza, et al., 2012). However, these analytical solutions assume infinitely long electrodes which are not the case in clinical practice and do not incorporate the non-linear changes in tissue conductivity due to electroporation. Therefore, there is a need for simple, quick, and accurate methods to provide physicians with predicted IRE zones of ablation during surgery when one of the pulse parameters needs to be adjusted. To this end, the inventors have adapted the Cassini curve in an effort to provide researchers and physicians with a graphical representation of IRE zones of ablation, for example, in in vivo porcine liver. The goal of this work is to provide a correlation between experimentally produced zones of ablations in in vivo porcine liver tissue with the corresponding IRE pulse parameters and electrode configuration. These Cassini curves are calibrated to experimental IRE ablations, and incorporate the dynamic changes in tissue conductivity, a limitation of the analytical approach.

The Cassini oval is a plane curve that derives its set of values based on the distance of any given point, a, from the fixed location of two foci, $q_1$ and $q_2$, located at $(x_1, y_1)$ and $(x_2, y_2)$. The equation is similar to that of an ellipse, except that it is based on the product of distances from the foci, rather than the sum. This makes the equation for such an oval $$[(x_1-a)^2+(y_1-a)^2]\cdot[(x_2-a)^2+(y_2-a)^2]=b^4 \qquad (3)$$

where $b^4$ is a scaling factor to determine the value at any given point. For incorporation of this equation into shapes that mimic the electric field distribution, it is assumed that the two foci were equidistantly located on the x-axis at $(\pm x, 0)$. The flexibility of the Cassini curve is crucial since it allows for fitting a wide range of shapes by adjusting the 'a' and/or 'b' parameters from Equation 3 simultaneously and fitting them to the experimental lesion dimensions or the locations at which a particular electric field value results from the computational simulations. The new approach in this analysis is that it is not assumed that the parameter 'a' is related to the separation distance between the electrodes used in IRE treatments for example but will be a second parameter to match the width/depth of any distribution thus allowing for more flexibility between the shapes achieved with the Cassini Oval as can be seen in FIGS. 16A and 16B.

The in vivo experimental data in porcine liver was provided from published studies performed at the Applied Radiology Laboratory of Hadassah Hebrew University Medical Center (P. A. Garcia, et al., 2011). All experiments were performed with Institutional Animal Care and Use Committee approval from the Hebrew University Medical Center. The treatments were performed with a two-needle electrode configuration, 1.5 cm center-to-center separation, 2.0 cm electrode exposure, and an applied voltage of 2250 V. In this paper we only evaluate the effect of pulse number and pulse duration on the resulting 'a' and 'b' parameters required to fit the IRE zones of ablation with the Cassini curve. The NonlinearModelFit function in Wolfram Mathematica 9 was used to determine the 'a' and 'b' parameters (average±standard deviation) for each pulse parameter resulting in three curves for each condition. This same technique can be used to fit the 'a' and 'b' parameters to match the electric field shape at any particular electric field value as well thus providing an avenue to capture the shape for any IRE lesion independent of the tissue or patient.

Figure 17:
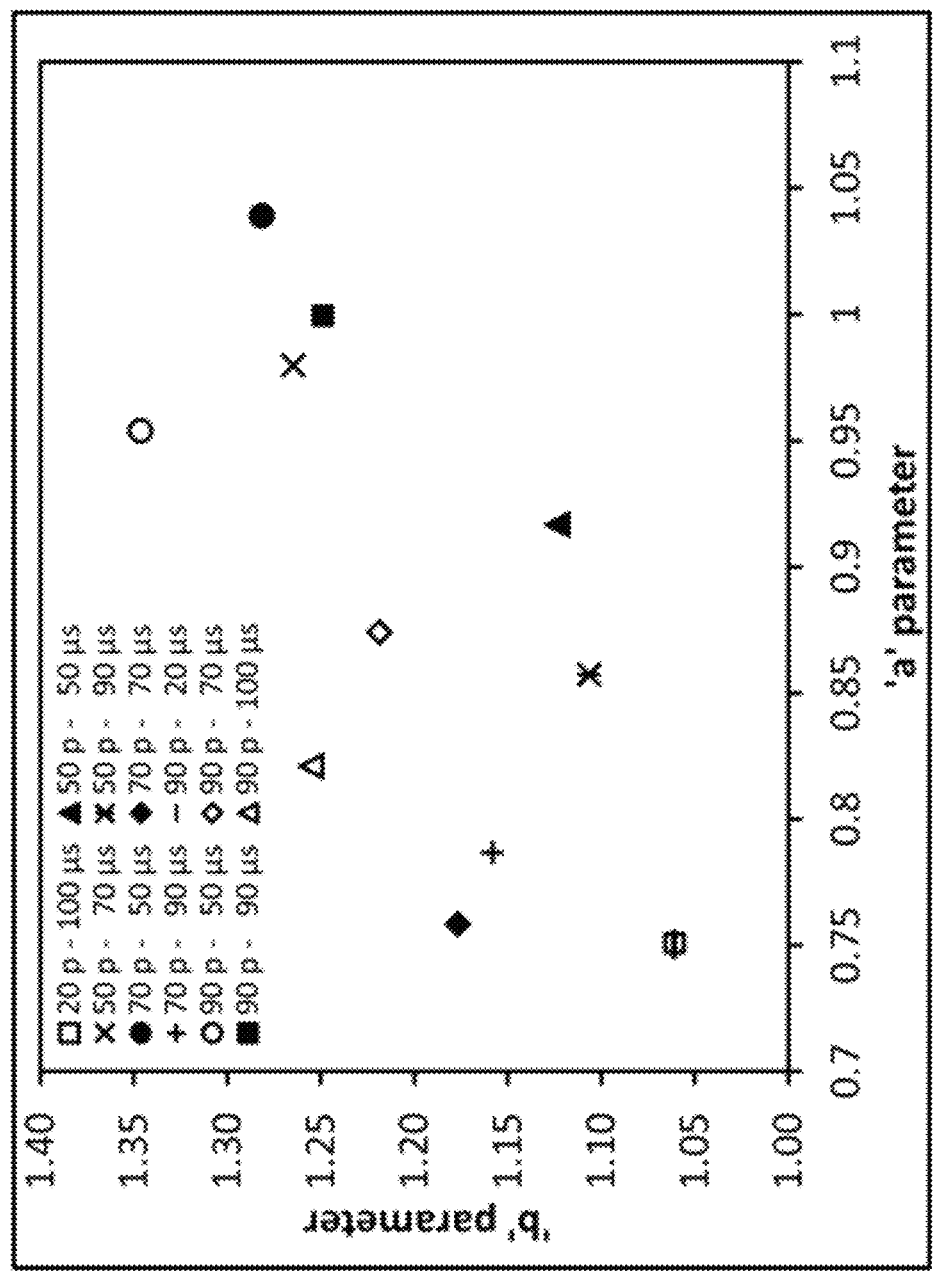
FIG. 17 is a graph showing NonlinearModelFit results for the 'a' and 'b' parameters used to generate the Cassini curves that represent the experimental IRE zones of ablation in porcine liver.

The NonlinearModelFit results for the 'a' and 'b' parameters to generate the Cassini curves are provided in FIG. 17. The 'a' parameter ranged from 0.75-1.04 and the 'b' from 1.06-1.35 for the average IRE zones of ablation in the in vivo porcine liver. From these data it can be seen that each pulse parameter used results in a unique 'a' and 'b' combination except for the twenty 100-µs pulses and ninety 20-µs pulses which overlap since they had identical IRE ablations. Therefore, consideration should be given to pulse length and total number of pulses when planning treatments to ensure maximum accuracy when using Cassini curves to rapidly predict treatment zones.

Figure 18:
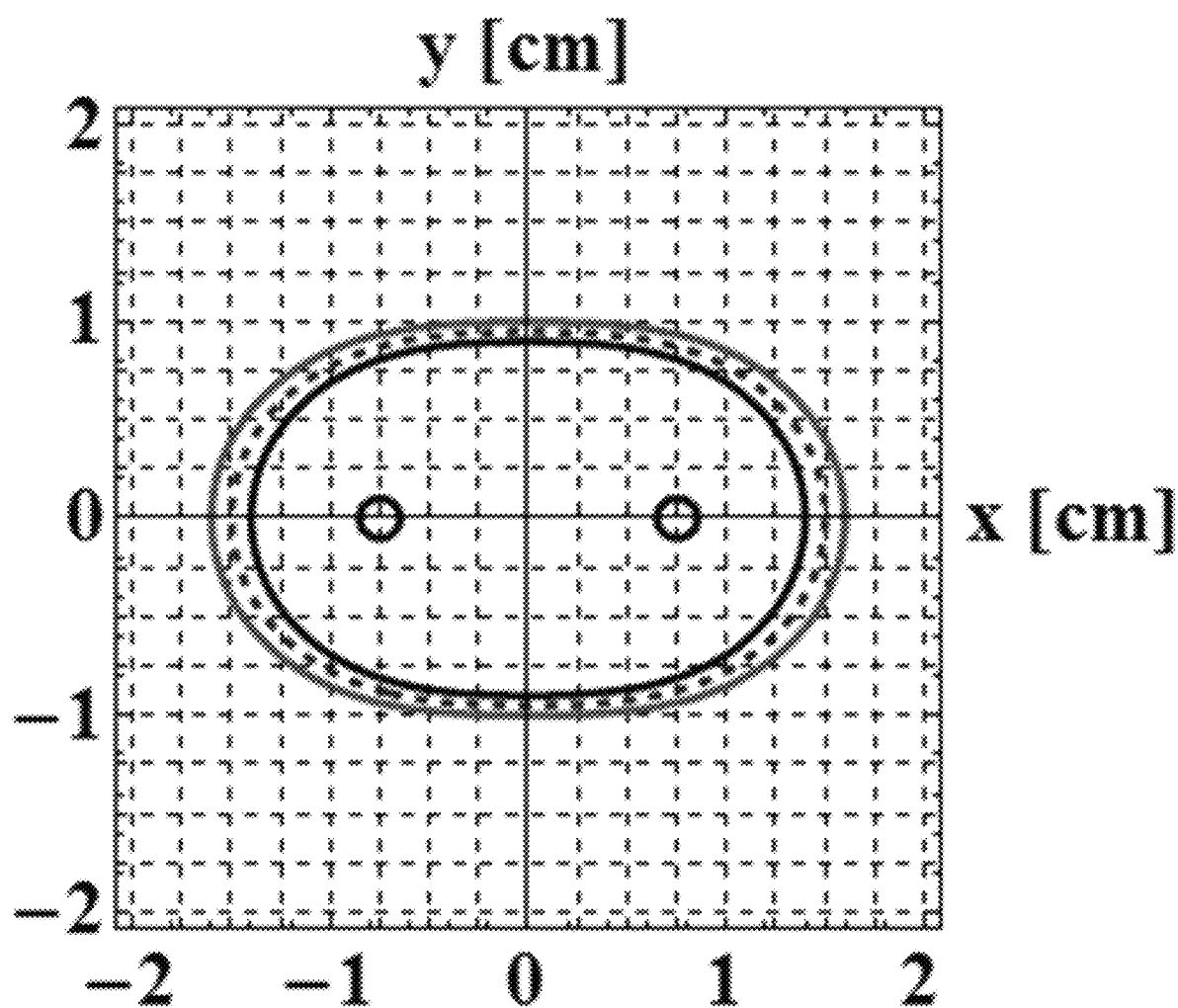
FIG. 18 shows Cassini curves from a ninety 100-µs pulse IRE treatment that represent the average zone of ablation (blue dashed), +SD (red solid), and −SD (black solid) according to a=0.821±0.062 and b=1.256±0.079 using two single needle electrodes.

FIG. 18 provides a representation of the average IRE zone of ablation and also includes the experimentally achieved standard deviations. This Cassini curve is the most clinically relevant as ninety 100-µs pulses is the recommended setting by the manufacturer that is currently being used by physicians to treat several types of cancer. The Cassini curves in FIG. 18 were generated using two single needle electrodes with a=0.821±0.062 and b=1.256±0.079 that corresponded to IRE ablations that were 3.0±0.2 cm in width and 1.9±0.1 cm in depth (P. A. Garcia, et al., 2011). The results suggest that the Cassini curve is a viable method to represent experimentally achieved IRE zones of ablation. These curves can be used to provide physicians with simple, quick, and accurate prediction of IRE treatments. The parameters generated in this study were achieved from porcine liver ablations data. The parameters for other tissues and/or tumors can be determined in a similar manner. Cassini curve parameters should be re-calibrated if the pulse parameters or electrode configuration (i.e. separation or exposure) deviate from the typical protocols in Ben-David et al. Additionally, there is a need to calibrate these Cassini curves to electric and temperature distributions in order to take advantage of the relatively simple curves in representing simulated solutions that account for other pulse parameters and electrode configuration including different electrode separations, diameter, exposure, and voltages. A method to represent IRE zones of ablation in a computationally efficient manner and based on experimental data is thus presented. Such methods can be used to predict IRE ablation in liver in order to provide physicians with an immediate tool for treatment planning.

Figure 19:
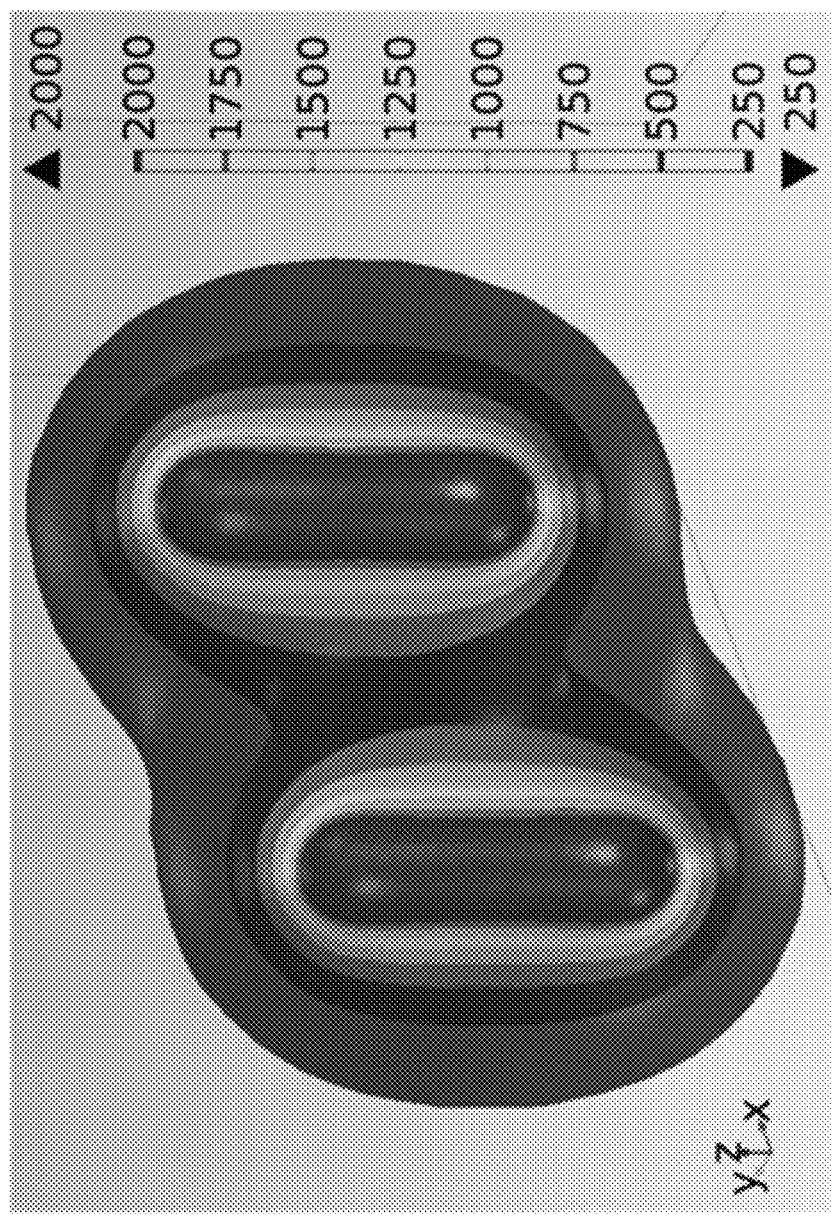
FIG. 19 is a representation of the Finite Element Analysis (FEA) model for a 3D Electric Field [V/cm] Distribution in Non-Electroporated (Baseline) Tissue with 1.5-cm Single Needle Electrodes at a Separation of 2.0 cm and with 3000 V applied.

FIG. 19 is a representation of the 3D Electric Field [V/cm] Distribution in Non-Electroporated (Baseline) Tissue with 1.5-cm Single Needle Electrodes at a Separation of 2.0 cm and 3000 V applied.

FIGS. 20A-D are representations of the Electric Field [V/cm] Distributions from the 3D Non-Electroporated (Baseline) Models with 1.5-cm Electrodes at a Separation of 2.0 cm and 3000 V (cross-sections), wherein FIG. 20A is a representation of the x-y plane mid-electrode length, FIG. 20B is a representation of the x-z plane mid-electrode diameter, FIG. 20C is a representation of the y-z plane mid electrode diameter, and FIG. 20D is a representation of the y-z plane between electrodes.

Figure 21:
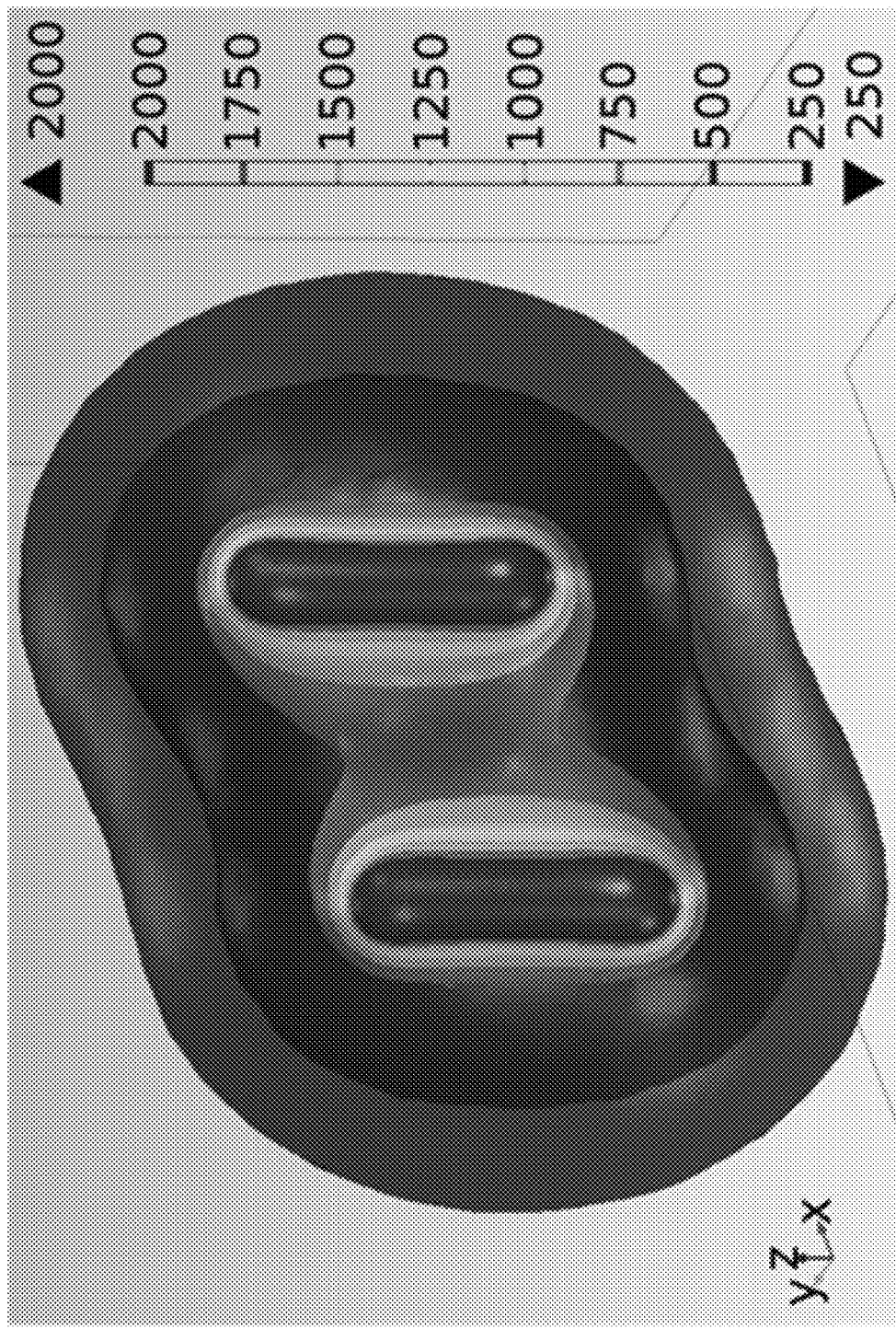
FIG. 21 is a representation of the Finite Element Analysis (FEA) model for a 3D Electric Field [V/cm] Distribution in Electroporated Tissue with 1.5-cm Single Needle Electrodes at a Separation of 2.0 cm and 3000 V applied assuming $\sigma_{max}/\sigma_0=3.6$.

FIG. 21 is a representation of the 3D Electric Field [V/cm] Distribution in Electroporated Tissue with 1.5-cm Single Needle Electrodes at a Separation of 2.0 cm and 3000 V applied assuming $\sigma_{max}/\sigma_0 = 3.6$.

Figure 22A:
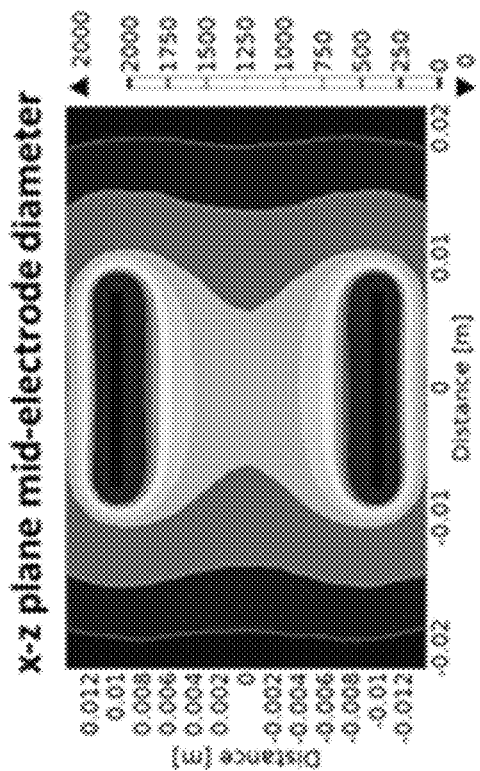
Figure 22B:
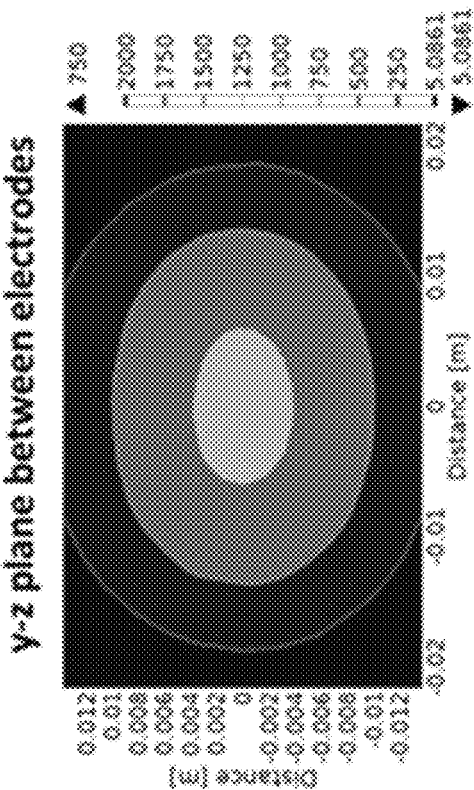
Figure 22C:
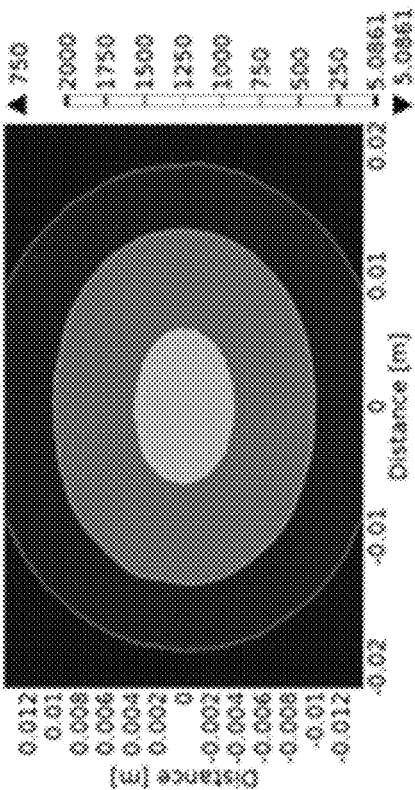
Figure 22D:
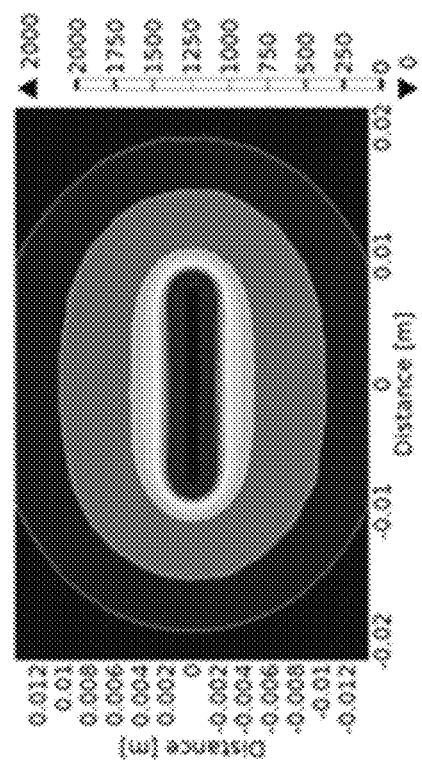

FIGS. 22A-22D are representations of the Electric Field [V/cm] Distributions from the 3D Electroporated Models with 1.5-cm Electrodes at a Separation of 2.0 cm and 3000 V (cross-sections) assuming $\sigma_{max}/\sigma_0 = 3.6$, wherein FIG. 22A is a representation of the x-y plane mid-electrode length, FIG. 22B is a representation of the x-z plane mid-electrode diameter, FIG. 22C is a representation of the y-z plane mid electrode diameter, FIG. 22D is a representation of the y-z plane between electrodes.

Example 7: The Cassini Oval Equation

In mathematics, a Cassini oval is a set (or locus) of points in the plane such that each point p on the oval bears a special relation to two other, fixed points $q_1$ and $q_2$: the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \quad (2)$$

where b is a constant.

Nevertheless, in embodiments the 'b' parameter can be modified to manipulate the shape of the Cassini curve and illustrate the desired electric field distribution. Therefore, the 'b' is a variable parameter that is determined based on the specific location (distance) of a particular electric field threshold to be displayed.

The points $q_1$ and $q_2$ are called the foci of the oval.

Suppose $q_1$ is the point (a,0), and $q_2$ is the point (−a,0). Then the points on the curve satisfy the equation:

$$((x-a)^2 + y^2)((x+a)^2 + y^2) = b^4 \quad (3)$$

The equivalent polar equation is:

$$r^4 - 2a^2 r^2 \cos 2\theta = b^4 - a^4 \quad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on grid 200. By taking pairs of probes for each firing sequence, the first probe is set as qi being the point (a,0) and the second probe is set as $q_2$ being the point (−a,0). This original Cassini oval formulation was revised by modifying the assumption of the 'a' parameter being related to the position of the electrodes. In the revised formulation the 'a' is a variable parameter that is adjusted depending on the width and length of the Cassini oval in order to intercept the zone of ablation in the x- and y-directions.

In summary, the 'a' and 'b' variable parameters should be determined in order to have the ability to generate a Cassini curve that could fit the shape of any electric field isocontour. Specifically from the electric field simulations or experimental irreversible electroporation zones of ablation the user should determine the distance along the x-axis and y-axis that the Cassini curve should intersect.

For example in the case of a Finite Element Analysis (FEA) simulation using two 1-mm in diameter electrodes, separated by a center-to-center distance of 2.0 cm, 1.5 cm in exposure, and an applied voltage of 3000 V to one electrode and ground to the other electrode the distances from the point in between the electrodes to a specific electric field contour is given below (Table 8 for the baseline (non-electroporated) and $\sigma_{max}/\sigma_0 = 3.6$ (electroporated) models.

TABLE 8

| E-field [V/cm] | Baseline $(p_{1x}, 0)$ [cm] | Baseline $(0, p_{2y})$ [cm] | $\sigma_{max}/\sigma_0 = 3.6$ $(p_{3x}, 0)$ [cm] | $\sigma_{max}/\sigma_0 = 3.6$ $(0, p_{4y})$ [cm] |
|---|---|---|---|---|
| 300 | 1.97 | 0.92 | 2.38 | 1.39 |
| 400 | 1.81 | 0.69 | 2.17 | 1.18 |
| 500 | 1.70 | 0.49 | 1.99 | 1.01 |

Using the 500 V/cm electric field isocontour as an example it can be determined that the Cassini oval using the baseline model will intersect the points (1.70,0) and (0,0.49) and the model using $\sigma_{max}/\sigma_0 = 3.6$ will intersect the point (1.99,0) and (0,1.01). Using the two points that will be intersected by the Cassini oval of each specific model type (non-electroporated vs. electroporated) allows for determination of the 'a' and 'b' variable parameter and still satisfy the mathematical condition outlined above in the first paragraph of this section by way of least square fits such as the NonlinearModelFit function in Mathematica or via interpolation tables as the one presented below.

The interpolation method involves assuming values for the 'a' parameter from 0.00 cm to 3.00 cm in steps of 0.01 cm and calculating the 'b' parameter using the specific points from the previous paragraph. The distance and steps were arbitrarily chosen and can vary depending on the specific Cassini oval that is being developed. In the case of Table 9 the point p1x=(1.70 cm, 0 cm) and the point p2y=(0 cm, 0.49 cm) and the corresponding distances to either q1 (−a,0) or q2 (a,0) are calculated.

TABLE 9

| 'a' | d(q1, p1x) = d1 | d(q2, p1x) = d2 | d1*d2 | d(q1, p2y) = d3 | d(q2, p2y) = d4 | d3*d4 | d1*d2/ d3*d4 |
|---|---|---|---|---|---|---|---|
| 1.04 | 0.66 | 2.74 | 1.808 | 1.150 | 1.150 | 1.322 | 1.37 |
| 1.05 | 0.65 | 2.75 | 1.788 | 1.159 | 1.159 | 1.343 | 1.33 |
| 1.06 | 0.64 | 2.76 | 1.766 | 1.168 | 1.168 | 1.364 | 1.30 |
| 1.07 | 0.63 | 2.77 | 1.745 | 1.177 | 1.177 | 1.385 | 1.26 |
| 1.08 | 0.62 | 2.78 | 1.724 | 1.186 | 1.186 | 1.407 | 1.23 |
| 1.09 | 0.61 | 2.79 | 1.702 | 1.195 | 1.195 | 1.428 | 1.19 |
| 1.1 | 0.60 | 2.80 | 1.680 | 1.204 | 1.204 | 1.450 | 1.16 |
| 1.11 | 0.59 | 2.81 | 1.658 | 1.213 | 1.213 | 1.472 | 1.13 |
| 1.12 | 0.58 | 2.82 | 1.636 | 1.222 | 1.222 | 1.495 | 1.09 |
| 1.13 | 0.57 | 2.83 | 1.613 | 1.232 | 1.232 | 1.517 | 1.06 |
| 1.14 | 0.56 | 2.84 | 1.590 | 1.241 | 1.241 | 1.540 | 1.03 |
| 1.15 | 0.55 | 2.85 | 1.568 | 1.250 | 1.250 | 1.563 | 1.00 |
| 1.16 | 0.54 | 2.86 | 1.544 | 1.259 | 1.259 | 1.586 | 0.97 |
| 1.17 | 0.53 | 2.87 | 1.521 | 1.268 | 1.268 | 1.609 | 0.95 |
| 1.18 | 0.52 | 2.88 | 1.498 | 1.278 | 1.278 | 1.633 | 0.92 |
| 1.19 | 0.51 | 2.89 | 1.474 | 1.287 | 1.287 | 1.656 | 0.89 |
| 1.2 | 0.50 | 2.90 | 1.450 | 1.296 | 1.296 | 1.680 | 0.86 |
| 1.21 | 0.49 | 2.91 | 1.426 | 1.305 | 1.305 | 1.704 | 0.84 |
| 1.22 | 0.48 | 2.92 | 1.402 | 1.315 | 1.315 | 1.729 | 0.81 |
| 1.23 | 0.47 | 2.93 | 1.377 | 1.324 | 1.324 | 1.753 | 0.79 |
| 1.24 | 0.46 | 2.94 | 1.352 | 1.333 | 1.333 | 1.778 | 0.76 |

In the baseline case analyzed above when the variable parameter 'a' was 1.15 cm the calculated $b^2$ were 1.568 and 1.563 for the d1*d2 and d3*d4, respectively. The last column calculates the ratio of both $b^2$ values in order to determine the location at which they are the same (or closest) which happens when (d1*d2)/(d3*d4)=1.00.

Once it is determined that 'a'=1.15 cm provides the closest ratio to one, the average of the d1*d2 (1.568) and d3*d4 (1.563) quantities is calculated and used to determine the corresponding 'b' parameter by taking the square root as shown in the equation below.

$$b = \sqrt{\frac{(d1*d2)+(d3*d4)}{2}} = \sqrt{\frac{1.568+1.563}{2}} = \sqrt{1.5655} = 1.2512 \quad (5)$$

Once the 'a' and 'b' parameters are determined then any plotting software can be used to illustrate the Cassini curve in Cartesian coordinates using the modified equation $$y = \pm\sqrt{-a^2 - x^2 \pm \sqrt{b^4 + 4a^2x^2}} \quad (6)$$

The steps outlined in the previous paragraphs just above can also be used to determine the 'a' and 'b' parameters using the same methodology and with points p3x=(1.99 cm, 0 cm) and p4y=(0 cm, 1.01 cm) and results in 'a'=1.21 cm and 'b'=1.578 cm as the Cassini parameters for the electroporated model when $\sigma_{max}/\sigma_0=3.6$.

TABLE 10

| 'a' | d(q1, p3x) = d5 | d(q2, p3x) = d6 | d5*d6 | d(q1, p4y) = d7 | d(q2, p4y) = d8 | d7*d8 | d5*d6/ d7*d8 |
|---|---|---|---|---|---|---|---|
| 1.1 | 0.89 | 3.09 | 2.750 | 1.493 | 1.493 | 2.230 | 1.23 |
| 1.11 | 0.88 | 3.10 | 2.728 | 1.501 | 1.501 | 2.252 | 1.21 |
| 1.12 | 0.87 | 3.11 | 2.706 | 1.508 | 1.508 | 2.275 | 1.19 |
| 1.13 | 0.86 | 3.12 | 2.683 | 1.516 | 1.516 | 2.297 | 1.17 |
| 1.14 | 0.85 | 3.13 | 2.661 | 1.523 | 1.523 | 2.320 | 1.15 |
| 1.15 | 0.84 | 3.14 | 2.638 | 1.531 | 1.531 | 2.343 | 1.13 |
| 1.16 | 0.83 | 3.15 | 2.615 | 1.538 | 1.538 | 2.366 | 1.11 |
| 1.17 | 0.82 | 3.16 | 2.591 | 1.546 | 1.546 | 2.389 | 1.08 |
| 1.18 | 0.81 | 3.17 | 2.568 | 1.553 | 1.553 | 2.413 | 1.06 |
| 1.19 | 0.80 | 3.18 | 2.544 | 1.561 | 1.561 | 2.436 | 1.04 |
| 1.2 | 0.79 | 3.19 | 2.520 | 1.568 | 1.568 | 2.460 | 1.02 |
| 1.21 | 0.78 | 3.20 | 2.496 | 1.576 | 1.576 | 2.484 | 1.00 |
| 1.22 | 0.77 | 3.21 | 2.472 | 1.584 | 1.584 | 2.509 | 0.99 |
| 1.23 | 0.76 | 3.22 | 2.447 | 1.592 | 1.592 | 2.533 | 0.97 |
| 1.24 | 0.75 | 3.23 | 2.423 | 1.599 | 1.599 | 2.558 | 0.95 |
| 1.25 | 0.74 | 3.24 | 2.398 | 1.607 | 1.607 | 2.583 | 0.93 |
| 1.26 | 0.73 | 3.25 | 2.373 | 1.615 | 1.615 | 2.608 | 0.91 |
| 1.27 | 0.72 | 3.26 | 2.347 | 1.623 | 1.623 | 2.633 | 0.89 |
| 1.28 | 0.71 | 3.27 | 2.322 | 1.630 | 1.630 | 2.659 | 0.87 |
| 1.29 | 0.70 | 3.28 | 2.296 | 1.638 | 1.638 | 2.684 | 0.86 |
| 1.3 | 0.69 | 3.29 | 2.270 | 1.646 | 1.646 | 2.710 | 0.84 |

Figure 23:
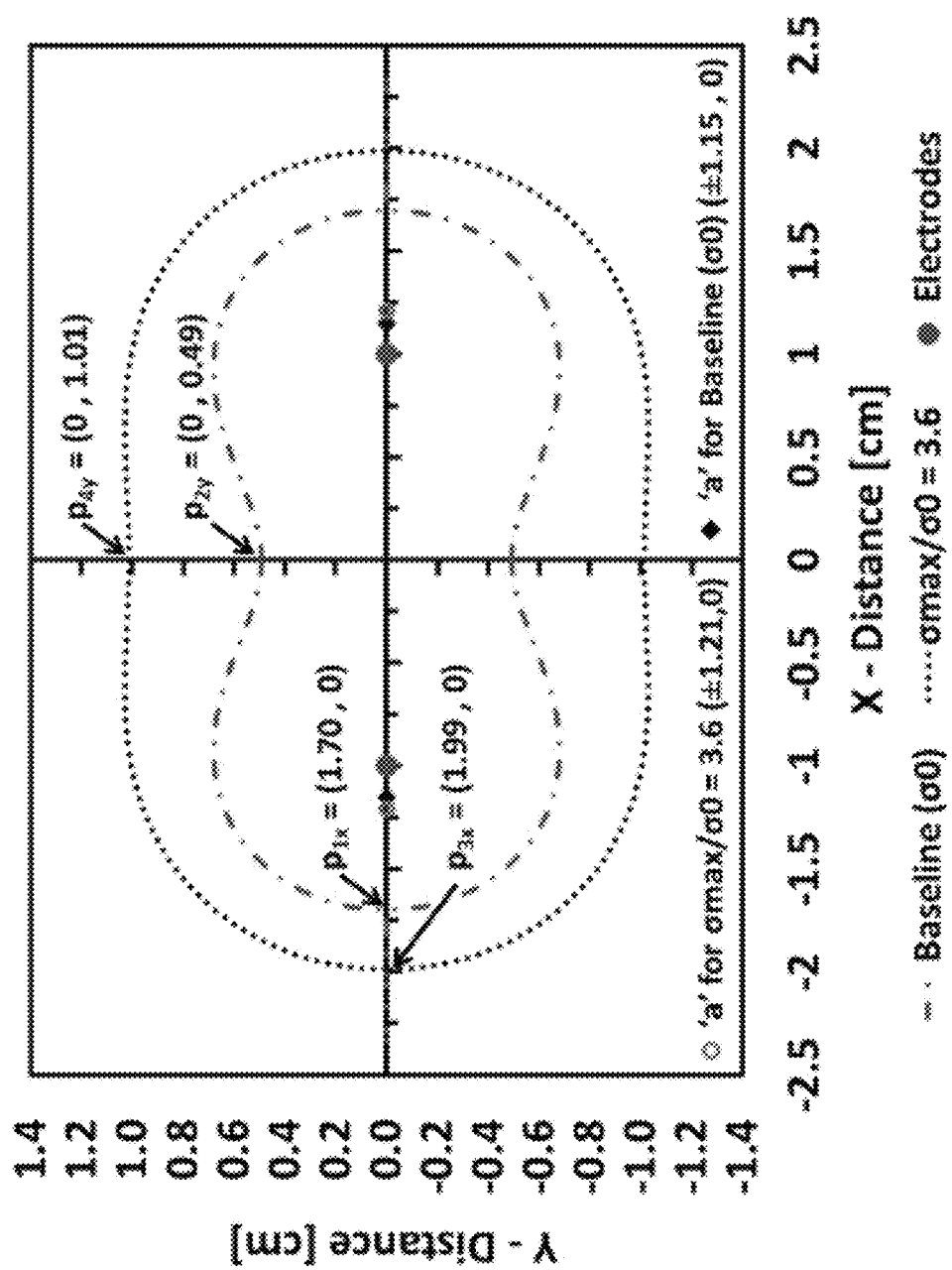
FIG. 23 is a representative Cassini curve showing zones of ablation derived using two single needle electrodes and the pre-pulse procedure to determine the ratio of maximum conductivity to baseline conductivity. For comparison purposes the baseline electric field isocontour is also presented in which no electroporation is taken into account.
Figure 24:
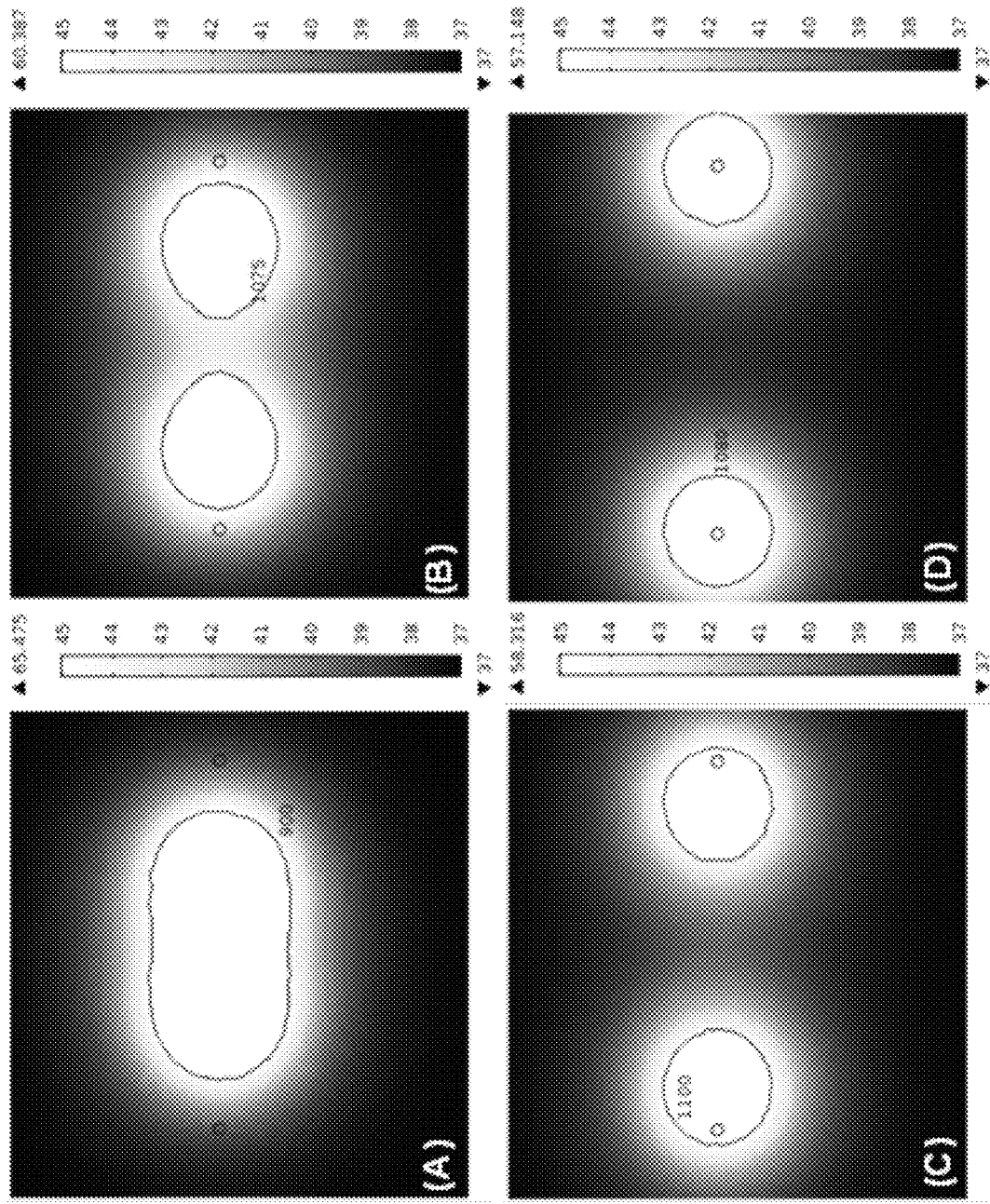
FIGS. 24A-24D are representative surface plots showing finite element temperature calculations at different electrode spacings. The surface plots show temperature distributions at t=90 seconds (Ninety pulses of 100 µs each) for 3000 V treatments with (A) 1.0 cm, (B) 1.5 cm, (C) 2.0 cm, and (D) 2.5 cm electrode spacing. Contour lines show approximate electric field correlating to T=45° C. (A) 900 V/cm, (B) 1075 V/cm, (C) 1100 V/cm, and (D) 1080 V/cm.
Figure 25:
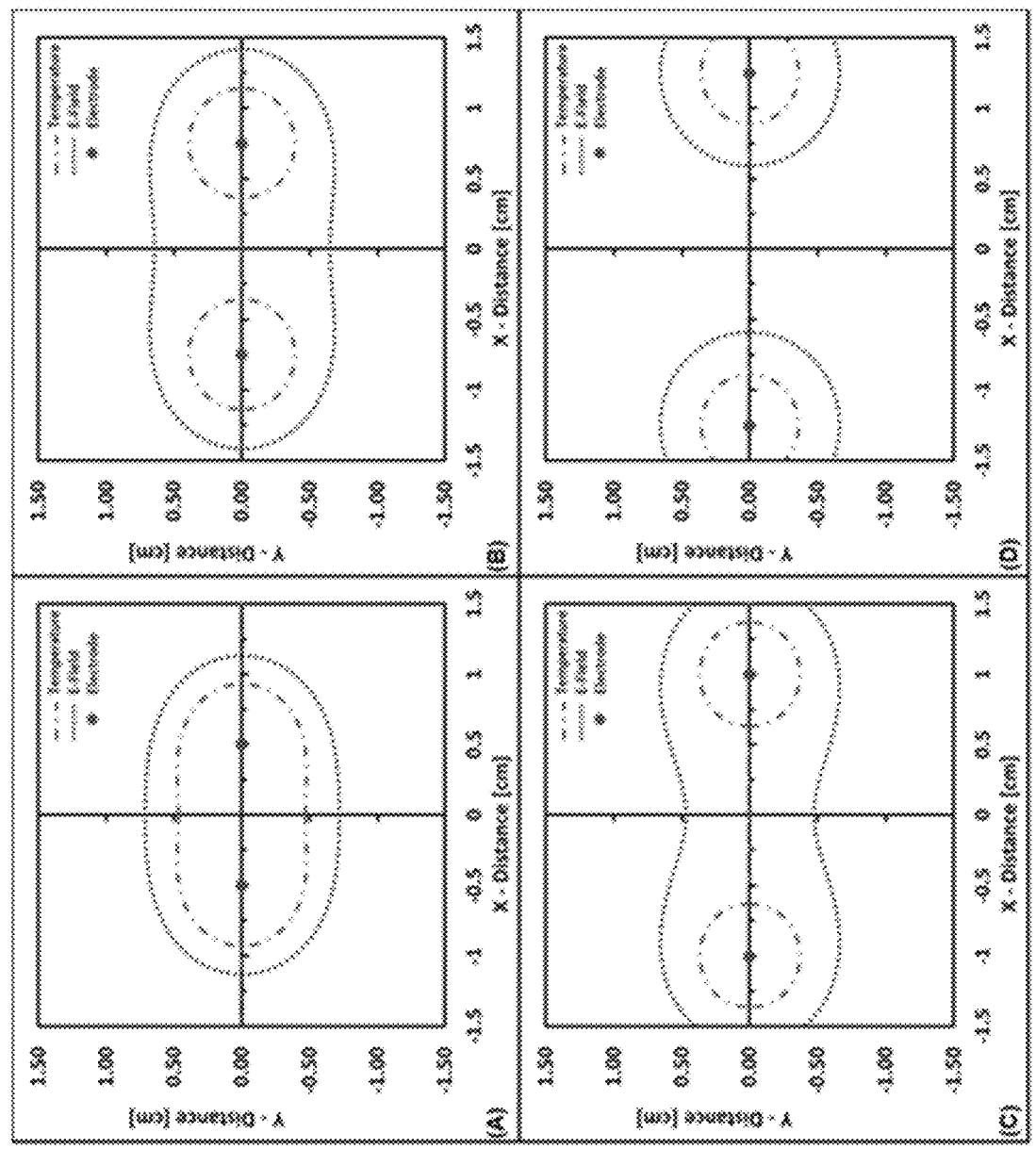
FIGS. 25A-25D are representative surface plots showing Cassini Oval Approximations at different electrode spacings. The surface plots show the temperature distribution at t=90 seconds (Ninety pulses of 100 µs each) for 3000 V treatments with (A) 1.0 cm, (B) 1.5 cm, (C) 2.0 cm, and (D) 2.5 cm electrode spacing. Red dashed lines show the Cassini oval correlating to T=45° C. and the black dotted lines show the Cassini oval correlating to 500 V/cm.
Figure 26:
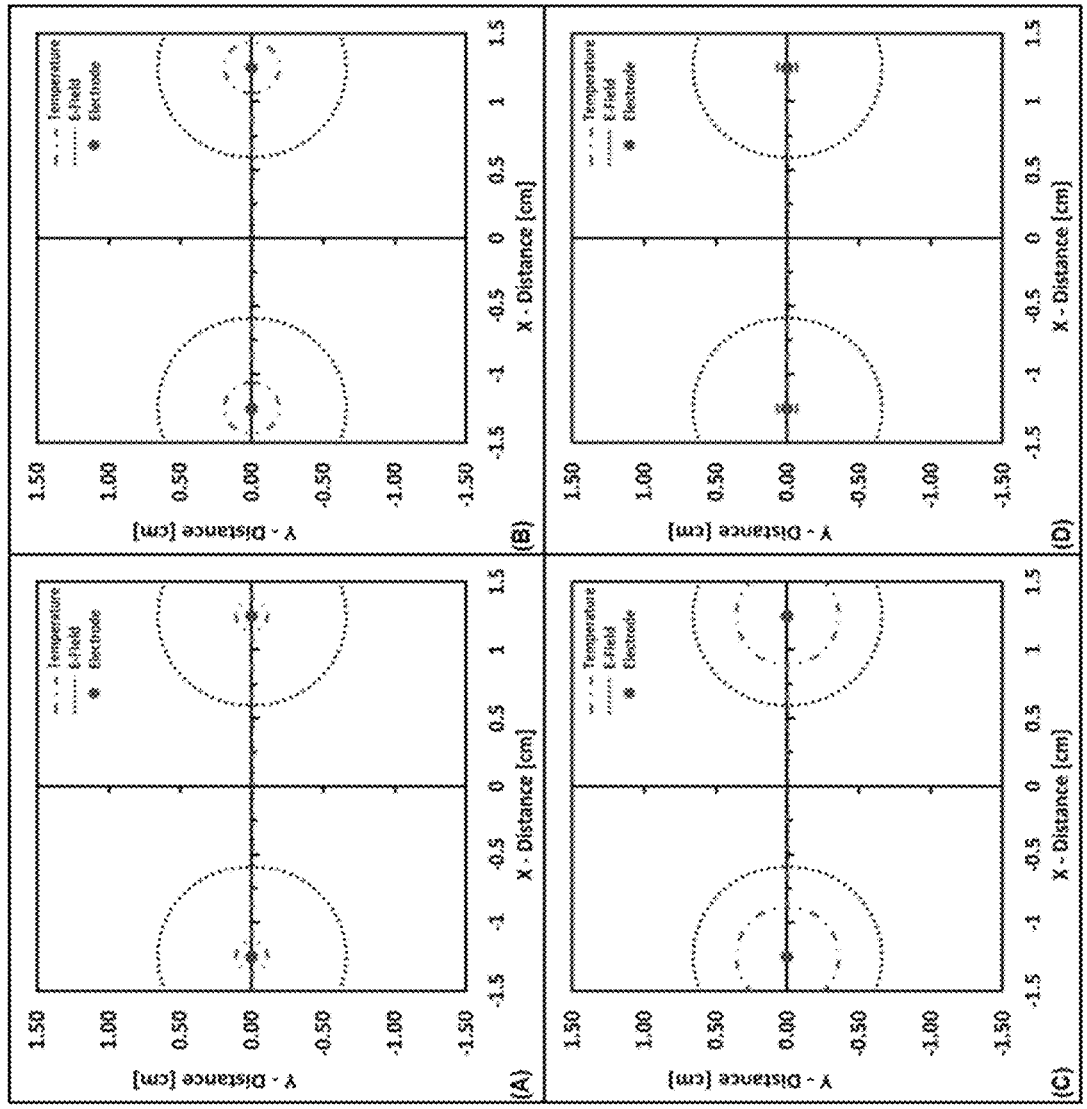
FIGS. 26A-26D are representative surface plots showing Cassini Oval Approximations at different times. The surface plots show the temperature distribution at (A) t=10 seconds, (B) t=40 seconds, (C) t=90 seconds, and (D) t=200 seconds. Treatment parameters were held constant at 3000 V, 1.5 cm exposure, and 2.5 cm electrode spacing. Red dashed lines show the Cassini oval correlating to T=45° C. and the black dotted lines show the Cassini oval correlating to 500 V/cm. The pulses were programmed with 100 µs duration.
Figure 27:
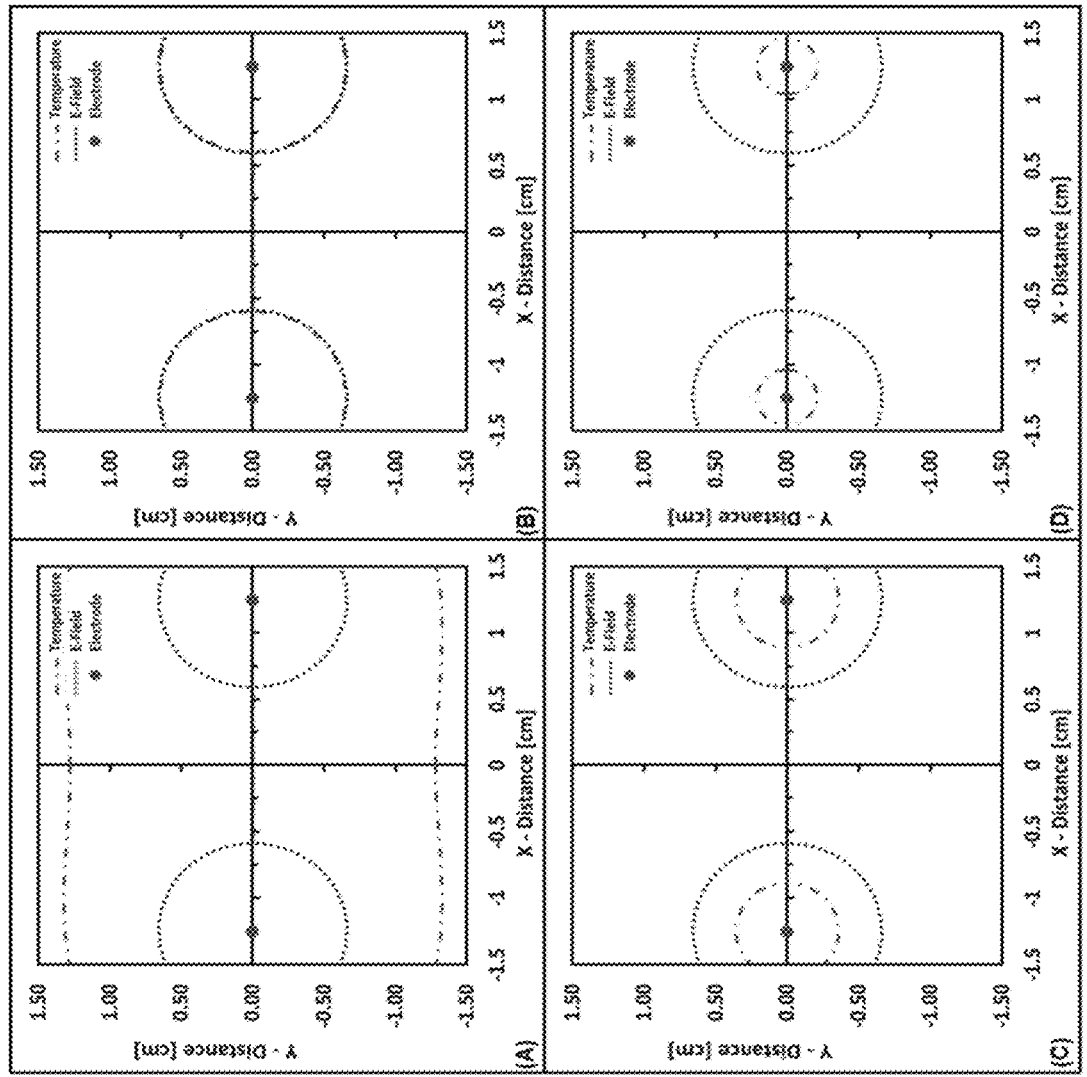
FIGS. 27A-27D are representative surface plots showing Cassini Oval Approximations at different temperatures. The surface plots show the temperature distribution at A) T=37.2° C., B) T=40° C., C) T=45° C., and D) T=50° C. Treatment parameters were held constant at 3000V, 1.5 cm exposure, and 2.5 cm electrode spacing at a time=90 seconds (Ninety pulses of 100 µs each). Red dashed lines show the Cassini oval correlating to the specified temperatures and the black dotted lines show the Cassini oval correlating to 500 V/cm.

In FIG. 23, it can be seen that with the implementation of the pre-pulse concept to determine the ratio of maximum conductivity to baseline conductivity one can derive a Cassini curve representing zones of ablation. In this case the 500 V/cm isocontour was specified but this technique could be used for any other isocontour that perhaps could represent the lethal IRE threshold for any other tissue/tumor type.

The polar equation for the Cassini curve could also be used because since it provides an alternate method for computation. The current Cartesian coordinate algorithm can work equally as well by using the polar equation of the Cassini curve. By solving for $r^2$ from eq. (4) above, the following polar equation was developed:

$$r^2 = a^2 \cos(2*\theta) +/- \sqrt{b^4 - a^4 \sin^2(2*\theta)} \quad (5)$$

and the 'a' and 'b' parameters should be determined as previously described in this application.

Example 8: Mapping of Electric Field and Thermal Contours Using a Simplified Data Cross-Referencing Approach This method can be used to identify the volume of tissue which will be elevated above a specific temperature (e.g. 45° C.) for specific treatment parameters. This contour can then be correlated with electric field intensity. This data in turn can be used to fit a contour using the Cassini oval software in the NANOKNIFE® System.

Methods: A mathematical model was built with COMSOL Multiphysics (Version 4.2a, Comsol Inc., Burlington, MA, USA) to estimate the temperature rise within tissue due to Joule heating effects. The electric field distribution within the simulation domain was solved using the Joule Heating module, as described by the Laplace Equation:

$$\nabla^2 \phi = 0$$

where $\phi$ is the electric potential, this equation is solved with boundary conditions:

$\vec{n} \cdot \vec{J} = 0$ at the boundaries $\phi = V_{in}$ at the boundary of the first electrode $\phi = 0$ at the boundary of the second electrode wherein $\vec{n}$ is the normal vector to the surface, $\vec{J}$ is the electrical current and $V_{in}$ is the electrical potential applied. Heat transfer in the solid domain was calculated as:

$$\rho C_p \frac{\partial T}{\partial t} = \nabla \cdot (k \nabla T) + Q_{jh} \left[\frac{W}{m^3}\right]$$

where ρ is the density, $C_p$ is the heat capacity, k is the thermal conductivity, and $Q_{jh}$ are the resistive losses $$Q_{jh} = J \cdot E \left[ \frac{W}{m^3} \right]$$

where J is the induced current density $$J = \sigma E \left[ \frac{A}{m^2} \right]$$

and σ is the tissue conductivity and E is the electric field $$E = -\nabla \phi \left[ \frac{V}{m} \right]$$

To account for the pulsed nature of the applied electric field, the Joule heating term in COMSOL was adjusted by adding in a duty cycle term equal to 100×10-6, the pulse duration (100 µs) (See P. A. Garcia, et al., "A Parametric Study Delineating Irreversible Electroporation from Thermal Damage Based on a Minimally Invasive Intracranial Procedure," Biomed Eng Online, vol. 10, p. 34, Apr. 30 2011).

In the Joule Heating Model equation view, the equation for resistive losses was modified to:

jh.Qrh=((jh.Jix+jh.Jex)*duty_cycle*jh.Ex+(jh.Jiy+jh.Jey)*duty_cycle*jh.Ey+(jh.Jiz+jh.Jez)*duty_cycle*jh.Ez)*(t<=90)+0*(t>90)

The resulting behavior was to calculate Joule heating only for the first 90 seconds (Ninety pulses of 100 µs each) of the simulation, after which, heat was allowed to dissipate within the tissue domain without additional heating. The parameters used in the simulations are provided in Table 11 below.

TABLE 11

Parameters used in COMSOL finite element model

| Parameter | Value | Unit | Description |
|---|---|---|---|
| r_e | 0.0005 | [m] | electrode radius |
| l_e | 0.15 | [m] | electrode length |
| l_t | 0.15 | [m] | tissue radius |
| h_t | 0.1 | [m] | tissue thickness |
| gap | 0.015 | [m] | center-to-center spacing |
| epsi_e | 0 | — | electrode permittivity |
| epsi_i | 0 | — | insulation permittivity |
| epsi_t | 0 | — | tissue permittivity |
| sigma_e | 2.22E+16 | [S/m] | electrode conductivity |
| sigma_i | 6.66E−16 | [S/m] | insulation conductivity |
| sigma_t | 0.2 | [S/m] | tissue conductivity |
| rho | 1080 | [kg/m3] | tissue density |
| Cp | 3890 | (J/(kg*K)] | tissue heat capacity |
| k | 0.547 | [W/(m*K)] | tissue thermal conductivity |
| duty_cycle | 1.00E−04 | — | pulse duty cycle |

Results: The COMSOL model was used to solve for temperature distributions at times between 0 and 900 seconds (10 second increment 0-100 s, 100 second increment 100-900 seconds). Electric Field and Temperature distributions were exported along lines on the x- (width) and y-axis (depth) with 100 micrometer spacing between data points. These values were imported into Excel and used as the basis for the Cassini oval calculations. FIGS. 24A-D shows the temperature distributions determined in COMSOL at 90 seconds (Ninety pulses of 100 µs each) for 3000 V treatments with 1.0 cm, 1.5 cm, 2.0 cm, and 2.5 cm electrode spacing and an electrode exposure of 1.5 cm. Contours on this figure show an approximate electric field which corresponds to tissue temperatures greater than 45° C. Simulations of each parameter required approximately 30 minutes to complete for a total computational duration of 15 hours.

FIGS. 25A-D shows the Cassini oval approximations for the temperature and electric field distributions based on the finite element simulation results. Iso-contour lines correspond to the tissue with temperature elevated above 45° C. and electric field above 500 V/cm, at the end of a 90 second IRE treatment (Ninety pulses of 100 µs).

The Cassini oval spreadsheet has been programmed so that the user can plot contour lines for specified voltages (500, 1000, 1500, 2000, 2500, 3000 V), electrode separations (0.5, 1.0, 1.5, 2.0, 2.5 cm), Simulation times (0-900 seconds), Temperatures (37-Tmax ° C.), and electric field intensities (0-infinity V/cm). FIGS. 26A-D shows the temperature distributions for a 3000 V, 2.5 cm spacing treatment at 10, 40, 90, and 200 seconds. The simulation accounts for Joule heating up to 90 seconds. After 90 seconds, Joule heating is no longer calculated and the temperature dissipates over time since the ninety-pulse delivery is completed.

The Cassini oval approximation can also be used to investigate the contours of any temperature. FIG. 27A-D shows the volumes of tissue that have been heated by at least 0.2, 3.0, 8.0, and 13.0° C. At 3000V, 1.5 cm exposure, and 2.5 cm electrode spacing at a time=90 seconds (Ninety pulses of 100 µs each), only a very small volume of tissue outside the ablation zone (500 V/cm) experiences any temperature increase.

Figure 28:
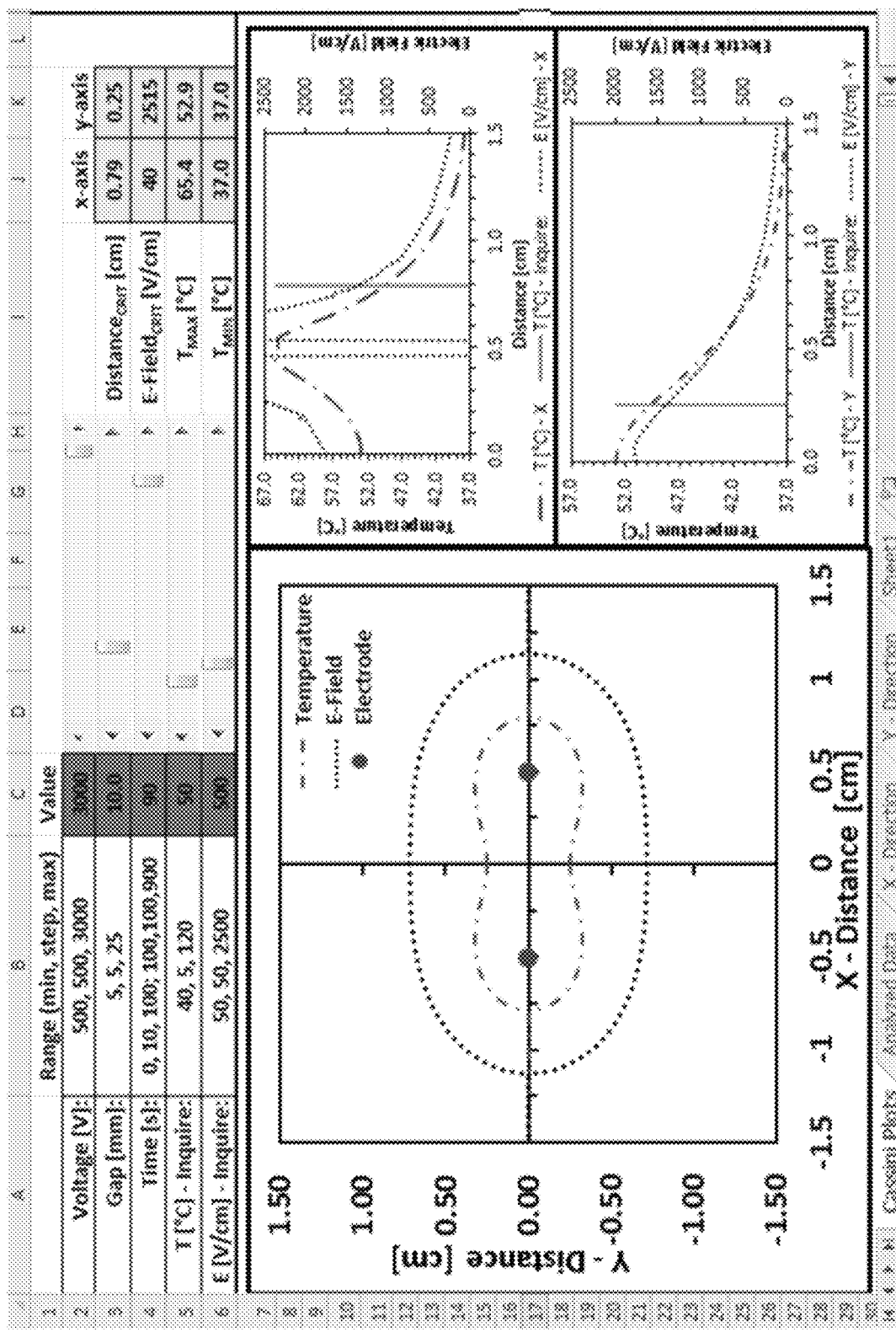
FIG. 28 is a screenshot of the Cassini Oval Approximation Tool using the following parameters: Voltage=3000 V, Gap=10 mm, Time=90 seconds (Ninety pulses of 100 µs each), Temperature=50° C., and Electric Field=500 V/cm. The red dashed line shows the Cassini oval correlating to 50° C. and the black dotted lines show the Cassini oval correlating to 500 V/cm.
Figure 29:
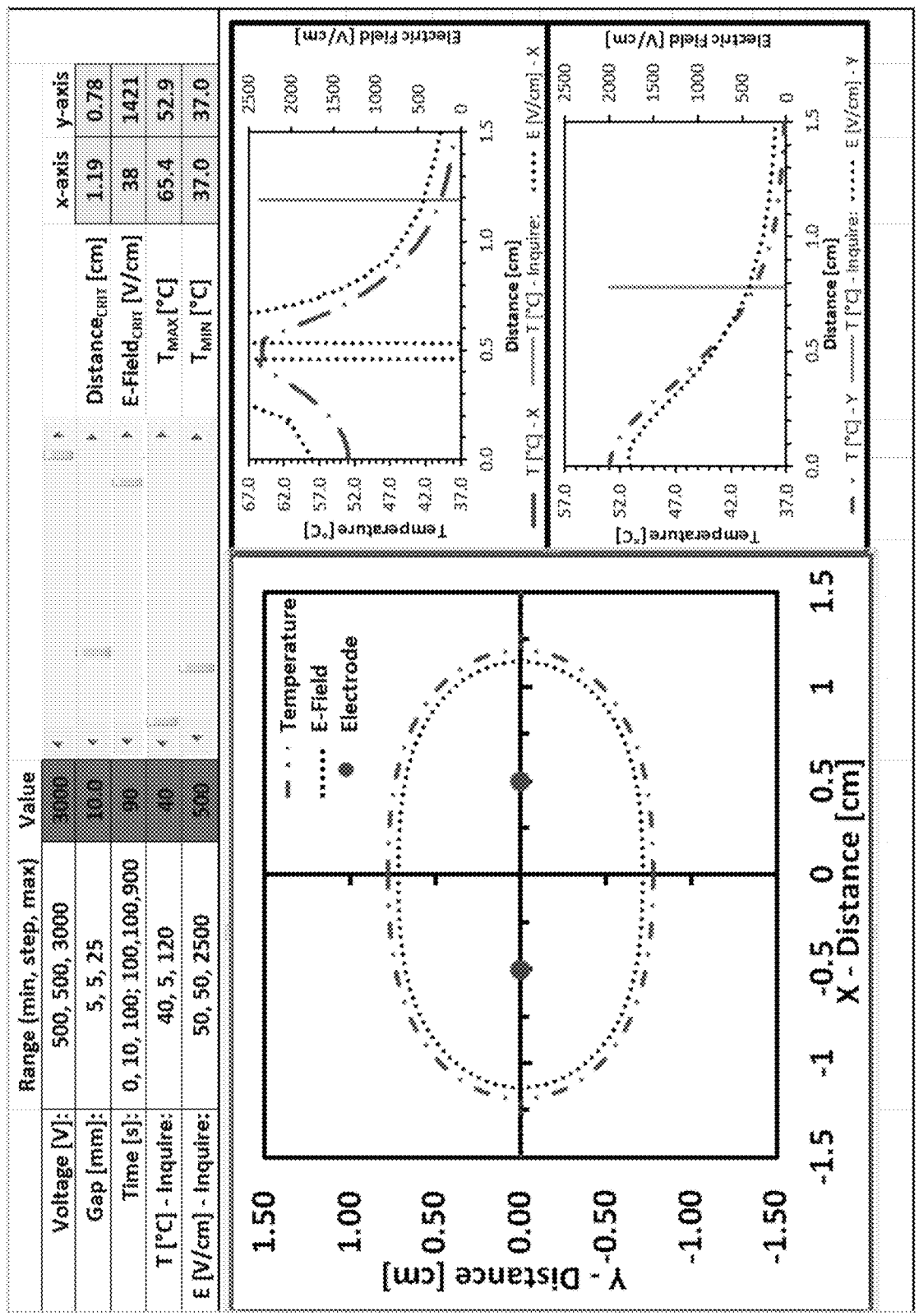
FIG. 29 is a screenshot of the Cassini Oval Approximation Tool using the following parameters: Voltage=3000 V, Gap=10 mm, Time=90 seconds (Ninety pulses of 100 µs each), Temperature=40° C., and Electric Field=500 V/cm. The red dashed lines show the Cassini oval correlating to 40° C. and the black dotted line show the Cassini oval correlating to 500 V/cm.
Figure 30A:
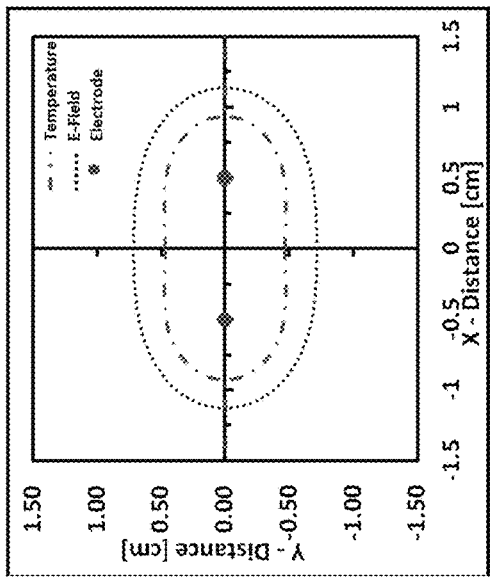
FIGS. 30A-30D are representative surface plots showing Cassini Oval Approximations at different temperature thresholds. The surface plots show the temperature and electric field distribution at A) T=40° C., B) T=45° C., C) T=50° C., and D) T=55° C. The other parameters are the same as those for FIGS. 28 and 29. The red dashed lines show the Cassini oval correlating to the specified temperatures and the black dotted lines show the Cassini oval correlating to 500 V/cm.
Figure 30B:
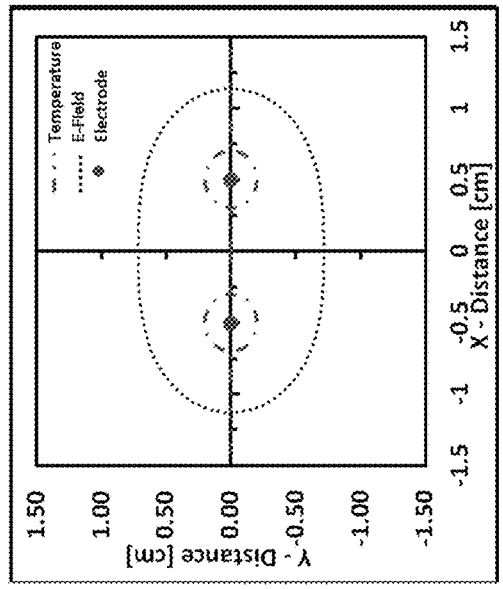
Figure 30C:
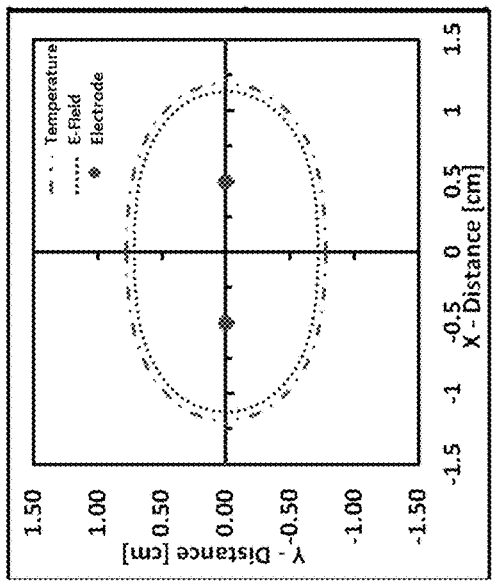
Figure 30D:
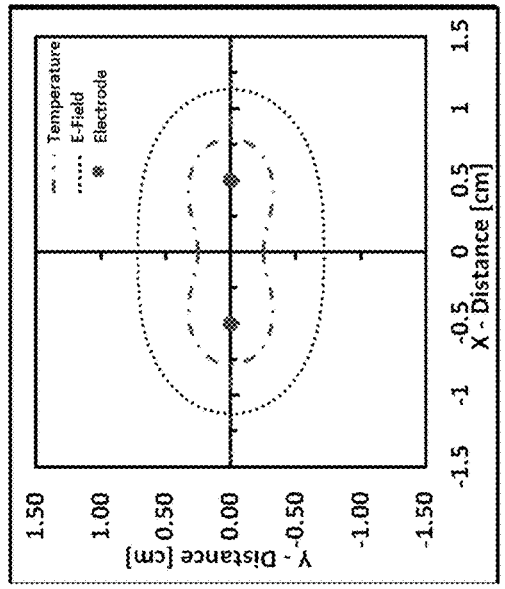
Figure 31A:
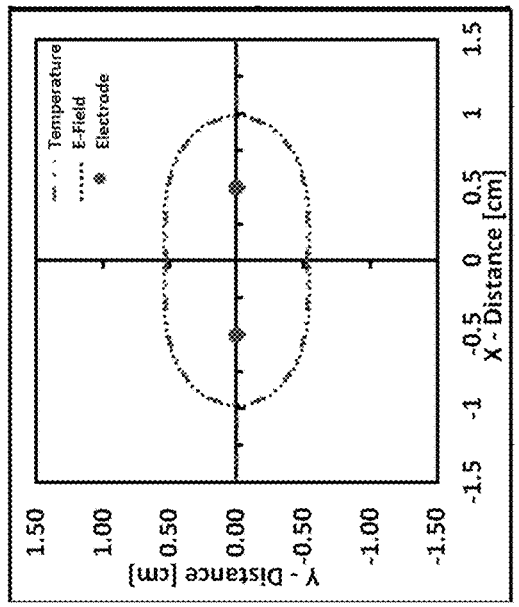
FIGS. 31A-31D are representative surface plots showing Cassini Oval Approximations at different voltages. The surface plots show the temperature and electric field distribution at A) 3000 V, B) 2000 V C) 1500 V and D) 1000 V. Other parameters were Gap=10 mm, Time=90 seconds (Ninety pulses of 100 µs each), Temperature=40° C., and Electric Field=500 V/cm. The red dashed lines show the Cassini oval correlating to 40° C. and the black dotted lines show the Cassini oval correlating to 500 V/cm.
Figure 31B:
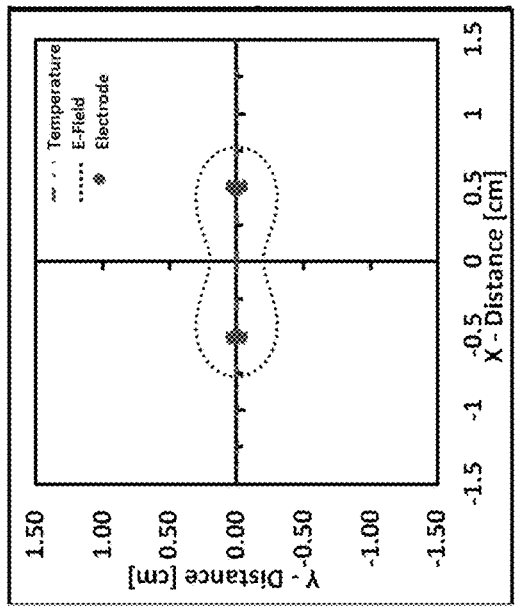
Figure 31C:
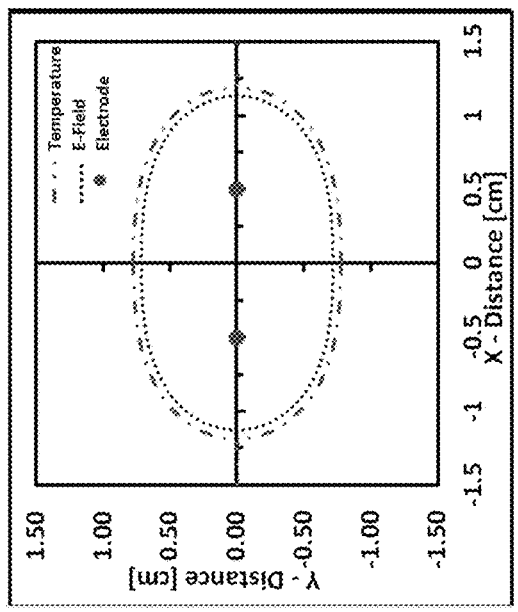
Figure 31D:
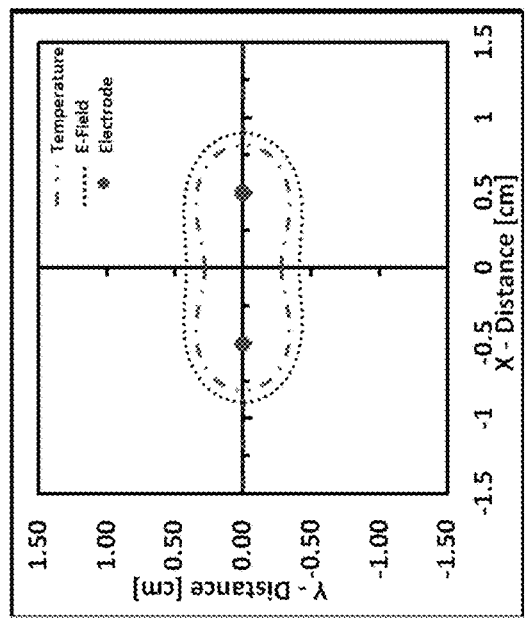
Figure 32A:
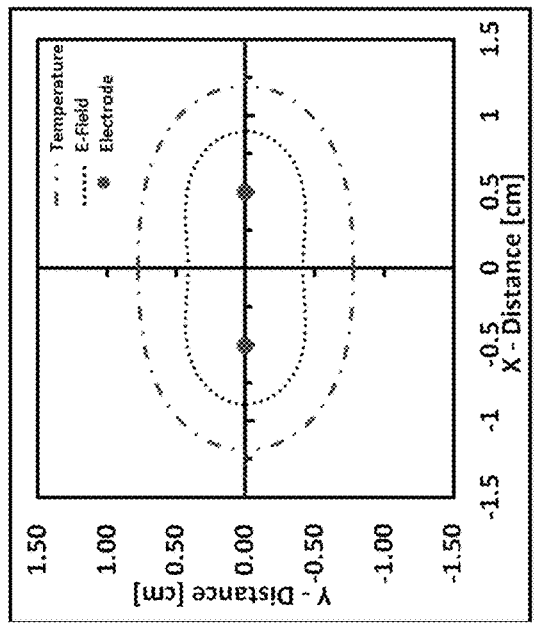
FIGS. 32A-32D are representative surface plots showing Cassini Oval Approximations at different electric field thresholds. The surface plots show the temperature and electric field distribution at A) 500 V/cm, B) 1000 V/cm, C) 1500 V/cm, and D) 2000 V/cm. Other parameters were Voltage=3000 V, Gap=10 mm, Time=90 seconds (Ninety pulses of 100 µs each), Temperature=40° C. The red dashed lines show the Cassini oval correlating to 40° C. and the black dotted lines show the Cassini oval correlating to the specified electric field thresholds.
Figure 32B:
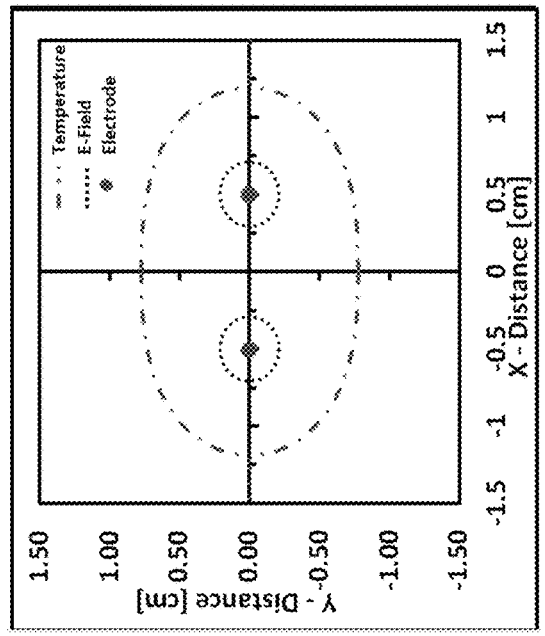
Figure 32C:
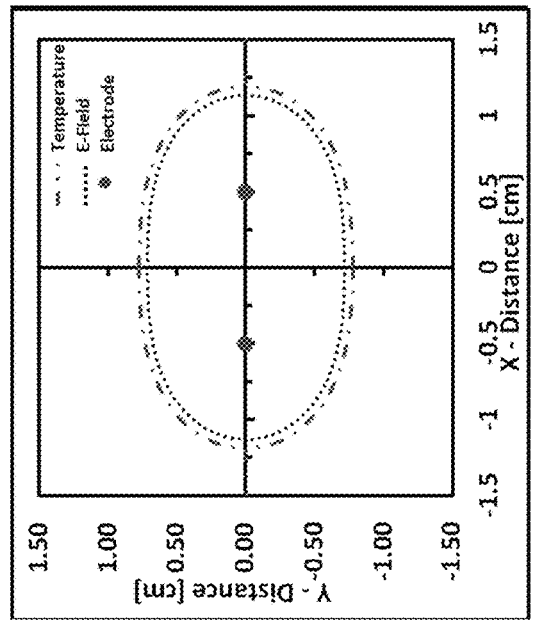
Figure 32D:
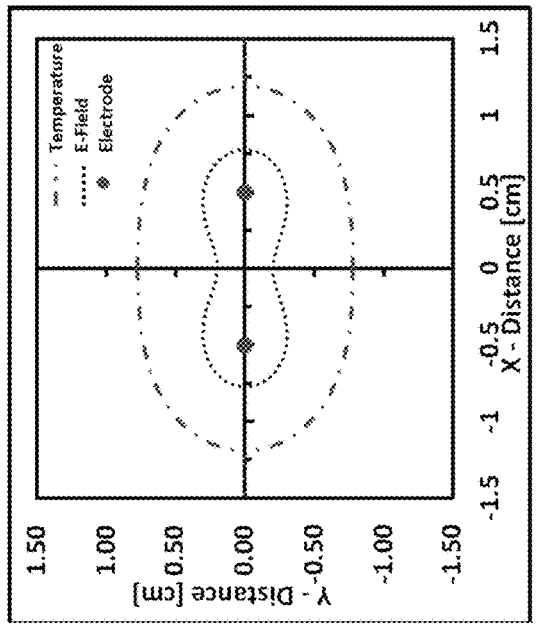

The Cassini oval approximation tool provides a rapid method for determining the temperature distribution expected for a given set of treatment parameters (FIGS. 28 and 29). Voltage, Electrode Spacing (Gap), Time, Temperature, and Electric Field can be selected by moving the slider or editing values in the green boxes. In embodiments, baseline conductivity of the target treatment area, and/or a conductivity for a specific tissue type, and/or a change in conductivity for the target treatment area can also, and/or alternatively, be selected. Voltage is selectable in 500 V discrete steps between 500 and 3000 V. Electrode Spacing (Gap) is selectable in 5.0 mm discrete steps between 5.0 mm and 25 mm. Time is selectable in 10 second discrete steps between 0 and 100 seconds and 100 second discrete steps between 100 and 900 seconds. The temperature contour line is selectable for any value between 37° C. and $T_{max}$, where $T_{max}$ is the maximum temperature in the tissue at a given treatment time. Additionally, the electric field distribution within the tissue can be set for any value.

Additional examples of usage of the Cassini oval approximation tool are shown in the following figures. FIGS. 30A-D show temperature contour lines for 40° C. (FIG. 30A), 45° C. (FIG. 30B), 50° C. (FIG. 30C), and 55° C. (FIG. 30D) for a 90 second IRE treatment (Ninety pulses of 100 µs each) with a voltage of 3000 V and electrode spacing of 10 mm. An electric field contour line of 500 V/cm is shown for comparison. As can be seen, the figures show a temperature gradient that expectedly increases from the 500 V/cm contour line toward the electrodes.

FIGS. 31A-D show contour lines representing a 40° C. temperature and a 500 V/cm electric field for a 90 second IRE treatment (Ninety pulses of 100 µs each) and electrode spacing of 10 mm at different voltages (3000V (FIG. 31A), 2000V (FIG. 31B), 1500V (FIG. 31C), and 1000V (FIG.

31D)). The figures show that the size of the electric field and heated area decreases in proportion to the decrease in voltage.

FIGS. 32A-D show electric field contour lines for 500 V/cm (FIG. 32A), 1000 V/cm (FIG. 32B), 1500 V/cm (FIG. 32C), and 2000 V/cm (FIG. 32D) fora 90 second IRE treatment (Ninety pulses of 100 µs each) with a voltage of 3000 V and electrode spacing of 10 mm. As can be seen, the figures show an electric field gradient that expectedly increases from the 40° C. contour line toward the electrodes.

Figure 33A:
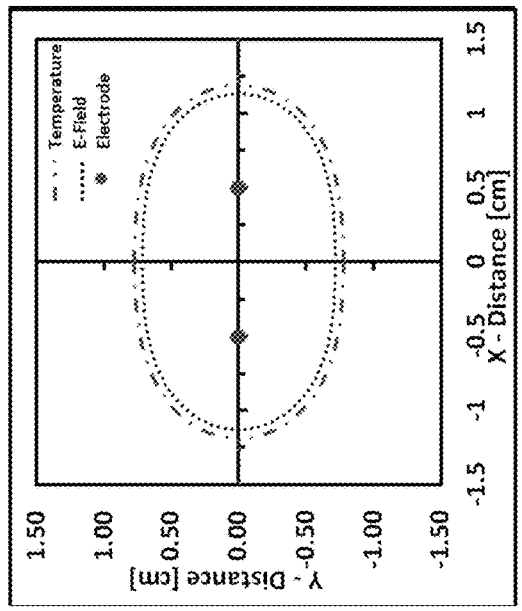
FIGS. 33A-33D are representative surface plots showing Cassini Oval Approximations at different electrode spacings. The surface plots show the temperature and electric field distribution at an electrode spacing of 5 mm, 10 mm, 15 mm, and 20 mm. Other parameters were Voltage=3000 V, Time=90 seconds (Ninety pulses of 100 µs each), Temperature=40° C., and Electric Field=500 V/cm. The red dashed lines show the Cassini oval correlating to 40° C. and the black dotted lines show the Cassini oval correlating to 500 V/cm.
Figure 33B:
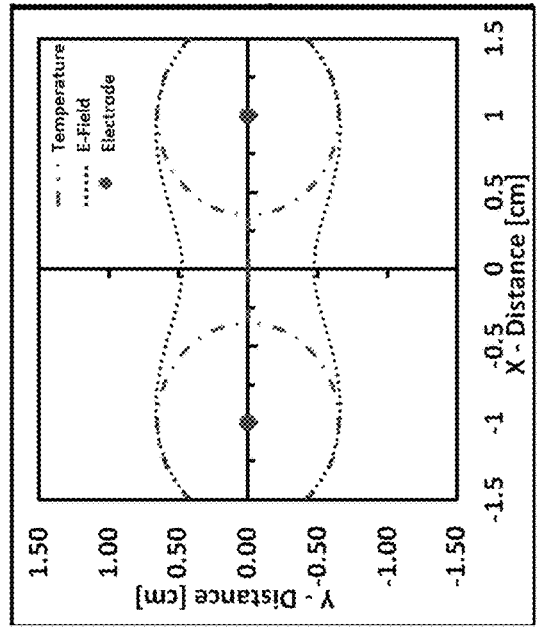
Figure 33C:
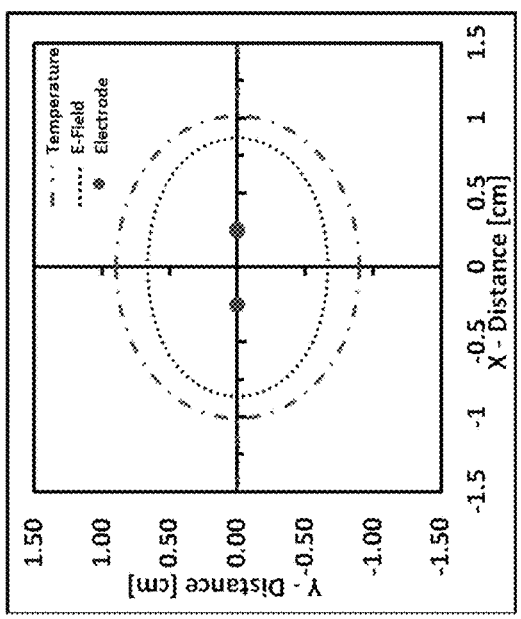
Figure 33D:
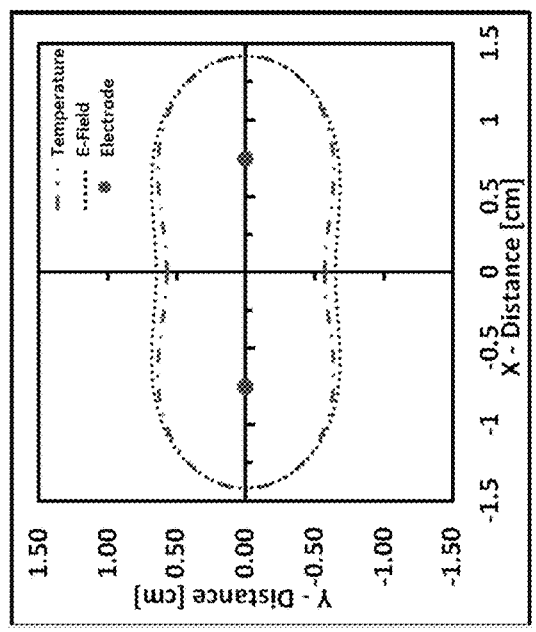
Figure 34A:
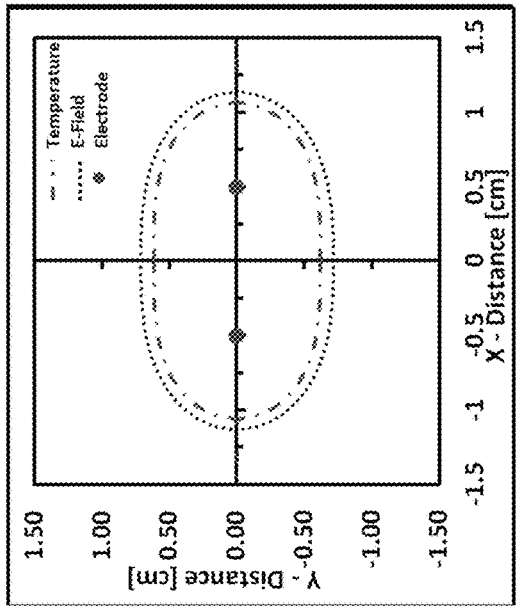
FIGS. 34A-34D are representative surface plots showing Cassini Oval Approximations at different times. The surface plots show the temperature and electric field distribution at A) 90 seconds (Ninety pulses of 100 µs each), B) 60 seconds (Sixty pulses of 100 µs each), C) 30 seconds (Thirty pulses of 100 µs each), and D) 10 seconds (Ten pulses of 100 µs each). Other parameters were Voltage=3000 V, Gap=10 mm, Temperature=40° C., and Electric Field=500 V/cm. The red dashed lines show the Cassini oval correlating to 40° C. and the black dotted lines show the Cassini oval correlating to 500 V/cm.
Figure 34B:
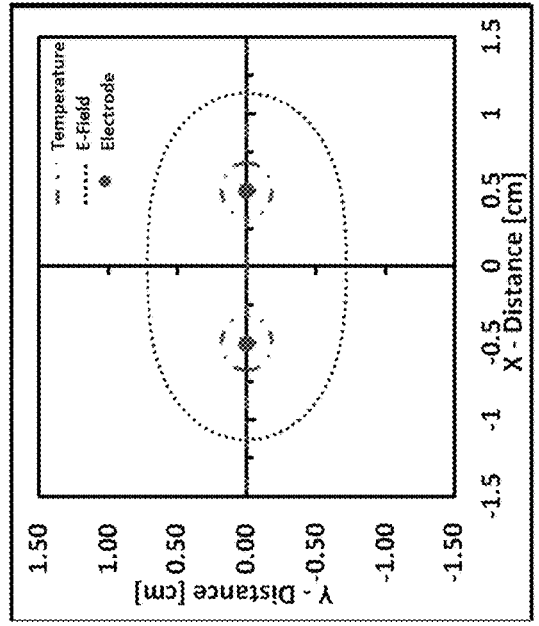
Figure 34C:
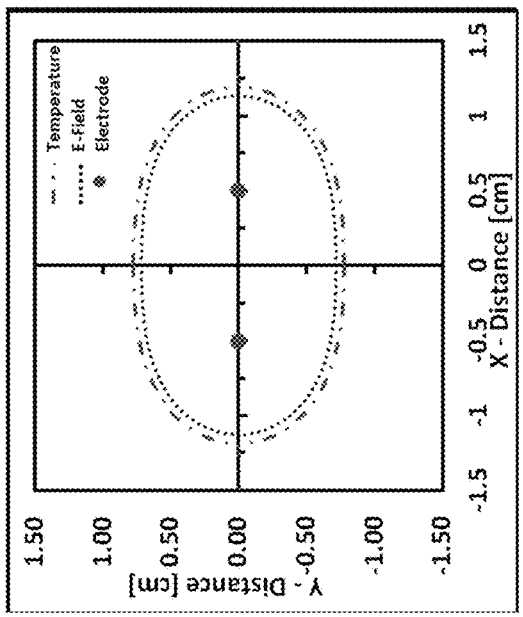
Figure 34D:
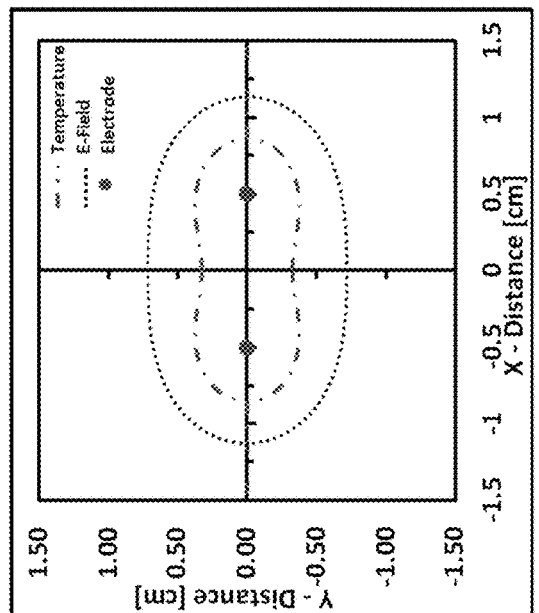

FIGS. 33A-D show contour lines representing a 40° C. temperature and a 500 V/cm electric field for a 90 second IRE treatment (Ninety pulses of 100 µs each) and voltage of 3000V at different electrode spacings (5 mm (FIG. 33A), 10 mm (FIG. 33B), 15 mm (FIG. 33C), 20 mm FIG. 33D)). As can be seen, increasing the electrode distance up to 15 mm widens the electric field and temperature contour. At an electrode distance of 20 mm, the electric field contour line widens and narrows, but the area heated to at least 40° C. is limited to a radius around each electrode.

FIGS. 34A-D show contour lines representing a 40° C. temperature and a 500 V/cm electric field for an IRE treatment of 3000V and an electrode spacing of 10 mm at different durations of treatment (90 seconds (Ninety pulses of 100 µs each) (FIG. 34A), 60 seconds (Sixty pulses of 100 µs each) (FIG. 34B), 30 seconds (Thirty pulses of 100 µs each) (FIG. 34C), 10 seconds (Ten pulses of 100 µs each) (FIG. 34D)). The graphs show that decreasing the durations of treatment reduces the area heated at least 40° C., but not the area of the electric field.

Figure 35:
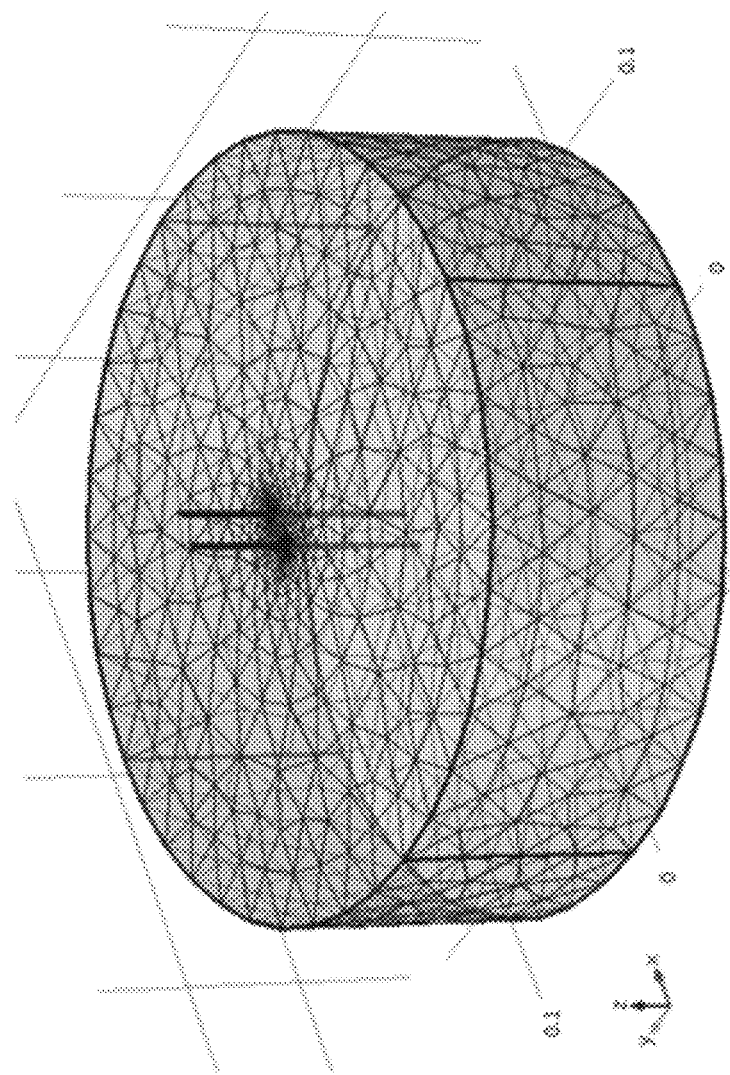
FIG. 35 is a representation of the COMSOL three-dimensional finite element domain and mesh used to calculate Cassini Oval values for the electric and thermal curves.

Model Limitations: This model was designed to give a rapid approximation for the temperature distribution within a volume of tissue without the need for complex finite element simulations. The data used to fit the Cassini oval curves uses values calculated assuming a constant conductivity of 0.2 S/m. This represents an approximate conductivity of human tissue, though conductivities of tissue vary between patients, tissue types, locations, and pathologies. Changing conductivity due to temperature increases or electroporation effects were not included. FIG. 35 shows the COMSOL three-dimensional finite element domain mesh used to calculate the electric field and temperature information to create the Cassini Oval values and curves.

The effects of blood flow and perfusion through the tissue, metabolic heat generation, or diffusion of heat at the tissue domain boundaries were not considered. It is anticipated that these effects will result in lower temperatures. Therefore, the visualization tool provides a conservative (worst case scenario) estimate as to the zones exposed to critical temperatures. The effects of changing conductivity and conductivities other than 0.2 S/m were not considered. Elevated conductivities are anticipated to result in higher temperatures within the tissue. Blood flow, metabolic heat generation, tissue conductivity, and ratios of changing conductivity are tissue type specific and will require the inclusion of in-vivo derived data.

Conclusions: In this Example, a real time visualization package plots the isocontour lines for an arbitrary temperature and electric field based on applied voltage, electrode spacing, and time. This data can be used to build intuition and instruct clinicians on reasonable expectations of temperature increases to prevent damage to critical structures of organs in the proximity of the treatment.

Example 9: Visualization Of Electric Field Distributions Using Different Configurations Of Bipolar Probes FIGS. 36A-36C show a representation of a visualization tool providing the 650 V/cm electric field distributions using different configurations of bipolar probes and includes dynamic change (3.6×) in electrical conductivity from the non-electroporated baseline for runs 7, 8, and 9 of the visualization. FIG. 36D is a table showing parameters of each run including electrode length, separation distance (insulation), and applied voltage. FIG. 36E is a table showing lesion dimensions for runs 7, 8, and 9. The results show that as the length of the bipolar electrode increases, the size of the zone of ablation increases.

Example 10: Determining the IRE Threshold for Different Tissues According to Conductivity In this Example, as shown in the following figures, the "Goldberg" data (red-dashed line), is from pre-clinical data for a particular treatment (2700V, 90 pulses, 100 µs energized per pulse). By adjusting one or more treatment parameters, a user can determine the electric field threshold for these types of tissues (black-solid line).

An important aspect of this model is that the tissue conductivity is allowed to change as a function of electric field to simulate what happens when the tissue becomes irreversibly electroporated. This function is 'sigmoidal' or 'S' shaped and increases from a baseline (non-electroporated) to a conductivity multiplier (electroporated). This transition happens at a specific electric field intensity.

Figure 37:
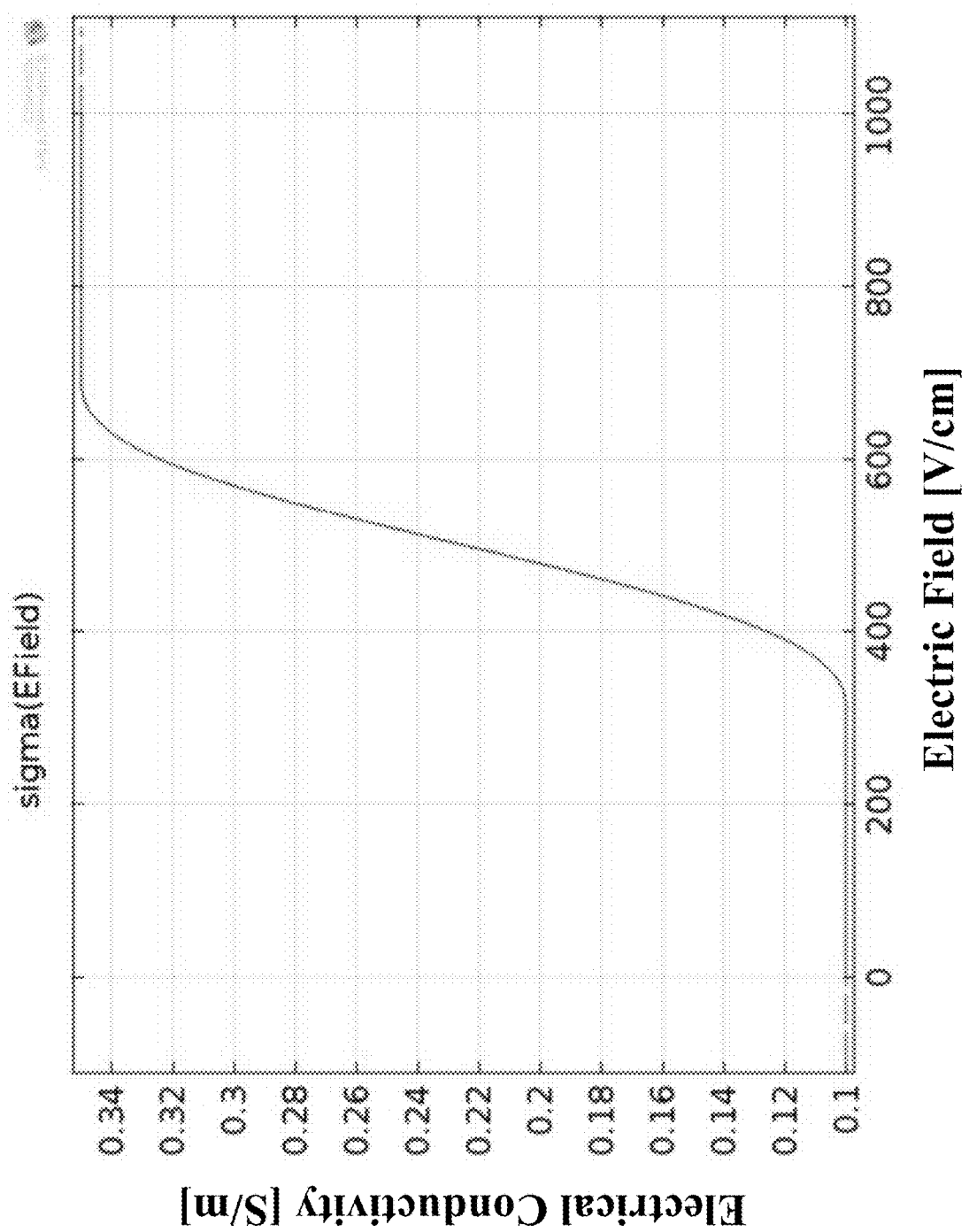
FIG. 37 is a graph showing electrical conductivity (S/m, y-axis) plotted against electric field strength (V/cm, x-axis).
Figures 38A, 38B, 38C:
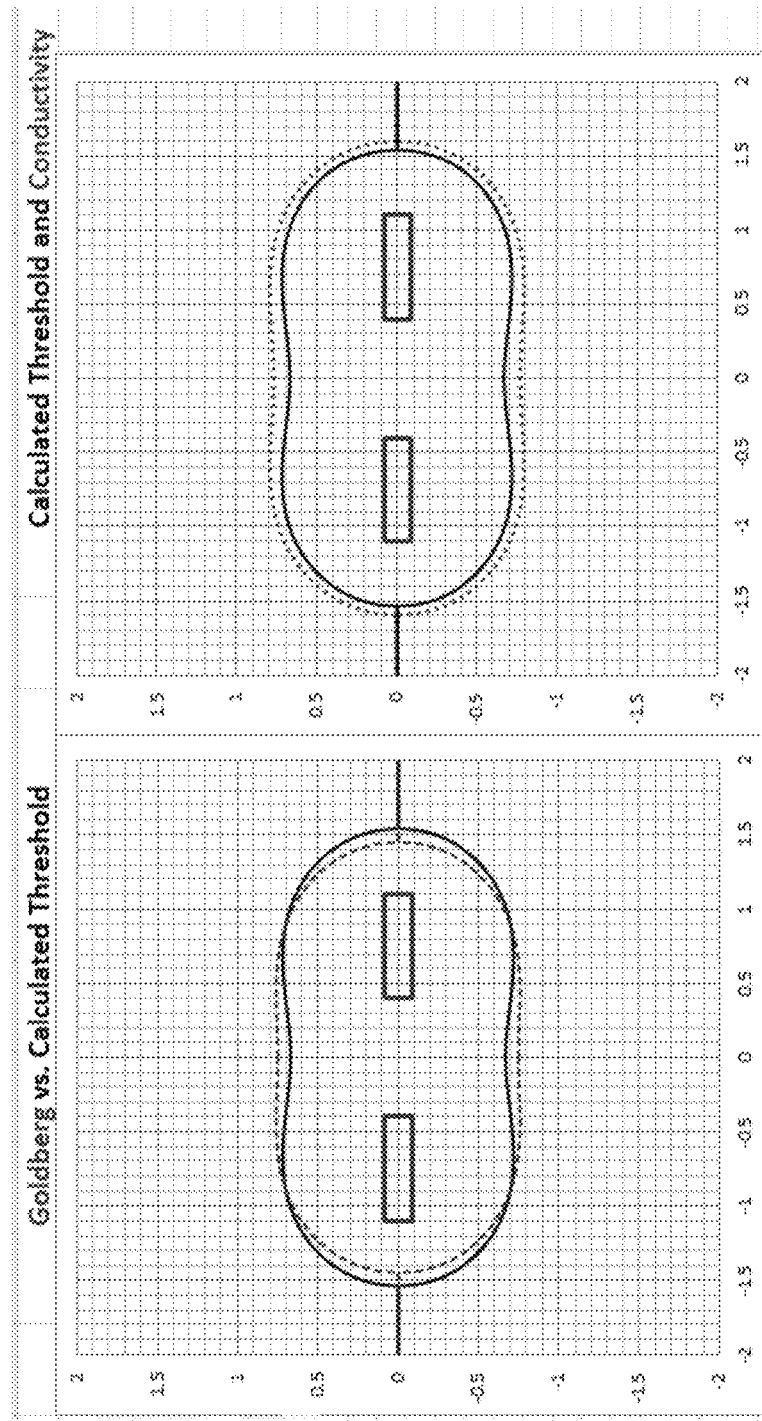
FIG. 38A is a representative contour plot showing the "Goldberg" data (red dashed line) vs a calculated threshold (solid black line) based on the parameters shown in FIG. 38C. The x and y axes represent distance [cm].
FIG. 38B is a representative contour plot showing the conductivity (blue dotted line) vs. a calculated threshold (solid black line) based on the parameters shown in FIG. 38C. The x and y axes represent distance [cm].
FIG. 38C is a table showing the parameters used to generate the contour plots of FIGS. 38A and 38B.

In FIG. 37, the conductivity changes from 0.1 to 0.35 at an electric field centered at 500 V/cm. A user can change/shift all of the values in this curve to fit the experimental data. FIG. 38A is a contour plot comparing the "Goldberg" data (red dashed line) with a calculated threshold (solid black line) based on the parameters shown in FIG. 38C, explained below. FIG. 38B is a contour plot comparing the conductivity (blue dotted line) with a calculated threshold (solid black line) based on the parameters shown in FIG. 38C.

IRE Threshold [V/cm]: This parameter is the electric field at which the change in conductivity occurs for the sigmoidal curve. By changing this value, the sigmoidal curve shifts to the left or right. A value of 500 V/cm has been found to fit the data best.

Transition zone: This is the 'width' of the transition zone. By changing this value, the rate at which the conductivity increase changes. In FIG. 37, this value is set to 0.49, the widest transition possible. It has been found that a transition of 0.2 matches the experimental data best.

Sigma: This is the baseline conductivity before treatment. It has been found that a value of 0.067 (or 0.1) works well.

Conductivity Multiplier: This is how much the conductivity increases by when the tissue has been irreversibly electroporated. A 3.6× increase has been found experimentally for liver and fits the data well.

E-Field: This is the parameter that is adjusted to find the in-vivo irreversible electroporation threshold. With the values set for the other parameters above, it has been found that IRE should occur at a threshold of 580 V/cm to match the lesions found in-vivo.

Figure 39A:
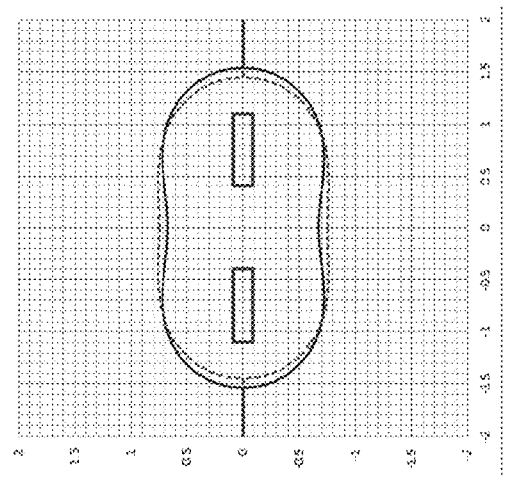
FIGS. 39A-39C are representative contour plots showing the "Goldberg" data (red dashed line) and calculated threshold (solid black line) and FIGS. 39D-39F are contour plots showing the conductivity (blue dotted line) and calculated threshold (solid black line) for conductivities of 2, 3, and 4, respectively. The other parameters are the same as those in the table of FIG. 38C. The x and y axes represent distance [cm].
Figure 39B:
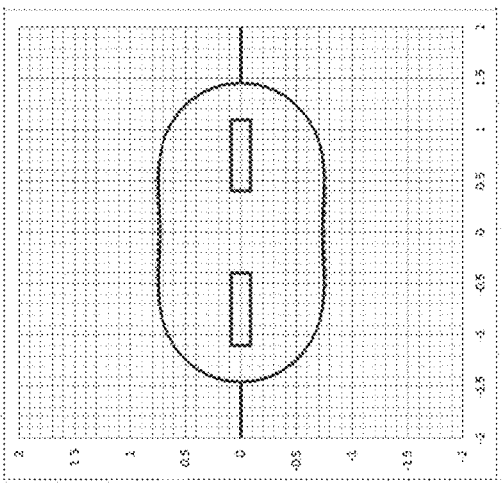
Figure 39C:
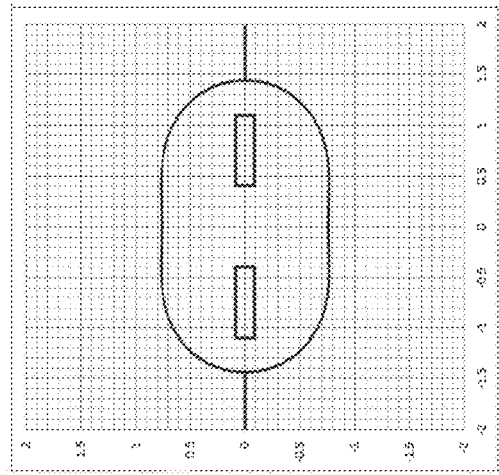
Figure 39D:
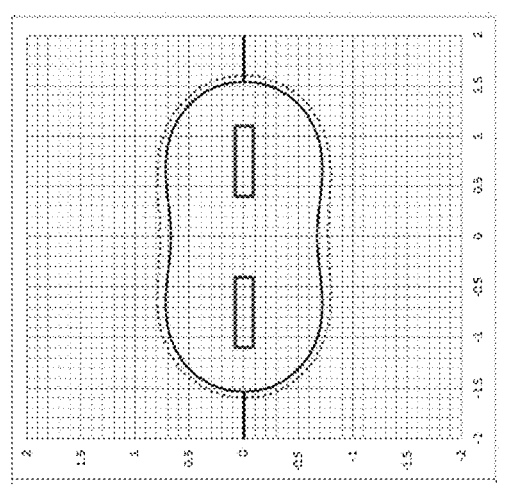
Figure 39E:
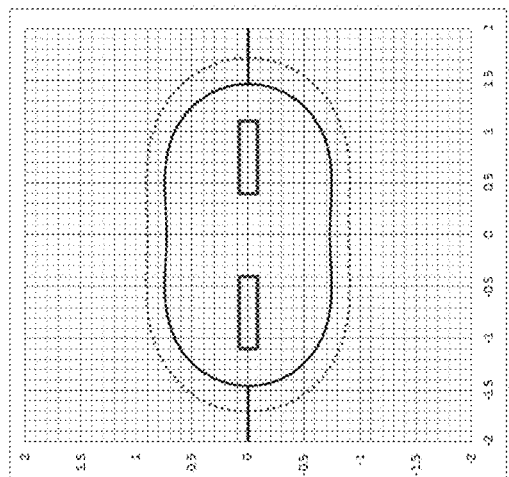
Figure 39F:
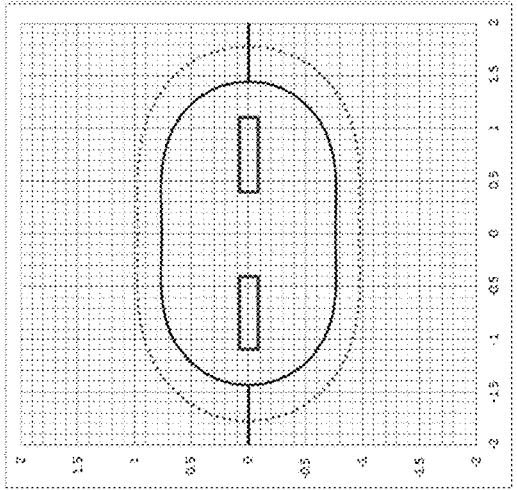

The following figures show how modifying the conductivity of the tissue changes the calculated zone of ablation. FIGS. 39A-39F were performed according to the parameters in FIG. 38C, except the conductivity of the tissue was modified. FIGS. 39A-39C show the "Goldberg" data and calculated threshold and FIGS. 39D-39F show the conductivity and calculated threshold for conductivity multipliers of 2, 3, and 4, respectively. As can be seen, the calculated ablation zone increases in comparison to the Goldberg preclinical data as conductivity increases.

Figure 40A:
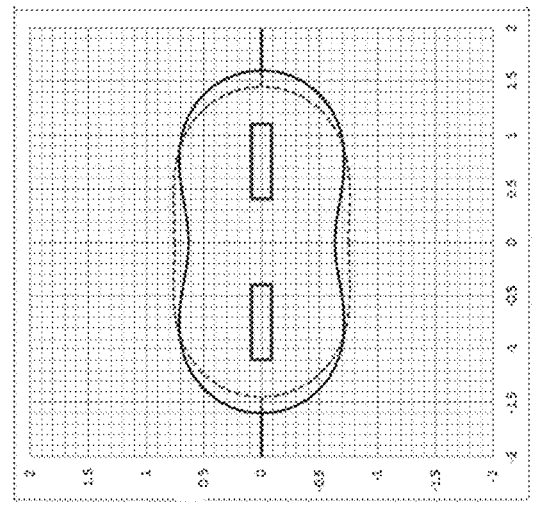
FIGS. 40A-40C are representative contour plots showing the "Goldberg" data (red dashed line) and calculated threshold (solid black line) and FIGS. 40D-40F are contour plots showing the conductivity (blue dotted line) and calculated threshold (solid black line) for conductivity multipliers of 2, 3, and 4, respectively. Other parameters used to generate the plots of FIGS. 40A-40F include an IRE Threshold of 600 V/cm, a transition zone of 0.4, a Voltage of 700 V, an E-Field of 700 V/cm, and a Sigma (baseline electrical conductivity) of 0.20 S/m. The x and y axes represent distance [cm].
Figure 40B:
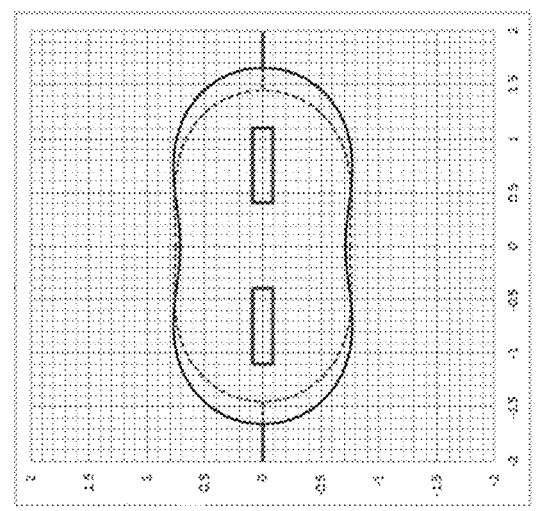
Figure 40C:
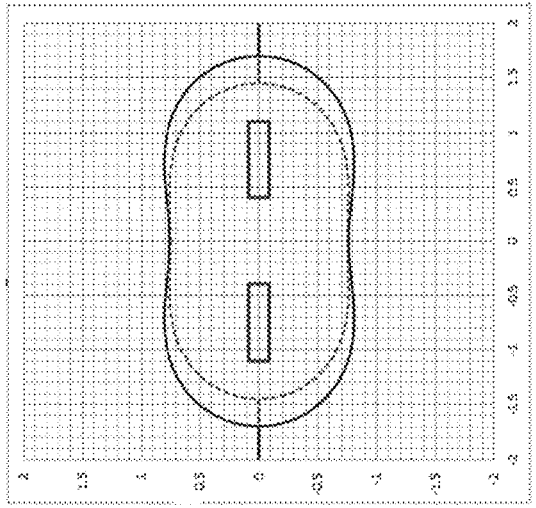
Figure 40D:
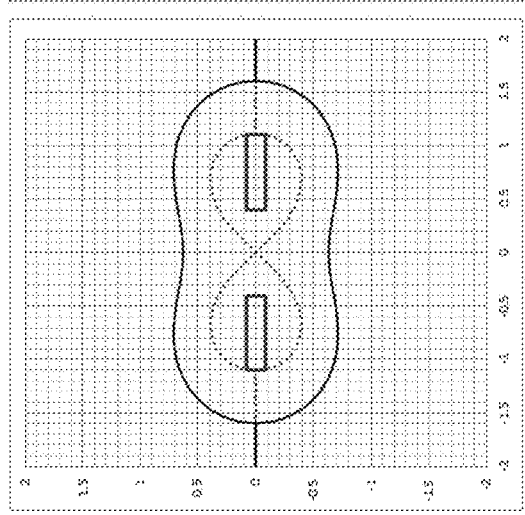
Figure 40E:
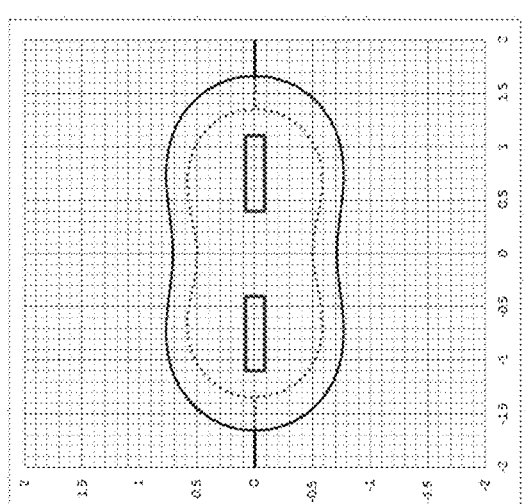
Figure 40F:
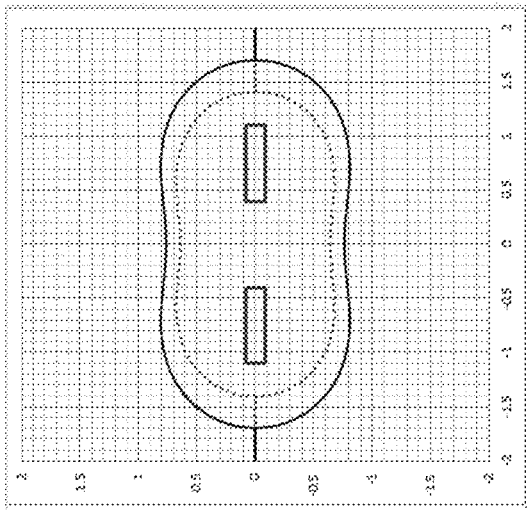

FIGS. 40A-40F were performed for an IRE Threshold of 600 V/cm, a transition zone of 0.4, a Voltage of 700 V, an E-Field of 700 V/cm, and a Sigma (electrical conductivity) of 0.20 S/m. FIGS. 40A-40C show the "Goldberg" data and calculated threshold and FIGS. 40D-40F show the conductivity and calculated threshold for conductivity multipliers of 2, 3, and 4, respectively.

Figure 41A:
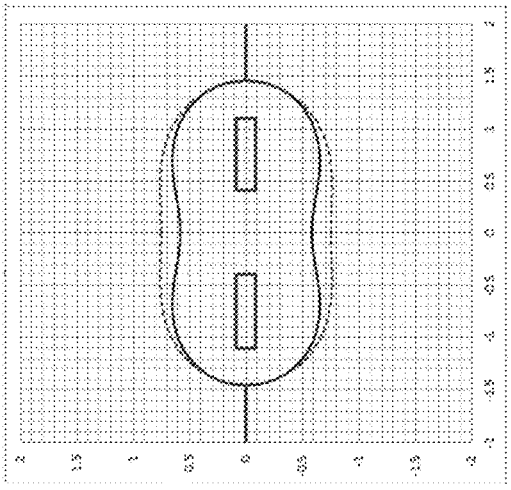
FIGS. 41A-41C are representative contour plots showing the "Goldberg" data (red dashed line) and calculated threshold (solid black line) and FIGS. 41D-41F are contour plots showing the conductivity (blue dotted line) and calculated threshold (solid black line) for conductivity multipliers of 2, 3, and 4, respectively. Other parameters used to generate the plots of FIGS. 41A-41F include an IRE Threshold of 1000 V/cm, transition zone of 0.2, Voltage of 2700 V, E-Field of 700 V/cm, and Sigma (baseline electrical conductivity) of 0.20 S/m. The x and y axes represent distance [cm].
Figure 41B:
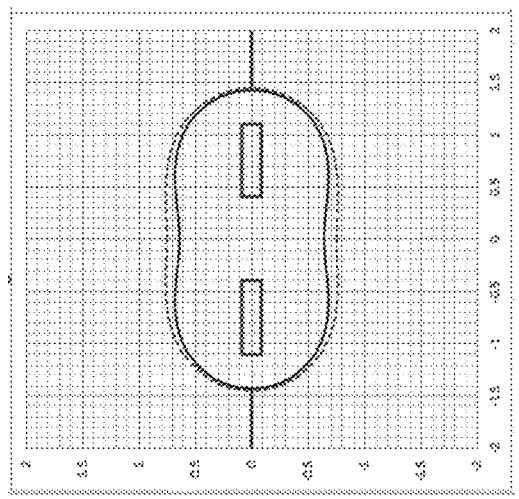
Figure 41C:
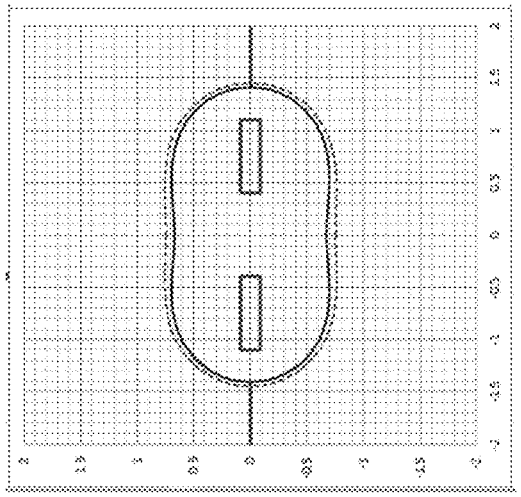
Figure 41D:
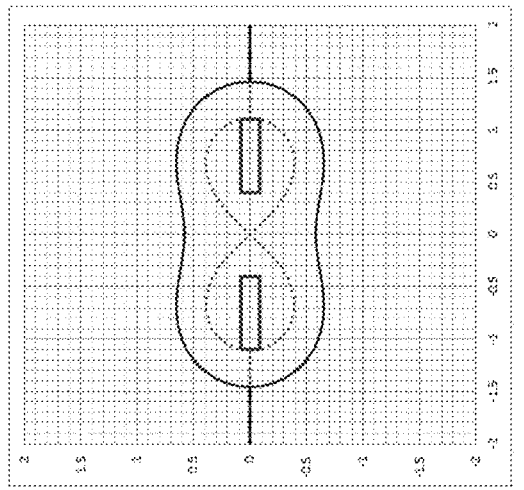
Figure 41E:
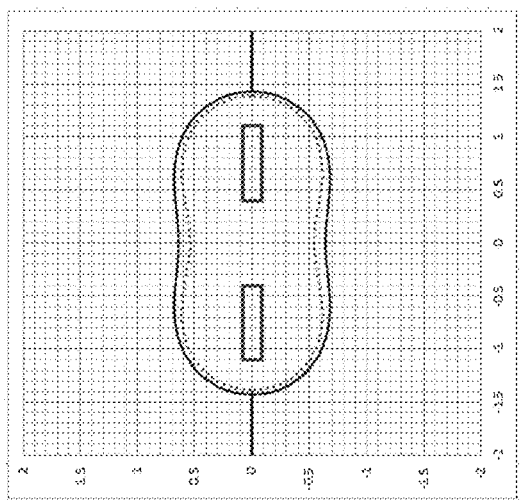
Figure 41F:
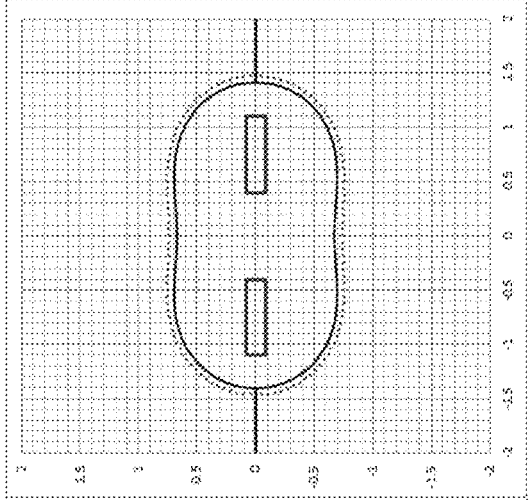

FIGS. 41A-41F were performed for an IRE Threshold of 1000 V/cm, a transition zone of 0.2, a Voltage of 2700 V, an E-Field of 700 V/cm, and a Sigma (electrical conductivity) of 0.20 S/m. FIGS. 41A-41C show the "Goldberg" data and calculated threshold and FIGS. 41D-41F show the conductivity and calculated threshold for conductivity multipliers of 2, 3, and 4, respectively.

As can be seen, the calculated ablation zone increases in comparison to the Goldberg preclinical data as the conductivity multiplier increases.

Example 11: Correlating Experimental And Numerical IRE Lesions Using The Bipolar Probe Purpose: To establish a function that correlates experimentally produced zones of ablations in in vivo porcine tissue with the corresponding IRE pulse parameters (duration, number, strength) and single needle electrode configuration.

A mathematical function was developed that captures the IRE response in liver tissue as a function of applied voltage, pulse number, and pulse duration for the bipolar electrode configuration. It is important to note that the inventors used a rate equation that was fit to the 1.5 cm×2.9 cm IRE zone of ablation but this has not been validated experimentally (See Golberg, A. and B. Rubinsky, *A statistical model for multidimensional irreversible electroporation cell death in tissue*. Biomed Eng Online, 2010. 9(1): p. 13). The results below provide insight as to the effect of different pulse parameters and electrode/insulation dimensions in the resulting zone of IRE ablation in order to optimize the bipolar probe electrode for clinical use. In order to perform a computationally efficient study, the models were constructed in a 2-D axis-symmetric platform which generates results that are representative of the 3-D space.

Figure 42:
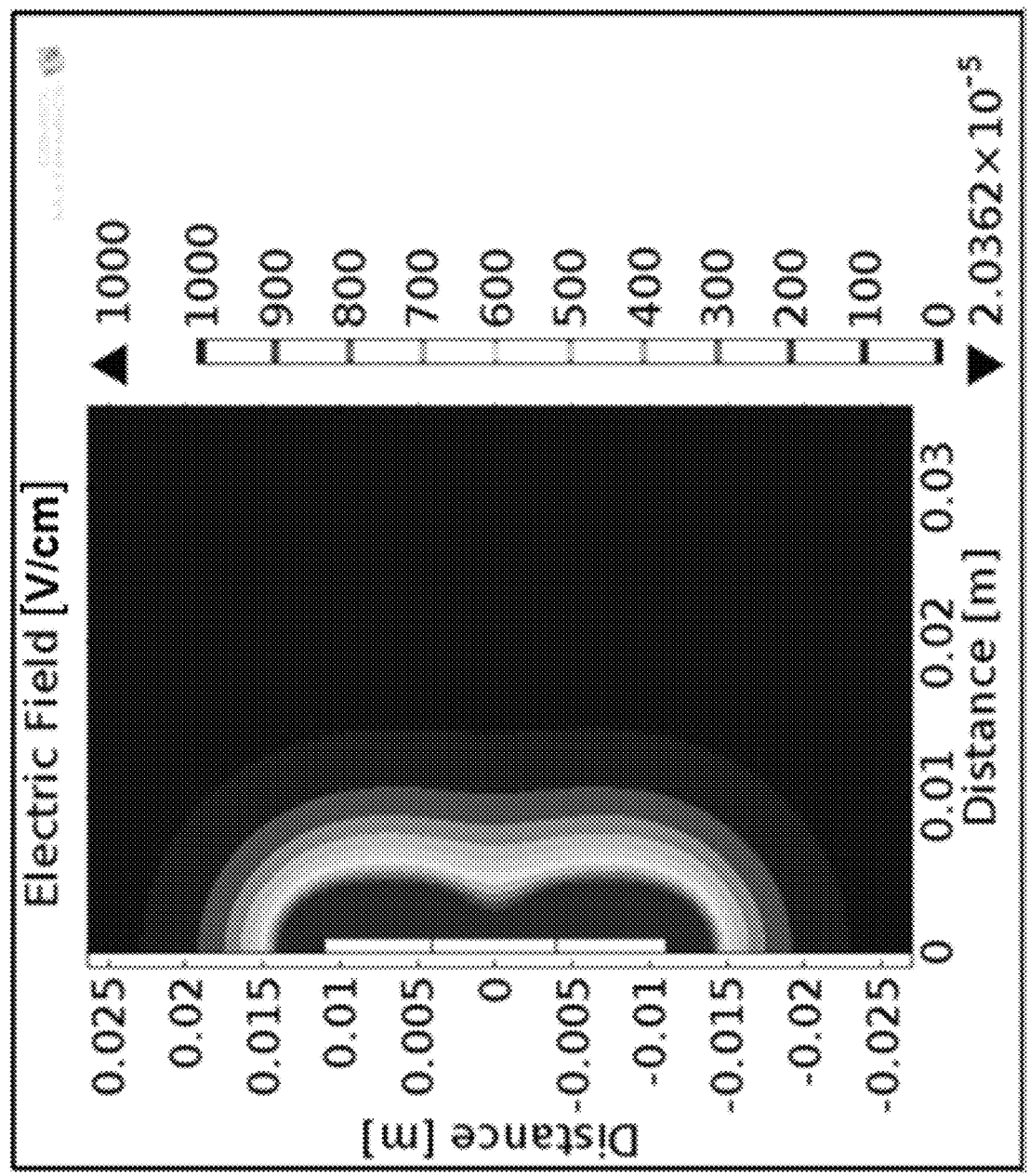
FIG. 42 is a representative contour plot of the electric field distribution assuming a static electrical conductivity using a bipolar probe. The model assumes an applied voltage of 2700 V with 7 mm long electrodes separated by an 8 mm insulation shaft.
Figure 43:
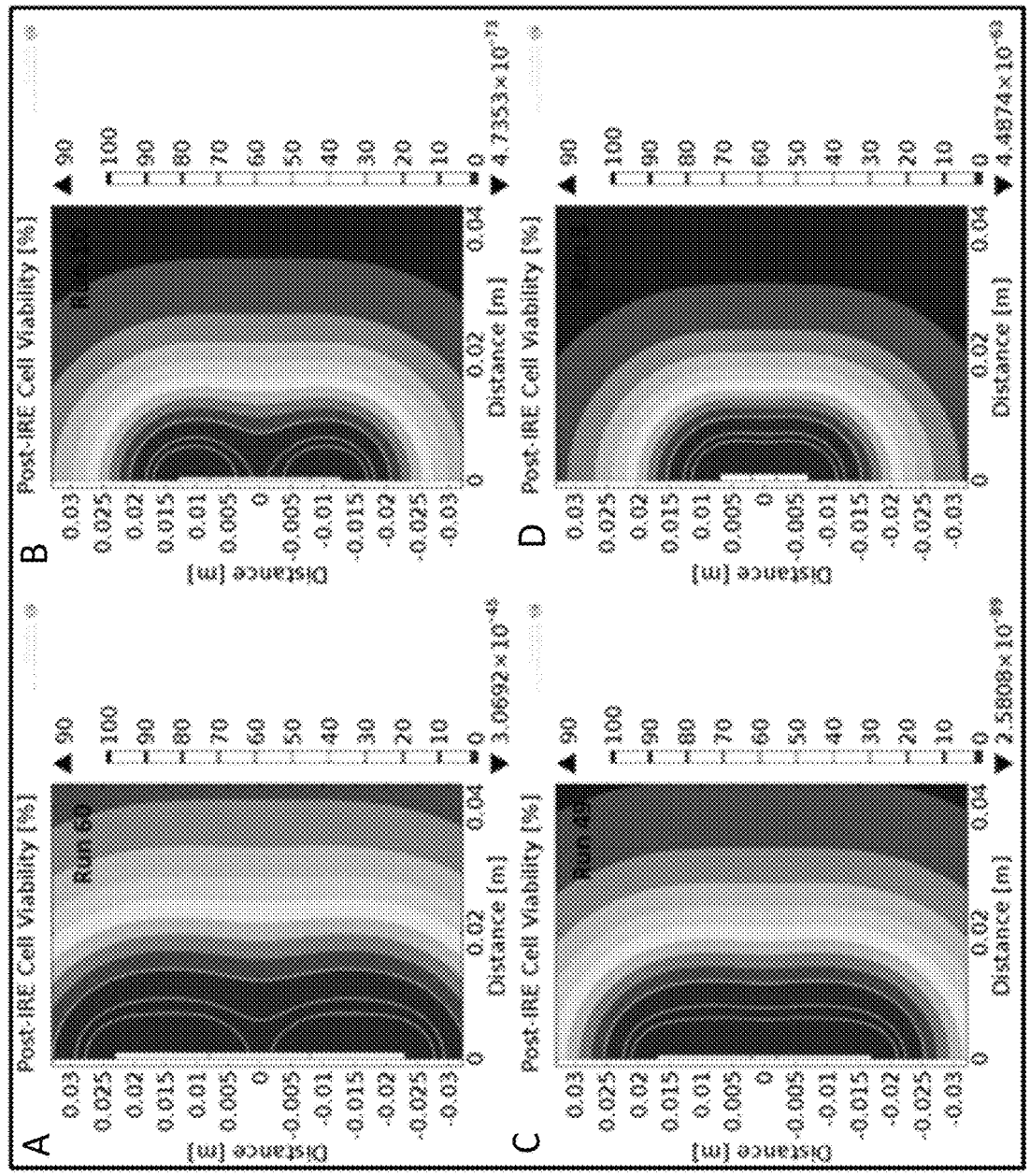
FIGS. 43A-43D are representative contour plots of post-IRE cell viability predictions with the colored curves illustrating different cell viability levels. The model assumes using ninety 100-µs pulses at a rate of one pulse per second with 2700 V, and a viability value of 0.1% (S=0.001) as the complete cell death due to IRE exposure.

Part 1: The work from Part 1 determined the electric field threshold for 0.7 cm electrodes with a 0.8 cm insulation to be 572.8 V/cm assuming a static electric conductivity (Table 12). This threshold is the average between the width (349.5 V/cm) and length (795.1 V/cm) electric field thresholds that matched the experimental lesion of 1.5 cm (width) by 2.9 cm (length). It is important to note that due to the mismatch between the electric field thresholds, the predicted width will be underestimated and the predicted length will be overestimated when using the average value of 572.8 V/cm. The model assumes an applied voltage of 2700 V, ninety 100-μs pulses, at a repetition rate of 1 pulse per second, and a viability value of 0.1% (S=0.001) as the complete cell death due to IRE exposure (FIG. 42). The rate equation used in the analysis is given by $S=e^{-k \cdot E \cdot t}$ where S is the cell viability post-IRE, E is the electric field, t is the cumulative exposure time, and k is the rate constant that dictates cell death. Specifically during this Part, it was determined that k=1.33996 assuming an E=572.8 V/cm, S=0.001, and t=0.009 s (90×100-μs). The k parameter was scaled by the duty cycle of the pulses (0.0001 s) in order to reflect the cell viability in the time scale in which the pulses were delivered (i.e. one pulse per second).

TABLE 12

Electric field thresholds for the static modeling approach from experimental IRE lesions in liver.

| Conductivity | Lesion Dimensions | E-field [V/cm] | Average [V/cm] | Threshold [V/cm] |
|---|---|---|---|---|
| Static - $\sigma_0$ | x = 1.5 cm | 349.5 | 349.5 | 572.8 |
| Static - $\sigma_0$ | y = 2.9 cm (distal) | 796.2 | 795.1 | |
| Static - $\sigma_0$ | y = 2.9 cm (proximal) | 795.6 | | |

A parametric study was constructed in order to explore the effect of electrode diameter (18G=1.27 mm, 16G=1.65 mm, 14G=2.11 mm), electrode spacing (0.4 cm, 0.8 cm, 1.2 cm, 1.6 cm), and electrode length (0.5 cm, 0.75 cm, 1.0 cm, 1.25 cm, and 1.5 cm). In order to provide a comprehensive analysis of all iterations we computed the volumes of tissue that would achieve a cell viability, S<0.001, and these results are reported in the table of FIG. 48A-B. The results with the specific minimum and maximum parameters from Part 1 are presented in Table 13 and demonstrate that with increasing probe diameter and electrode length a larger area/volume of IRE ablation is achieved for ninety 100-μs pulses delivered at 2700 V at a repetition rate of one pulse per second. FIGS. 43A-D shows the predicted regions of post-IRE cell viability isocontour levels with the solid white curve illustrating the 0.1%, 1.0%, and 10% cell viability levels. Of importance is the fact that if the electrodes are spaced too far apart, the resulting IRE zone of ablation is not contiguous and the treatment would fail between the electrodes as shown with Runs 60 and 10, respectively.

TABLE 13

Predicted IRE lesion dimensions for the min. and max. parameters investigated in Part 1.

| Run | Diameter | Spacing (cm) | Length (cm) | Area (cm²) | Volume (cm³) | x(cm) | y(cm) | x:y |
|---|---|---|---|---|---|---|---|---|
| 60 | 14 G = 2.11 mm | 1.6 | 1.5 | 2.705 | 6.232 | 0.311 | 5.550 | 0.056 |
| 10 | 18 G = 1.27 mm | 1.6 | 0.5 | 1.042 | 1.689 | 0.227 | 3.390 | 0.067 |
| 49 | 18 G = 1.27 mm | 0.4 | 1.5 | 2.242 | 4.626 | 1.257 | 4.210 | 0.299 |
| 3 | 14 G = 2.11 mm | 0.4 | 0.5 | 1.120 | 2.241 | 1.221 | 2.190 | 0.558 |

In an effort to better understand the effects of the electrode geometry on the ablation region an extra set of values (Table 14) was generated. The closest outputs to a 1.5 cm×2.9 cm lesion size from parameters in Table 13 were modified to better approximate the targeted lesion. Considering all 60 different runs, number 15 is closest to the targeted values with a lesion geometry of 1.301 cm×2.84 cm.

TABLE 14

Predicted IRE lesion dimensions for parameters approximating a 1.5 cm × 2.9 cm ablation region.

| Run | Diameter | Spacing (cm) | Length (cm) | Area (cm²) | Volume (cm³) | x(cm) | y(cm) | x:y |
|---|---|---|---|---|---|---|---|---|
| 3 | 14 G = 2.11 mm | 0.4 | 0.5 | 1.120 | 2.241 | 1.221 | 2.190 | 0.558 |

TABLE 14-continued

Predicted IRE lesion dimensions for parameters approximating a 1.5 cm × 2.9 cm ablation region.

| Run | Diameter | Spacing (cm) | Length (cm) | Area (cm$^2$) | Volume (cm$^3$) | x(cm) | y(cm) | x:y |
|---|---|---|---|---|---|---|---|---|
| 1 | 18 G = 1.27 mm | 0.4 | 0.5 | 0.943 | 1.590 | 1.037 | 2.170 | 0.478 |
| 15 | 14 G = 2.11 mm | 0.4 | 0.75 | 1.483 | 3.215 | 1.301 | 2.840 | 0.458 |
| 18 | 14 G = 2.11 mm | 0.8 | 0.75 | 1.680 | 3.652 | 1.181 | 3.250 | 0.363 |

Figure 44:
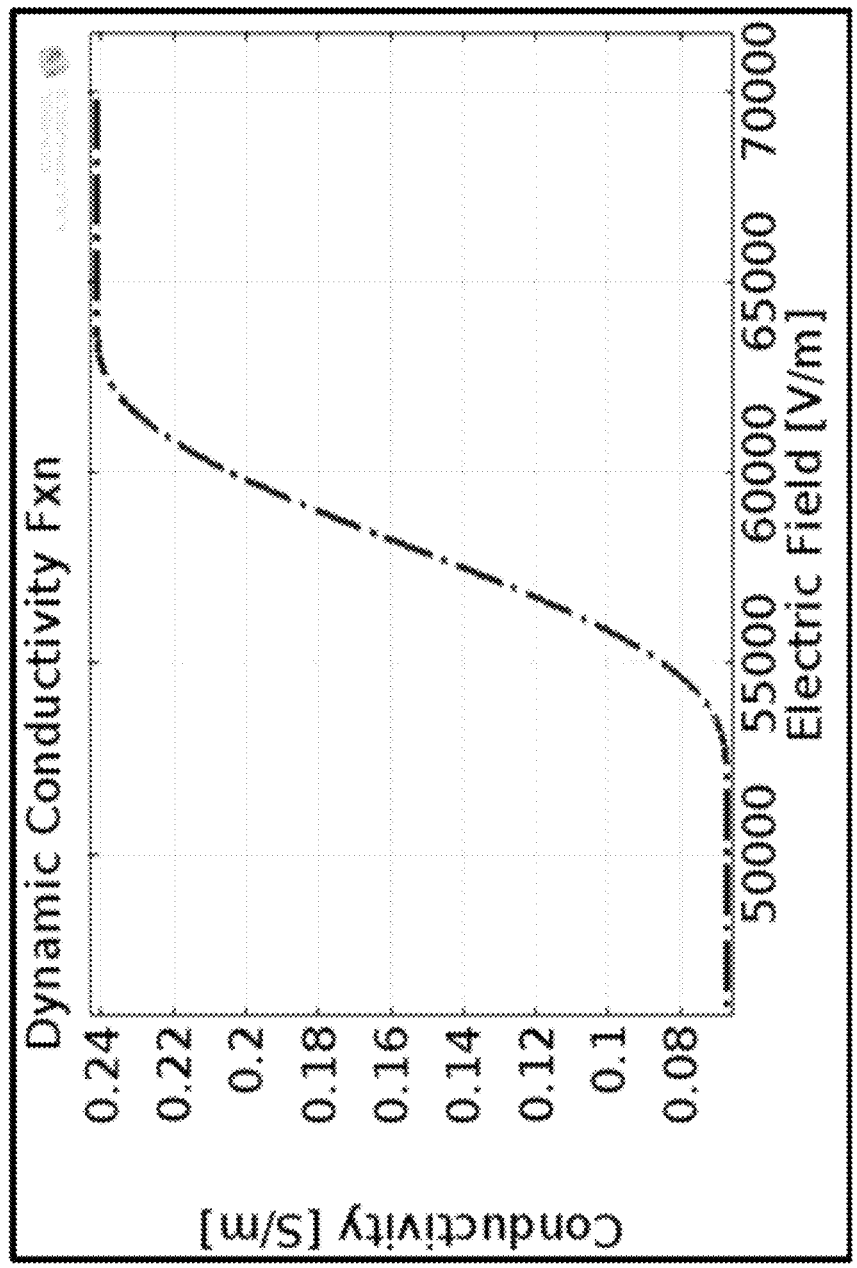
FIG. 44 is a graph showing the dynamic electric conductivity function of liver tissue undergoing electroporation. The sigmoid function includes a baseline of 0.067 S/m and maximum conductivity of 0.241 S/m.

Part 2: In Part 2 the electric field distribution assuming a dynamic electric conductivity was used to determine the threshold of cell death due to IRE exposure. Specifically during this Part, a sigmoid function (FIG. 44) with a baseline (0.067 S/m) and maximum (0.241 S/m) conductivity values was used (see Sel, D., et al., *Sequential finite element model of tissue electropermeabilization*. IEEE Trans Biomed Eng, 2005. 52(5): p. 816-27). This published function assumes that reversible electroporation starts at 460 V/cm and is irreversible at 700 V/cm as reported by Sel. et al. Using the dynamic conductivity function resulted in a more consistent electric field threshold between the width (615.7 V/cm) and the length (727.4 V/cm); therefore, using the average (670.1 V/cm) provides a better prediction of the IRE lesions being achieved in vivo versus the ones predicted in Part 1 that assume a static conductivity (Table 15). The electric field threshold for IRE using the dynamic conductivity approach resulted in a revised k=1.14539 assuming an E=670.1 V/cm, S=0.001, and t=0.009 s (90×100 μs). The k parameter was scaled by the duty cycle of the pulses (0.0001 s) in order to reflect the cell viability in the time scale in which the pulses were delivered (i.e. one pulse per second).

TABLE 15

Electric field thresholds for the dynamic modeling approach from experimental IRE lesions in liver.

| Conductivity | IRE Dimension | E-field [V/cm] | Average | Threshold [V/cm] |
|---|---|---|---|---|
| Dynamic - σ(E) | x = 1.5 cm | 615.7 | 615.7 | 670.1 |
| Dynamic - σ(E) | y = 2.9 cm (distal) | 720.7 | 727.4 | |
| Dynamic - σ(E) | y = 2.9 cm (proximal) | 734.0 | | |

Figure 45:
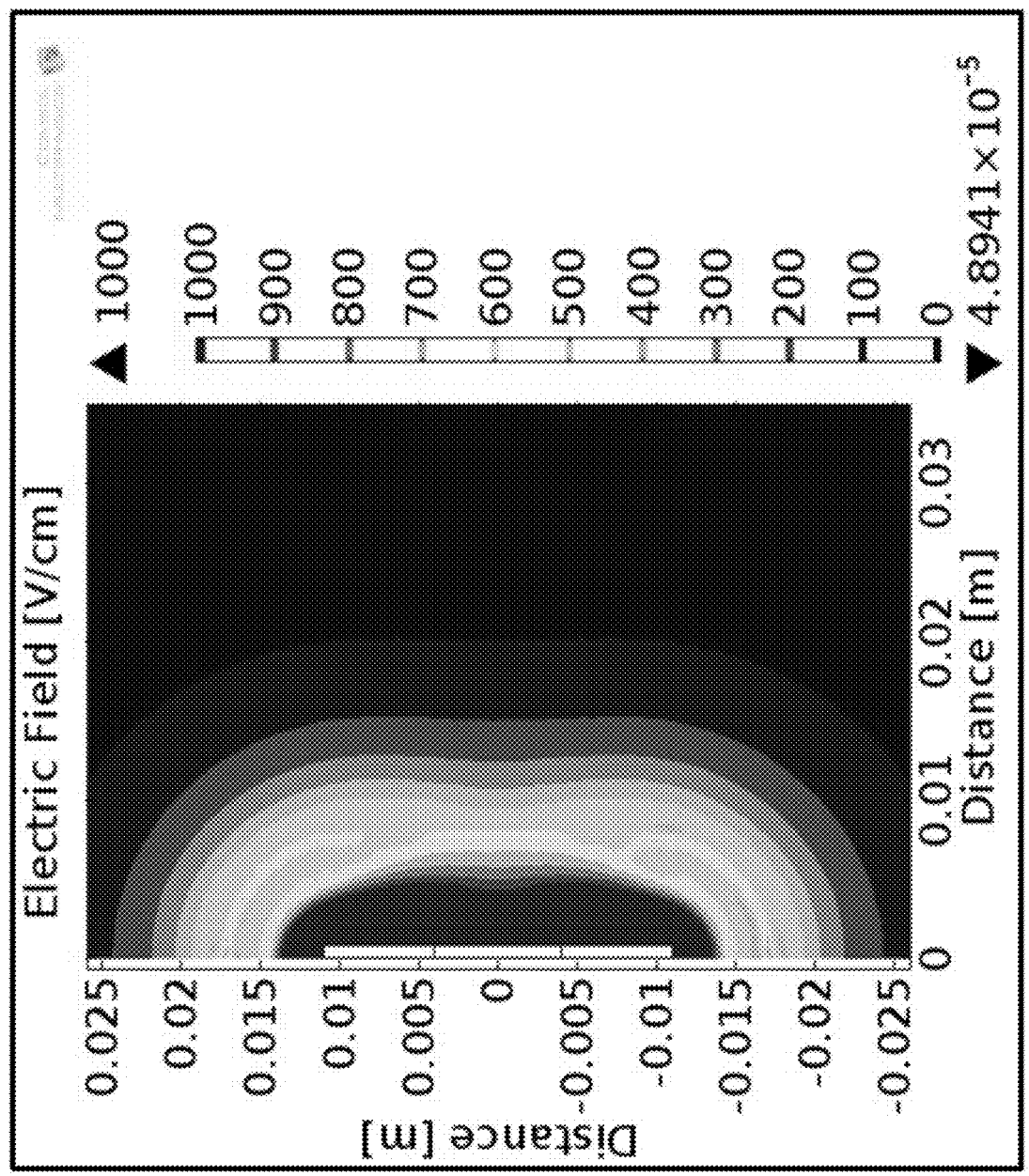
FIG. 45 is a representative contour plot showing the electric field distribution assuming a dynamic electrical conductivity using the bipolar probe with 3000 V with 7 mm long electrodes separated by an 8 mm insulation shaft.

In Part 2, the effect of pulse strength (2000 V, 2250 V, 2500 V, 2750 V, 3000 V) and pulse number (20, 40, 60, 80, 100) was explicitly investigated and the results of the parametric study are provided in the table of FIG. 49 and a representative plot provided in FIG. 45. The results with the specific minimum and maximum parameters from Part 2 are presented in Table 16 and demonstrate that with increasing pulse strength and pulse number a larger volume of IRE ablation is achieved at a repetition rate of one pulse per second (FIGS. 46A-D). In order to compare the results to the electric field threshold, both areas/volumes were computed and are provided as well. Similar to the results from Part 1, the white solid curve represents the 0.1%, 1.0%, and 10% cell viability isocontour levels due to IRE. For all voltages investigated, delivering one hundred 100-μs pulses covers a greater area/volume than the prediction by the 670.1 V/cm electric field threshold assumed with the dynamic conductivity function.

TABLE 16

Predicted lesion dimensions for the minimum and maximum parameters investigated in Part 2.

| Run | Voltage (V) | Number | Area (cm$^2$) | Volume (cm$^3$) | E-Field (cm$^2$) | E-Field (cm$^3$) | x(cm) | y(cm) | x:y |
|---|---|---|---|---|---|---|---|---|---|
| 3 | 2000 | 20 | 0.080 | 0.050 | 0.970 | 1.575 | 0.216 | 2.350 | 0.092 |
| 6 | 2000 | 100 | 1.209 | 2.238 | 0.970 | 1.575 | 0.646 | 1.630 | 0.396 |
| 27 | 3000 | 20 | 0.209 | 0.170 | 1.493 | 3.171 | 0.221 | 1.800 | 0.123 |
| 30 | 3000 | 100 | 1.900 | 4.604 | 1.493 | 3.171 | 0.946 | 1.130 | 0.837 |

Figures 47A, 47B:
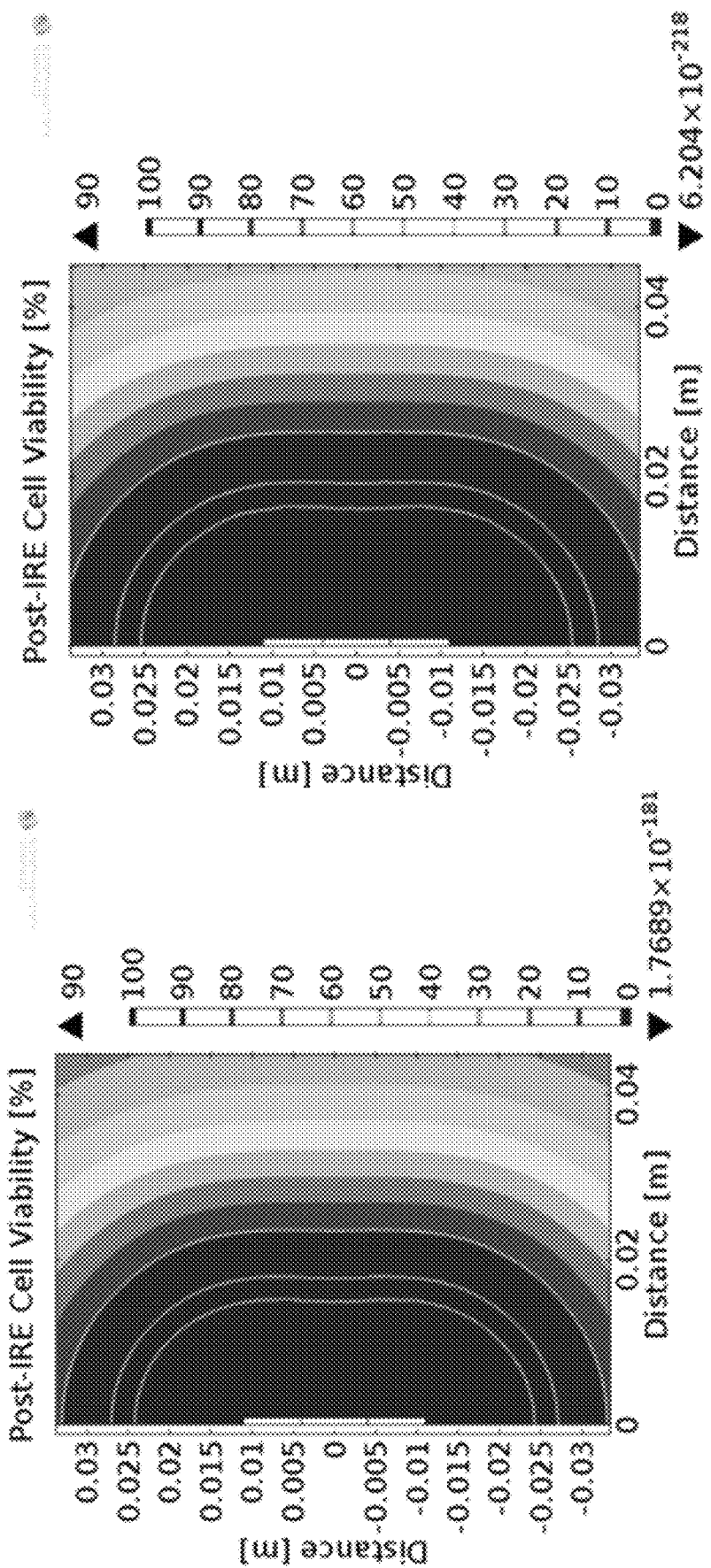
FIGS. 47A and 47B are representative contour plots showing post-IRE cell viability after three hundred (FIG. 47A) and three hundred and sixty (FIG. 47B) 100-µs pulses at a rate of one pulse per second with an applied voltage of 3000 V.

Part 3: In this Part the exposure of liver tissue to 300 (5×60) and 360 (4×90) pulses were simulated at an applied voltage of 3000 V, 100-μs pulses, at a repetition rate of one pulse per second. From the cell viability plots in FIG. 47A-B it can be seen that with increasing number of pulses, larger zones of IRE ablation are achieved with the corresponding areas and volumes included in Table 17 and the table of FIG. 50. It is important to note that in this case the simulation assumes that there is sufficient thermal relaxation time between sets of pulses; thus preventing any potential thermal damage from Joule heating which is not simulated in this work.

TABLE 17

Predicted lesion dimensions for the 5 × 60 and 4 × 90 IRE pulses investigated in Part 3.

| Run | Voltage (V) | Number | Area (cm$^2$) | Volume (cm$^3$) | E-Field (cm$^2$) | E-Field (cm$^3$) | x(cm) | y(cm) | x:y |
|---|---|---|---|---|---|---|---|---|---|
| 16 | 3000 | 5 × 60 | 6.135 | 27.282 | 1.493 | 3.171 | 2.877 | 4.900 | 0.587 |
| 19 | 3000 | 4 × 90 | 6.950 | 33.202 | 1.493 | 3.171 | 3.287 | 5.540 | 0.593 |

Models with exploratory geometries were developed that include multiple voltage sources and current diffusers (balloons). FIGS. 51A-C present images of the raw geometries being tested and FIGS. 51D-F show the corresponding electric field distribution. In general, the most influential parameter remains the size of the electrodes and insulation. According to the values generated from these simulations, it seems like substantial helps to achieve more spherical lesions.

TABLE 18

Predicted IRE lesion dimensions for exploratory models in Appendix D.

| Run | Diameter | Spacing (cm) | Length (cm) | Area (cm$^2$) | Volume (cm$^3$) | x(cm) | y(cm) | x:y |
|---|---|---|---|---|---|---|---|---|
| 61 | 0.211 | 0.4 | 0.5 | 1.453 | 1.807 | 1.201 | 2.850 | 0.421 |
| 62 | 0.211 | 0.4 | 1 | 1.617 | 2.129 | 1.321 | 3.670 | 0.360 |
| 63 | 0.211 | 0.4 | 1 | 2.008 | 3.041 | 1.241 | 2.955 | 0.420 |
| 64 | 0.211 | 0.4 | 0.5 | 1.389 | 1.929 | 1.261 | 2.810 | 0.449 |
| 65 | 0.211 | 0.4 | 0.5 | 0.976 | 1.142 | 1.421 | 2.000 | 0.711 |

The present invention has been described with reference to particular embodiments having various features. In light of the disclosure provided, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. In particular, for method embodiments, the order of steps is merely exemplary and variations appreciated by a skilled artisan are included in the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method comprising:
   obtaining an image of a patient tissue;
   identifying a target treatment area in the image of the patient tissue;
   modeling an estimated treatment zone in the target treatment area based on one or more electrical energy treatment parameters and one or more tissue-specific conductivity parameters, wherein the tissue-specific conductivity parameters include a measured baseline electrical conductivity, a change in electrical conductivity, a rate at which electrical conductivity changes, an electric field at which the change in electrical conductivity occurs, and/or an electric field at which irreversible electroporation occurs;
   providing a graphical representation of the estimated treatment zone;
   providing a treatment protocol based on the modeling; and
   administering electrical pulses to the target treatment area of the patient tissue according to the treatment protocol.

2. The method of claim 1, wherein the graphical representation is a 3D graphical representation of the estimated treatment zone.

3. The method of claim 2, wherein the image and/or the 3D graphical representation includes one or more of cells, organs, vessels, heart, kidney, liver, lung, spleen, pancreas, brain, prostrate, breast, small intestine, large intestine, stomach, or mesenchymal tissue.

4. The method of claim 1, wherein the identifying of the target treatment area in the image of the patient tissue is performed automatically by software; and/or
   wherein the target treatment area is modified by a user.

5. The method of claim 1, wherein the graphical representation comprises the estimated treatment zone and a safety margin.

6. The method of claim 1, wherein the change in electrical conductivity is due to temperature.

7. The method of claim 1, wherein the electrical energy treatment parameters are chosen from one or more of voltage, electrode spacing, electrode diameter, electrode length, number of pulses, treatment duration, pulse width, electric field intensity.

8. The method of claim 1, wherein the graphical representation comprises a modeled electrical field distribution derived from Cassini oval calculations.

9. The method of claim 1, wherein the graphical representation is an image generated from Computed Tomography (CT), Magnetic Resonance Imaging (MRI), Ultrasound imaging, Positron Emission Tomography (PET) or fluoroscopic imaging.

10. The method of claim 1, wherein the modeling comprises virtual placement of one or more electrodes.

11. The method of claim 10, further comprising determining a lethal electric field threshold for IRE ($E_{IRE}$).

12. A method comprising:
    obtaining an image of a patient tissue;
    identifying a target treatment area in the image of the patient tissue;
    segmenting the target treatment area from surrounding tissue;
    modeling an estimated treatment zone in the target treatment area based on one or more treatment parameters and one or more tissue-specific conductivity parameters, wherein the tissue-specific conductivity parameters include a measured baseline electrical conductivity, a change in electrical conductivity, a rate at which electrical conductivity changes, an electric field at which the change in electrical conductivity occurs, and/or an electric field at which irreversible electroporation occurs;
    providing a graphical representation of the estimated treatment zone;
    identifying one or more area within the estimated treatment zone that may be subject to thermal damage based on the modeling;
    modifying one or more of the treatment parameters through one or more iterations to provide modified treatment parameters capable of preventing thermal damage within the one or more area of the estimated treatment zone; and
    providing a modified graphical representation of the estimated treatment zone based on the modified treatment parameters and providing a treatment protocol based on the modeling that prevents thermal damage within the one or more area within the estimated treatment zone.

13. The method of claim 12, wherein the graphical representation and/or the modified graphical representation is a 3D graphical representation.

14. The method of claim 12, wherein the identifying of the target treatment area in the image of the patient tissue is performed automatically by software; and/or
    wherein the target treatment area is modified by a user.

15. The method of claim 12, wherein the graphical representation and/or the modified graphical representation comprises the estimated treatment zone and a safety margin.

16. The method of claim 12, wherein the treatment parameters and/or the modified treatment parameters are chosen from one or more of voltage, electrode spacing, electrode diameter, electrode length, number of pulses, treatment duration, pulse width, electric field intensity, a baseline electrical conductivity for the target treatment area, or an electrical conductivity for a specific tissue type.

17. The method of claim 12, wherein the graphical representation or the modified graphical representation is derived from Cassini oval calculations.

18. The method of claim 12, further comprising administering the treatment protocol to the patient.

19. A method comprising:
obtaining an image of a patient tissue;
identifying a target treatment area in the image of the patient tissue;
virtually placing one or more simulated electrodes in the target treatment area;
modeling an estimated treatment zone in the target treatment area based on one or more treatment parameters, the virtually placed electrodes, and one or more tissue-specific conductivity parameters, wherein the tissue-specific conductivity parameters include a measured baseline electrical conductivity, a change in electrical conductivity, a rate at which electrical conductivity changes, an electric field at which the change in electrical conductivity occurs, and/or an electric field at which irreversible electroporation occurs;
providing a graphical representation of the estimated treatment zone;
providing a treatment protocol based on the modeling;
placing one or more electrodes into the target area based on the treatment protocol; and
administering the treatment protocol to the patient.

* * * * *